(12) United States Patent
Forsgren et al.

(10) Patent No.: US 10,183,071 B2
(45) Date of Patent: *Jan. 22, 2019

(54) INTERACTION OF MORAXELLA CATARRHALIS WITH EPITHELLAL CELLS, EXTRACELLULAR MATRIX PROTEINS AND THE COMPLEMENT SYSTEM

(71) Applicant: ARNE FORSGREN AB, Falsterbo (SE)

(72) Inventors: Arne Forsgren, Falstebro (SE); Kristian Riesbeck, Malmo (SE)

(73) Assignee: ARNE FORSGREN AB, Falsterbo (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/486,513

(22) Filed: Apr. 13, 2017

(65) Prior Publication Data

US 2017/0281746 A1 Oct. 5, 2017

Related U.S. Application Data

(62) Division of application No. 14/986,104, filed on Dec. 31, 2015, now Pat. No. 9,657,067, which is a division of application No. 14/508,033, filed on Oct. 7, 2014, now Pat. No. 9,255,127, which is a division of application No. 13/666,941, filed on Nov. 1, 2012, now Pat. No. 8,895,030, which is a division of application No. 13/314,727, filed on Dec. 8, 2011, now Pat. No. 8,323,667, which is a division of application No. 12/063,408, filed as application No. PCT/SE2006/000931 on Aug. 8, 2006, now Pat. No. 8,092,811.

(60) Provisional application No. 60/707,148, filed on Aug. 11, 2005, provisional application No. 60/706,745, filed on Aug. 10, 2005.

(51) Int. Cl.

| A61K 39/104 | (2006.01) |
| C07K 14/195 | (2006.01) |
| C07K 14/21 | (2006.01) |
| C12N 15/10 | (2006.01) |
| C07K 14/78 | (2006.01) |
| G01N 30/02 | (2006.01) |
| C12N 15/09 | (2006.01) |
| A61K 39/02 | (2006.01) |
| C07K 19/00 | (2006.01) |

(52) U.S. Cl.
CPC ........ *A61K 39/1045* (2013.01); *A61K 39/104* (2013.01); *C07K 14/195* (2013.01); *C07K 14/212* (2013.01); *C07K 14/78* (2013.01); *C12N 15/101* (2013.01); *G01N 30/02* (2013.01); *A61K 39/02* (2013.01); *C07K 19/00* (2013.01); *C12N 15/09* (2013.01)

(58) Field of Classification Search
CPC .............. C07K 14/212; C07K 2319/00; C07K 14/285; A61K 39/1045; A61K 39/0208; A61K 39/092; A61K 39/145; A61K 39/00; A61K 39/102
See application file for complete search history.

(56) References Cited

U.S. PATENT DOCUMENTS

| 5,721,115 | A | 2/1998 | Krivan et al. | |
| 8,092,811 | B2* | 1/2012 | Forsgren .............. | C07K 14/212 424/190.1 |
| 8,323,667 | B2 | 12/2012 | Forsgren et al. | |
| 8,617,565 | B2 | 12/2013 | Forsgren et al. | |
| 8,895,030 | B2* | 11/2014 | Forsgren .............. | C07K 14/212 424/190.1 |
| 9,255,127 | B2* | 2/2016 | Forsgren .............. | C07K 14/212 |
| 9,309,293 | B2 | 4/2016 | Forsgren et al. | |
| 9,657,067 | B2* | 5/2017 | Forsgren .............. | C07K 14/212 |
| 9,744,225 | B2 | 8/2017 | Forsgren et al. | |
| 2010/0062027 | A1 | 3/2010 | Forsgren et al. | |
| 2015/0071956 | A1 | 3/2015 | Forsgren et al. | |
| 2017/0326223 | A1 | 11/2017 | Forsgren et al. | |

FOREIGN PATENT DOCUMENTS

| CN | 101374859 B | 11/2014 |
| EP | 0 163 623 A2 | 12/1985 |
| EP | 1254234 B1 | 11/2002 |
| JP | 5275814 B2 | 8/2013 |
| JP | 6008747 B2 | 10/2016 |
| KR | 101737464 B1 | 5/2017 |
| WO | WO 96/34960 A1 | 11/1996 |
| WO | WO 98/28333 A2 | 7/1998 |
| WO | WO 2001/061013 A1 | 8/2001 |
| WO | WO 2002/028889 A2 | 4/2002 |
| WO | WO 2004/031236 A2 | 4/2004 |
| WO | WO 2005/111066 A2 | 11/2005 |

OTHER PUBLICATIONS

Li et al (Proc. Natl. Acad. Sci. USA 77:3211-3214, 1980).*
Lederman et al (Molecular Immunology 28:1171-1181, 1991).*
LaFontaine et al., "The UspA1 Protein and a Second Type of UspA2 Protein Mediate Adherence of *Moraxella catarrhalis* to Human Epithelial Cells in Vitro," J. Bacteriol. 182(5): 1364-1373 (2000).
Möllenkvist et al., "The *Moraxella catarrhalis* Immunoglobulin D-Binding Protein MID Has Conserved Sequences and Is Regulated by a Mechanism Corresponding to Phase Variation," J. Bacteriol. 185(7): 2285-2295 (2003).

(Continued)

*Primary Examiner* — Padmavathi Baskar
(74) *Attorney, Agent, or Firm* — Finnegan, Henderson, Farabow, Garrett & Dunner, LLP

(57) ABSTRACT

The present disclosure relates to surface proteins of *Moraxella catarrhalis* and their ability to interact with epithelial cells via cell-associated fibronectin and laminin, and also to their ability to inhibit the complement system. These surface proteins are useful in the preparation of vaccines. The present disclosure also provides peptides interacting with fibronectin, laminin and the complement system.

5 Claims, 34 Drawing Sheets

Specification includes a Sequence Listing.

(56) References Cited

OTHER PUBLICATIONS

Strott, "Sulfonation and Molecular Action," Endocrine Reviews 23(5): 703-732 (2002).
Lederman et al., "A Single Amine Acid Substitution in a Common African Allele of the CD4 Molecule Ablates Binding of the Monoclonal Antibody, OKT4," Mol. Immunol. 28(11): 1171-1181 (1991).
Li et al., "b-Endorphin omission analogs: Dissociation of immunoreactivity from other biological activities," Proc. Natl. Acad. Sci. USA 77(6): 3211-3214 (1980).
Cope et al., "Characterization of the *Moraxella catarrhalis uspA1* and *uspA2* Genes and Their Encoded Products," J. Bacteriol. 181(13): 4026-4034 (1999).
Database UNIProtKB/TREMBL entry with accession No. Q9XD55 dated Nov. 1, 1999 (3 pages).
Tan et al., "The Respiratory Pathogen *Moraxella catarrhalis* Adheres to Epithelial Cells by Interacting With Fibronectin through Ubiquitous Surface Proteins A1 and A2," J. Infectious Diseases 192: 1029-1038 (2005).
McMichael et al., "Isolation and Characterization of Two Proteins from *Moraxella catarrhalis* That Bear a Common Epitope," Infection and Immunity 66(9): 4374-4381 (1998).
Aebi et al., "A Protective Epitope of *Moraxella catarrhalis* Is Encoded by Two Different Genes," Infection and Immunity 65(11): 4367-4377 (1997).
Nordström et al., "Ionic Binding of C3 to the Human Pathogen *Moraxella catarrhalis* Is a Unique Mechanism for Combating Innate Immunity," Journal of Immunology 175(6): 3628-3636 (2005).
Nordström, "*Moraxella catarrhalis* Outer Membrane Proteins and Interactions with the Human Immune System," Lund University Dissertations, Scripts Academica Lundensia, Medicinsk Mikrobiologi Institutionen för Laboratorie Medicin Universitetssjukhuset MAS Lunds Universitet, pp. 1-4 (2005).
Nordström et al., "The Emerging Pathogen *Moraxella catarrhalis* Interacts with Complement Inhibitor C4b Binding Protein through Ubiquitous Surface Proteins A1 and A2", J. Immunol. 173: 4598-4606 (2004).
Blom, "Strategies developed by bacteria and virus for protection from the human complement system", Scand. J. Clin. Lab. Invest. 64: 479-495 (2004).
Database UniProtKB/TrEMBL entry with Accession No. Q8RT89, Ubiquitous surface protein A2 (uspA2) (Date sequence integrated to UniProtKB/TrEMBL database: Jun. 1, 2002).
Office Action, dated Feb. 23, 2010, for U.S. Appl. No. 12/063,408, filed Feb. 8, 2008.
Office Action, dated Jun. 29, 2010, for U.S. Appl. No. 12/063,408, filed Feb. 8, 2008.
Final Office Action, dated Dec. 28, 2010, for U.S. Appl. No. 12/063,408, filed Feb. 8, 2008.
Notice of Allowance, dated Sep. 9, 2011, for U.S. Appl No. 12/063,408, filed Feb. 8, 2008.
Office Action, dated Jun. 13, 2012, for U.S. Appl. No. 13/314,727, filed Dec. 8, 2011.
Notice of Allowance and Interview Summary, dated Aug. 2, 2012, for U.S. Appl. No. 13/314,727, filed Dec. 8, 2011.
Notice of Allowance, dated Aug. 2, 2012, for U.S. Appl. No. 13/314,727 filed Dec. 8, 2011.
Notice of Allowance, dated Jul. 7, 2014, for U.S. Appl. No. 13/666,941 filed Nov. 1, 2012.
Notice of Allowance, dated Mar. 21, 2014, for U.S. Appl. No. 13/666,941 filed Nov. 1, 2012.
Office Action, dated Nov. 22, 2013, for U.S. Appl. No. 13/666,941 filed Nov. 1, 2012.
Notice of Allowance, dated Oct. 1, 2015, for U.S. Appl. No. 14/508,033 filed Oct. 7, 2014.
Notice of Allowance, dated Oct. 26, 2015, for U.S. Appl. No. 14/508,033 filed Oct. 7, 2014.
Office Action, dated Jun. 24, 2015, for U.S. Appl. No. 14/508,033 filed Oct. 7, 2014.
Notice of Allowance, dated Jan. 17, 2017, for U.S. Appl. No. 14/986,104 filed Dec. 31, 2015.
Bowie, J. et al., "Deciphering the Message in Protein Sequences: Tolerance to Amino Acid Substitutions", Science, 257(4948):1306-1310 (1990).
Colman, P. "Effects of amino acid sequence changes on antibody-antigen interactions", Res. Immunology, 145(a):38-36 (1994).
Greenspan, et al., "Defining epitopes: It's not as easy as it seems", Nature Biotechnology, 17:936-937 (1999).
Musacchio, A., et al., "Recombinant Opc meningococcal protein, folded in vitro, elicits bactericidal antibodies after immunization", Vaccine, 15(b/7):751-758 (1997).
Fleischmann, R., et al., "Whole-genome random sequencing and assembly of Haemophilus influenzae Rd.," Science, vol. 269, pp. 469-512 (1995).
Harrison, a., et al., "Genomic Sequence of an Otitis Media Isolate of Nontypeable Haemophilus influenzae: Comparative Study with H. influenzae Serotype d, Strain KW20" Journal of Bacteriology, vol. 187, No. 13, pp. 4627-4636 (2005).
Ronander, E., et al., "Nontypeable Haemophilus influenzae adhesin protein E: Characterization and Biological Activity," The Journal of Infectious Diseases, vol. 199, pp. 522531 (2009).
International Search Report issued in International Application No. PCT/SE2007/000034, dated Apr. 17, 2007.
European Search Report issued in European Patent Application No. EP 17 19 6588.
Extended European Search Report issued in European Patent Application No. 17196588, dated Feb. 13, 2018.

\* cited by examiner

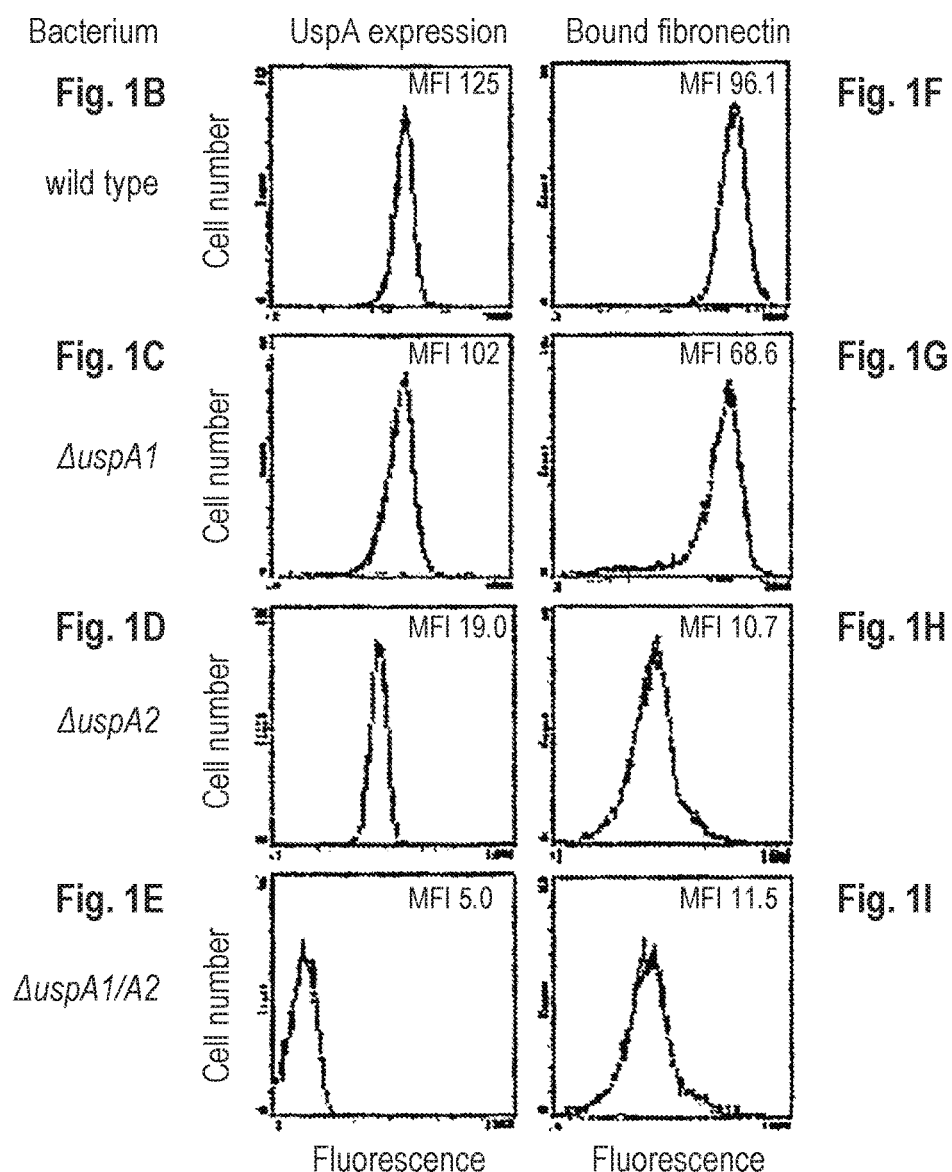

Fig. 3A  *M. catarrhalis* wild type
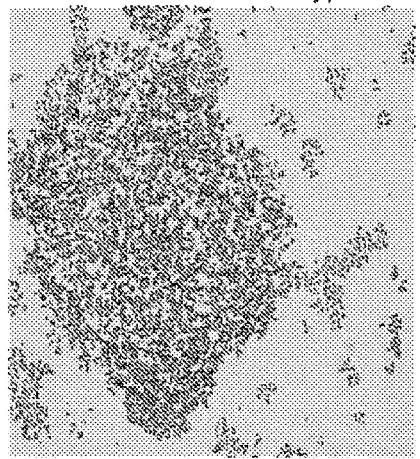
Fig. 3B  Δ*uspA1* mutant
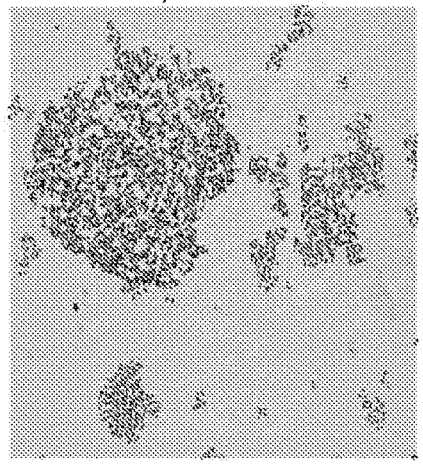
Fig. 3C  Δ*uspA2* mutant
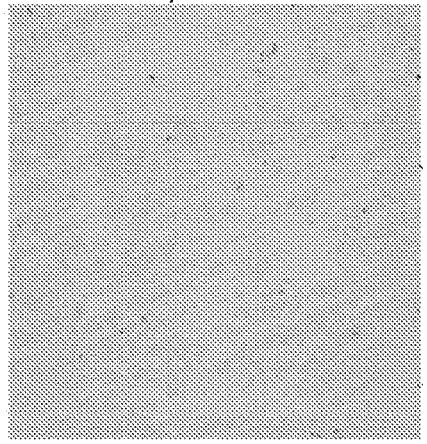
Fig. 3D  Δ*uspA1/A2* double mutant

Fig. 6

```
UspA1 300-453    TGNGTVSVGKKGKERQIVHVGAGEISDTST
UspA2 165-318    --KDAIAKNNESIED-LYDFGH-EVAES--

UspA1 300-453    DAVNGSQLHVLATVVAQNKADIKDLDDEVG
UspA2 165-318    ---IG-EIHAHN--EAQNET----LK---G

UspA1 300-453    LLGEEINSLEGEIFNNQDAIAKNQADIKTL
UspA2 165-318    LI---TNSIE--NTNN---ITKNKADIQAL

UspA1 300-453    ESNVEEGLLDLSGRLLDQKADIDNNINNIY
UspA2 165-318    ENNVVEELFNLSGRLIDQKADIDNNINNIY

UspA1 300-453    ELAQQDQHSSDIKTLKNNVEEGLLDLSGR
UspA2 165-318    ELAQQDQHSSDIKTLKKNVEEGLLELSDH

UspA1 300-453    LIDQ--------------------------
UspA2 165-318    IIDQKTDIAQNQANIQDLATYNELQDQYAQ

UspA1 300-453    -
UspA2 165-318    K
```

C3

C3met

Covalently Bound C3b

Microbial surface

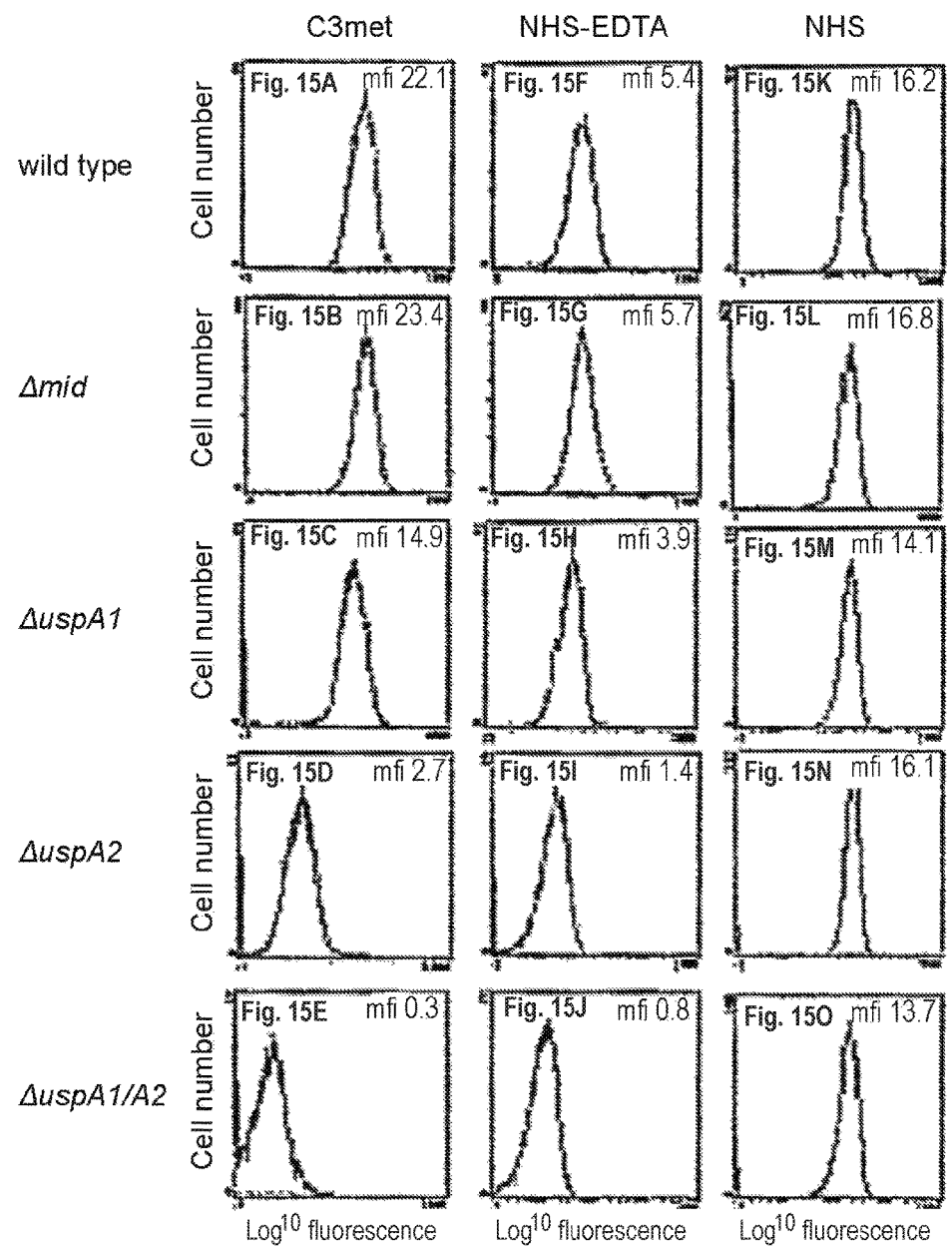

Fig. 19A

Pileup – beginning and end of the fibronectin binding domain marked with { and }

```
                         *        20         *        40         *
USPA1_O12E  : MNKIYKVKKNAAGHLVACSEFAKGHTKKAVLGSLLIVG LGMATTASAQ-  :  49
USPA1_P44   : MNKIYKVKKNAAGHLVACSEFAKGHTKKAVLGSLLIVG LGMATTASAQ-  :  49
USPA1_ATCC  : MNKIYKVKKNAAGHLVACSEFAKGHTKKAVLGSLLIVG LGMATTASAQ-  :  49
USPA1_O46E  : MNKIYKVKKNAAGHLVACSEFAKGHTKKAVLGSLLIVGALGMATTASAQ-  :  49
USPA1_TTA3  : MNKIYKVKKNAAGHLVACSEFAKGHTKKAVLGSLLIVG LGMATTASAQQ :  50
USPA1_O35E  : MNKIYKVKKNAAGHLVACSEFAKGHTKKAVLGSLLIVGALGMATTASAQ-  :  49
USPA1_TTA2  : MNKIYKVKKNAAGHLVACSEFAKGHTKKAVLGSLLIVG LGMATTASAQ-  :  49
USPA1_V117  : MNKIYKVKKNAAGHLVACSEFAKGHTKKAVLGSLLIVG LGMATTASAQ-  :  49

60         *        80     §   *       100
USPA1_O12E  : ----KAANTTNQASGRHT--------YVGGGDNNQATCMTSF  FFNQ :  87
USPA1_P44   : ----AIN-------TGQGT--------VVDQ-NGNEAICN TAS  DNNQ :  80
USPA1_ATCC  : -----KVGKATNKISGGDNNTANGTYLTIGGGDYNKTKCPYST  LFNE :  95
USPA1_O46E  : ---ATKGTGKHVVDN--KDNKAKGDYSTASGGKDNEAKCNKSTV  DYNE :  95
USPA1_TTA3  : TIARQGKGMHSIIGGGNDNEANGDYSTVSGGDYNEAKCDSST  YNNE : 100
USPA1_O35E  : -----ATNS---------------------KCTGAH  VNNNNE :  67
USPA1_TTA2  : ----MATTPSAQVVKTNN-----------KKNCTHPF  DYNT :  79
USPA1_V117  : -----QNNQ--------------------KSCKYPF  GYNN :  68

*       120         *       140         *
USPA1_O12E  : T NHL  CSANQAKCN      CGDCNETT THCT    CCDS------- : 130
USPA1_P44   : K N  AS  CSGNTAECN   ASCCLNT E N  STASCCLG------- : 123
USPA1_ATCC  : TNE  S   CCGYNE TNQ  CT   STASCCGDN------- : 138
USPA1_O46E  : K N  SV  CSSNTAKCEK   CCDTND MT ST CC--------- : 136
USPA1_TTA3  : N DSS   CFYNEAKCES   CCDNNS TNMC T  CCDNNSATGRY : 150
USPA1_O35E  : P D 8F   SCGYNKA CP A  CCLFNK TNE STVCCGY------- : 110
USPA1_TTA2  : TK N P   CHFNTAECN  V CCFTNE I KNSTV CCFT------- : 122
USPA1_V117  : VD K P   CLFNIA GK P  CCGAHNK NT ST  CCSY------- : 111

*       160         *       180         *       200
USPA1_O12E  : ------KAECTHST  CCYDNTAK THST IVCCRKNP ECNYS  AG : 172
USPA1_P44   : ------TAKCKYST VACCANNQAKCDYS ASCCSGNTAECNYS  AG : 165
USPA1_ATCC  : ------TAKCRYST  CCGYNEATIENS VGCCGYNQAKCRNST  AG : 180
USPA1_O46E  : ------YYSRAICDSST  CCGYYNQATCEKST VACCRNNQATCNNST  AG : 180
USPA1_TTA3  : STIAGGWL QATCHSST VACGWLNQATNENSTV CCGRENQATCRNST  AG : 200
USPA1_O35E  : ------KAECRYST  CCSNNEATNEYSTIV CCGDLNKATCRYST  IGG : 152
USPA1_TTA2  : ------EAMCEYST VACCANNQAKCNYSTI VCCGNGNKAIGNNST  VG : 164
USPA1_V117  : ------EANCEKST  CCDNNTAKCNHST V CCGYKNEATCKYST  GG : 153

*       220         *       240         *
USPA1_O12E  : GDNNQA CGNNST VCGSKNQA CAGSPAAC TNQAKTEN VACGN NT G : 222
USPA1_P44   : GKNNQA GLNSTV CGSDNQA CTGSPAAC GNKA EN VACGN NTI R : 215
USPA1_ATCC  : GYNNEA CTDSTII GCRKNQACKGSPAAGIDNKA DN VACGN NTI R : 230
USPA1_O46E  : GSYNQA CNNSTV CGSHNQA CEGSPAAC NN VACKNN ID : 230
USPA1_TTA3  : CYKNKA CVDSTI GCRNQANCIGSPAACIDNQA NNITVACGN NIIK : 250
USPA1_O35E  : GDNNTAECEYSTV CGKNNQA CTGSPAAC BNQA EN VAVCK NIIE : 202
USPA1_TTA2  : GSNNQAKCEHSTI GCKNNQA CNGSPAAC NNAD NN VACGN NTIE : 214
USPA1_V117  : CNSNKAECTDSTII GCKNNQAKCEGSPAAC NNKA EN VAVCK NSIE : 203
```

Fig. 19B

```
                   260         *         280         *         300
USPA1_O12E  : ET SVAIGS N ED QDVE LGSN--TTN Q GSVLLG N SGK A A : 270
USPA1_P44   : E  SVAIGS N ET  E V LGG--TGVT NSVLLG K  E A A : 263
USPA1_ATCC  : E  SVAIGS N KK QQ   LGSNTD PN QNGSVLLCHN G  A I : 280
USPA1_O46E  : D  SVAIGS N IDS Q VE LGSSTN PN Q GSVLLCHN AG KA A : 280
USPA1_TTA3  : KD SVAIGS N ET  E VE LGS--NTKD H NSVLLG E TGKAAT : 298
USPA1_O35E  : E  SVAIGSEN  KTEHK VE LGS--GTGVT NSVLLG E T GQA T : 250
USPA1_TTA2  : ET SVAIGS N  KT E VE LGSNTN EN Q GSVLLG N AGKA T : 264
USPA1_V117  : KD SVAIGSEN  ENN Q VE LGS--K SG Q NSVLLG E TGKA T : 251

*         320         *         340         *
USPA1_O12E  : SSATV R K  G VSQANQA-NSG VSVC AGSERQIV VGAG   : 319
USPA1_P44   : ND TVN   T KN  GVS T----GNG VSVG ENH RQIV VGACK  : 309
USPA1_ATCC  : NS EV  S    GAS T----GNG VSVGKK ERQIV HVGAGE  : 326
USPA1_O46E  : SS AKV  T GN  GAS TG----NG VSVGKK ENN RQIV VGACN  : 326
USPA1_TTA3  : EN AK   S    VGAS ANT--NNG VSVG KQ GKERQIV VGACN R : 346
USPA1_O35E  : KN EV  IS    GES AEN----GV VSVG E GGERQIV VGAGE D : 296
USPA1_TTA2  : NN EVN  T ENF GVS ANANN-IG VSVG ENN ERQIV VGAC   : 313
USPA1_V117  : EN EV  IS    CAS ANANANIG VSVG QGK ERQIV VGAC I : 301
                                       {

360         *         380         *         400
USPA1_O12E  : STDAVNGSQL ALA A SQN----------------QDNILTNRVDIQE K : 355
USPA1_P44   : DSTDAVNGSQL ALA V AKNK-------SDITKNQAETLVNRVNIKE E : 352
USPA1_ATCC  : STDAVNGSQL ALA V AQN------------------KADIKD D : 355
USPA1_O46E  : DSTDAVNGSQL YALA A KAD---------------------ADENFKA T : 356
USPA1_TTA3  : DSTDAVNGSQL ALA A  -----------------------DAEFRT T : 372
USPA1_O35E  : STDAVNGSQL ALA V DDNQYDIVNNRADILNNQDDIKDLQKEVKG D : 346
USPA1_TTA2  : STDAVNGSQL ALAKA AKN---------------KSDIKGLNKGVKE D : 349
USPA1_V117  : STDAVNGSQL ALASTIDEE----------------------VDL G : 327

*         420         *         440         *
USPA1_O12E  : RKQENDIKEVVEMQNAIAEQADI----NKNH QD AKAQLAGVAVMEE DK : 402
USPA1_P44   : RKQENDIKEVVEMQNAIAEQADK----NKNH QD AKAQLAGVTVMEE NK : 399
USPA1_ATCC  : DEVG----------------------------LLG------------ : 362
USPA1_O46E  : KTQN----------TLIEQGE--------------AQDALIAQNQT : 378
USPA1_TTA3  : QTQN----------ALIEQGEA----INQELEG ADYTNAQDEKILKNQT : 408
USPA1_O35E  : NEVGELSRDINSLHDVTDNQQD--------D KEL KRGVKELDNEVGV SR : 389
USPA1_TTA2  : KEVGVLSRDINSLHDDVADNQDSIAKNKAD KG NKEVKELDKEVGV SR : 399
USPA1_V117  : EEINSLEGEIFNNQDAIAKNQA--------D ATNKTNIETNGSKITN GT : 370

460         *         480         *         500
USPA1_O12E  : HVEDLYEATNE LDK SQLDGAVFNNTQNIEDLAAYNELQDAYAKQQTEA : 452
USPA1_P44   : HVEDLYEATND LDK SQLDGAVFN------------------------ : 424
USPA1_ATCC  : -------------EE NSLEGE FN------------------------ : 374
USPA1_O46E  : DITANKT IER FNRTVV GFE EK------------------------ : 403
USPA1_TTA3  : DITANKT IEQ FNRTVT GFE EK------------------------ : 433
USPA1_O35E  : DINSLHDDVAD QDD AK KAD KGLNKEVKELDKEVG--------VLSRD : 432
USPA1_TTA2  : DIGSLHDDVAD QDS AK KAD KGLNKEVKELDKEVG--------VLSRD : 442
USPA1_V117  : LYATVTK VGN TQGVAA KAD TKNKADIQDLDDEVG--------VLSQD : 413

*         520         *         540         *
USPA1_O12E  : IDALNKASSE TQN IAKNSNH K TLES V  LL LSGRL DQKADIDNN : 502
USPA1_P44   : ---------- TQN IAKNSNH K TLE  V  LL LSGRL DQKADIDNN : 464
USPA1_ATCC  : ---------- NQDA IAKN   K ELES V  GL D SGRL DQKADIDNN : 414
USPA1_O46E  : ---------- NKAG IAKN   K IQ LE  VG  LL LSGRL DQKADIDNN : 443
USPA1_TTA3  : ---------- NKAG IAKN   K IQ LLE D GK LL LSGRL DQKADIDNN : 473
```

Fig. 19C

```
USPA1_O35E : IGSLHDDVATNQADIAKNAAIKTLEAVAEALLALSGRLIDQKADIDNN : 482
USPA1_TTA2 : IGSLHDDVATNQADIAKNAAIKTLEAVAEALLALSGRLIDQKADIDNN : 492
USPA1_V117 : IGSLHDDVATNQADIAKNAAIQTLEAVAEALLALSGRLIDQKADIDNN : 463

560         *         580         *         600
USPA1_O12E : INHIYELAQQQDQHSSDIKTLK------------------------------- : 525
USPA1_P44  : INTIYELAQQQDQHSSDIKTLK..............................A : 514
USPA1_ATCC : INTIYELAQQQDQHSSDIKTLK..............................A : 464
USPA1_O46E : INTIDLAQQQDQHSSDIKTLKK..............................T : 493
USPA1_TTA3 : INTIYELAQQQDQHSSDIKTLK..............................A : 523
USPA1_O35E : INTIYELAQQQDQHSSDIKTLK------------------------------- : 505
USPA1_TTA2 : INTIYELAQQQDQHSSDIKTLK..............................T : 542
USPA1_V117 : INTIYELAQQQDQHSSDIKTLK..............................T : 513
                                                              }

*         620         *         640         *
USPA1_O12E : --NVEEGLLDLSGRLIDQKADIAK............NCADIQDLAAYNELQDAYA : 573
USPA1_P44  : KNNVEEGLLDLSGRLIDQKADIAK............NCADIQDLAAYNELQDAYA : 564
USPA1_ATCC : KSNVEEGLLDLSGRLIDQKADIAK............NCADIQDLAAYNELQDAYA : 514
USPA1_O46E : KNNVEEGLLDLSGRLIDQKADIAK............NCADIQDLAAYNELQDAYA : 543
USPA1_TTA3 : KNNVEEGLLDLSGRLIDQKADIAK--------NCADIQDLAAYNELQDAYA : 566
USPA1_O35E : --NVEEGLLDLSGRLIDQKADIAK............NCADIQDLAAYNELQDAYA : 553
USPA1_TTA2 : KNNVEEGLLDLSGRLIDQKADIAK............NCADIQDLAAYNELQDAYA : 592
USPA1_V117 : KSNVEEGLLDLSGRLIDQKADIAK............NCADIQDLAAYNELQDAYA : 563

660         *         680         *         700
USPA1_O12E : KQQTEAIDALNKASSANT........................................ : 623
USPA1_P44  : KQQTEAIDALNKASSANT........................................ : 614
USPA1_ATCC : KQQTEAIDALNKASSANT........................................ : 564
USPA1_O46E : QKQTEAIDALNKASSANT........................................ : 593
USPA1_TTA3 : QKQTEAIDALNKASSANT........................................ : 616
USPA1_O35E : QKQTEAIDALNKASSENIQ--------------------------------- : 572
USPA1_TTA2 : QKQTEAIDALNKASSANT........................................ : 642
USPA1_V117 : QKQTEAIDALNKASSANT........................................ : 613

*         720         *         740         *
USPA1_O12E : .................................................NQADIAN : 673
USPA1_P44  : .................................................NQADIAN : 664
USPA1_ATCC : .................................................NQADIAN : 614
USPA1_O46E : .................................................NQADIAN : 643
USPA1_TTA3 : N-----------------------------------------------NQADIAN : 624
USPA1_O35E : ------------------------------------------------NNQADIAN : 583
USPA1_TTA2 : .................................................NQADIAN : 692
USPA1_V117 : .................................................NQADIAN : 663

760         *         780         *         800
USPA1_O12E : NIINIYELAQQQDQHSSDIKTLAKVSAANTDRIAKNKAEADASFETLTKN : 723
USPA1_P44  : NIINIYELAQQQDQHSSDIKTLAKVSAANTDRIAKNKAEADASFETLTKN : 714
USPA1_ATCC : NIINIYELAQQQDQHSSDIKTLAKVSAANTDRIAKNKAEADASFETLTKN : 664
USPA1_O46E : NIINIYELAQQQDQHSSDIKTLAKVSAANTDRIAKNKAEADASFETLTKN : 693
USPA1_TTA3 : NIINIYELAQQQDQHSSDIKTLAKVSAANTDRIAKNKAEADASFETLTKN : 674
USPA1_O35E : NINIYELAQQQDQHSSDIKTLAKVSAANTDRIAKNKAEADASFETLTKN  : 633
USPA1_TTA2 : NIINIYELAQQQDQHSSDIKTLAKVSAANTDRIAKNKAEADASFETLTKN : 742
USPA1_V117 : NIINIYELAQQQDQHSSDIKTLAKVSAANTDRIAKNKAEADASFETLTKN : 713

```
USPA1_O12E : QNTLIEQGEALVEQNKAINQELEGFAAHAD QDKQILQNQADIT NK A  : 773
USPA1_P44  : QNTLIEQGEALVEQNKAINQELEGFAAHAD QDKQILQNQADIT NK A  : 764
USPA1_ATCC : QNTLIEQGEALVEQNKAINQELEGFAAHAD QDKQILQNQADIT NK A  : 714
USPA1_O46E : QNTLIEQGEALVEQNKAINQELEGFAAHAD QDKQILQNQADIT NKAA  : 743
USPA1_TTA3 : QNTLIEQGEALVEQNKAINQELEGFAAHAD QDKQILQNQADIT ANK A : 724
USPA1_O35E : QNTLIEQGEALVEQNKAINQELEGFAAHAD I QDKQILQNQADIT NK A : 683
USPA1_TTA2 : QNTLIEQGEALVEQNKAINQELEGFAAHAD QDKQILQNQADIT NK A  : 792
USPA1_V117 : QNTLIEQGEALVEQNKAINQELEGFAAHAD QDKQILQNQADIT NK A  : 763

860         *         880        *        900
USPA1_O12E : EQNINRTVANGFEIEKNKAGIATNKQELILQ DRLN INETNN HQDQKID : 823
USPA1_P44  : EQNINRTVANGFEIEKNKAGIATNKQELILQ DRLN INETNN RQDQKID : 814
USPA1_ATCC : EQNINRTVANGFEIEKNKAGIATNKQELILQ DRLN INETNN HQDQKID : 764
USPA1_O46E : EQNINRTVANGFEIEKNKAGIATNKQELILQ DRLQ INETNN RQDQKID : 793
USPA1_TTA3 : EQNINRTVANGFEIEKNKAGIATNKQELILQH DRLN INETNN RQDQKID : 774
USPA1_O35E : EQNINRTVANGFEIEKNKAGIATNKQELILQ DRLN INETNN RQDQKID : 733
USPA1_TTA2 : EQNINRTVANGFEIEKNKAGIATNKQELILQ DRLNQ INETNN HQDQKID : 842
USPA1_V117 : EQNINRTVANGFEIEKNKAGIATNKQELILQ DRLN INETNN HQDQKID : 813

*           920         *         940           *
USPA1_O12E : QLGYALKEQGQHFNNRISAVERQTAGGIANAIAIATLPSPSRAGEHHVL  : 873
USPA1_P44  : QLGYALKEQGQHFNNRISAVERQTAGGIANAIAIATLPSPSRAGEHHVL  : 864
USPA1_ATCC : QLGYALKEQGQHFNNRISAVERQTAGGIANAIAIATLPSPSRAGEHHVL  : 814
USPA1_O46E : QLGYALKEQGQHFNNRISAVERQTAGGIANAIAIATLPSPSRAGEHHVL  : 843
USPA1_TTA3 : QLGYALKEQGQHFNNRISAVERQTAGGIANAIAIATLPSPSRAGEHHVL  : 824
USPA1_O35E : QLGYALKEQGQHFNNRISAVERQTAGGIANAIAIATLPSPSRAGEHHVL  : 783
USPA1_TTA2 : QLGYALKEQGQHFNNRISAVERQTAGGIANAIAIATLPSPSRAGEHHVL  : 892
USPA1_V117 : QLGYALKEQGQHFNNRISAVERQTAGGIANAIAIATLPSPSRAGEHHVL  : 863

960          *          980         *
USPA1_O12E : GSGYHNGQAAVSLGAAGLSDTGKSTYKIGLSWSDAGGLSGGVGGSYRWK : 922
USPA1_P44  : GSGYHNGQAAVSLGAAGLSDTGKSTYKIGLSWSDAGGLSGGVGGSYRWK : 913
USPA1_ATCC : GSGYHNGQAAVSLGAAGLSDTGKSTYKIGLSWSDAGGLSGGVGGSYRWK : 863
USPA1_O46E : GSGYHNGQAAVSLGAAGLSDTGKSTYKIGLSWSDAGGLSGGVGGSYRWK : 892
USPA1_TTA3 : GSGYHNGQAAVSLGAAGLSDTGKSTYKIGLSWSDAGGLSGGVGGSYRWK : 873
USPA1_O35E : GSGYHNGQAAVSLGAAGLSDTGKSTYKIGLSWSDAGGLSGGVGGSYRWK : 832
USPA1_TTA2 : GSGYHNGQAAVSLGAAGLSDTGKSTYKIGLSWSDAGGLSGGVGGSYRWK : 941
USPA1_V117 : GSGYHNGQAAVSLGAAGLSDTGKSTYKIGLSWSDAGGLSGGVGGSYRWK : 912
```

Fig. 20A

PileUp multiple alignment of full length UspA2 protein sequences

```
                           *         20         *         40         *
q848s1_morca    : MNKIYKVKKNAAGHIVACSEFAKGHTKKAVLGSLLIVGALCMATTASAQ-L : 50
q91961_morca    : MNKIYKVKKNAAGHIVACSEFAKGHTKKAVLGSLLIVGALCMATTASAQ L : 51
q8rtb2_morca    : ~~~~~~~~~~~~~~~~~~~~~~~~~~~~~~~~~~~~~~~~~~~~~~~~~~ : -
q91963_morca    : ~~~~~~~~~~~~~~~~~~~~~~~~~~~~~~~~~~~~~~~~~~~~~~~~~~ : -
o54407_morca    : ~~~~~~~~~~~~~~~~~~~~~~~~~~~~~~~~~~~~~~~~~~~~~~~~~~ : -
q9xd51_morca    : ~~~~~~~~~~~~~~~~~~~~~~~~~~~~~~~~~~~~~~~~~~~~~~~~~~ : -
q58xp4_morca    : ~~~~~~~~~~~~~~~~~~~~~~~~~~~~~~~~~~~~~~~~~~~~~~~~~~ : -
q8gh86_morca    : ~~~~~~~~~~~~~~~~~~~~~~~~~~~~~~~~~~~~~~~~~~~~~~~~~~ : -
q91962_morca    : ~~~~~~~~~~~~~~~~~~~~~~~~~~~~~~~~~~~~~~~~N         K : 10
forsgren_uspa2  : ~~~~~~~~~~~~~~~~~~~~~~~~~~~~~~~~~~~~~~~~~~~~~~~~~~ : -
q9xd55_morca    : ~~~~~~~~~~~~~~~~~~~~~~~~~~~~~~~~~~~~~~~~~~~~~~~~~~ : -
q848s2_morca    : ~~~~~~~~~~~~~~~~~~~~~~~~~~~~~~~~~~~~~~~~~~~~~~~~~~ : -
q9xd53_morca    : ~~~~~~~~~~~~~~~~~~~~~~~~~~~~~~~~~~~~~~~~~~~~~~~~~~ : -

60        *         80         *        100
q848s1_morca    : VST P        GN  I SSWSIIGAG DN V SA-NSGII GYKN V : 101
q91961_morca    : VSTNKP---------N QVK WSIIGAGE N V SA  SGII G KNIV : 93
q8rtb2_morca    : ~~~~~~~~~~~~~~~~~~~~~~~~~~~~~~~~~~~~~~~~~~~~~~~~~~ : -
q91963_morca    : ~~~~~~~~~~~~~~~~~~~~~~~~~~~~~~~~~~~~~~~~~~~~~~~~~~ : -
o54407_morca    : ~~~~~~~~~~~~~~~~~~~~~~~~~~~~~~~~~~~~~~~~~~~~~~~~~~ : -
q9xd51_morca    : ~~~~~~~~~~~~~~~~~~~~~~~~~~~~~~~~~~~~~~~~~~~~~~~~~~ : -
q58xp4_morca    : ~~~~~~~~~~~~~~~~~~~~~~~~~~~~~~~~~~~~~~~~~~~~~~~~~~ : -
q8gh86_morca    : ~~~~~~~~~~~~~~~~~~~~~~~~~~~~~~~~~~~~~~~~~~~~~~~~~~ : -
q91962_morca    : S ACSEFAKG  AVL  I   L  A TASAQ      A N N        : 61
forsgren_uspa2  : ~~~~~~~~~~~~~~~~~~~~~~~~~~~~~~~~~~~~~~~~~~~~~~~~~~ : -
q9xd55_morca    : ~~~~~~~~~~~~~~~~~~~~~~~~~~~~~~~~~~~~~~~~~~~~~~~~~~ : -
q848s2_morca    : ~~~~~~~~~~~~~~~~~~~~~~~~~~~~~~~~~~~~~~~~~~~~~~~~~~ : -
```

Fig. 20B

```
q9xd53_morca    : ~~~~~~~~~~~~~~~~~~~~~~~~~~~~~~~~~~~~~~~~~~~~~~~~~ : -

*         120         *         140         *
q848s1_morca    : NG TSAVGGYDNE  CR YTFVGGGYKNLAEG  S  GGGY N AEGDNA  : 152
q91961_morca    : NG TSAVGGY NE  G  YTFVGGGYKNLA GN    GGGYKNLAEGDNA  : 144
q8rtb2_morca    : ~~~~~~~~~~~~~~~~~~~~~~~~~~~~~~~~~~~~~~~~~~~~~~~~~ : -
q91963_morca    : ~~~~~~~~~~~~~~~~~~~~~~~~~~~~~~~~~~~~~~~~~~~~~~~~~ : -
o54407_morca    : ~~~~~~~~~~~~~~~~~~~~~~~~~~~~~~~~~~~~~~~~~~~~~~~~~ : -
q9xd51_morca    : ~~~~~~~~~~~~~~~~~~~~~~~~~~~~~~~~~~~~~~~~~~~~~~~~~ : -
q58xp4_morca    : ~~~~~~~~~~~~~~~~~~~~~~~~~~~~~~~~~~~~~~~~~~~~~~~~~ : -
q8gh86_morca    : ~~~~~~~~~~~~~~~~~~~~~~~~~~~~~~~~~~~~~~~~~~~~~~~~~ : -
q91962_morca    : GV    GG  N  GN  VGGG  N A GN VG  GG  N A G    I   : 112
forsgren_uspa2  : ~~~~~~~~~~~~~~~~~~~~~~~~~~~~~~~~~~~~~~~~~~~~~~~~~ : -
q9xd55_morca    : ~~~~~~~~~~~~~~~~~~~~~~~~~~~~~~~~~~~~~~~~~~~~~~~~~ : -
q848s2_morca    : ~~~~~~~~~~~~~~~~~~~~~~~~~~~~~~~~~~~~~~~~~~~~~~~~~ : -
q9xd53_morca    : ~~~~~~~~~~~~~~~~~~~~~~~~~~~~~~~~~~~~~~~~~~~~~~~~~ : -

160         *         180         *         200
q848s1_morca    : TAGG  N A GN S   GGY N  A G  D  T AGG  EN AEG  SA  GG  : 203
q91961_morca    : TAGG  NLA  G  N  TAGG EN AEG  DS V GGY NOA G  S VAGGSN : 195
q8rtb2_morca    : ~~~~~~~~~~~~~~~~~~~~~~~~~~~~~~~~~~~~~~~~~~~~~~~~~~ : -
q91963_morca    : ~~~~~~~~~~~~~~~~~~~~~~~~~~~~~~~~~~~~~~~~~~~~~~~~~~ : -
o54407_morca    : ~~~~~~~~~~~~~~~~~~~~~~~~~~~~~~~~~~~~~~~~~~~~~~~~~~ : -
q9xd51_morca    : ~~~~~~~~~~~~~~~~~~~~~~~~~~~~~~~~~~~~~~~~~~~~~~~~~~ : -
q58xp4_morca    : ~~~~~~~~~~~~~~~~~~~~~~~~~~~~~~~~~~~~~~~~~~~~~~~~~~ : -
q8gh86_morca    : ~~~~~~~~~~~~~~~~~~~~~~~~~~~~~~~~~~~~~~~~~~~~~~~~~~ : -
q91962_morca    : TAGG SN  A G NST AGG  NOA G  STVAGG  NOA G NS  AG  N : 163
forsgren_uspa2  : ~~~~~~~~~~~~~~~~~~~~~~~~~~~~~~~~~~~~~~~~~~~~~~~~~~ : -
q9xd55_morca    : ~~~~~~~~~~~~~~~~~~~~~~~~~~~~~~~~~~~~~~~~~~~~~~~~~~ : -
q848s2_morca    : ~~~~~~~~~~~~~~~~~~~~~~~~~~~~~~~~~~~~~~~~~~~~~~~~~~ : -
q9xd53_morca    : ~~~~~~~~~~~~~~~~~~~~~~~~~~~~~~~~~~~~~~~~~~~~~~~~~~ : -
```

Fig. 20C

```
                            *         220         *         240         *
q848s1_morca   : NLAAG.YI.GGG.EN.A.GNOS....GGYANLAEG..ATI.GG..N.AKG : 254
q91961_morca   : NLA.G...AIGGC..NEA.G..STVSGGY.NLAEG.S..IGGG..N.AIG : 246
q8rtb2_morca   : ~~~~~~~~~~~~~~~~~~~~~~~~~~~~~~~~~~~~~~~~~~~~~~~~~~ : -
q91963_morca   : ~~~~~~~~~~~~~~~~~~~~~~~~~~~~~~~~~~~~~~~~~~~~~~~~~~ : -
o54407_morca   : ~~~~~~~~~~~~~~~~~~~~~~~~~~~~~~~~~~~~~~~~~~~~~~~~~~ : -
q9xd51_morca   : ~~~~~~~~~~~~~~~~~~~~~~~~~~~~~~~~~~~~~~~~~~~~~~~~~~ : -
q58xp4_morca   : ~~~~~~~~~~~~~~~~~~~~~~~~~~~~~~~~~~~~~~~~~~~~~~~~~~ : -
q8gh86_morca   : ~~~~~~~~~~~~~~~~~~~~~~~~~~~~~~~~~~~~~~~~~~~~~~~~~~ : -
q91962_morca   : A...NAAG.I...SA.CS....I....NVTI.C..TTNA..GS       : 214
forsgren_uspa2 : ~~~~~~~~~~~~~~~~~~~~~~~~~~~~~~~~~~~~~~~~~~~~~~~~~~ : -
q9xd55_morca   : ~~~~~~~~~~~~~~~~~~~~~~~~~~~~~~~~~~~~~~~~~~~~~~~~~~ : -
q848s2_morca   : ~~~~~~~~~~~~~~~~~~~~~~~~~~~~~~~~~~~~~~~~~~~~~~~~~~ : -
q9xd53_morca   : ~~~~~~~~~~~~~~~~~~~~~~~~~~~~~~~~~~~~~~~~~~~~~~~~~~ : -

260         *         280         *         300
q848s1_morca   : N.VK....Q....S.GG-----ENP.EGID.SV.SG...TC.UGAQ     : 300
q91961_morca   : NATI..RQ....S.DK.SV.C-----EQN.IGKY.S..ISG.RQNE.SCER : 292
q8rtb2_morca   : ~~MKTMKLLPLKIAVLSAMI.GLGAASTANAQ-----A.ETELPNLEDNEY : 44
q91963_morca   : ~~MKTMKLLPLKIAVLSAMVGLC.ASTANAQ.KSPK.ETELPNLEDNDN    : 49
o54407_morca   : ~~MKTMKLLPLKIAVLSAMIVGLGA.ST.NAC-----WEC.EN.E.N.N     : 44
q9xd51_morca   : ~~MKTMKLLPLKIAVLSAMIVGLGA.ST.NAC-----WEC.EN.E.N.N     : 44
q58xp4_morca   : ~~MKTMKLLPLKIAVLSA.LVGLGAASTANAC.QQ..K.E.TELPNLE.YNEY : 49
q8gh86_morca   : ~~MKTMKLLPLKIAVLSA.LVGLC.ASTANAQVK.P.NQKI----------Q : 42
q91962_morca   : ..ETSGK....AV..ARYNGL.LK.....KADNG.V.---------GSQ    : 258
forsgren_uspa2 : ~~MKTMKLLPLKIAVLSAMI.GLGAASTANAQA.N----I---------T   : 36
q9xd55_morca   : ~~MKTMKLLPLKIAVLSAMI.GLGAASTANAQA.N----I---------T   : 36
q848s2_morca   : ~~MKTMKLLPLKIAVLSA.LVGLCA.TNAQC.ESLDQI----------IT    : 42
q9xd53_morca   : ~~MKTMKLLPLKIAVLSAMI.GLGAASTANAC.SPDRSLE.I---------IS : 42

*         320         *         340         *
q848s1_morca   : -.V.E.NN.TE.SS.I.GG.I.AT..GSE.D.EVENK.NA.N.VA.GK
```

```
              : 287
o54407_morca  : K----------------------------------------------------
              : 242
q9xd51_morca  : K----------------------------------------------------
              : 242
q58xp4_morca  : DLYK EE DS E----HA NKA  TI D T  E        AD
              : 288
q8gh86_morca  : KNQADIQTLENNVEE II LSG I DQKADIDNN N YELAQQQDQHSSD
              : 239
q91962_morca  : KNQADI TLENNVEE II LSGRI DQKADIDNN NH YELAQQQDQHSSD
              : 428
forsgren_uspa2: KN ADIQ LENNV EI NLSGRI DQKADIDNN N YELAQQQDQHSSD
              : 269
q9xd55_morca  : KN ADIQ LENNV EI NLSGRI DQKADIDNN N YELAQQQDQHSSD
              : 269
q848s2_morca  : KN---------------------KADIDNN NH YELAQQQDQHSSD
              : 254
q9xd53_morca  : KN---------------------KADIDNN NH YELAQQQDQHSSD
              : 240

*       580         *       600        *
q848s1_morca  : KTLKNNVEEGLLELSGHL IDQKADLTKDIKALE NVEEGLLD--------
              : 558
q91961_morca  : KTLK NVEEGLLELSGHL IDQKADLTKDIKALESNVEEGLLD
              : 577
q8rtb2_morca  : KTL NN EEGLLELSGHL IDQKADLTKDIKALESNVEEGLLD
              : 325
q91963_morca  : KTL NN EEGLLELSGHL IDQKADLTKDIKALESNVEEGLLD
              : 330
o54407_morca  : K L NVEEGLLELSGHL IDQKADLTKDIKALESNVEEGLLD
              : 285
q9xd51_morca  : K L NVEEGLLELSGHL IDQKADLTKDIKALESNVEEGLLD
              : 285
q58xp4_morca  : K L NNV E L LSG I DQKADLTKDIK LESNVEEGLL
              : 331
q8gh86_morca  : KTLK NVEEGLLELSGHL IDQK D        N     II DQYAQEQT
              : 290
q91962_morca  : KTLK NVEEGLLELSGHL IDQKAD       D         II DQYAQ QT
              : 479
forsgren_uspa2: KTLK NVEEGLLELS H IDQK E-------
              : 299
q9xd55_morca  : KTLK NVEEGLLELSGHL IDQK E-------
              : 299
q848s2_morca  : KTLKNNVEEGLLELSGHL IDQKADLTKDIK LE--------
              : 288
q9xd53_morca  : KTLKNNVEEGLLELSGHL IDQKADLTKDIKALE--------
              : 274

620        *        640        *       660
q848s1_morca  : --------------------------------LSGRL DQKADIAKNQA
              : 576
q91961_morca  : --------------------------------LSGRL DQK--------A
              : 588
q8rtb2_morca  : --------------------------------LSGRL DQKADIAKNQA
              : 343
q91963_morca  : --------------------------------LSGRL DQK--------A
              : 341
o54407_morca  : --------------------------------LSGRL DQKADIAKNQA
              : 303
```

```
                    : 388
q8gh86_morca    :  QQA---------ANQNIQDLAAYNELQDYAQQTEATDALNKASSEN
                    : 406
q91962_morca    :  QQEATDALNKASSENTQNIQDLAAYNELQDAYAKQQTEATDALNKASSEN
                    : 632
forsgren_uspa2  :  QQA---------ENQNIQDLAAYNELQDAYAKQQTEATDALNKASSEN
                    : 368
q9xd55_morca    :  QAS---------ENQNIQDLAAYNELQDAYAKQQTEATDALNKASSEN
                    : 368
q848s2_morca    :  -QA---------ANQNIQDLAAYNELQDAYAQQTEATDALNKASSEN
                    : 354
q9xd53_morca    :  QQA---------ANQNIQDLAAYNELQDAYAQQTEATDALNKASSEN
                    : 362

*       780         *       800        *
q848s1_morca    :  TQNIEDLAAYNELQDAYAKQQTEATDALNKASSENTQNIAKNQADIANNIN
                    : 666
q91961_morca    :  TQNIEDLAAYNELQDAYAKQQTEATDALNKASSENTQNIAKNQADIANNIN
                    : 678
q8rtb2_morca    :  TQNIEDLAAYNELQDAYAKQQTEATDALNKASSENTQNIAKNQADIANNIN
                    : 468
q91963_morca    :  TQNIEDLAAYNELQDAYAKQQTEATDALNKASSENTQNIAKNQADIANNIN
                    : 466
o54407_morca    :  ---IDLAAYNELQDAYAKQQTEATDALNKASSENTQNIAKNQADIANNIN
                    : 358
q9xd51_morca    :  TQNIEDLAAYNELQDAYAKQQTEATDALNKASSENTQNIAKNQADIANNIN
                    : 456
q58xp4_morca    :  TQNIEDLAAYNELQDAYAKQQTEATDALNKASSENTQNIAKNQADIANNIN
                    : 439
q8gh86_morca    :  TQNIEDLAAYNELQDAYAKQQTEATDALNKASSENTQNIAKNQADIANNIN
                    : 457
q91962_morca    :  TQNIDLAAYNELQDAYAKQQTEATDALNKASSENTQNIAKNQADIANNIN
                    : 683
forsgren_uspa2  :  TQNIEDLAAYNELQDAYAKQQTEATDALNKASSENTQNIAKNQADIANNI
                    : 419
q9xd55_morca    :  TQNIEDLAAYNELQDAYAKQQTEATDALNKASSENTQNIAKNQADIANNIN
                    : 419
q848s2_morca    :  TQNIEDLAAYNELQDAYAKQQTEATDALNKASSENTQNIAKNQADIANNIN
                    : 405
q9xd53_morca    :  TQNIEDLAAYNELQDAYAKQQTEATDALNKASSENTQNIAKNQADIANNIN
                    : 413

820         *       840         *       860
q848s1_morca    :  NIYELAQQQDQHSSDIKTLAKASAANTDRIAKNKADADASFETLTKNQNTL
                    : 717
q91961_morca    :  NIYELAQQQDQHSSDIKTLAKASAANTDRIAKNKADADASFETLTKNQNTL
                    : 729
q8rtb2_morca    :  NIYELAQQQDQHSSDIKTLAKASAANTDRIAKNKADADASFETLTKNQNTL
                    : 519
q91963_morca    :  NIYELAQQQDQHSSDIKTLAKASAANTDRIAKNKADADASFETLTKNQNTL
                    : 517
o54407_morca    :  NIYELAQQQDQHSSDIKTLAKASAANTDRIAKNKADADASFETLTKNQNTL
                    : 409
q9xd51_morca    :  NIYELAQQQDQHSSDIKTLAKASAANTDRIAKNKADADASFETLTKNQNTL
                    : 507
q58xp4_morca    :  NIYELAQQQDQHSSDIKTLAKASAANTDRIAKNKADADASFETLTKNQNTL
                    : 490
q8gh86_morca    :  NIYELAQQQDQHSSDIKTLAKASAANTDRIAKNKADADASFETLTKNQNTL
                    : 508
```

Fig. 20I

```
q91962_morca   : NIYELAQQQDQHSSDIKTLAKASAANTDRIAKNKADADASFETLTKNQNTL
: 734
forsgren_uspa2 : NIYELAQQQD H SDIKTLAK SAANTDRIAKNKAD DASFETLTKNQNTL
: 470
q9xd55_morca   : NIYELAQQQDQHSSDIKTLAKASAANTDRIAKNKADADASFETLTKNQNTL
: 470
q848s2_morca   : NIYELAQQQDQHSSDIKTLAKASAANTDRIAKNKADADASFETLTKNQNTL
: 456
q9xd53_morca   : NIYELAQQQDQHSSDIKTLAKASAANT RI------A A
: 458

*        880         *        900         *         9
q848s1_morca   : IEKDKEHDKLITANKTAIDANKASADTKFAATADAITKNGNAITKNAKSIT
: 768
q91961_morca   : IEKDKEHDKLITANKTAIDANKASADTKFAATADAITKNGNAITKNAKSIT
: 780
q8rtb2_morca   : IEKDKEHDKLITANKTAIDANKASADTKFAATADAITKNGNAITKNAKSIT
: 570
q91963_morca   : IEKDKEHDKLITANKTAIDANKASADTKFAATADAITKNGNAITKNAKSIT
: 568
o54407_morca   : IEKDKEHDKLITANKTAIDANKASADTKFAATADAITKNGNAITKNAKSIT
: 460
q9xd51_morca   : IEKDKEHDKLITANKTAIDANKASADTKFAATADAITKNGNAITKNAKSIT
: 558
q58xp4_morca   : IEKDKEHDKLITANKTAID NKASADTKFAATADAITKNGNAITKNAKSIT
: 541
q8gh86_morca   : IEKDKEHDKLITANKTAIDANK SADTKFAATADAITKNGNAITKNAKSIT
: 559
q91962_morca   : IEKDKEHDKLITANKTAIDANKASADTKFAATADAITKNGNAITKNAKSIT
: 785
forsgren_uspa2 : IEKDKEHDKLITANKTAIDANKASADTKFAATADA TKNGNAITKNAKSIT
: 521
q9xd55_morca   : IEKDKEHDKLITANKTAIDANKASADTKFAATADAITKNGNAITKNAKSIT
: 521
q848s2_morca   : IEKDKEHDKLITANKTAID NKASADTKFAATADAITKNGNAITKNAKSIT
: 507
q9xd53_morca   : I K ------ANKTAID NKASADTKFAATADAITKNGNAITKNAKSIT
: 504

20         *        940         *        960
q848s1_morca   : DLGTKVDGFDGRVT-------ALDTKVNAFDGRITALDSKVENGMAAQAAI
: 812
q91961_morca   : DLGTKVDGFDGRVT-------ALDTKVNAFDGRITALDSKVENGMAAQAAI
: 824
q8rtb2_morca   : DLGTKVDGFDGRVTALDTKVNALDTKVNAFDGRITALDSKVENGMAAQAAI
: 621
q91963_morca   : DLGTKVDGFDGRVTALDTKVNALDTKVNAFDGRITALDSKVENGMAAQAAI
: 619
o54407_morca   : DLGTKVDGFDGRVTALDTKVNALDTKVNAFDGRITALDSKVENGMAAQAAI
: 511
q9xd51_morca   : DLGTKVDGFDGRVTALDTKVNALDTKVNAFDGRITALDSKVENGMAAQAAI
: 609
q58xp4_morca   : DLGTKVDGFDGRVT-------ALDTKVNAFDGRITALDSKVENGMAAQAAI
: 585
q8gh86_morca   : DLGTKVD FD RVT-------ALDTKVNAFDGRITALDSKVENGMAAQAAI
: 603
q91962_morca   : DLGTKVDGFDGRVT-------ALDTKVNAFDGRITALDSKVENGMAAQAAI
: 829
forsgren_uspa2 : DLGTKVDGFD RVT-------ALDTKVNAFDGRITALDSKVENGMAAQAAI
```

Fig. 20J

```
             :  565
q9xd55_morca : DLGTKVDGFDGRVT-------ALDTKVNAEDGRITALDSKVENGMAAQAAL
             :  565
q848s2_morca : DLGTKVDGFDGRVT-------ALDTKVNAEDGRITALDSKVENGMAAQAAL
             :  551
q9xd53_morca : DLGTKVDGFDGRVT-------ALDTKVNAEDGRITALDSKVENGMAAQAAL
             :  548

*        980         *       1000         *       1020
q848s1_morca    : SGLFQPYSVGKFNATAALGGYGSKSAVAIGAGYRVNPNLAFKAGAAINTSC
                : 863
q91961_morca    : SGLFQPYSVGKFNATAALGGYGSKSAVAIGAGYRVNPNLAFKAGAAINTSC
                : 875
q8rtb2_morca    : SGLFQPYSVGKFNATAALGGYGSKSAVAIGAGYRVNPNLAFKAGAAINTSC
                : 672
q91963_morca    : SGLFQPYSVGKFNATAALGGYGSKSAVAIGAGYRVNPNLAFKAGAAINTSC
                : 670
o54407_morca    : SGLFQPYSVGKFNATAALGGYGSKSAVAIGAGYRVNPNLAFKAGAAINTSC
                : 562
q9xd51_morca    : SGLFQPYSVGKFNATAALGGYGSKSAVAIGAGYRVNPNLAFKAGAAINTSC
                : 660
q58xp4_morca    : SGLFQPYSVGKFNATAALGGYGSKSAVAIGAGYRVNPNLAFKAGAAINTSC
                : 636
q8gh86_morca    : SGLFQPYSVGKFNATAALGGYGSKSAVAIGAGYRVNPNLAFKAGAAINTSC
                : 654
q91962_morca    : SGLFQPYSVGKFNATAALGGYGSKSAVAIGAGYRVNPNLAFKAGAAINTSC
                : 880
forsgren_uspa2  : SGLFQPYSVGKFNATAALGGYGSKSAVAIGAGYRVNPNLAFKAGAAINTSC
                : 616
q9xd55_morca    : SGLFQPYSVGKFNATAALGGYGSKSAVAIGAGYRVNPNLAFKAGAAINTSC
                : 616
q848s2_morca    : SGLFQPYSVGKFNATAALGGYGSKSAVAIGAGYRVNPNLAFKAGAAINTSC
                : 602
q9xd53_morca    : SGLFQPYSVGKFNATAALGGYGSKSAVAIGAGYRVNPNLAFKAGAAINTSC
                : 599

*
q848s1_morca   : NKKGSYNIGVNYEE : 877
q91961_morca   : NKKGSYNIGVNYEE : 889
q8rtb2_morca   : NKKGSYNIGVNYEE : 686
q91963_morca   : NKKGSYNIGVNYEE : 684
o54407_morca   : NKKGSYNIGVNYEE : 576
q9xd51_morca   : NKKGSYNIGVNYEE : 674
q58xp4_morca   : NKKGSYNIGVNYEE : 650
q8gh86_morca   : NKKGSYNIGVNYEE : 668
q91962_morca   : NKKGSYNIGVNYEE : 894
forsgren_uspa2 : NKKGSYNIGVNYEE : 630
q9xd55_morca   : NKKGSYNIGVNYEE : 630
q848s2_morca   : NKKGSYNIGVNYEE : 616
q9xd53_morca   : NKKGSYNIGVNYEE : 613
```

Fig. 21

% identity in regions identified on Forsgren sequence

|  | 30-177 laminin binding | 165-318 fibronectin binding | 302-458 C3-binding |
|---|---|---|---|
| q848s1_morca | 8 | 19 | 74 |
| q9l961_morca | 6 | 41 | 73 |
| q8rtb2_morca | 9 | 22 | 67 |
| q9l963_morca | 10 | 23 | 68 |
| o54407_morca | 10 | 17 | 53 |
| q9xd51_morca | 10 | 19 | 66 |
| q58xp4_morca | 10 | 16 | 75 |
| q8gh86_morca | 18 | 43 | 69 |
| q9l962_morca | 9 | 36 | 64 |
| q9xd55_morca | 99 | 98 | 96 |
| q848s2_morca | 35 | 54 | 74 |
| q9xd53_morca | 29 | 52 | 64 |

INTERACTION OF MORAXELLA CATARRHALIS WITH EPITHELLAL CELLS, EXTRACELLULAR MATRIX PROTEINS AND THE COMPLEMENT SYSTEM

CROSS REFERENCE TO RELATED APPLICATIONS

This application is a divisional of U.S. patent application Ser. No. 14/986,104, filed Dec. 31, 2015, and now issued as U.S. Pat. No. 9,657,067, which is a divisional of U.S. patent application Ser. No. 14/508,033, filed Oct. 7, 2014, now issued as U.S. Pat. No. 9,255,127, which is a divisional of U.S. patent application Ser. No. 13/666,941, filed Nov. 1, 2012, and now issued as U.S. Pat. No. 8,895,030, which is a divisional of U.S. patent application Ser. No. 13/314,727, filed Dec. 8, 2011, and now issued as U.S. Pat. No. 8,323,667, which is a divisional of U.S. application Ser. No. 12/063,408, filed on Feb. 8, 2008, and now issued as U.S. Pat. No. 8,092,811, which is a national stage filing under 35 U.S.C. § 371 of International Application No. PCT/SE2006/000931, filed on Aug. 8, 2006, which claims the benefit of priority of U.S. Provisional Application No. 60/706,745, filed on Aug. 10, 2005, and of U.S. Provisional Application No. 60/707,148, filed on Aug. 11, 2005. All seven applications are incorporated herein by reference in their entireties.

SEQUENCE LISTING

The instant application contains a Sequence Listing, which is hereby incorporated by reference in its entirety. A computer readable copy of the Sequence Listing (ASCII copy) is submitted concurrently herewith to the U.S. Patent and Trademark Office via EFS-Web as part of a file created on created on Nov. 1, 2012, named SequenceListing.txt, and being 199,367 bytes in size.

Technical Field of the Invention

The present invention relates to *Moraxella catarrhalis* and their ability to interact with epithelial cells via extracellular matrix proteins such as fibronectin and laminin, and also to their ability to inhibit the complement system. The interaction with these extracellular proteins is useful in the preparation of vaccines.

Background Art

The ability to bind epithelial cells is of great importance for several bacterial species. For example, *Staphylococcus aureus* and *Streptococcus pyogenes* possess fibronectin binding proteins (FnBP) with related sequence organization. These FnBP are known as Microbial Surface Components Recognizing Adhesive Matrix Molecules (MSCRAMMs). They exploit the modular structure of fibronectin forming extended tandem beta-zippers in its binding to fibronectin. [27, 39, 47, 73] The function is to mediate bacterial adhesion and invasion of host cells.

The important mucosal pathogen *Moraxella catarrhalis* is the third leading bacterial cause of acute otitis media in children after *Streptococcus pneumoniae* and *Haemophilus influenzae*.[14, 40, 55] *M. catarrhalis* is also one of the most common inhabitants of the pharynx of healthy children.

Furthermore, *M. catarrhalis* is also a common cause of sinusitis and lower respiratory tract infections in adults with chronic obstructive pulmonary disease (COPD). [74] The success of this species in patients with COPD is probably related in part to its large repertoire of adhesins.

Recent years focus of research has been on the outer membrane proteins and their interactions with the human host.[6, 48, 56] Some of these outer membrane proteins appear to have adhesive functions including amongst others, *M. catarrhalis* IgD binding protein (MID, also designated Hag), protein CD, *M. catarrhalis* adherence protein (McaP) and the ubiquitous surface proteins (Usp).[1, 22, 33, 48, 61, 81, 84]

SUMMARY OF THE INVENTION

In view of the fact that *M. catarrhalis* has been found to be such a leading cause of infections in the upper and lower airways, there is a current need to develop vaccines which can be used against *M. catarrhalis*.

The aim of the present invention has therefore been to find out in which way *M. catarrhalis* interacts with epithelial cells in the body and affects the immune system. In this way, substances that can act as vaccines against *M. catarrhalis* can be developed.

In this study, using *M. catarrhalis* mutants derived from clinical isolates, the inventors have been able to show that both UspA1 and A2 bind fibronectin and laminin. Furthermore, the inventors have been able to show that *M. catarrhalis* interfere with the classical pathway of the complement system, and also to elucidate in which way they interfere.

Many bacteria adhere to epithelial cells via fibronectin binding MSCRAMMS.[54, 77] *Pseudomonas aeruginosa* has a FnBP that binds to cellular associated fibronectin on nasal epithelial cells.[69] Blocking the bacteria-fibronectin protein interactions may help the host tissue to overcome the infection. In fact, it has been shown that antibodies against a *S. aureus* FnBP resulted in rapid clearance of the bacteria in infected mice.[71]

Recombinant truncated UspA1/A2 proteins together with smaller fragments spanning the entire molecule have been tested according to the present invention for fibronectin binding. Both UspA1 and A2 bound fibronectin and the fibronectin binding domains were found to be located within UspA1$^{299-452}$ and UspA2$^{165-318}$. These two truncated proteins both inhibited binding of *M. catarrhalis* to Chang conjunctival epithelial cells to a similar extent as anti-fibronectin antibodies. The observations made show that both *M. catarrhalis* UspA1 and A2 are involved in the adherence to epithelial cells via cell-associated fibronectin. The biologically active sites within UspA1$^{299-452}$ and UspA2$^{165-318}$ are therefore suggested as potential candidates to be included in a vaccine against *M. catarrhalis*.

Further, the inventors have studied and characterized binding of *M. catarrhalis* to laminin. *M. catarrhalis* is a common cause of infectious exacerbations in patients with COPD. The success of this species in patients with COPD is probably related in part to its large repertoire of adhesins. In addition, there are pathological changes such as loss of epithelial integrity with exposure of basement membrane where the laminin layer itself is thickened in smokers.[4] Some pathogens have been shown to be able to bind laminin and this may contribute to their ability to adhere to such damaged and denuded mucosal surfaces. These include pathogens known to cause significant disease in the airways such as *S. aureus* and *P. aeruginosa* amongst others.[7, 63] The present inventors have been able to show that *M. catarrhalis* ubiquitous surface protein (Usp) A1 and A2 also bind to laminin. Laminin binding domains of UspA1 and A2 were, amongst others, found within the N-terminal halves of UspA1$^{50-491}$ and UspA2$^{30-351}$. These domains are also containing the fibronectin binding domains. However, the smallest fragments that bound fibronectin, UspA1$^{299-452}$ and UspA2$^{165-318}$, did not bind laminin to any appreciable extent. Fragments smaller than the N-terminal half of UspA1 (UspA1$^{53-491}$) lose all its laminin binding ability, whereas with UspA2, only UspA2$^{30-170}$ bound laminin albeit at a lower level than the whole recombinant protein (UspA2$^{30-539}$). These findings suggest that different parts of the molecule might have different functional roles. UspA1$^{50-770}$ was also found to have laminin binding properties.

Comparing the smallest laminin binding regions of UspA1 and A2, we find that there is, however, little similarity by way of amino acid homology between UspA2$^{30-170}$ and UspA1$^{50-491}$ (data not shown). This is not surprising as it is a known fact that both proteins have a 'lollipop'-shaped globular head structure despite having only 22% identity in both N terminal halves.[2, 32]

The biologically active sites within UspA1$^{50-770}$ and UspA2$^{30-539}$ are suggested as potential candidates to be included in a vaccine against M. catarrhalis.

Finally, the inventors have studied the interaction between M. catarrhalis ubiquitous surface proteins A1 and A2 and the innate immune system, and have found that M. catarrhalis interferes with the complement system. The complement system is one of the first lines of innate defence against pathogenic microorganisms, and activation of this system leads to a cascade of protein deposition on the bacterial surface resulting in formation of the membrane attack complex or opsonization of the pathogen followed by phagocytosis. [85, 86] One of the most important complement proteins is C3, which is present in the circulation in a concentration similar to some immunoglobulins (1-1.2 mg/ml). C3 does not only play a crucial role as an opsonin, but also is the common link between the classical, lectin and alternative pathways of the complement activation. The alternative pathway functions as amplification loop for the classical and lectin pathways and can also be spontaneously activated by covalent attachment of C3 to the surface of a microbe in the absence of complement inhibitors. C3 deposition requires the presence of an internal thioester bond, formed in the native protein by the proximity of a sulfhydryl group) (Cys$^{1010}$) and a glutamyl carbonyl (Gln$^{1012}$) on the C3 α-chain. [76] Proteolytic cleavage of a 77-residue peptide from the amino terminus of the C3 α-chain generates C3a (anaphylatoxin) and C3b. Attachment of C3b is then accomplished through a covalent link between the carbonyl group of the metastable thioester and either —NH$_2$ or —OH groups of proteins or carbohydrate structures on the activator surface. [36, 37] M. catarrhalis UspA1 and A2 have been found to non-covalently and in a dose dependent manner bind both the third component of complement (C3) from EDTA-treated serum and methylamine treated C3 (C3met). UspA1$^{50-770}$ and UspA2$^{30-539}$ have been found to bind to C3 and C3met. The C3-binding region for UspA2 was found to mainly be localised in UspA2$^{200-458}$. UspA1 has however been found to have a minor role in the interactions. The biologically active sites within UspA1$^{50-770}$ and UspA2$^{30-539}$ are suggested as potential candidates to be included in a vaccine against M. catarrhalis.

The UspA family consists of UspA1 (molecular weight 88 kDa), UspA2 (62 kDa), and the hybrid protein UspA2H (92 kDa).[2, 43] These proteins migrate as high molecular mass complexes in SDS-PAGE, are relatively conserved and hence important vaccine candidates. The amino acid sequences of UspA1 and A2 are 43% identical and have 140 amino acid residues that are 93% identical. [2] In a series of 108 M. catarrhalis nasopharyngeal isolates from young children with otitis media, uspA1 and uspA2 genes were detected in 107 (99%) and 108 (100%) of the isolates, respectively. Twenty-one percent were identified as having the hybrid variant gene uspA2H.[50] Moreover, it is known that naturally acquired antibodies to UspA1 and A2 are bactericidal.[15]

Several functions have been attributed to the UspA family of proteins. UspA1 expression is essential for the attachment of M. catarrhalis to Chang conjunctival epithelial cells and Hep-2 laryngeal epithelial cells.[43, 49] In a more recent study, UspA1 was shown to bind carcinoembryonic antigen related cell adhesion molecules (CEACAM) expressed in the lung epithelial cell line A549.[31] Purified UspA1 has also been shown to bind fibronectin in dot blot experiments while purified UspA2 did not.[49] Both UspA1 and A2 may play important roles for M. catarrhalis serum resistance.[1, 5, 58, 60]

The present invention demonstrates that both UspA1 and A2 are determinants for M. catarrhalis binding to fibronectin and laminin in the clinical isolates M. catarrhalis BBH18 and RH4. Interestingly, recombinant UspA1 and A2 derived from M. catarrhalis Bc5 both bound fibronectin to the same extent. The binding domains for fibronectin were found within amino acid residues 299 to 452 of UspA1 and 165 to 318 of UspA2. These two domains share 31 amino acid residues sequence identity. Importantly, truncated protein fragments containing these residues in UspA1 and UspA2 were able to inhibit M. catarrhalis binding to Chang epithelial cells suggesting that the interactions with these cells were via cell-associated fibronectin.

The binding domains for laminin were found within the amino acid residues mentioned above. Binding assays with recombinant proteins revealed that the major binding regions were localized in the N-terminal parts, where both proteins form a globular head.

Bacterial factors mediating adherence to tissue and extracellular matrix (ECM) components are grouped together in a single family named "microbial surface components recognizing adhesive matrix molecules" (MSCRAMMS). Since UspA1/A2 both bind fibronectin and laminin, these proteins can be designated MSCRAMMS.

According to one aspect the present invention provides a peptide having sequence ID no. 1, and fragments, homologues, functional equivalents, derivatives, degenerate or hydroxylation, sulphonation or glycosylation products and other secondary processing products thereof.

According to another aspect the present invention provides a peptide having sequence ID no. 2, and fragments, homologues, functional equivalents, derivatives, degenerate or hydroxylation, sulphonation or glycosylation products and other secondary processing products thereof.

According to a further aspect the present invention provides a peptide having sequence ID no. 3, and fragments, homologues, functional equivalents, derivatives, degenerate or hydroxylation, sulphonation or glycosylation products and other secondary processing products thereof.

According to another aspect the present invention provides a peptide having sequence ID no. 4, and fragments, homologues, functional equivalents, derivatives, degenerate or hydroxylation, sulphonation or glycosylation products and other secondary processing products thereof.

According to a further aspect the present invention provides a peptide having sequence ID no. 5, and fragments, homologues, functional equivalents, derivatives, degenerate or hydroxylation, sulphonation or glycosylation products and other secondary processing products thereof.

According to a further aspect the present invention provides a peptide having sequence ID no. 6, and fragments, homologues, functional equivalents, derivatives, degenerate or hydroxylation, sulphonation or glycosylation products and other secondary processing products thereof.

According to another aspect the present invention provides a peptide having sequence ID no. 7, and fragments, homologues, functional equivalents, derivatives, degenerate or hydroxylation, sulphonation or glycosylation products and other secondary processing products thereof.

According to another aspect the present invention provides a peptide having sequence ID no. 8, and fragments, homologues, functional equivalents, derivatives, degenerate or hydroxylation, sulphonation or glycosylation products and other secondary processing products thereof.

According to another aspect the present invention provides a peptide having sequence ID no. 9, and fragments, homologues, functional equivalents, derivatives, degenerate or hydroxylation, sulphonation or glycosylation products and other secondary processing products thereof.

According to another aspect the present invention provides a peptide having sequence ID no. 10, and fragments, homologues, functional equivalents, derivatives, degenerate or hydroxylation, sulphonation or glycosylation products and other secondary processing products thereof.

According to another aspect, the present invention provides use of at least one peptide according to the invention for the production of a medicament for the treatment or prophylaxis of an infection, preferably an infection caused by *M. catarrhalis*, in particular caused by carriage of *M. catarrhalis* on mucosal surfaces.

According to another aspect, the invention further provides a ligand comprising a fibronectin binding domain, said ligand consisting of an amino acid sequence selected from the group consisting of Sequence ID No. 1, Sequence ID No. 2 and Sequence ID No. 3, and fragments, homologues, functional equivalents, derivatives, degenerate or hydroxylation, sulphonation or glycosylation products and other secondary processing products thereof.

The invention further provides a ligand comprising a laminin binding domain, said ligand consisting of an amino acid sequence selected from the group consisting of Sequence ID No. 4 to Sequence ID No. 8, and fragments, homologues, functional equivalents, derivatives, degenerate or hydroxylation, sulphonation or glycosylation products and other secondary processing products thereof.

Further, the present invention provides a ligand comprising a C3 or C3met binding domain, said ligand consisting of an amino acid sequence selected from the group consisting of Sequence ID No. 4, Sequence ID No. 6, Sequence ID No. 9 and Sequence ID No. 10, and fragments, homologues, functional equivalents, derivatives, degenerate or hydroxylation, sulphonation or glycosylation products and other secondary processing products thereof.

Further, the present invention provides a medicament comprising one or more ligands according to the invention and one or more pharmaceutically acceptable adjuvants, vehicles, excipients, binders, carriers, or preservatives.

The present invention further provides a vaccine comprising one or more ligands according to the present invention and one or more pharmaceutically acceptable adjuvants, vehicles, excipients, binders, carriers, or preservatives.

The present invention also provides a method of treating or preventing an infection in an individual, preferably an infection caused by *M. catarrhalis*, in particular caused by carriage of *M. catarrhalis* on mucosal surfaces, comprising administering a pharmaceutically effective amount of a medicament or vaccine according to the present invention.

Finally, the present invention also provides a nucleic acid sequence encoding a ligand, protein or peptide of the present invention, as well as homologues, polymorphisms, degenerates and splice variants thereof.

Further disclosure of the objects, problems, solutions and features of the present invention will be apparent from the following detailed description of the invention with reference to the drawings and the appended claims.

The expression ligand as it is used herein is intended to denote both the whole molecule which binds to the receptor and any part thereof which includes the receptor binding domain such that it retains the receptor binding property. Ligands comprising equivalent receptor binding domains are also included in the present invention.

The expressions fragment, homologue, functional equivalent and derivative relate to variants, modifications and/or parts of the peptides and protein fragments according to the invention which retain the desired fibronectin, laminin, C3 or C3met binding properties.

A homologue of UspA1 according to the present invention is defined as a sequence having at least 72% sequence identity, as can be seen from table 1 below.

A fragment according to the present invention is defined as any of the homologue sequences which are truncated or extended by 1, 2, 5, 10, 15, 20 amino acids at the N-terminus and/or truncated or extended by 1, 2, 5, 10, 15, 20 amino acids at the C-terminus.

The expressions degenerate, hydroxylation, sulphonation and glycosylation products or other secondary processing products relate to variants and/or modifications of the peptides and protein fragments according to the invention which have been altered compared to the original peptide or protein fragment by degeneration, hydroxylation, sulphonation or glycosylation but which retain the desired fibronectin, laminin, C3 or C3met binding properties.

The present invention concerns especially infections caused by *Moraxella catarrhalis*. A peptide according to the present invention can be used for the treatment or prophylaxis of otitis media, sinusitis or lower respiratory tract infections.

TABLE 1

Multiple alignment of full length UspA1 protein sequences, associated identity percentages

|          | O12E | O35E | O46E | P44 | TTA24 | TTA37 | V1171 |
|----------|------|------|------|-----|-------|-------|-------|
| ATCC25238 | 81   | 75   | 83   | 83  | 84    | 79    | 84    |
| O12E     |      | 74   | 77   | 83  | 76    | 72    | 75    |
| O35E     |      |      | 72   | 74  | 83    | 73    | 78    |
| O46E     |      |      |      | 81  | 81    | 82    | 80    |
| P44      |      |      |      |     | 81    | 75    | 77    |
| TTA24    |      |      |      |     |       | 76    | 84    |
| TTA37    |      |      |      |     |       |       | 78    |

TABLE 2

UspA2 Pileup Analysis - Strains and sequences used

| | acc | Strain | des | sl |
|---|---|---|---|---|
| TREMBL:O54407_MORCA | O54407 | O35E | Ubiquitous surface protein A 2. | 576 |
| TREMBL:Q58XP4_MORCA | Q58XP4 | MC317 | UspA2. | 650 |
| TREMBL:Q848S1_MORCA | Q848S1 | E22 | Ubiquitous surface protein A2H. | 877 |
| TREMBL:Q848S2_MORCA | Q848S2 | V1122 | Ubiquitous surface protein A2. | 616 |
| TREMBL:Q8GH86_MORCA | Q8GH86 | P44 | UspA2. | 668 |
| TREMBL:Q9L961_MORCA | Q9L961 | TTA37 | USPA2H. | 889 |
| TREMBL:Q9L962_MORCA | Q9L962 | O46E | USPA2H. | 894 |
| TREMBL:Q9L963_MORCA | Q9L963 | O12E | USPA2 (Ubiquitous surface protein A2). | 684 |
| TREMBL:Q9XD51_MORCA | Q9XD51 | V1171 | UspA2. | 674 |
| TREMBL:Q9XD53_MORCA | Q9XD53 | TTA24 | UspA2. | 613 |
| TREMBL:Q8RTB2_MORCA | Q8RTB2 | SP12-5 | UspA2 | 686 |
| TREMBL:Q9XD55_MORCA | Q9XD55 | ATCC25238 | UspA2. | 630 |
| Forsgren_UspA2 | | | UspA2. | 630 |

Accordingly, the present invention provides a ligand isolated from *Moraxella catarrhalis* outer membrane protein which has laminin and/or fibronectin and/or C3-binding, wherein said ligand is a polypeptide comprising or consisting of an amino acid sequence selected from the group consisting of SEQ ID NO: 1-10 which are derived from the full-length *Moraxella catarrhalis* BC5 UspA1 & UspA2 sequences shown below, or a fragment, homologue, functional equivalent, derivative, degenerate or hydroxylation, sulphonation or glycosylation product or other secondary processing product thereof.

Full-length UspA1 from *Moraxella catarrhalis* strain BC5 (SEQ ID NO: 32):

```
MNKIYKVKKN AAGHLVACSE FAKGHTKKAV LGSLLIVGIL

GMATTASAQK VGKATNKISG GDNNTANGTY LTIGGGDYNK

TKGRYSTIGG GLFNEATNEY STIGSGGYNK AKGRYSTIGG

GGYNEATNQY STIGGGDNNT AKGRYSTIGG GGYNEATIEN

STVGGGGYNQ AKGRNSTVAG GYNNEATGTD STIAGGRKNQ

ATGKGSFAAG IDNKANADNA VALGNKNTIE GENSVAIGSN

NTVKKGQQNV FILGSNTDTT NAQNGSVLLG HNTAGKAATI

VNSAEVGGLS LTGFAGASKT GNGTVSVGKK GKERQIVHVG

AGEISDTSTD AVNGSQLHVL ATVVAQNKAD IKDLDDEVGL

LGEEINSLEG EIFNNQDAIA KNQADIKTLE SNVEEGLLDL

SGRLLDQKAD IDNNINNIYE LAQQQDQHSS DIKTLKNNVE

EGLLDLSGRL IDQKADLTKD IKALESNVEE GLLDLSGRLI

DQKADIAKNQ ADIAQNQTDI QDLAAYNELQ DAYAKQQTEA

IDALNKASSA NTDRIATAEL GIAENKKDAQ IAKAQANENK

DGIAKNQADI QLHDKKITNL GILHSMVARA VGNNTQGVAT

NKADIAKNQA DIANNIKNIY ELAQQQDQHS SDIKTLAKVS

AANTDRIAKN KAEADASFET LTKNQNTLIE QGEALVEQNK

AINQELEGFA AHADVQDKQI LQNQADITTN KTAIEQNINR

TVANGFEIEK NKAGIATNKQ ELILQNDRLN RINETNNHQD
```

QKIDQLGYAL KEQGQHFNNR ISAVERQTAG GIANAIAIAT

LPSPSRAGEH HVLFGSGYHN GQAAVSLGAA GLSDTGKSTY

KIGLSWSDAG GLSGGVGGSY RWK

Full-length UspA2 from *Moraxella catarrhalis* strain BC5 (SEQ ID NO: 33):

```
MKTMKLLPLK IAVTSAMIIG LGAASTANAQ AKNDITLEDL

PYLIKKIDQN ELEADIGDIT ALEKYLALSQ YGNILALEEL

NKALEELDED VGWNQNDIAN LEDDVETLTK NQNAFAEQGE

AIKEDLQGLA DFVEGQEGKI LQNETSIKKN TQRNLVNGFE

IEKNKDAIAK NNESIEDLYD FGHEVAESIG EIHAHNEAQN

ETLKGLITNS IENTNNITKN KADIQALENN VVEELFNLSG

RLIDQKADID NNINNIYELA QQQDQHSSDI KTLKKNVEEG

LLELSDHIID QKTDIAQNQA NIQDLATYNE LQDQYAQKQT

EAIDALNKAS SENTQNIEDL AAYNELQDAY AKQQTEAIDA

LNKASSENTQ NIEDLAAYNE LQDAYAKQQA EAIDALNKAS

SENTQNIAKN QADIANNITN LYELAQQQDK HRSDIKTLAK

TSAANTDRIA KNKADDDASF ETLTKNQNTL IEKDKEHDKL

ITANKTAIDA NKASADTKFA ATADAFTKNG NAITKNAKSI

TDLGTKVDGF DSRVTALDTK VNAFDGRITA LDSKVENGMA

AQAALSGLFQ PYSVGKFNAT AALGGYGSKS AVAIGAGYRV

NPNLAFKAGA AINTSGNKKG SYNIGVNYEF
```

In a preferred embodiment, the ligand is a polypeptide [or polypeptide truncate compared with a wild-type polypeptide] comprising or consisting of an amino acid sequence selected from the group consisting of SEQ ID NO: 1-10, or a fragment, homologue, functional equivalent, derivative, degenerate or hydroxylation, sulphonation or glycosylation product or other secondary processing product thereof.

The term ligand is used herein to denote both the whole molecule which binds to laminin and/or fibronectin and/or C3 and any part thereof which includes a laminin and/or fibronectin and/or C3-binding domain such that it retains the respective binding property. Thus "ligand" encompasses molecules which consist only of the laminin and/or fibronectin and/or C3-binding domain i.e. the peptide region or regions required for binding.

For the purposes of this invention laminin, fibronectin or C3-binding properties of a polypeptide can be ascertained as follows:

For the purposes of this invention laminin, fibronectin or C3-binding properties of a polypeptide can be ascertained as follows: Polypeptides can be labelled with $^{125}$Iodine or other radioactive compounds and tested for binding in radio immunoassays (RIA) as fluid or solid phase (e.g., dot blots). Moreover, polypeptides can be analysed for binding with enzyme-linked immunosorbent assays (ELISA) or flow cytometry using appropriate antibodies and detection systems. Interactions between polypeptides and laminin, fibronectin, or C3 can further be examined by surface plasmon resonance (Biacore). Examples of methods are exemplified in detail in the Material and Methods section.

In another preferred embodiment, the polypeptide [or polypeptide truncate compared with a wild-type polypeptide] comprises or consists of at least one of the conserved sequences from within SEQ ID NO: 1-10 which are identified in the alignment shown herein. Hence, in this embodiment, the polypeptide [or polypeptide truncate compared with a wild-type polypeptide] comprises of consists of at least one of:

From UspA1 (conserved fragments from the fibronectin binding domain—'/' separating alternative choices of an amino acid at a position)

(SEQ ID NO: 34)
G T/V V S V G S/K Q/E/K/A G/N K/N/G/H/S E R

Q I V N/H V G A G Q/N/E/K I S/R A/D T/D S T

D A V N G S Q L H/Y A L A S/K/T T/A/V I/V (SEQ ID NO: 35)
S T D A V N G S Q L (SEQ ID NO: 36)
L L N/D L S G R L L/I D Q K A D I D N N I N

N/H I Y E/D L A Q Q Q D Q H S S D I K T L K (SEQ ID NO: 37)
D Q K A D I D N N I N (SEQ ID NO: 38)
L A Q Q Q D Q H S S D I K T L K

From UspA2 (conserved fragments from the fibronectin binding domain—'/' separating alternative choices of an amino acid at a position)

(SEQ ID NO: 39)
K A D I D N N I N N/H I Y E L A Q Q Q D Q H S S D (SEQ ID NO: 40)
I K/Q T/A L K/E K/N/S N V/I E/V E G/E L L/F E/N

L S D/G H/R I/L I D Q K T/A D I/L A/T Q/K N/D

From UspA2 (conserved fragments from the C3-binding domain—'/' separating alternative choices of an amino acid at a position)

(SEQ ID NO: 41)
I E/Q D L A A Y N E L Q D A Y A K Q Q A/T E A I

D A L N K A S S E N T Q N I A K N Q A D I A N N

I T/N N I Y E L A Q Q Q D K/Q H R/S S D I K T L

A K T/A S A A N T D/N R I (SEQ ID NO: 42)
D L A A Y N E L Q D A Y A K Q Q (SEQ ID NO: 43)
E A I D A L N K A S S E N T Q N I A K N Q A D I

A N N I

It will be understood that the polypeptide ligands of the invention can comprise a laminin and/or fibronectin and/or C3-binding domain of sequence recited herein which is modified by the addition or deletion of amino acid residues to or from the sequences recited herein at either or both the N or C termini, which modified peptides retain the ability to bind laminin and/or fibronectin and/or C3, respectively. Accordingly, the invention further provides a ligand comprising or consisting of a polypeptide in which 50, 40, 30, 20, 10, 5, 3 or 1 amino acid residues have been added to or deleted from an amino acid sequence recited herein at either or both the N or C termini, wherein said modified polypeptide retains the ability to bind laminin and/or fibronectin and/or C3; and/or elicit an immune response against the non-modified peptide. By extension it is meant lengthening the sequence using the context of the peptide from the full-length amino acid sequence from which it is derived.

As regards fragments of the polypeptides of the invention, any size fragment may be used in the invention (based on the homologue sequences/conserved regions/functional domatins discussed herein) provided that the fragment retains the ability to bind laminin and/or fibronectin and/or C3. It may be desirable to isolate a minimal peptide which contains only those regions required for receptor binding.

Polypeptide ligands according to the invention may be derived from known Moraxella catarrhalis UspA1 or UspA2 proteins by truncation at either or both of the N- and C-termini. Truncates are not the full-length native UspA1 or A2 molecules. Accordingly, the invention further provides a wild-type UspA1 sequence lacking at least (or exactly) 20, 30, 40, 50, 60, 70, 80, 100, 120, 140, 160 etc to 298 amino acids from the N-terminus, and/or lacking at least (or exactly) 20, 30, 40, 50, 60, 70, 80, 100, 120, 140, 160, 180, 200 etc to 450 amino acids from the C-terminus. Preferably, the truncate retains fibronectin binding function (optionally also laminin and/or C3-binding).

TABLE 3

Possible combinations of truncations to the N- and C-termini of wild-type UspA1 protein.
No. of amino acids lacking, at least or exactly:

| From the N-terminus | From the C-terminus | | | | | | | | | | | | | |
|---|---|---|---|---|---|---|---|---|---|---|---|---|---|---|
| 0 | X | 20 | 30 | 40 | 50 | 60 | 70 | 80 | 100 | 120 | 140 | 160 | 180 | 200 | 220 |
| 20 | 0 | 20 | 30 | 40 | 50 | 60 | 70 | 80 | 100 | 120 | 140 | 160 | 180 | 200 | 220 |
| 30 | 0 | 20 | 30 | 40 | 50 | 60 | 70 | 80 | 100 | 120 | 140 | 160 | 180 | 200 | 220 |
| 40 | 0 | 20 | 30 | 40 | 50 | 60 | 70 | 80 | 100 | 120 | 140 | 160 | 180 | 200 | 220 |
| 50 | 0 | 20 | 30 | 40 | 50 | 60 | 70 | 80 | 100 | 120 | 140 | 160 | 180 | 200 | 220 |
| 60 | 0 | 20 | 30 | 40 | 50 | 60 | 70 | 80 | 100 | 120 | 140 | 160 | 180 | 200 | 220 |
| 70 | 0 | 20 | 30 | 40 | 50 | 60 | 70 | 80 | 100 | 120 | 140 | 160 | 180 | 200 | 220 |
| 80 | 0 | 20 | 30 | 40 | 50 | 60 | 70 | 80 | 100 | 120 | 140 | 160 | 180 | 200 | 220 |
| 100 | 0 | 20 | 30 | 40 | 50 | 60 | 70 | 80 | 100 | 120 | 140 | 160 | 180 | 200 | 220 |
| 120 | 0 | 20 | 30 | 40 | 50 | 60 | 70 | 80 | 100 | 120 | 140 | 160 | 180 | 200 | 220 |
| 140 | 0 | 20 | 30 | 40 | 50 | 60 | 70 | 80 | 100 | 120 | 140 | 160 | 180 | 200 | 220 |
| 160 | 0 | 20 | 30 | 40 | 50 | 60 | 70 | 80 | 100 | 120 | 140 | 160 | 180 | 200 | 220 |
| 180 | 0 | 20 | 30 | 40 | 50 | 60 | 70 | 80 | 100 | 120 | 140 | 160 | 180 | 200 | 220 |
| 200 | 0 | 20 | 30 | 40 | 50 | 60 | 70 | 80 | 100 | 120 | 140 | 160 | 180 | 200 | 220 |
| 220 | 0 | 20 | 30 | 40 | 50 | 60 | 70 | 80 | 100 | 120 | 140 | 160 | 180 | 200 | 220 |
| 240 | 0 | 20 | 30 | 40 | 50 | 60 | 70 | 80 | 100 | 120 | 140 | 160 | 180 | 200 | 220 |
| 260 | 0 | 20 | 30 | 40 | 50 | 60 | 70 | 80 | 100 | 120 | 140 | 160 | 180 | 200 | 220 |
| 280 | 0 | 20 | 30 | 40 | 50 | 60 | 70 | 80 | 100 | 120 | 140 | 160 | 180 | 200 | 220 |
| 298 | 0 | 20 | 30 | 40 | 50 | 60 | 70 | 80 | 100 | 120 | 140 | 160 | 180 | 200 | 220 |

| From the N-terminus | From the C-terminus | | | | | | | | | | |
|---|---|---|---|---|---|---|---|---|---|---|---|
| 0 | 240 | 260 | 280 | 300 | 320 | 340 | 360 | 380 | 400 | 420 | 440 | 450 |
| 20 | 240 | 260 | 280 | 300 | 320 | 240 | 360 | 380 | 400 | 420 | 440 | 450 |
| 30 | 240 | 260 | 280 | 300 | 320 | 240 | 360 | 380 | 400 | 420 | 440 | 450 |
| 40 | 240 | 260 | 280 | 300 | 320 | 240 | 360 | 380 | 400 | 420 | 440 | 450 |
| 50 | 240 | 260 | 280 | 300 | 320 | 240 | 360 | 380 | 400 | 420 | 440 | 450 |
| 60 | 240 | 260 | 280 | 300 | 320 | 240 | 360 | 380 | 400 | 420 | 440 | 450 |
| 70 | 240 | 260 | 280 | 300 | 320 | 240 | 360 | 380 | 400 | 420 | 440 | 450 |
| 80 | 240 | 260 | 280 | 300 | 320 | 240 | 360 | 380 | 400 | 420 | 440 | 450 |
| 100 | 240 | 260 | 280 | 300 | 320 | 240 | 360 | 380 | 400 | 420 | 440 | 450 |
| 120 | 240 | 260 | 280 | 300 | 320 | 240 | 360 | 380 | 400 | 420 | 440 | 450 |
| 140 | 240 | 260 | 280 | 300 | 320 | 240 | 360 | 380 | 400 | 420 | 440 | 450 |
| 160 | 240 | 260 | 280 | 300 | 320 | 240 | 360 | 380 | 400 | 420 | 440 | 450 |
| 180 | 240 | 260 | 280 | 300 | 320 | 240 | 360 | 380 | 400 | 420 | 440 | 450 |
| 200 | 240 | 260 | 280 | 300 | 320 | 240 | 360 | 380 | 400 | 420 | 440 | 450 |
| 220 | 240 | 260 | 280 | 300 | 320 | 240 | 360 | 380 | 400 | 420 | 440 | 450 |
| 240 | 240 | 260 | 280 | 300 | 320 | 240 | 360 | 380 | 400 | 420 | 440 | 450 |
| 260 | 240 | 260 | 280 | 300 | 320 | 240 | 360 | 380 | 400 | 420 | 440 | 450 |
| 280 | 240 | 260 | 280 | 300 | 320 | 240 | 360 | 380 | 400 | 420 | 440 | 450 |
| 298 | 240 | 260 | 280 | 300 | 320 | 240 | 360 | 380 | 400 | 420 | 440 | 450 |

Accordingly the invention further provides a wild-type UspA2 sequence lacking at least (or exactly) 20, 30, 40, 50, 60, 70, 80, 100, 120, 140, 160, 164 amino acids from the N-terminus, and/or lacking at least (or exactly) 20, 30, 40, 50, 60, 70, 80, 100, 120, 140, 180, 200 etc to 312 amino acids from the C-terminus. Preferably, the truncate retains fibronectin binding function (optionally also laminin and/or C3-binding). Possible truncates may be selected from those shown in the following table, all of which are within the scope of the invention.

TABLE 4

Possible combinations of truncations to the N- and C-termini of wild-type UspA2 protein
No. of amino acids lacking, at least or exactly

| From the N-terminus | From the C-terminus | | | | | | | | | | | | | | | | | | | |
|---|---|---|---|---|---|---|---|---|---|---|---|---|---|---|---|---|---|---|---|---|
| 0 | X | 20 | 30 | 40 | 50 | 60 | 70 | 80 | 100 | 120 | 140 | 160 | 180 | 200 | 220 | 240 | 260 | 280 | 300 | 312 |
| 20 | 0 | 20 | 30 | 40 | 50 | 60 | 70 | 80 | 100 | 120 | 140 | 160 | 180 | 200 | 220 | 240 | 260 | 280 | 300 | 312 |
| 30 | 0 | 20 | 30 | 40 | 50 | 60 | 70 | 80 | 100 | 120 | 140 | 160 | 180 | 200 | 220 | 240 | 260 | 280 | 300 | 312 |
| 40 | 0 | 20 | 30 | 40 | 50 | 60 | 70 | 80 | 100 | 120 | 140 | 160 | 180 | 200 | 220 | 240 | 260 | 280 | 300 | 312 |
| 50 | 0 | 20 | 30 | 40 | 50 | 60 | 70 | 80 | 100 | 120 | 140 | 160 | 180 | 200 | 220 | 240 | 260 | 280 | 300 | 312 |
| 60 | 0 | 20 | 30 | 40 | 50 | 60 | 70 | 80 | 100 | 120 | 140 | 160 | 180 | 200 | 220 | 240 | 260 | 280 | 300 | 312 |
| 70 | 0 | 20 | 30 | 40 | 50 | 60 | 70 | 80 | 100 | 120 | 140 | 160 | 180 | 200 | 220 | 240 | 260 | 280 | 300 | 312 |
| 80 | 0 | 20 | 30 | 40 | 50 | 60 | 70 | 80 | 100 | 120 | 140 | 160 | 180 | 200 | 220 | 240 | 260 | 280 | 300 | 312 |
| 100 | 0 | 20 | 30 | 40 | 50 | 60 | 70 | 80 | 100 | 120 | 140 | 160 | 180 | 200 | 220 | 240 | 260 | 280 | 300 | 312 |
| 120 | 0 | 20 | 30 | 40 | 50 | 60 | 70 | 80 | 100 | 120 | 140 | 160 | 180 | 200 | 220 | 240 | 260 | 280 | 300 | 312 |
| 140 | 0 | 20 | 30 | 40 | 50 | 60 | 70 | 80 | 100 | 120 | 140 | 160 | 180 | 200 | 220 | 240 | 260 | 280 | 300 | 312 |
| 160 | 0 | 20 | 30 | 40 | 50 | 60 | 70 | 80 | 100 | 120 | 140 | 160 | 180 | 200 | 220 | 240 | 260 | 280 | 300 | 312 |
| 164 | 0 | 20 | 30 | 40 | 50 | 60 | 70 | 80 | 100 | 120 | 140 | 160 | 180 | 200 | 220 | 240 | 260 | 280 | 300 | 312 |

Accordingly the invention further provides a wild-type UspA2 sequence lacking at least (or exactly) 5, 10, 15, 20, 25 or 29 amino acids from the N-terminus, and/or lacking at least (or exactly) 20, 30, 40, 50, 60, 70, 80, 100, 120, 140, 160, 180, 200 etc to 453 amino acids from the C-terminus. Preferably, the truncate retains laminin binding function (optionally also fibronectin and/or C3-binding). Possible truncates may be selected from those shown in the following table, all of which are within the scope of the invention.

TABLE 5

Possible combinations of truncations to the N- and C-termini of wild-type UspA2 protein
No. of amino acids lacking, at least or exactly:

| From the C-terminus | From the N-terminus | | | | | | |
|---|---|---|---|---|---|---|---|
| 0 | X | 5 | 10 | 15 | 20 | 25 | 29 |
| 20 | 0 | 5 | 10 | 15 | 20 | 25 | 29 |
| 30 | 0 | 5 | 10 | 15 | 20 | 25 | 29 |
| 40 | 0 | 5 | 10 | 15 | 20 | 25 | 29 |
| 50 | 0 | 5 | 10 | 15 | 20 | 25 | 29 |
| 60 | 0 | 5 | 10 | 15 | 20 | 25 | 29 |
| 70 | 0 | 5 | 10 | 15 | 20 | 25 | 29 |
| 80 | 0 | 5 | 10 | 15 | 20 | 25 | 29 |
| 100 | 0 | 5 | 10 | 15 | 20 | 25 | 29 |
| 120 | 0 | 5 | 10 | 15 | 20 | 25 | 29 |
| 140 | 0 | 5 | 10 | 15 | 20 | 25 | 29 |
| 160 | 0 | 5 | 10 | 15 | 20 | 25 | 29 |
| 180 | 0 | 5 | 10 | 15 | 20 | 25 | 29 |
| 200 | 0 | 5 | 10 | 15 | 20 | 25 | 29 |
| 220 | 0 | 5 | 10 | 15 | 20 | 25 | 29 |
| 240 | 0 | 5 | 10 | 15 | 20 | 25 | 29 |
| 260 | 0 | 5 | 10 | 15 | 20 | 25 | 29 |
| 280 | 0 | 5 | 10 | 15 | 20 | 25 | 29 |
| 300 | 0 | 5 | 10 | 15 | 20 | 25 | 29 |
| 320 | 0 | 5 | 10 | 15 | 20 | 25 | 29 |
| 340 | 0 | 5 | 10 | 15 | 20 | 25 | 29 |
| 360 | 0 | 5 | 10 | 15 | 20 | 25 | 29 |
| 380 | 0 | 5 | 10 | 15 | 20 | 25 | 29 |
| 400 | 0 | 5 | 10 | 15 | 20 | 25 | 29 |
| 420 | 0 | 5 | 10 | 15 | 20 | 25 | 29 |
| 440 | 0 | 5 | 10 | 15 | 20 | 25 | 29 |
| 453 | 0 | 5 | 10 | 15 | 20 | 25 | 29 |

Accordingly the invention further provides a wild-type UspA2 sequence lacking (or exactly) 20, 30, 40, 50, 60, 70, 80, 100, 120, 140, 160 etc. to 301 amino acids from the N-terminus, and/or lacking at least (or exactly) 20, 30, 40, 50, 60, 70, 80, 100, 120, 140, 160 or 172 amino acids from the C-terminus. Preferably, the truncate retains C3 binding function (optionally also fibronectin and/or laminin binding). Possible truncates may be selected from those shown in the following table, all of which are within the scope of the invention.

TABLE 6

Possible combinations of truncations to the N- and C-termini of wild-type UspA2 protein
No. of amino acids lacking, at least or exactly:

| From the N-terminus | From the C-terminus | | | | | | | | | | | |
|---|---|---|---|---|---|---|---|---|---|---|---|---|
| 0 | X | 20 | 30 | 40 | 50 | 60 | 70 | 80 | 100 | 120 | 140 | 160 | 172 |
| 20 | 0 | 20 | 30 | 40 | 50 | 60 | 70 | 80 | 100 | 120 | 140 | 160 | 172 |
| 30 | 0 | 20 | 30 | 40 | 50 | 60 | 70 | 80 | 100 | 120 | 140 | 160 | 172 |
| 40 | 0 | 20 | 30 | 40 | 50 | 60 | 70 | 80 | 100 | 120 | 140 | 160 | 172 |
| 50 | 0 | 20 | 30 | 40 | 50 | 60 | 70 | 80 | 100 | 120 | 140 | 160 | 172 |
| 60 | 0 | 20 | 30 | 40 | 50 | 60 | 70 | 80 | 100 | 120 | 140 | 160 | 172 |
| 70 | 0 | 20 | 30 | 40 | 50 | 60 | 70 | 80 | 100 | 120 | 140 | 160 | 172 |
| 80 | 0 | 20 | 30 | 40 | 50 | 60 | 70 | 80 | 100 | 120 | 140 | 160 | 172 |
| 100 | 0 | 20 | 30 | 40 | 50 | 60 | 70 | 80 | 100 | 120 | 140 | 160 | 172 |
| 120 | 0 | 20 | 30 | 40 | 50 | 60 | 70 | 80 | 100 | 120 | 140 | 160 | 172 |
| 140 | 0 | 20 | 30 | 40 | 50 | 60 | 70 | 80 | 100 | 120 | 140 | 160 | 172 |
| 160 | 0 | 20 | 30 | 40 | 50 | 60 | 70 | 80 | 100 | 120 | 140 | 160 | 172 |
| 180 | 0 | 20 | 30 | 40 | 50 | 60 | 70 | 80 | 100 | 120 | 140 | 160 | 172 |
| 200 | 0 | 20 | 30 | 40 | 50 | 60 | 70 | 80 | 100 | 120 | 140 | 160 | 172 |
| 220 | 0 | 20 | 30 | 40 | 50 | 60 | 70 | 80 | 100 | 120 | 140 | 160 | 172 |
| 240 | 0 | 20 | 30 | 40 | 50 | 60 | 70 | 80 | 100 | 120 | 140 | 160 | 172 |
| 260 | 0 | 20 | 30 | 40 | 50 | 60 | 70 | 80 | 100 | 120 | 140 | 160 | 172 |
| 280 | 0 | 20 | 30 | 40 | 50 | 60 | 70 | 80 | 100 | 120 | 140 | 160 | 172 |
| 290 | 0 | 20 | 30 | 40 | 50 | 60 | 70 | 80 | 100 | 120 | 140 | 160 | 172 |
| 301 | 0 | 20 | 30 | 40 | 50 | 60 | 70 | 80 | 100 | 120 | 140 | 160 | 172 |

Known wild-type UspA1 sequences that may be truncated in this way are those of strains ATCC25238 (MX2; GenBank accession no. AAD43465), P44 (AAN84895), O35E (AAB96359), TTA37 (AAF40122), O12E (AAF40118), O46E (AAF36416), V1171 (AAD43469), TTA24 (AAD43467) (see Table 1/FIGS. 19A through 19D); or BC5 (see above). Known wild-type UspA2 sequences that may be truncated in this way are those of strains O35E (GenBank accession no. 04407), MC317 (GenBank accession no. Q58XP4), E22 (GenBank accession no. Q848S1), V1122 (GenBank accession no. Q848S2), P44 (GenBank accession no. Q8GH86), TTA37 (GenBank accession no. Q9L961), O46E (GenBank accession no. Q9L962), O12E (GenBank accession no. Q9L963), V1171 (GenBank accession no. Q9XD51), TTA24 (GenBank accession no. Q9XD53), SP12-5 (GenBank accession no. Q8RTB2), ATCC25238 (GenBank accession no. Q9XD55) (see Table 2/FIGS. 20A through 20J); or BC5 [Forsgren_UspA2] (see above).

Ideally the UspA1 or UspA2 truncate of this embodiment comprises or consists of an amino acid sequence selected from the group consisting of SEQ ID NO: 1-10 or a fragment, homologue, functional equivalent, derivative, degenerate or hydroxylation, sulphonation or glycosylation product or other secondary processing product thereof; or comprises or consists of at least one of the conserved sequences from within these regions which are identified in the alignment shown in herein, for example:

From UspA1 (conserved fragments from the fibronectin binding domain—'/' separating alternative choices of an amino acid at a position)

(SEQ ID NO: 44)
G T/V V S V G S/K Q/E/K/A G/N K/N/G/H/S E R Q I

V N/H V G A G Q/N/E/K I S/R A/D T/D S T D A V N

G S Q L H/Y A L A S/K/T T/A/V I/V (SEQ ID NO: 45)
S T D A V N G S Q L (SEQ ID NO: 46)
L L N/D L S G R L L/I D Q K A D I D N N I N N/H

I Y E/D L A Q Q Q D Q H S S D I K I L K (SEQ ID NO: 47)
D Q K A D I D N N I N (SEQ ID NO: 48)
L A Q Q Q D Q H S S D I K I L K

From UspA2 (conserved fragments from the fibronectin binding domain—'/' separating alternative choices of an amino acid at a position)

(SEQ ID NO: 49)
K A D I D N N I N N/H I Y E L A Q Q Q D Q H S S D (SEQ ID NO: 50)
I K/Q T/A L K/E K/N/S N V/I E/V E G/E L L/F E/N

L S D/G H/R I/L I D Q K T/A D I/L A/T Q/K N/D

From UspA2 (conserved fragments from the C3-binding domain—'/' separating alternative choices of an amino acid at a position)

(SEQ ID NO: 51)
I E/Q D L A A Y N E L Q D A Y A K Q Q A/T E A I

D A L N K A S S E N T Q N I A K N Q A D I A N N

I T/N N I Y E L A Q Q Q D K/Q H R/S S D I K T L

A K T/A S A A N T D/N R I (SEQ ID NO: 52)
D L A A Y N E L Q D A Y A K Q Q (SEQ ID NO: 53)
E A I D A L N K A S S E N T Q N I A K N Q A D I

A N N I

It may be convenient to produce fusion proteins containing polypeptide ligands as described herein. Accordingly, in a further embodiment, the invention provides fusion proteins comprising polypeptide ligands according to the invention. Preferably a fusion protein according to this embodiment is less than 50% identical to any known fully length sequence over its entire length. Such fusions can constitute a derivative of the polypeptides of the invention. Further derivatives can be the use of the polypeptides of the invention to as a carrier to covalently couple peptide or saccharide moieties. They may be coupled for instance to pneumococcal capsular oligosaccharides or polysaccharides, or *Moraxella catarrhalis* lipooligosaccaharides, or non-typeable *Haemophilus influenzae* lipooligosaccaharides.

Homologous peptides of the invention may be identified by sequence comparison. Homologous peptides are preferably at least 60% identical, more preferably at least 70%, 80%, 90%, 95% or 99% identical in ascending order of preference to the peptide sequence disclosed herein or fragments thereof or truncates of the invention over their entire length. Preferably the homologous peptide retains the ability to bind fibronectin and/or laminin and/or C3; and/or elicit an immune response against the peptide sequences disclosed herein or fragment thereof.

FIGS. 19A through 19D and 20A through 20J show an alignment of peptide sequences of UspA1 and UspA2 of different origin which indicates regions of sequence that are capable of being modified to form homologous sequences whilst retained function (i.e. fibronectin and/or laminin and/or C3 binding ability). Homologous peptides to the BC5 SEQ ID NO: 1-10 peptides are for instance those sequences corresponding to the BC5 sequence from other strains in FIGS. 19A through 19D and 20A through 20J.

Vaccines of the Invention

The polypeptides/peptides/functional domains/homologues/fragments/truncates/derivatives of the invention should ideally be formulated as a vaccine comprising an effective amount of said component(s) and a pharmaceutically acceptable excipient.

The vaccines of the invention can be used for administration to a patient for the prevention or treatment of *Moraxella catarrhalis* infection or otitis media or sinusitis or lower respiratory tract infections. They may be administered in any known way, including intramuscularly, parenternally, mucosally and intranasally.

Combination Vaccines of the Invention

The vaccines of the present invention may be combined with other *Moraxella catarrhalis* antigens for prevention or treatment of the aforementioned diseases.

The present inventors have found in particular that *Moraxella catarrhalis* has at least 2 means of hampering the host immune system from attacking the organism. In addition to the interaction with C3 (and C4BP) mentioned in the Examples below, *M. catarrhalis* has a strong affinity for soluble and membrane bound human IgD through protein MID (also known as OMP106). *Moraxella*-dependent IgD-binding to B lymphocytes results in a polyclonal immunoglobulin synthesis which may prohibit production of specific monoclonal anti-*moraxella* antibodies. The fact that *M. catarrhalis* hampers the human immune system in several ways might explain why *M. catarrhalis* is such a common inhabitant of the respiratory tract.

The inventors believe that the combination of antigens involved in the IgD-binding function (MID) and C3-binding function (UspA1 and/or UspA2) can provide an immunogenic composition giving the host enhanced defensive capabilities against *Moraxella's* hampering of the human immune system thus providing an enhanced decrease in *M. catarrhalis* carriage on mucosal surfaces.

A further aspect of the invention is therefore a vaccine composition comprising an effective amount of UspA1 and/or UspA2 (particularly the latter) (for instance full-length polypeptides or polypeptides/peptides/functional domains/homologues/fragments/truncates/derivatives of the invention as described herein, preferably which retains a C3-binding function) in combination with an effective amount of protein MID (for instance full-length polypeptides or polypeptides/peptides/functional domains/homologues/fragments/truncates/derivatives thereof, preferably which retain a human IgD-binding function), and a pharmaceutically acceptable excipient.

Protein MID, and IgD-binding homologous/fragments/trun-cates thereof is described in WO 03/004651 (incorporated by reference herein). Particularly suitable fragments for this purpose is a polypeptide comprising (or consisting of) the F2 fragment described in WO 03/004651, or sequences with at least 60, 70, 80, 90, 95, 99% identity thereto which preferably retain human IgD-binding activity.

The MID and UspA components of this combination vaccine may be separate from each other, or may be conveniently fused together by known molecular biology techniques.

BRIEF DESCRIPTION OF THE DRAWINGS

FIGS. 1A through 1I shows thirteen *M. catarrhalis* strains tested for fibronectin binding (FIG. 1A). Strong fibronectin binding correlated to UspA1/A2 expression as detected by anti-UspA1/A2 pAb (FIG. 1B (wild type) FIG. 1C (ΔuspA1), FIG. 1D (ΔuspA2), FIG. 1E (ΔuspA1/A2), FIG. 1F (wild type), FIG. 1G (ΔuspA1), FIG. 1H (ΔuspA2), FIG. 1I (ΔuspA1/A2)). Flow cytometry profiles of *M. catarrhalis* BBH18 wild type and UspA1/A2 deficient mutants show an UspA1/A2-dependent binding to soluble fibronectin. The profiles of wild type clinical isolate (FIG. 1B and. 1F) and corresponding mutants devoid of UspA1 (FIG. 1C and FIG. 1G), or UspA2 (FIG. 1D and FIG. 1H), and double mutants (FIG. 1E and FIG. 1I) lacking both UspA1 and UspA2 are shown. Bacteria were incubated with rabbit anti-UspA1/A2 or fibronectin followed by an anti-fibronectin pAb. FITC-conjugated rabbit pAb was subsequently added followed by flow cytometry analysis. A typical experiment out of three with the mean fluorescence intensity (MFI) for each profile is shown.

FIGS. 3A through 3D shows pictures that verify that *M. catarrhalis* mutants devoid of UspA1 and UspA2 do not bind to immobilized fibronectin. *M. catarrhalis* wild type was able to adhere at a high density on fibronectin coated glass slides (FIG. 3A). *M. catarrhalis* ΔuspA1 mutant was also retained at a high density (FIG. 3B), whereas *M. catarrhalis* ΔuspA2 and ΔuspA1/A2 double mutants adhered poorly (FIG. 3C and FIG. 3D). Glass slides were coated with fibronectin and incubated with *M. catarrhalis* RH4 and its corresponding UspA1/A2 mutants. After several washes, bacteria were Gram stained.

FIG. 6 shows the sequence according to sequence ID No. 1, and the sequence homology between UspA1$^{300-453}$ (SEQ ID NO: 87) and UspA2$^{165-318}$ (SEQ ID NO: 3). The 31 identical amino acid residues are within brackets.

FIG. 9B) shows the binding of recombinant UspA1 and A2 laminin in a dose-dependent manner. Specific laminin binding is shown for UspA1$^{50-770}$ and UspA2$^{30-539}$. Both UspA proteins (40 nM) were coated on microtiter plates and incubated with increasing concentrations of laminin followed by detection with rabbit anti-laminin pAb and HRP-conjugated anti-rabbit pAb. Mean values of three separate experiments are shown and error bars indicate SD.

(FIG. 11A) The C3-molecule in serum consists of one α-chain and one β-chain. (FIG. 11B) The α-chain contains an internal thioester site that after activation can attach covalently to a microbial surface. (FIG. 11C) The C3 has been treated with methylamine, which becomes covalently attached to the thioester.

(FIG. 12A) *M. catarrhalis* RH4 wild-type (wt), the ΔuspA1, the ΔuspA2 or the ΔuspA1/A2 mutants were incubated in the presence of 10% NHS. (FIG. 12B) The ΔuspA1/A2 mutant was incubated with 10% NHS supplemented with either EDTA or Mg-EGTA. Bacteria were collected at the indicated time points. After overnight incubation, colony forming units (cfu) were counted. The number of bacteria at the initiation of the experiments was defined as 100%. Mean values of three separate experiments are shown and error bars indicate S.D. (FIG. 12A) The mean values after 5 min for the ΔuspA1, the ΔuspA2 or the ΔuspA1/A2 mutants were significantly different from the wild-type (P<0.05). (FIG. 12B) The mean values after 5 min for the ΔuspA1/A2 mutant and after 10 min for the ΔuspA1/A2 mutant incubated Mg-EGTA were significantly different from the wild-type (P<0.05).

(FIG. 14B) The mean fluorescence intensity (mfi) of each profile in panel (FIG. 14A) is shown in (. 14B). (FIG. 14C) C3met binding of RH4 decreases with increasing concentrations of NaCl. Bacteria were incubated with C3met with or without NaCl as indicated. C3met binding was measured by flow cytometry as described in FIG. 3. Error bars indicate SD. * P≤0.05,  P≤0.01, * P≤0.001.

FIGS. 15A through 15O illustrates that flow cytometry profiles of *M. catarrhalis* RH4 wild type and UspA1/A2 deficient mutants show a UspA1/UspA2-dependent C3met/C3 binding. The profiles of a wild type clinical isolate (FIG. 15A, FIG. 15F, FIG. 15K) and corresponding mutants devoid of protein MID (FIG. 15B, 15G, FIG. 15L), UspA1 (FIG. 15C, FIG. 15H, FIG. 15M), UspA2 (FIG. 15D, FIG. 15I, FIG. 15N), or both UspA1 and UspA2 (FIG. 15E, FIG. 15J, FIG. 15O) are shown. Bacteria were incubated with C3met (FIGS. 15A through 15E). FIGS. 15F through 15J) or NHS (FIGS. 15K through 15O) and detected as outlined in FIG. 3. One typical experiment out of three with the mean fluorescence intensity (mfi) for each profile is shown.

(FIG. 16A) The recombinant UspA1$^{50-770}$ and UspA2$^{30-539}$ were immobilized on a nitrocellulose membrane. The membrane was incubated with [$^{125}$I]-labelled C3met overnight and bound protein was visualized with a Personal FX (Bio-Rad) using intensifying screens. The recombinant protein MID$^{962-1200}$ was included as a negative control. (FIG. 16B) UspA1$^{50-770}$, UspA2$^{30-539}$ and a series of truncated UspA2 proteins were coated on microtiter plates and incubated with C3met, followed by incubation with goat anti-human C3 pAb and HRP-conjugated anti-goat pAb. The mean values out of three experiments are shown. The background binding was subtracted from all samples. Error bars correspond to S.D. * P≤0.05,  P≤0.01, * P≤0.001.

(FIG. 17C) RH4ΔuspA1/A2 was incubated with 10% NHS or NHS-Mg-EGTA. For inhibition, the NHS-Mg-EGTA was incubated with 100 nM UspA1$^{50-770}$ and/or UspA2$^{30-539}$ before addition of bacteria. Bacteria were collected at the indicated time points. The number of bacteria at the initiation of the experiments was defined as 100%. Mean values of three separate experiments are shown and error bars indicate S.D. The time points 10, 20 and 30 min for the ΔuspA1/A2 mutant preincubated with recombinant proteins were significantly different from the ΔuspA1/A2 mutant incubated with Mg-EGTA alone (P<0.05).

FIGS. 19A through 19D F illustrate a pileup-analysis of UsPa1 for eight different strains, to show the homology of different parts of UspA1 (SEQ ID NOS 11-18 are disclosed respectively in order of appearance). Each page, and hence each of FIGS. 19A through 19D, represents a different portion of the alignment, which was too large to fit in one page.

FIGS. 20A through 20J illustrate a pileup-analysis of UsPa2 for thirteen different strains to show the homology of different parts of UspA2 (SEQ ID NOS 19-31 are disclosed respectively in order of appearance). Each page, and hence each of FIGS. 20A through 20J, represents a different portion of the alignment, which was too large to fit in one page.

FIG. 21 illustrates % identity in regions identified on Forsgren sequence computed as the ratio between the number of exact matches and the length of the region alignment, where the region alignment is that part of the above total alignment containing the Forsgren region.

MATERIALS AND METHODS

Interaction Between *M. catarrhalis* and Fibronectin

Bacterial Strains and Culture Conditions

Figure 1A:
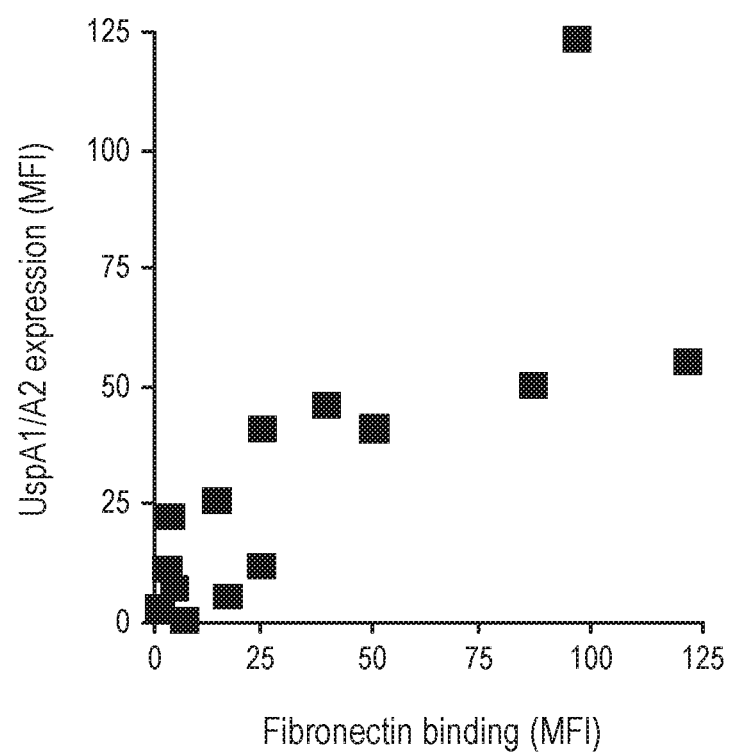

The sources of the clinical *M. catarrhalis* strains are listed in table 7. *M. catarrhalis* BBH18 and RH4 mutants were constructed as previously described.[23, 58] The *M. catarrhalis* strains were routinely cultured in brain heart infusion (BHI) liquid broth or on BHI agar plates at 37° C. The UspA1-deficient mutants were cultured in BHI supplemented with 1.5 μg/ml chloramphenicol (Sigma, St. Louis, Mo.), and UspA2-deficient mutants were incubated with 7 μg/ml zeocin (Invitrogen, Carlsbad, Calif.). Both chloramphenicol and zeocin were used for growth of the double mutants.

TABLE 7

Clinical strains of *M. catarrhalis* used in the present study

| Strain | Clinical Source | Reference |
| --- | --- | --- |
| BBH18 | Sputum | [53] |
| D1 | Sputum | [53] |
| Ri49 | Sputum | [53] |
| C10 | Sputum | [10] |
| F16 | Sputum | [10] |
| Bro2 | Respiratory tract | [53] |
| Z14 | Pharynx | [10] |
| S6-688 | Nasopharynx | [23] |
| Bc5 | Nasopharynx | [20] |
| RH4 | Blood | [53] |

TABLE 7-continued

Clinical strains of *M. catarrhalis* used in the present study

| Strain | Clinical Source | Reference |
| --- | --- | --- |
| RH6 | Blood | [53] |
| R14 | Unknown | [10] |
| R4 | Unknown | [10] |
| SÖ-1914 | Tympanic cavity aspirate | [23] |

Note:
The strains C10, R4 did not have the uspA1 gene, whereas F16, R14, Z14 lacked the uspA2 gene.
[10] The remaining strains contained both uspA1 and A2 genes (data not shown).

DNA Method

To detect the presence uspA1, A2, and A2H genes in those strains which this was unknown, primers and PCR conditions as described by Meier et al. was used. [50] Partial sequencing was also carried out with the UspA1$^{299-452}$ and UspA2$^{165-3185}$, and 3' primers of the respective uspA1 and uspA2 gene of RH4 and BBH18. Confirmation of the presence of the amino acid residues "DQKADIDNNINNI-YELAQQQDQHSSDIKTLK" (SEQ ID NO: 1) was also performed by PCR with a primer (5'-CAAAGCTGACATC-CAAGCACTTG-3') (SEQ ID NO: 54) designed from the 5' end of this sequence and 3' primers for uspA1 and A2 as described by Meier at al. [50]

Recombinant Proteins Construction and Expression

Recombinant UspA1$^{50-770}$ and UspA2$^{30-539}$ which are devoid of their hydrophobic C-termini, has recently been described.[58] The genomic DNA was extracted from *M. catarrhalis* Bc5 using a DNeasy tissue kit (Qiagen, Hilden, Germany). In addition, recombinant proteins corresponding to multiple regions spanning UspA1$^{50-770}$ and UspA2$^{30-539}$ were also constructed by the same method. The primers used are listed in table 8. All constructs were sequenced according to standard methods. Expression and purification of the recombinant proteins were done as described previously. [59] Proteins were purified using columns containing a nickel resin (Novagen) according to the manufacturer's instructions for native conditions. The recombinant proteins were analyzed on SDS-PAGE as described.[21]

TABLE 8

Primers used in this present study (5' primers are disclosed as SEQ ID NOS 55-69, respectively, in order of appearance; 3' primers are disclosed as SEQ ID NOS 70-84, respectively, in order of appearance.

| Protein | 5' primer | 3' primer |
| --- | --- | --- |
| UspA1$^{50-770}$ | gcgtctgcggatccagtaggcaaggcaacc | ccctgaagctttagtgcataacctaattg |
| UspA1$^{50-491}$ | gcgtctgcggatccagtaggcaaggcaacc | ttgagcaagcttagcttggttttttagcg |
| UspA1$^{50-197}$ | gcgtctgcggatccagtaggcaaggcaacc | acctgtggcaagcttcttcctgcc |
| UspA1$^{50-321}$ | gcgtctgcggatccagtaggcaaggcaacc | ggtgtcactaagcttacctgcaccaacatgaac |
| UspA1$^{299-452}$ | ggatttgcaggtgcatcggatcctggtaatggtact | gtcttttgtaagatcaagcttttgatcaat |
| UspA1$^{433-580}$ | catagctctgatatggatccacttaaaaac | catgctgagaagcttacctagattgg |
| UspA1$^{557-704}$ | gccaaagcacaagcgatccaaataaagac | ggtcttattggtagtaagcttagcttggttttg |

TABLE 8-continued

Primers used in this present study (5' primers are disclosed as SEQ ID NOS 55-69, respectively, in order of appearance; 3' primers are disclosed as SEQ ID NOS 70-84, respectively, in order of appearance.

| Protein | 5' primer | 3' primer |
|---|---|---|
| UspA1$^{680-770}$ | gttgagcaaaaggatccc atcaatcaagag | ccctgaagctttagtgcat aacctaattg |
| UspA2$^{30-539}$ | cgaatgcggatcctaaaa atgatataactttagagg | cattaagcttggtgtctaa tgcagttac |
| UspA2$^{30-177}$ | cgaatgcggatcctaaaa atgatataactttagagg | ctcatgaccaaaatcaagc ttatcttcgatagactc |
| UspA2$^{101-240}$ | gatattgcggatccggaa gatgatgttgaaac | gatcaataagcttaccgct tagattgaatagttcttc |
| UspA2$^{101-318}$ | gatattgcggatccggaa gatgatgttgaaac | gtcaatcgcttcaagcttc ttttgagcatactg |
| UspA2$^{165-318}$ | gagattgagaaggatcca gatgctattgct | gtcaatcgcttcaagcttc ttttgagcatactg |
| UspA2$^{302-458}$ | gctcaaaaccaagcggat ccccaagatctg | ggtgagcgtacaagctagc atcagcatcggc |
| UspA2$^{446-539}$ | gcaagtgctgcggatcct gatcgtattgct | cattaagcttggtgtctaa tgcagttac |

Antibodies

Rabbit anti-UspA1/A2 polyclonal antibodies (pAb) were recently described in detail.[58] The other antibodies used were rabbit anti-human fibronectin pAb, swine FITC-conjugated anti-rabbit pAb, swine horseradish peroxidase (HRP) conjugated anti-rabbit pAb and finally a mouse anti-human CD54 (ICAM1) monoclonal antibody (mAb). Antibodies were from Dakopatts (Glostrup, Denmark).

Flow Cytometry Analysis

The UspA1/A2-protein expression and the capacity of M. catarrhalis to bind fibronectin were analyzed by flow cytometry. M. catarrhalis wild type strains and UspA1/A2-deficient mutants were grown overnight and washed twice in phosphate buffered saline containing 3% fish gelatin (PBS-gelatin). The bacteria (10$^8$) were then incubated with the anti-UspA1/A2 antiserum or 5 μg fibronectin (Sigma, St Louis, Mo.). They were then washed and incubated for 30 min at room temperature (RT) with FITC-conjugated anti-rabbit pAb (diluted according to the manufacturer's instructions) or with 1/100 dilution of rabbit anti-human fibronectin pAb (if fibronectin was first added) for 30 min at RT before incubation with the FITC-conjugated anti-rabbit pAb. After three additional washes, the bacteria were analyzed by flow cytometry (EPICS, XL-MCL, Coulter, Hialeah, Fla.). All incubations were kept in a final volume of 100 μl PBS-gelatin and the washings were done with the same buffer. Anti-fibronectin pAb and FITC-conjugated anti-rabbit pAb were added separately as a negative control for each strain analyzed. Fibronectin inhibition studies were carried out by pre-incubating 0.25 μmoles of UspA fragments for 1 h with 2 μg of fibronectin before incubation with M. catarrhalis bacteria (10$^8$). The residual free amount of fibronectin that bound to M. catarrhalis was determined by flow cytometry as outlined above.

Binding of M. catarrhalis to Immobilized Fibronectin

Glass slides were coated with 30 μl aliquots of fibronectin (1 mg/ml) and air dried at RT. After washing once with PBS, the slides were incubated in Petri dishes with pre-chilled bacteria at late exponential phase (optical density (OD) at 600 nm=0.9). After 2 h at RT, glass slides were washed once with PBS followed by Gram staining.

Protein Labeling and Radio Immunoassay (RIA)

Fibronectin was $^{125}$Iodine labeled (Amersham, Buckinghamshire, England) to a high specific activity (0.05 mol iodine per mol protein) with the Chloramine T method.[21] M. catarrhalis strains BBH18 and RH4 together with their corresponding mutants were grown overnight on solid medium and were washed in PBS with 2% bovine serum albumin (BSA). Bacteria (10$^8$) were incubated for 1 h at 37° C. with $^{125}$I-labeled fibronectin (1600 kcpm/sample) in PBS containing 2% BSA. After three washings with PBS 2% BSA, $^{125}$I-labeled fibronectin bound to bacteria was measured in a gamma counter (Wallac, Espoo, Finland).

Enzyme-Linked Immunosorbent Assay (ELISA)

Microtiter plates (Nunc-Immuno Module; Roskilde, Denmark) were coated with 40 nM of purified recombinant UspA1$^{50-770}$ and UspA2$^{30-539}$ proteins in 75 mM sodium carbonate, pH 9.6 at 4° C. overnight. Plates were washed four times with washing buffer (50 mM Tris-HCl, 0.15 M NaCl, and 0.1% Tween 20, pH 7.5) and blocked for 2 h at RT with washing buffer containing 3% fish gelatin. After four additional washings, the wells were incubated for 1 h at RT with fibronectin (120 μg/ml) diluted in three-fold step in 1.5% fish gelatin (in wash buffer). Thereafter, the plates were washed and incubated with rabbit anti-human fibronectin pAb for 1 h. After additional washings, HRP-conjugated anti-rabbit pAb was added and incubated for 1 h at RT. Both the antihuman fibronectin and HRP-conjugated anti-rabbit pAb were diluted 1:1,000 in washing buffer containing 1.5% fish gelatin. The wells were washed four times and the plates were developed and measured at OD$_{450}$. ELISAs with truncated proteins spanning UspA1$^{50-770}$ and UspA2$^{30-539}$ were performed with fixed doses of fibronectin at 80 μg/ml and 120 μg/ml, respectively.

Cell Line Adherence Inhibition Assay

Chang conjunctival cells (ATCC CCL 20.2) were cultured in RPMI 1640 medium (Gibco BRL, Life Technologies, Paisley, Scotland) supplemented with 10% fetal calf serum, 2 mM L-glutamine, and 12 μg of gentamicin/ml. On the day before adherence inhibition experiments, cells were harvested, washed twice in gentamicin-free RPMI 1640, and added to 96 well tissue culture plates (Nunc) at a final concentration of 10$^4$ cells/well in 200 μl of gentamicin-free culture medium. Thereafter, cells were incubated overnight at 37° C. in a humidified atmosphere of 5% CO$_2$ and 95% air. On the day of experiments, inhibition of M. catarrhalis adhesion was carried out by pre-incubating increasing concentration of recombinant UspA1/A2 truncated proteins containing the fibronectin binding domains (UspA1$^{299-452}$ and UspA2$^{165-318}$) or rabbit anti-human fibronectin pAb (diluted 1:50) for 1 h. Nonfibronectin binding recombinant proteins (UspA1$^{433-580}$ and UspA2$^{30-177}$) were used as controls. Chang epithelial cells are known to express ICAM1. [18] Hence an anti-ICAM1 antibody was used to differentiate if the inhibitory effect of the anti-fibronectin antibody was secondary to steric hindrance. Subsequently, M. catarrhalis RH4 (10$^6$) in PBS-gelatin was inoculated onto the confluent monolayers. In all experiments, tissue culture plates were centrifuged at 3,000×g for 5 min and incubated at 37° C. in 5% CO$_2$. After 30 min, infected monolayers were rinsed several times with PBS-gelatin to remove non-adherent bacteria and were then treated with trypsin-EDTA (0.05% trypsin and 0.5 mM EDTA) to release the Chang cells from the plastic support. Thereafter, the resulting cell/bacterium suspension was seeded in dilution onto agar plates containing BHI and incubated overnight at 37° C. in 5% $CO_2$.

Determination of Fibronectin Expression in Chang Conjunctival Epithelial Cells

Chang conjunctival epithelial cells were harvested by scraping followed by re-suspension in PBS-gelatin. Cells ($1 \times 10^6$/ml) were labeled with rabbit anti-human fibronectin pAb followed by washing and incubation with a FITC-conjugated anti-rabbit pAb. After three additional washes, the cells were analyzed by flow cytometry as outlined above.

Interaction Between *M. catarrhalis* and Laminin

Bacterial Strains and Culture Conditions

The clinical *M. catarrhalis* strains BBH18 and RH4 and their corresponding mutants were previously described.[58] Both strains have a relatively higher expression of UspA2 compared to UspA1.[58] The mutants expressed equal amount of *M. catarrhalis* immunoglobulin D-binding protein (MID) when compared to wild type strains. Bacteria were routinely cultured in brain heart infusion (BHI) broth or on BHI agar plates at 37° C. The UspA1-deficient, UspA2-deficient and double mutants were cultured in BHI supplemented with antibiotics as described.[58]

Recombinant Protein Construction and Expression

Recombinant $UspA1^{50-770}$ and $UspA2^{30-539}$, which are devoid of their hydrophobic C-termini, were manufactured.[58] In addition, recombinant proteins corresponding to multiple regions spanning $UspA1^{50-770}$ and $UspA2^{30-539}$ were used.[78]

Antibodies

Rabbit anti-UspA1/A2 and anti-MID polyclonal antibodies (pAb) were used.[22, 58] Rabbit anti-laminin pAb was from Sigma (St Louis, Mo., USA). Swine horseradish peroxidase (HRP)-conjugated anti-rabbit pAb was from Dakopatts (Glostrup, Denmark).

Binding of *M. catarrhalis* to Immobilized Laminin

Microtiter plates (Nunc-Immuno Module; Roskilde, Denmark) were coated with Engelbreth-Holm-Swarm mouse sarcoma laminin (Sigma, Saint Louis, USA) or bovine serum albumin (BSA) (30 μg/ml) in Tris-HCL, pH 9.0 at 4° C. overnight. The plates were washed with phosphate buffered saline and 0.05% Tween 20, pH 7.2 (PBS-Tween) and subsequently blocked with 2% BSA in PBS+0.1% Tween 20, pH 7.2. *M. catarrhalis* RH4 and BBH18 ($10^8$) in 100 μl were then added followed by incubation for 1 h. Unbound bacteria were removed by washing 3 times with PBS-Tween. Residual bound bacteria were detected by means of an anti-MID pAb, followed by detection with HRP-conjugated anti-rabbit pAb. The plates were developed and measured at $OD_{450}$ according to a standard protocol.

Enzyme-Linked Immunosorbent Assay (ELISA)

Microtiter plates (Nunc-Immuno Module) were coated with 40 nM of purified recombinant $UspA1^{50-770}$ and $UspA2^{30-539}$ proteins in 75 mM sodium carbonate, pH 9.6 at 4° C. Plates were washed four times with washing buffer (50 mM Tris-HCl, 0.15 M NaCl, and 0.1% Tween 20, pH 7.5) and blocked at RT with washing buffer containing 3% fish gelatin. After additional washings, the wells were incubated for 1 h at RT with laminin at different dilutions as indicated in 1.5% fish gelatin (in wash buffer). Thereafter, the plates were washed and incubated with rabbit anti-laminin pAb. After additional washings, HRP-conjugated anti-rabbit pAb was added and incubated at RT. Both the anti-laminin and HRP-conjugated anti-rabbit pAb were diluted 1:1,000 in washing buffer containing 1.5% fish gelatin. The wells were washed and the plates were developed and measured at $OD_{450}$. Uncoated wells incubated with identical dilutions of laminin were used as background controls. ELISAs with truncated proteins spanning $UspA1^{50-770}$ and $UspA2^{30-539}$ were performed with fixed doses of laminin (20 μg/ml).

Interaction Between *M. catarrhalis* and C3 and C3met

Bacterial Strains and Culture Conditions

The clinical *M. catarrhalis* isolates and related subspecies have recently been described in detail.[21, 53] Type strains were from the Culture Collection, University of Gothenburg (CCUG; Department of Clinical Bacteriology, Sahlgrenska Hospital, Gothenburg, Sweden), or the American Type Culture Collection (ATCC; Manassas, Va.); *Neisseria gonorrheae* CCUG 15821, *Streptococcus pyogenes* CCUG 25570 and 25571, *Streptococcus agalactiae* CCUG 4208, *Streptococcus pneumoniae* ATCC 49619, *Legionella pneumophila* ATCC 33152, *Pseudomonas aeruginosa* ATCC 10145, *Staphylococcus aureus* ATCC 29213, and finally *Staphylococcus aureus* ATCC 25923. The remaining strains in Table 9 were clinical isolates from Medical Microbiology, Department of Laboratory Medicine, Malmö University Hospital, Lund University, Sweden.

TABLE 9

*M. catarrhalis* is a unique C3/C3met binding bacterium. Related *moraxella* subspecies and other common human pathogens do not bind C3/C3met (mfi <2.0). After incubation with EDTA-treated NHS or C3met, bacteria were analysed by flow cytometry using a rabbit anti-C3d pAb and a FITC-conjugated goat anti-rabbit pAb.

| Species | NHS-EDTA (mfi) | C3met (mfi) |
|---|---|---|
| *Moraxella catarrhalis* RH4 | 8.7 | 22.1 |
| *M. osloensis* | <2.0 | <2.0 |
| *M. bovis* | <2.0 | <2.0 |
| *M. caniculi* | <2.0 | <2.0 |
| *M. nonliquefacie* | <2.0 | <2.0 |
| *N. pharyngis* | <2.0 | <2.0 |
| *N. sicca* | <2.0 | <2.0 |
| *N. flava* | <2.0 | <2.0 |
| *N. subflava* | <2.0 | <2.0 |
| *Oligella ureolytica* (n = 2) | <2.0 | <2.0 |
| *Haemophilus influenzae* (n = 7) | <2.0 | <2.0 |
| *Streptococcus pneumoniae* (n = 11) | <2.0 | <2.0 |
| *Legionella pneumophila* (n = 2) | <2.0 | <2.0 |
| *Pseudomonas aeruginosa* (n = 2) | <2.0 | <2.0 |
| *Listeria monocytogenes* | <2.0 | <2.0 |
| *Yersinia entercolitica* | <2.0 | <2.0 |
| *Staphylococcus aureus* (n = 3) | <2.0 | <2.0 |
| *Streptococcus pyogenes* (n = 2) | <2.0 | <2.0 |
| *Streptococcus agalactia* | <2.0 | <2.0 |
| *Enterococcus faecalis* | <2.0 | <2.0 |
| *Helicobacter pylori* | <2.0 | <2.0 |
| *Escherichia coli* (n = 2) | <2.0 | <2.0 |
| *M. ovis* | <2.0 | <2.0 |
| *M. caviae* | <2.0 | <2.0 |
| *Neisseria gonorrheae* | <2.0 | <2.0 |
| *N. meningtidis* | <2.0 | <2.0 |
| *N. mucosa* | <2.0 | <2.0 |

The different non-*moraxella* species were grown on appropriate standard culture media. *M. catarrhalis* strains were routinely cultured in brain heart infusion (BHI) liquid broth or on BHI agar plates at 37° C. *M. catarrhalis* BBH18 and RH4 mutants were manufactured as previously described.[22, 23, 58] The MID-deficient mutants were grown in BHI containing 50 μg/ml kanamycin. The UspA1-deficient mutants were cultured in BHI supplemented with 1.5 μg/ml chloramphenicol (Sigma, St. Louis, Mo.), and UspA2-deficient mutants were incubated with 7 μg/ml zeocin (Invitrogen, Carlsbad, Calif.). Both chloramphenicol and zeocin were used for growth of the UspA1/A2 double mutants.

Antibodies

Rabbits were immunized intramuscularly with 200 μg recombinant full-length UspA1 emulsified in complete Freunds adjuvant (Difco, Becton Dickinson, Heidelberg, Germany), and boosted on days 18 and 36 with the same dose of protein in incomplete Freunds adjuvant.[22] Blood was drawn 3 weeks later. To increase the specificity, the anti-UspA1 antiserum was affinity-purified with Sepharose-conjugated recombinant UspA1$^{50-770}$.[58] The antiserum bound equally to UspA1 and UspA2 and was thus designated anti-UspA1/A2 pAb. The rabbit anti-human C3d pAb and the FITC-conjugated swine anti-rabbit pAb were purchased from Dakopatts (Glostrup, Denmark), and the goat anti-human C3 were from Advanced Research Technologies (San Diego, Calif.). The horseradish peroxidase (HRP)-conjugated donkey anti-goat pAb was obtained from Serotec (Oxford, UK).

Proteins and Iodine Labelling

The manufacture of recombinant UspA1$^{50-770}$ and UspA2$^{30-539}$ which are devoid of their hydrophobic C-termini, has recently been described.[23] The truncated UspA1 and UspA2 proteins were manufactured as described in detail by Tan et al.[78] C3b was purchased from Advanced Research Technologies. C3(H$_2$O) was obtained by freezing and thawing of purified C3. The C3b-like molecule (C3met) was made by incubation of purified C3 with 100 mM methylamine (pH 8.0) for 2 h at 37° C., and subsequent dialysis against 100 mM Tris-HCl (pH 7.5), 150 mM NaCl. For binding studies, C3met was labelled with 0.05 mol $^{125}$I (Amersham, Buckinghamshire, England) per mol protein, using the Chloramine T method.[25]

Flow Cytometry Analysis

Binding of C3 to *M. catarrhalis* and other species was analyzed by flow cytometry. Bacteria were grown on solid medium overnight and washed twice in PBS containing 2% BSA (Sigma) (PBS-BSA). Thereafter, bacteria (10$^8$ colony forming units; cfu) were incubated with C3met, C3b, C3(H$_2$O), or 10% NHS with or without 10 mM EDTA or 4 mM MgCl$_2$ and 10 mM EGTA (Mg-EGTA) in PBS-BSA for 30 min at 37° C. After washings, the bacteria were incubated with anti-human C3d pAb for 30 min on ice, followed by washings and incubation for another 30 min on ice with FITC-conjugated goat anti-rabbit pAb. After three additional washes, bacteria were analyzed by flow cytometry (EPICS, XL-MCL, Coulter, Hialeah, Fla.). All incubations were kept in a final volume of 100 μl PBS-BSA and the washings were done with the same buffer. The anti-human C3d pAb and FITC-conjugated anti-rabbit pAb were added separately as a negative control for each strain analyzed. In the inhibition studies, serum was preincubated with 100 nM of the recombinant UspA1$^{50-770}$ and UspA2$^{30-539}$ proteins for 30 min at 37° C. To analyze the characteristics of the *M. catarrhalis* and C3 interaction, increasing concentrations of NaCl (0-1.0 M) was added to bacteria and C3met. To analyze UspA1/A2 expression, bacteria (10$^8$ cfu) were incubated with the anti-UspA1/A2 pAb and washed as described above. A FITC-conjugated goat anti-rabbit pAb diluted according to the manufacturers instructions was used for detection. To assure that EDTA did not disrupt the outer membrane proteins UspA1 and UspA2, *M. catarrhalis* was incubated with or without EDTA followed by detection of UspA1/A2 expression. EDTA, at the concentrations used in the NHS-EDTA experiments, did not change the density of UspA1/A2.

Serum and Serum Bactericidal Assay

Normal human serum (NHS) was obtained from five healthy volunteers. The blood was allowed to clot for 30 min at room temperature and thereafter incubated on ice for 60 min. After centrifugation, sera were pooled, aliquoted and stored at −70° C. To inactivate both the classical and alternative pathways, 10 mM EDTA was added. In contrast, Mg-EGTA was included to inactivate the classical pathway. Human serum deficient in the C4BP was prepared by passing fresh serum through a HiTrap column (Amersham Biosciences) coupled with mAb 104, a mouse mAb directed against CCP1 of the □-chain of C4BP.[41] The flow through was collected and the depleted serum was stored in aliquots at −70° C. Serum depleted of C1q was obtained via the first step of C1q purification [79] using Biorex 70 ion exchange chromatography (Bio-Rad, Hercules, Calif.). The resulting sera displayed normal haemolytic activity. The factor D and properdin deficient serum was kindly provided by Dr. Anders Sjöholm (Department of Medical Microbiology, Lund University, Lund, Sweden). *M. catarrhalis* strains were diluted in 2.5 mM Veronal buffer, pH 7.3 containing 0.1% (wt/vol) gelatin, 1 mM MgCl$_2$, 0.15 mM CaCl$_2$, and 2.5% dextrose (DGVB$^{++}$). Bacteria (10$^3$ cfu) were incubated together with 10% NHS and EDTA or Mg-EGTA in a final volume of 100 μl. The bacteria/NHS was incubated at 37° C. and at various time points, 10 μl aliquots were removed and spread onto BHI agar plates. In inhibition studies, 10% serum was incubated with 100 nM of the recombinant UspA1$^{50-770}$ and UspA2$^{30-539}$ proteins for 30 min at 37° C. before bacteria were added.

Dot Blot Assays

Purified recombinant UspA1$^{50-770}$ and UspA2$^{30-539}$ diluted in three-fold steps (1.9-150 nM) in 100 μl of 0.1 M Tris-HCl, pH 9.0 were applied to nitrocellulose membranes (Schleicher & Schüll, Dassel, Germany) using a dot blot device. After saturation, the membranes were incubated for 2 h with PBS-Tween containing 5% milk powder at room temperature and washed four times with PBS-Tween. Thereafter, 5 kcpm [$^{125}$I]-labelled C3met in PBS-Tween with 2% milk powder was added overnight at 4° C. The bound protein was visualized with a Personal FX (Bio-Rad) using intensifying screens.

Surface Plasmon Resonance (Biacore)

The interaction between UspA1$^{50-770}$ or UspA2$^{30-539}$ and C3 was further analysed using surface plasmon resonance (Biacore 2000; Biacore, Uppsala, Sweden) as recently described for the UspA1/2-C4BP interaction.[58] The K$_D$ (the equilibrium dissociation constant) was calculated from a binding curve showing response at equilibrium plotted against the concentration using steady state affinity model supplied by Biaevaluation software (Biacore).

Enzyme-Linked Immunosorbent Assay (ELISA)

Microtiter plates (Nunc-Immuno Module; Roskilde, Denmark) were coated with triplets of purified recombinant UspA1$^{50-770}$, UspA2$^{30-539}$, or the truncated UspA1 and UspA2 fragments (40 nM in 75 mM sodium carbonate, pH 9.6) at 4° C. overnight. Plates were washed four times with washing buffer (PBS with 0.1% Tween 20, pH 7.2) and blocked for 2 hrs at room temperature with washing buffer supplied with 1.5% ovalbumin (blocking buffer). After washings, the wells were incubated overnight at 4° C. with 0.25 □g C3met in blocking buffer. Thereafter, the plates were washed and incubated with goat anti-human C3 in blocking buffer for 1 h at RT. After additional washings, HRP-conjugated donkey anti-goat pAbs was added for another 1 h at RT. The wells were washed four times and the plates were developed and measured at OD$_{450}$.

Haemolytic Assay

Rabbit erythrocytes were washed three times with ice-cold 2.5 mM Veronal buffer, pH 7.3 containing 0.1% (wt/vol) gelatin, 7 mM MgCl$_2$, 10 mM EGTA, and 2.5% dextrose (Mg$^{++}$EGTA), and resuspended at a concentration of 0.5×10$^9$ cells/ml. Erythrocytes were incubated with various concentrations (0 to 4%) of serum diluted in M$^{++}$EGTA. After 1 h at 37° C., erythrocytes were centrifuged and the amount of lysed erythrocytes was determined by spectrophotometric measurement of released hemoglobin at 405 nm. For inhibition with UspA1 and UspA2, 10% serum was preincubated with 100 nM of recombinant UspA1$^{50-770}$ and/or UspA2$^{30-539}$ proteins for 30 min at 37° C., and thereafter added to the erythrocytes at 0 to 4%.

Isolation of Polymorphonuclear Leukocytes and Phagocytosis

Human polymorphonuclear leukocytes (PMN) were isolated from fresh blood of healthy volunteers using macrodex (Pharmalink AB, Upplands Väsby, Sweden). The PMN were centrifuged for 10 min at 300 g, washed in PBS and resuspended in RPMI 1640 medium (Life Technologies, Paisley, Scotland). The bacterial suspension (0.5×10$^8$) was opsonized with 3% of either NHS or NHS-EDTA, or 20 □g of purified C3met for 15 min at 37° C. After washes, bacteria were mixed with PMN (1×10$^7$ cells/ml) at a bacteria/PMN ratio of 10:1 followed by incubation at 37° C. with end-over-end rotation. Surviving bacteria after 0, 30, 60, and 120 min of incubation was determined by viable counts. The number of engulfed NHS-treated bacteria was compared with bacteria phagocytosed in the absence of NHS. *S. aureus* opsonized with NHS was used as positive control.

Examples and Results

Interaction Between *M. catarrhalis* and Fibronectin
*M. catarrhalis* Devoid of UspA1 and A2 Does Not Bind Soluble or Immobilized Fibronectin.

We selected a random series of *M. catarrhalis* clinical strains (n=13) (table 7) and tested them for fibronectin binding in relation to their UspA1/A2 expression by flow cytometry analysis. High UspA1/A2 expression as determined by high mean fluorescence intensity (MFI) was correlated to UspA1/A2 expression (Pearson correlation coefficient 0.77, P<0.05) (FIG. 1A). However, to discriminate between UspA1 and A2 expression was not possible with our anti-UspA1/A2 pAb. Moreover, the presence of UspA2H protein contributing to the binding was unlikely as the uspA2H gene was not found in the strains used in this study (data not shown).

Two *M. catarrhalis* isolates (BBH18 and RH4) and their specific mutants lacking UspA1, UspA2 or both proteins were also analyzed by flow cytometry. *M. catarrhalis* BBH18 strongly bound fibronectin with a mean fluorescence intensity (MFI) of 96.1 (FIG. 1F). In contrast, BBH18ΔuspA1 showed a decreased fibronectin binding with an MFI of 68.6 (FIG. 1G). Fibronectin binding to BBH18ΔuspA2 and the double mutant BBH18ΔuspA1/A2 revealed an MFI of only 10.7 and 11.5, respectively (FIG. 1H, 1I). Similar results were obtained with UspA1/A2 mutants of the clinical strain *M. catarrhalis* RH4. Taken together, these results suggest that UspA1 and A2 bound fibronectin and that the ability of the bacteria to bind fibronectin strongly depended on UspA1/A2 expression.

Figure 2:
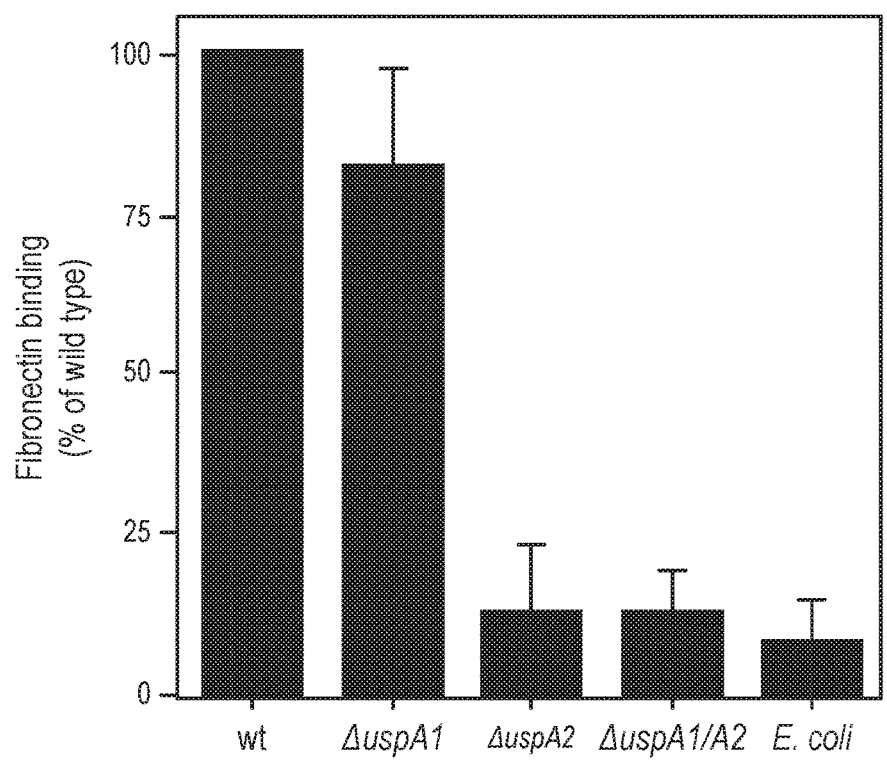
FIG. 2 shows that *M. catarrhalis* RH4 UspA2 deficient mutants do not bind $^{125}$I-labeled fibronectin. *E. coli* BL21 was included as a negative control not binding fibronectin. Bacteria were incubated with $^{125}$I-labeled fibronectin followed by several washes and analyzed in a gamma counter. Fibronectin binding to the RH4 wild type expressing both UspA1 and A2 was set as 100%. The mean values of three independent experiments are shown. Error bars represent standard deviations (SD). Similar results were obtained with *M. catarrhalis* BBH18.

To further analyze the interaction between fibronectin and *M. catarrhalis*, $^{125}$I-labeled fibronectin was incubated with two clinical *M. catarrhalis* isolates (BBH18 and RH4) and their respective mutants. The wild type *M. catarrhalis* RH4 strongly bound $^{125}$I-fibronectin while the corresponding ΔuspA1 mutant showed 80% binding of the wild type. In contrast, the ΔuspA2 and double mutant bound $^{125}$I-fibronectin at 14% and 12%, respectively, which was just above the background levels (5.0 to 10%) (FIG. 2). Similar results were obtained with *M. catarrhalis* BBH18 and the corresponding UspA1/A2 mutants. Thus, our results suggest that both UspA1 and A2 are required for the maximal binding of soluble fibronectin by *M. catarrhalis*.

To investigate the bacterial attachment to immobilized fibronectin, *M. catarrhalis* RH4 and its corresponding ΔuspA1/A2 mutants were applied onto fibronectin coated glass slides. After 2 h of incubation, slides were washed, and subsequently Gram stained. *M. catarrhalis* wild type and the ΔuspA1 mutant were found to strongly adhere to the fibronectin coated glass slides (FIGS. 3A and 3B). In contrast, *M. catarrhalis* ΔuspA2 and ΔuspA1/A2 double mutants weakly adhered to the fibronectin coated glass slide with only a few bacteria left after washing (FIGS. 3C and 3D, respectively). Experiments with another *M. catarrhalis* clinical isolate (BBH18) and its derived mutants showed a similar pattern indicating that UspA2 was of major importance for *M. catarrhalis* binding to immobilized fibronectin.

The Fibronectin Binding Domains Include Amino Acid Residues Located Between 299 and 452 of UspA1 and Between 165 and 318 of UspA2

Figure 4:
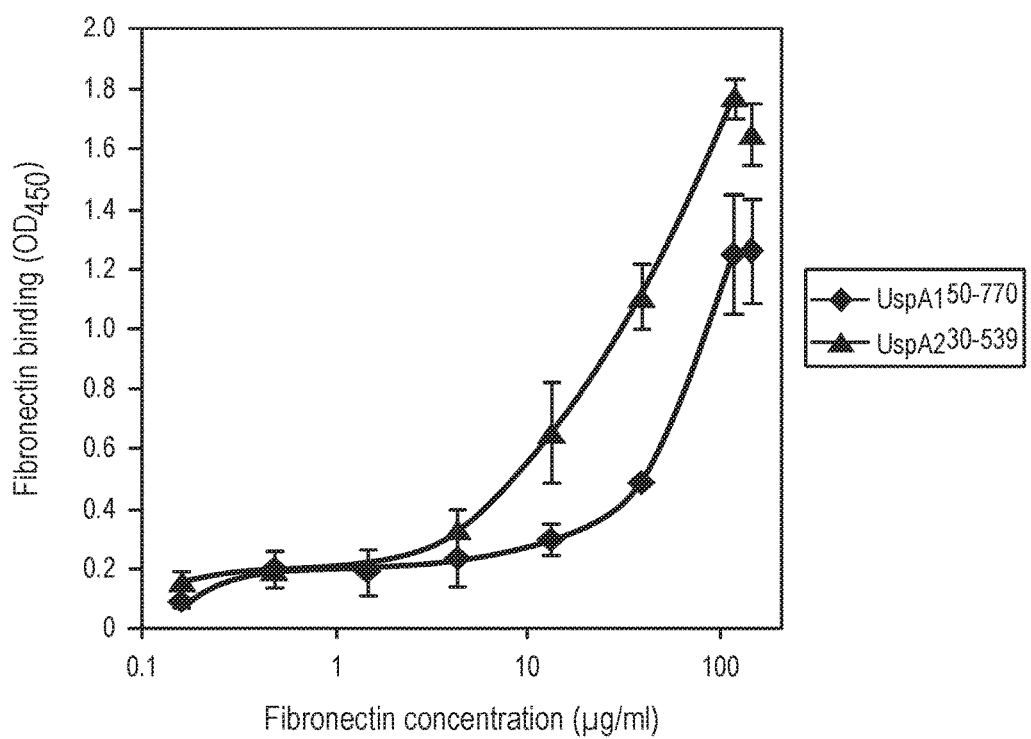
FIG. 4 is a graph showing that recombinant UspA1 and A2 bind to fibronectin in a dose-dependent manner. Specific fibronectin binding is shown for UspA1$^{50-770}$ and UspA2$^{30-539}$. Both UspA proteins (40 nM) were coated on microtiter plates and incubated with increasing concentrations of fibronectin followed by detection with rabbit anti-human fibronectin pAb and HRP-conjugated anti-rabbit pAb. Mean values of three separate experiments are shown and error bars indicate SD.

To further analyze the interactions of UspA1 and A2 with fibronectin, truncated UspA1$^{50-770}$ and UspA2$^{30-539}$ were recombinantly produced in *E. coli*, coated on microtiter plates and incubated with increasing concentrations of fibronectin. Bound fibronectin was detected with an anti-human fibronectin pAb followed by incubation with a horseradish peroxidase conjugated anti-rabbit pAb. Both recombinant UspA1$^{50-770}$ and UspA2$^{30-539}$ bound soluble fibronectin and the interactions were dose-dependent (FIG. 4).

Figure 5A:
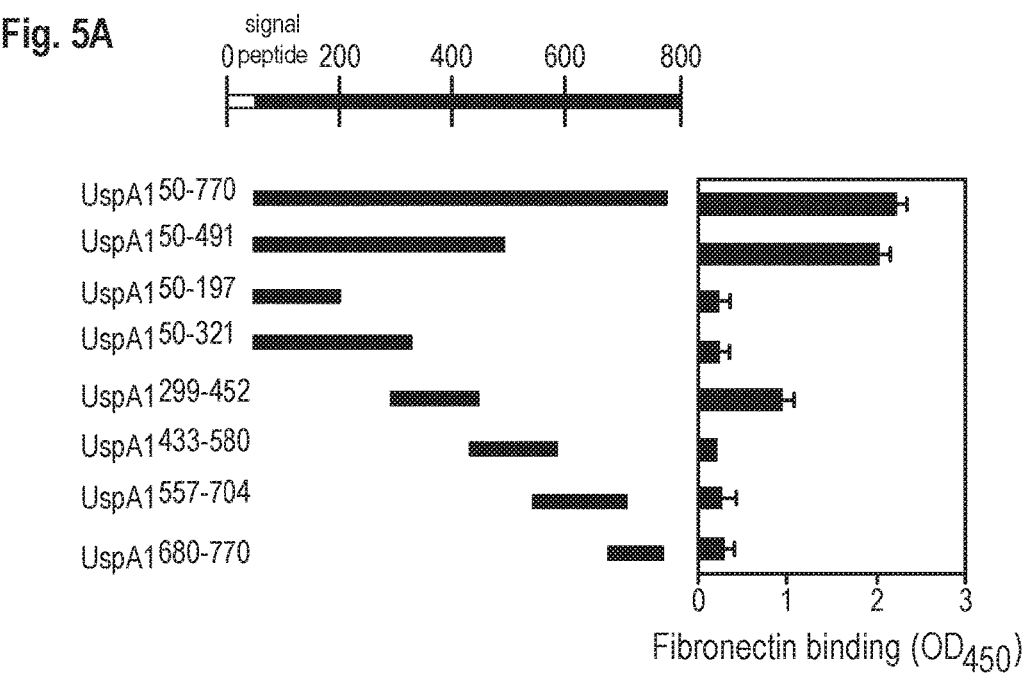
FIGS. 5A and 5B. The active fibronectin binding domains for UspA1 and UspA2 are located between amino acids 299 to 452 and 165 to 318, respectively. Truncated proteins derived from UspA1 (FIG. 5A) and UspA2 (FIG. 5B) are shown. All fragments were tested for fibronectin binding in ELISA. Forty nM of each truncated fragment was coated on microtiter plates and incubated with 80 μg/ml and 120 μg/ml fibronectin for UspA1 and UspA2, respectively. Bound fibronectin was detected with rabbit anti-fibronectin pAb followed by HRP-conjugated anti-rabbit pAb. Results are representative for three sets of experiments. Error bars represent SD.
Figure 5B:
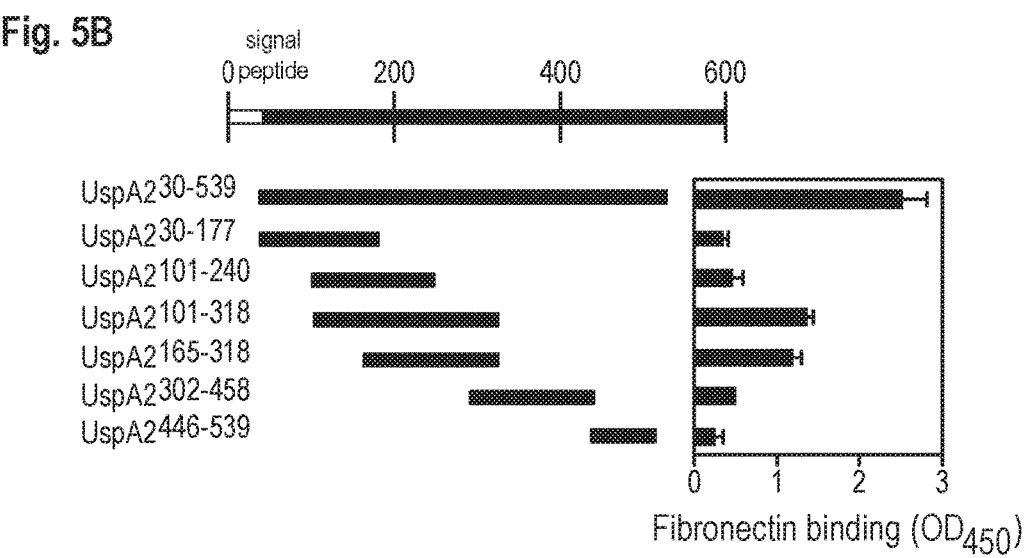

To define the fibronectin-binding domain of UspA1, recombinant proteins spanning the entire molecule of UspA1$^{50-770}$ were manufactured. Fibronectin was incubated with the immobilized UspA1 proteins fragments and the interactions were quantified by ELISA. UspA1$^{50-491}$ bound fibronectin almost as efficiently as UspA1$^{50-770}$ suggesting that the binding domain was within this part of the protein. Among the other truncated fragments, UspA1$^{299-452}$ efficiently bound fibronectin (FIG. 5A). In parallel, the interactions between fibronectin and several recombinant UspA2 fragments including amino acids UspA2$^{30-539}$ were analyzed. The two fragments UspA2$^{101-318}$ and UspA2$^{165-318}$ strongly bound fibronectin (FIG. 5B). Our findings provide significant evidence that the binding domains include residues found within UspA1$^{299-452}$ and UspA2$^{165-318}$. A sequence comparison between these two binding fragments revealed that the 31 amino acid residues "DQKADIDNNIN-NIYELAQQQDQHSSDIKTLK" (SEQ ID NO: 1) were identical for UspA1 and A2 (FIG. 6). Moreover, this repeat sequence was also found in the uspA1 and A2 gene of *M. catarrhalis* BBH18 and RH4 (data not shown).

Figure 7:
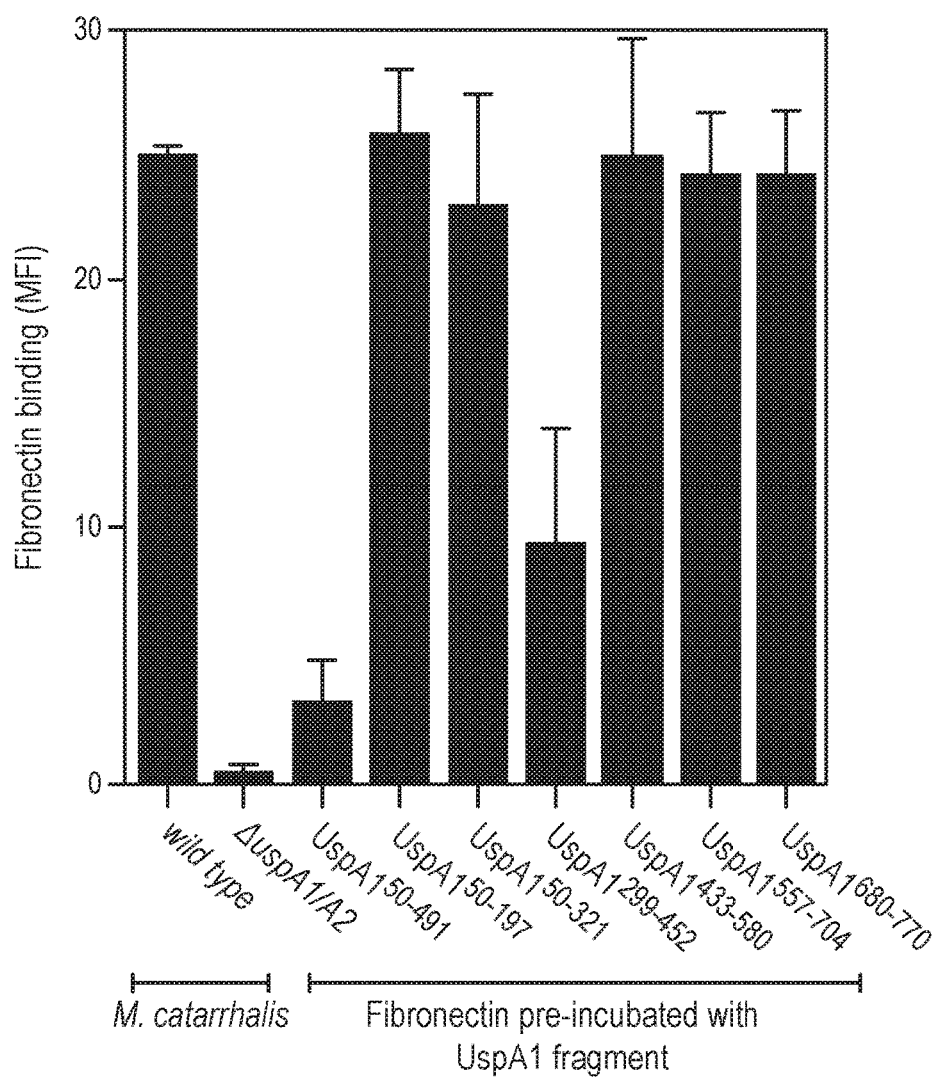
FIG. 7 shows that truncated UspA1$^{50-491}$ and UspA1$^{299-452}$ fragments competitively inhibit *M. catarrhalis* UspA-dependent fibronectin binding. *M. catarrhalis* ΔuspA1/A2 double mutants, which do not bind fibronectin, were included as negative controls. UspA1 recombinant proteins were pre-incubated with 2 mg/100 ml fibronectin before incubation with *M. catarrhalis*. The mean fluorescence values (MFI) of *M. catarrhalis* with bound fibronectin detected by FITC conjugated anti-fibronectin pAb in flow cytometry are shown. UspA1$^{50-491}$ and UspA1$^{299-452}$ resulted in 95% and 63% inhibition respectively. Error bars represent mean±SD of three independent experiments.

UspA1$^{50-491}$ and UspA1$^{299-452}$ Fragments Competitively Inhibit *M. catarrhalis* Fibronectin Binding To further validate our findings on the UspA1/A2 fibronectin binding domains, recombinant truncated UspA1 proteins were tested for their capacity to block fibronectin binding to *M. catarrhalis*. Fibronectin (2 μg) was preincubated with 0.25 μmoles of recombinant UspA1 fragments and subsequently incubated with *M. catarrhalis*. Finally, *M. catarrhalis* UspA-dependent fibronectin binding was measured by flow cytometry. Pre-incubation with UspA1$^{50-491}$ and UspA1$^{299-452}$ resulted in decreased fibronectin binding with a 95% reduction for UspA1$^{50-491}$ and a 63% reduction for UspA1$^{299-452}$ (FIG. 7). When fibronectin was pre-incubated with the truncated UspA2$^{101\text{-}318}$, an inhibition of 50% was obtained.

Thus, the fibronectin binding domains of UspA1 and A2 block the interactions between fibronectin and *M. catarrhalis*.

Figure 8A:
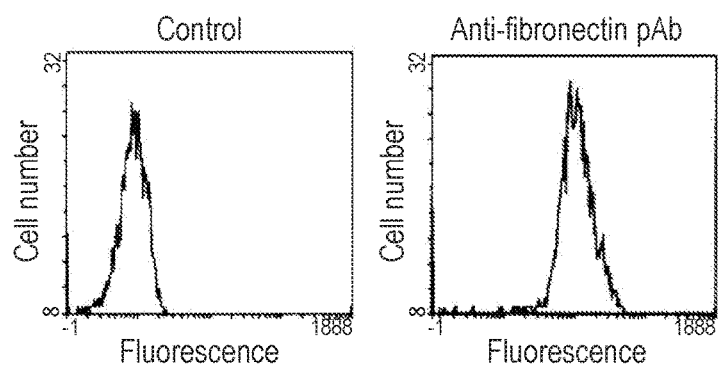
FIGS. 8A through 8B shows that UspA1$^{299-452}$ and UspA2$^{165-318}$ inhibit *M. catarrhalis* adherence to Chang conjunctival cells via cell-associated fibronectin. Chang epithelial cells expressed fibronectin on the surface as revealed by an anti-fibronectin pAb and flow cytometry (FIG. 8A). Pre-incubation with the fibronectin binding proteins UspA1$^{299-452}$, UspA2$^{165-318}$, or anti-fibronectin pAb resulted in significantly reduced binding by *M. catarrhalis* RH4 as compared to control recombinant proteins (UspA1$^{433-580}$ and UspA2$^{30-177}$) and a control antibody (anti-ICAM1 mAb) (FIG. 8B). $P<0.05$ by two-tailed paired Student's t test. Mean values of three separate experiments are shown and error bars indicate SD.

UspA1$^{299\text{-}452}$ and UspA2$^{165\text{-}318}$ Inhibit *M. catarrhalis* Adherence to Chang Epithelial Cells Epithelial cells are known to express fibronectin and many bacteria attach to epithelial cells via cell-associated fibronectin.[46, 54, 69, 77] Previous studies have shown that *M. catarrhalis* adhere to epithelial cells.[43, 49] We analyzed Chan conjunctival cells, which have frequently been used in adhesion experiments with respiratory pathogens. Chang cells strongly expressed fibronectin as revealed by flow cytometry analysis (FIG. 8A).

Figure 8B:
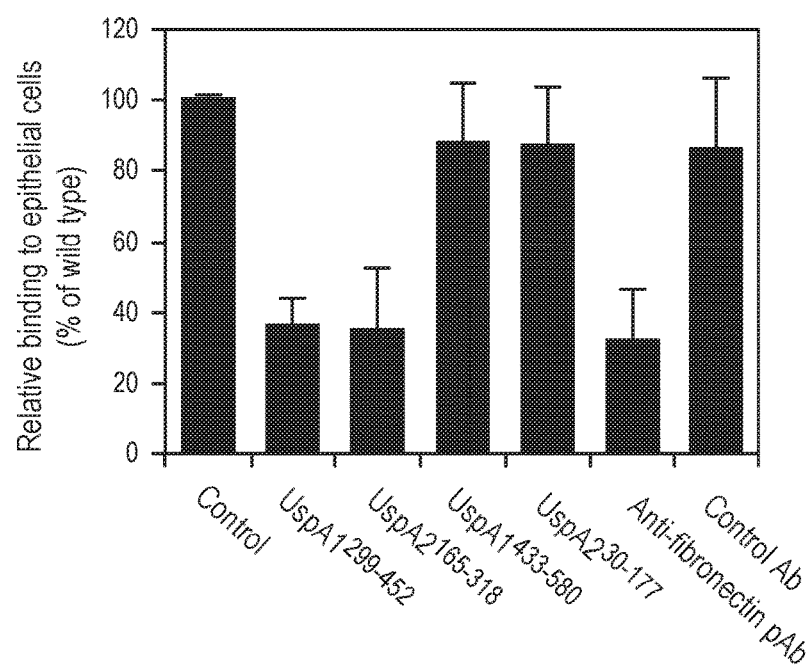

To analyze whether the UspA-dependent fibronectin binding was important for bacterial adhesion, Chang epithelial cells were pre-incubated with anti-human fibronectin pAb, or the recombinant proteins UspA1$^{299\text{-}452}$ and UspA2$^{165\text{-}318}$. Thereafter, *M. catarrhalis* RH4 was added and bacterial adhesion analyzed. The relative adherence (measured by the number of colony forming units) after pre-incubation with 0.4 μmoles per 200 μl of UspA1$^{299\text{-}452}$, UspA2$^{165\text{-}318}$, or an anti-human fibronectin pAb were 36%, 35% and 32%, respectively. Higher concentrations of recombinant peptides did not result in further inhibition. In contrast, the non-fibronectin binding fragments UspA1$^{433\text{-}583}$ and UspA2$^{30\text{-}177}$ did not inhibit the interactions between *M. catarrhalis* and the Chang epithelial cells (FIG. 8B). Thus, fibronectin on Chang epithelial cells may function as a receptor for *M. catarrhalis* and the amino acid residues 299-452 of UspA1 and 165-318 of UspA2 contain the ligand responsible for the interactions.

Interaction Between *M. catarrhalis* and Laminin
*M. catarrhalis* Binds Laminin Through UspA1 and A2

Figure 9A:
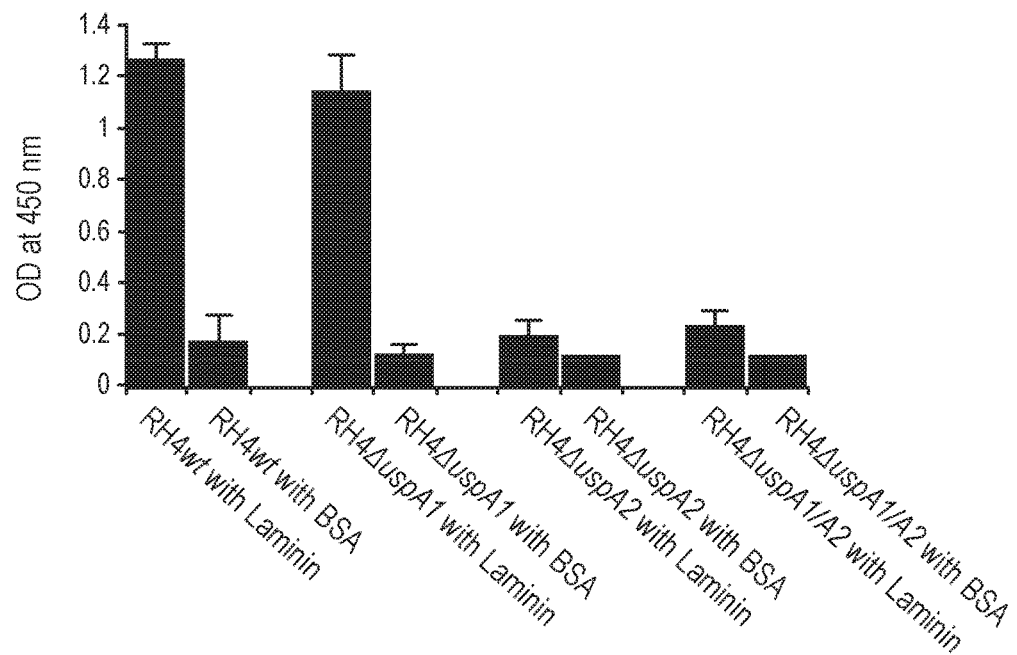
FIGS. 9A through 9B shows binding of *M. catarrhalis* RH4 to laminin via UspA1 and A2. *M. catarrhalis* RH4 wild type (wt) strongly bound to immobilized laminin with a mean OD of 1.27. RH4ΔuspA1 showed mean OD of 1.14 (89.8% of the wild type). RH4ΔuspA2 and the double mutant RH4ΔuspA1/A2 had a mean OD of 0.19 and 0.23 respectively (15.0% and 18.1% of the wild type). This was not significantly different from the residual adhesion to bovine serum albumin coated plates. Thirty μg/ml of laminin or bovine serum albumin were coated on microtiter plates. They were blocked followed by incubation with bacteria suspension and finally washed. Bound bacteria was detected with anti-MID pAb and HRP-conjugated anti-rabbit pAb. The mean results of 3 representative experiments are shown. Error bars represent standard deviations (SD).

Two clinical *M. catarrhalis* isolates (BBH18 and RH4) and their specific mutants lacking UspA1, UspA2 or both proteins were analyzed by a whole-cell ELISA. *M. catarrhalis* RH4 strongly bound to immobilized laminin. (FIG. 9A). In contrast, *M. catarrhalis* RH4 uspA1 mutant (RH4ΔuspA1) showed a laminin binding of 89.9% of the wild type. *M. catarrhalis* RH4 uspA2 mutant (RH4ΔuspA2) and the double mutant RH4ΔuspA1/A2 15.2% and 18.1% binding capacity of the wild type, respectively. This was not significantly different from the residual adhesion to BSA coated plates. Similar results were obtained with UspA1/A2 mutants originating from the clinical strain *M. catarrhalis* BBH18. In these two strains (BBH18 and RH4), UspA2 is the predominant protein expressed as compared to UspA1, explaining the minimal difference in binding between the wild type and RH4ΔuspA1. Taken together, these results show that UspA1 and A2 bound laminin.

Figure 9B:
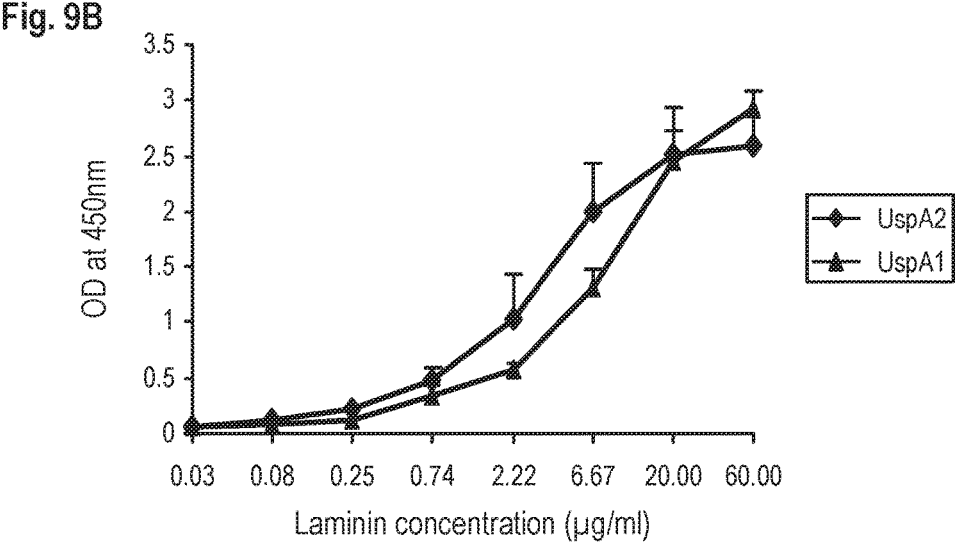

To further analyze the binding between UspA1/A2 and laminin, truncated UspA1$^{50\text{-}770}$ and UspA2$^{30\text{-}539}$ were produced in *E. coli*. Recombinant proteins were coated on microtiter plates and incubated with increasing concentrations of laminin. Bound laminin was detected with a rabbit anti-laminin pAb followed by incubation with an HRP-conjugated anti-rabbit pAb. Both recombinant UspA1$^{50\text{-}770}$ and UspA2$^{30\text{-}539}$ strongly bound soluble laminin and the binding was dose-dependent and saturable (FIG. 9B).

Figure 10A:
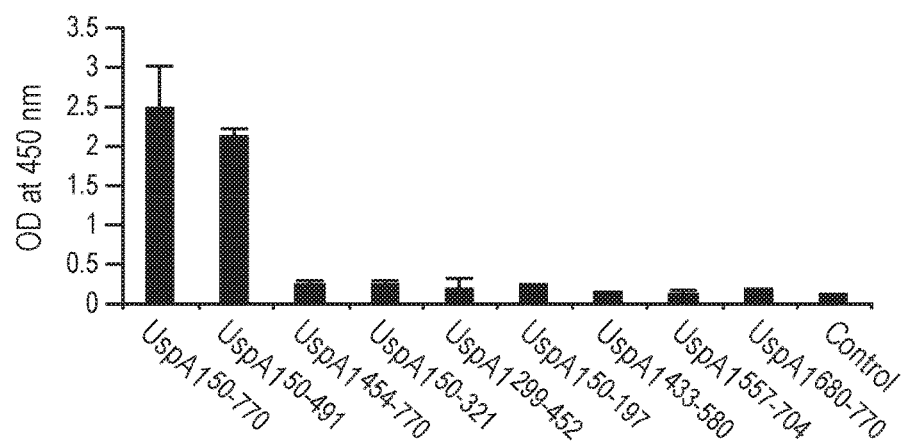
FIGS. 10A though 10B shows that the active laminin binding domains for UspA1$^{50-777}$ (FIG. 10A) and UspA2$^{30-539}$ (FIG. 10B) are located in the N-terminal halves. Forty nM of recombinant UspA1$^{50-770}$ and UspA2$^{30-539}$ together with the truncated proteins were coated on microtiter plates and incubated with 20 μg/ml of laminin followed by detection with rabbit anti-laminin pAb and HRP-conjugated anti-rabbit pAb. Mean values of three separate experiments are shown and error bars indicate SD.
Figure 10B:
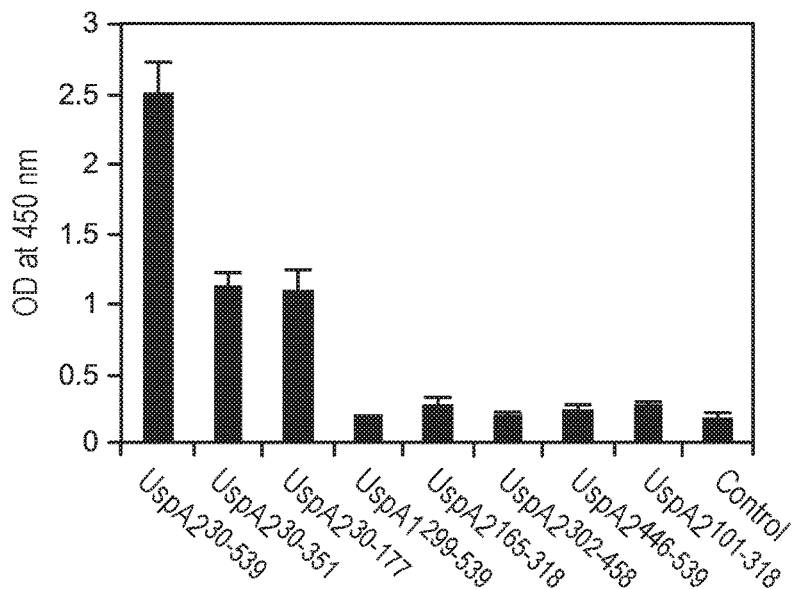

To define the laminin binding domains, recombinant UspA1 and A2 spanning the entire molecules were manufactured. Laminin was incubated with immobilized truncated UspA1 and A2 fragments and followed by quantification by ELISA. UspA1$^{50\text{-}491}$ bound to laminin almost as efficiently as UspA1$^{50\text{-}770}$ suggesting that the binding domain was within this part of the protein. However, among the other truncated fragments spanning this region, no other fragment appeared to bind laminin. The N-terminal part, UspA2$^{30\text{-}351}$, was able to retain 44.7% binding capacity as compared to the full length protein. The shorter protein UspA2$^{30\text{-}177}$ showed a 43.7% binding capacity. (FIG. 10B). These results show that the binding domains include residues found within the N-terminals of both UspA1 and UspA2.

Figure 12A:
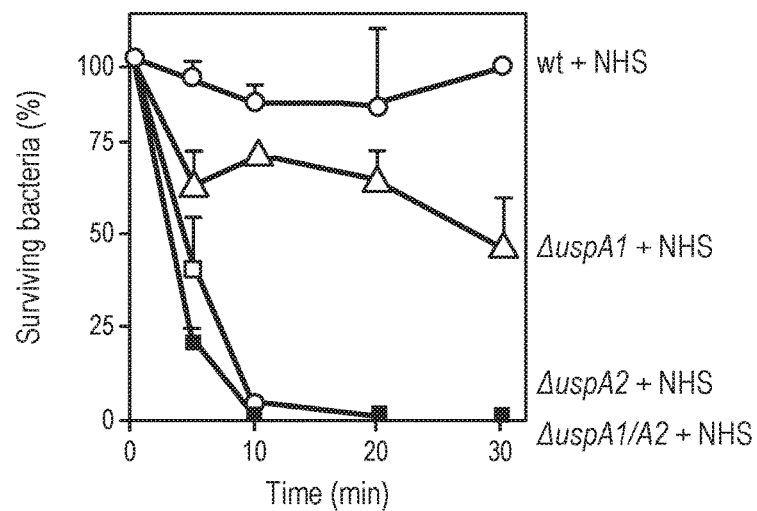
FIGS. 12A through 12B illustrates that *M. catarrhalis* counteracts the classical and alternative pathways of the complement system by the outer membrane proteins UspA1 and A2.
Figure 12B:
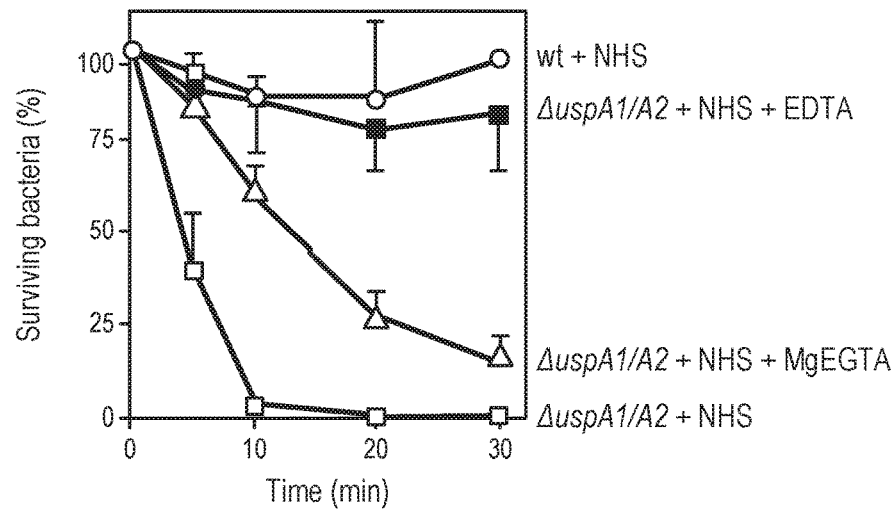

Interaction Between *M. catarrhalis* and C3 and C3met
*M. catarrhalis* Outer Membrane Proteins UspA1 and UspA2 Inhibit Both the Classical and the Alternative Pathway of the Complement Cascade UspA2 surface expression is crucial for *M. catarrhalis* survival in normal human serum (NHS) [1, 58], i.e., *moraxella* UspA2 deficient mutants are rapidly killed when exposed to NHS. We have recently shown that both UspA1 and A2 bind C4BP and thus might inhibit the classical pathway of complement activation [58]. To further shed light on *M. catarrhalis* interactions with the complement system, survival of UspA1/A2 double mutants was studied in serum treated with either EGTA with addition of MgCl$_2$ (Mg-EGTA) or EDTA. Mg-EGTA inhibits the classical and lectin pathways and thus allows separate analysis of the alternative pathway. In contrast, EDTA inhibits all complement pathways by absorbing divalent cations (Mg$^{2+}$ and Ca$^{2+}$). The *M. catarrhalis* RH4 wild type survived after 30 min of incubation, whereas RH4ΔuspA1/A2 double mutant was killed by intact NHS after 10 min (FIG. 12). When the classical pathway was inhibited (NHS+Mg-EGTA), the RH4ΔuspA1/A2 mutant survived for a significantly longer period of time as compared to NHS without any chelators, but not as long as the wild type bacterium. Furthermore, when both the classical and alternative pathways were blocked with EDTA, *M. catarrhalis* RH4ΔuspA1/A2 survived. A similar pattern was obtained with the *M. catarrhalis* BBH18 isolate and the corresponding BBH18 ΔuspA1/A2 mutants (not shown). In parallel, experiments with C1q and factor D/properdin deficient sera demonstrated that both the classical and the alternative pathways were inhibited by *M. catarrhalis* (not shown). Thus, *M. catarrhalis*, a pathogen that frequently colonizes the human respiratory tract, does not only counteract the classical pathway but also the alternative pathway of the complement system by the outer membrane proteins UspA1 and A2.

*M. catarrhalis* Absorbs C3 from EDTA-Inactivated Serum

Figure 11A:
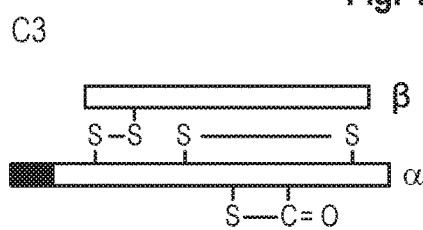
FIGS. 11A through 11C is a schematic illustration of C3, covalent bound C3b and C3met.
Figure 11C:
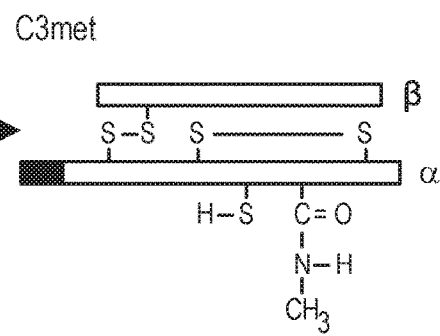
Figure 11B:
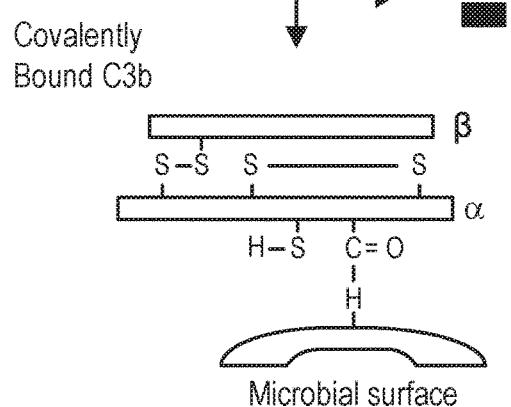
Figure 13A:
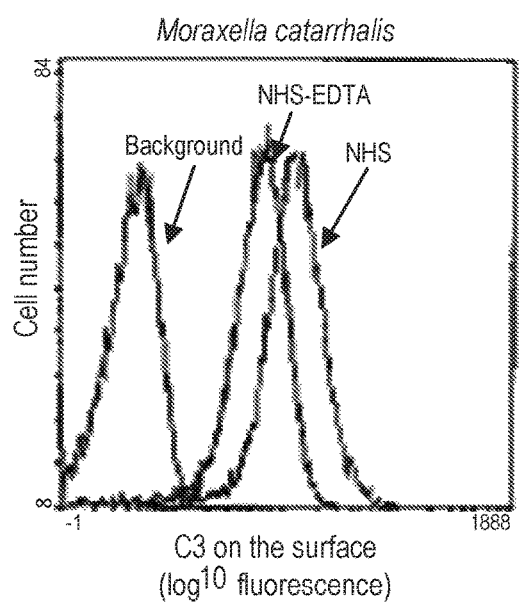
FIGS. 13A through 13B illustrates that *Moraxella catarrhalis* binds C3 in serum independently of complement activation. Flow cytometry profiles showing C3 binding to (FIG. 13A) *M. catarrhalis* RH4 or (FIG. 13B) *Streptococcus pneumoniae*. Bacteria were incubated with NHS or NHS pretreated with EDTA. Thereafter, a rabbit anti-human C3d pAb and as a secondary layer a FITC-conjugated goat anti-rabbit pAb were added followed by flow cytometry analysis. Bacteria in the absence of NHS, but in the presence of both pAb, were defined as background fluorescence. One representative experiment out of three is shown.
Figure 13B:
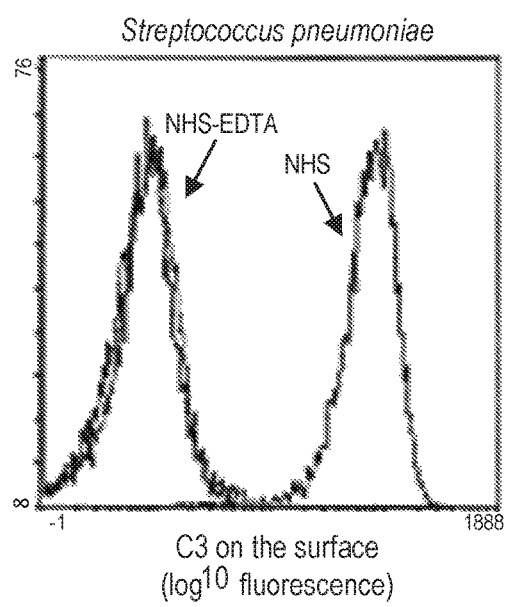

C3b covalently binds to the surface of a microbe and hence induces the alternative pathway (FIG. 11B). To analyze whether *M. catarrhalis* can interact with C3, our RH4 wild type strain was incubated with NHS or NHS treated with EDTA. Binding or deposition (via covalent link) of C3/C3b at the bacterial surface of *M. catarrhalis* RH4 was detected by flow cytometry analysis with a polyclonal antibody (pAb) directed against C3d recognizing both C3 and C3b. Incubation of bacteria with NHS containing intact complement led to deposition of C3 (FIG. 13). Interestingly, when the complement cascade was inactivated in the presence of EDTA, the *M. catarrhalis* RH4 still bound C3 (FIG. 13A). *Streptococcus pneumoniae* that was included for comparison did not absorb C3 from the EDTA-treated serum (FIG. 13B). In contrast to pneumococci, *M. catarrhalis* thus bound C3 irrespectively of complement activation. The internal thioester of C3 is spontaneously hydrolysed in fluid phase to C3(H$_2$O). Thus, intact C3 or C3(H$_2$O) was the most likely forms of C3 interacting with *M. catarrhalis*. Since *M. catarrhalis* also binds C4BP [58], we wanted to exclude that C4BP was involved in the C3 binding and for that purpose we used C4BP depleted serum. *M. catarrhalis* absorbed C3 from the C4BP depleted serum to the same extent as to NHS (not shown).

Binding of C3met to *M. catarrhalis* is Dose-Dependent and Non-Covalent

Figure 14A:
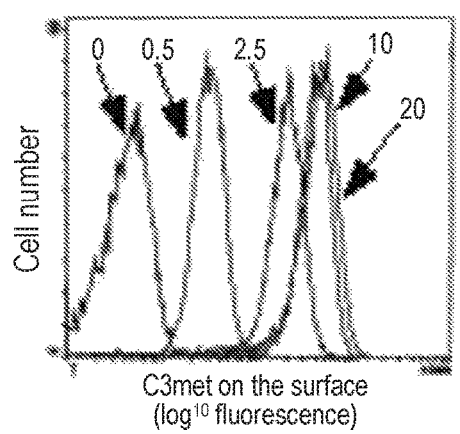
FIGS. 14A through 14C illustrates that *M. catarrhalis* non-covalently binds purified methylamine-treated C3 in a dose-dependent manner, and that the binding is based on ionic interactions. Flow cytometry profiles showing (FIG. 14A) binding with increasing concentrations of C3met.
Figure 14B:
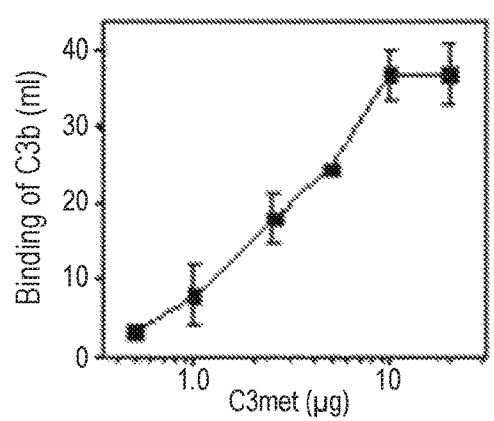
Figure 14C:
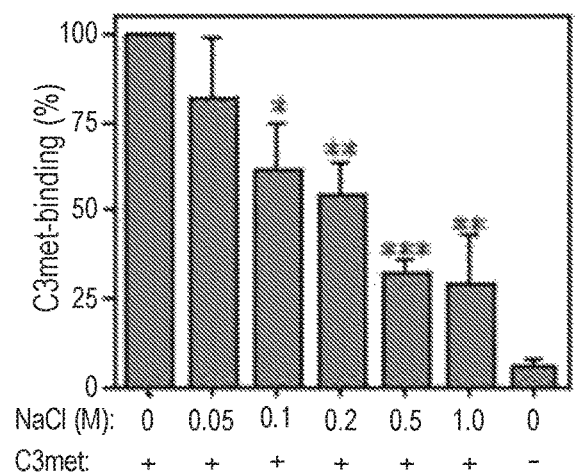

Our experiments implied that C3 bound to the surface of *M. catarrhalis* irrespectively of complement activation. Therefore, we analyzed whether converted C3, which is non-functional, could bind to the bacteria. Native C3 was purified from human serum and treated with methylamine, which converts C3 to a C3met molecule equivalent to C3b without the capacity to covalently bind to microbes (FIG. 11C). Flow cytometry analysis revealed that the *M. catarrhalis* RH4 wild type strain efficiently bound C3met in a dose-dependent and saturable manner (FIGS. 14A and B). This interaction was not mediated by the C3a part of the C3 molecule since C3b and C3($H_2O$) also bound *M. catarrhalis* (not shown). The binding between *M. catarrhalis* RH4 and C3met was based to a large extent on ionic interactions as increasing concentrations of NaCl inhibited the interaction (FIG. 14C). Similar results were obtained with the *M. catarrhalis* BBH18 wild type strain (not shown).

To determine whether the binding of C3 is a general feature of all *M. catarrhalis* strains, we selected a random series of clinical isolates (n=13) and analyzed their capacity to bind C3met. All *M. catarrhalis* strains bound C3met as revealed by a flow cytometry analysis with an anti-C3d pAb. The mfi values varied from 4 to 39. However, *S. pneumoniae* and *E. coli* that were included for comparison did not bind C3met.

*M. catarrhalis* is a Unique C3 and C3met Binding Bacterium

To extend our analysis of bacterial C3 absorption from NHS, related *moraxella* subspecies (n=13) as well as common human pathogens (n=13) were incubated in the presence of NHS-EDTA. Interestingly, among all the bacterial species tested, *M. catarrhalis* was the only bacterium binding C3 in complement-inactivated serum (Table 9). All related *moraxella* strains as well as the other human pathogens were also analyzed for binding of C3met. In parallel with the C3 binding, *M. catarrhalis* was the only species that bound C3met. Taken together, *M. catarrhalis* has a unique feature to strongly bind C3 and C3met in a non-covalent manner.

*M. catarrhalis* Binds C3met Via the Outer Membrane Proteins UspA1 and UspA2

To determine the *M. catarrhalis* protein responsible for the C3 binding, we tested a series of bacterial mutants devoid of the outer membrane proteins MID, UspA1 and/or UspA2 [22, 58]. Interestingly, the binding of C3met was significantly correlated with Usp expression (FIG. 15). *M. catarrhalis* RH4Δmid bound C3met to the same degree as the wild type counterpart (FIG. 15A-B). The RH4ΔuspA1 mutant showed only a slightly decreased binding, whereas the RH4ΔuspA2 was a weaker binder as compared to the wild type counterpart (FIG. 15C-D). In parallel, C3met binding to the double RH4ΔuspA1/A2 mutant was completely abolished (FIG. 15E). Furthermore, when the same experiments were performed using NHS-EDTA, the same pattern was seen (FIG. 15F-J). When normal human serum was used, all mutants showed similar amount of C3 on their surface since it was a mixture of covalent deposition and binding of C3 (FIG. 15K-O). Similar results were obtained with the *M. catarrhalis*☐BBH18 isolate and the corresponding BBH18 mutants.

Figure 16A:
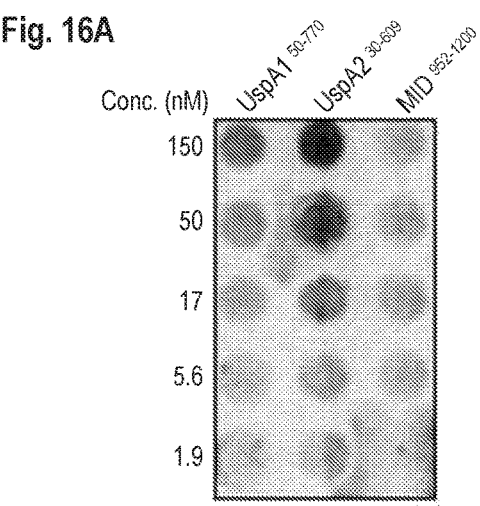
FIGS. 16A through 16B illustrates that C3met binds to purified recombinant UspA2$^{30-539}$, whereas only a weak C3met binding to UspA1$^{50-770}$ is observed. Furthermore, the C3met binding region of UspA2 was determined to be located between the amino acid residues 200 to 458.

To further analyze the interaction between C3 and UspA1/A2, UspA1$^{50-770}$ and UspA2$^{30-539}$ were produced in *E. coli* and purified. The recombinant proteins were dot blotted onto a nitrocellulose membrane followed by incubation with iodine-labelled C3met. Recombinant MID$^{962-1200}$, which is derived from the *M. catarrhalis* outer membrane protein MID [59], was included as a negative control. A weak binding to UspA1$^{50-770}$ was detected, whereas [$^{125}$I]-C3met strongly bound to UspA2$^{30-539}$ (FIG. 16A). These findings were further strengthened using surface plasmon resonance (i.e., Biacore). UspA1$^{50-770}$ and UspA2$^{30-539}$ were immobilized on the surface of a CM5 chip using amino coupling and C3met was injected until saturation was reached. The $K_D$ for the interaction between C3met and UspA2$^{30-539}$ or UspA1$^{50-770}$ was 3 and 14 μM, respectively. In conclusion, we found that UspA2 was the major C3met-binding protein of *M. catarrhalis*, whereas UspA1 contributed to the binding to a lower degree.

A C3 Binding Domain is Located Between Amino Acid Residues 200 and 458 of UspA2.

Figure 16B:
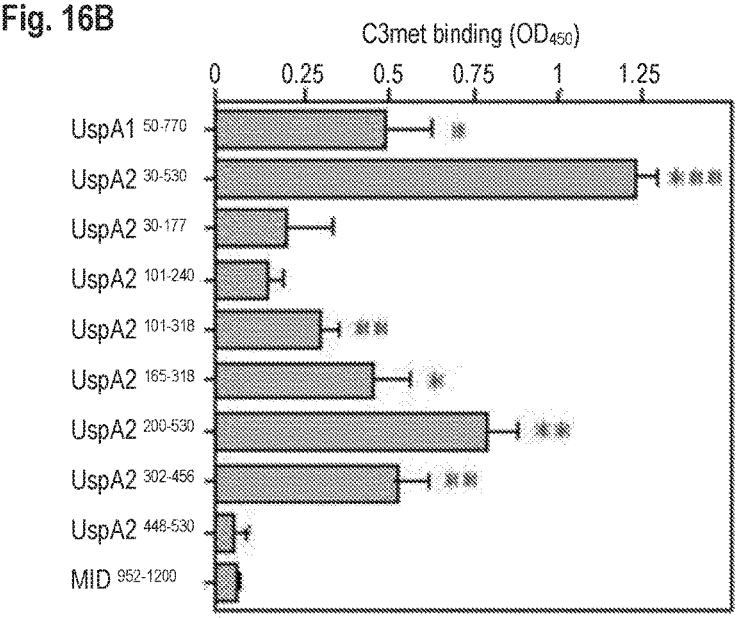

To define the C3 binding domain of UspA2, recombinant proteins spanning the entire UspA2$^{30-539}$ molecule were manufactured. C3met was incubated with the immobilized full length UspA1$^{50-770}$, UspA2$^{30-539}$ and a series of truncated UspA2 proteins. Thereafter, the interactions were quantified by ELISA. In agreement with the dot blot experiments (FIG. 16A), UspA1$^{50-770}$ bound C3met to a much lower extent compared to UspA2$^{30-539}$ in the ELISA (FIG. 16B). Among the truncated protein fragments, UspA2$^{165-318}$, UspA2$^{200-539}$ and UspA2$^{302-458}$ efficiently bound C3met, suggesting that a binding domain was within the amino acid residues 200 and 458.

Recombinant UspA1/A2 Neutralizes C3 Activity

Figure 17A:
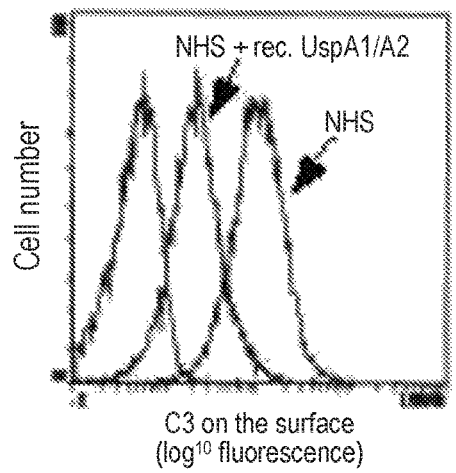
FIGS. 17A through 17C illustrates that addition of recombinant UspA1$^{50-770}$ and UspA2$^{30-539}$ to serum inhibit C3b deposition and killing of *M. catarrhalis* via the alternative pathway. Flow cytometry profiles show C3b-deposition on RH4ΔuspA1/A2 after incubation with (FIG. 17A) NHS or NHS preincubated with recombinant (rec.) UspA1$^{50-770}$ and UspA2$^{30-539}$, or (FIG. 17B) NHS-Mg-EGTA or NHS-Mg-EGTA preincubated with UspA1$^{50-770}$ and UspA2$^{30-539}$. After addition of the various NHS combinations, bacteria were analyzed as described in FIG. 13.
Figure 17B:
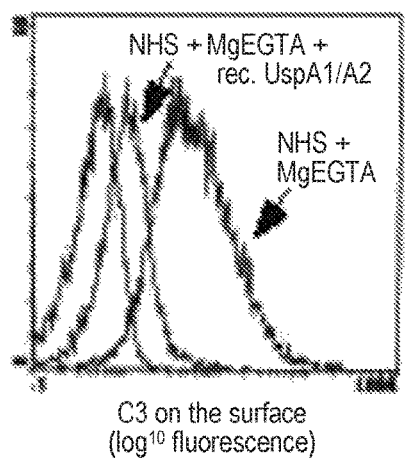

In order to in detail examine the role of UspA1/A2-dependent inhibition of the alternative pathway, a series of flow cytometry experiments was performed with bacteria incubated with 10% NHS or serum that had been preincubated with 100 nM recombinant UspA1$^{50-770}$ and UspA2$^{30-539}$. Interestingly, a significantly decreased C3 deposition/binding at the surface of *M. catarrhalis* RH4ΔuspA1/A2 was observed when NHS was pretreated with UspA1$^{50-770}$ and UspA2$^{30-539}$ (FIG. 17A). When the classical pathway was shut down with Mg-EGTA, similar results were obtained (FIG. 17B). Thus, the recombinant proteins UspA1$^{50-770}$ and UspA2$^{30-539}$ absorbed C3 from NHS and inhibited deposition/binding of C3.

Figure 17C:
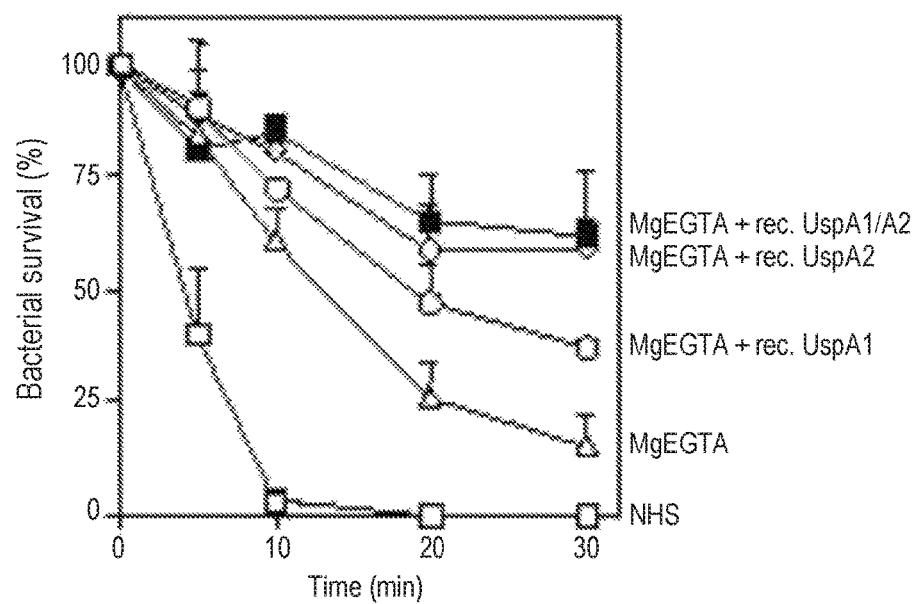

To determine whether absorption of C3 by recombinant UspA1$^{50-770}$ and UspA2$^{30-539}$ increased bacterial survival, the double mutant *M. catarrhalis* RH4ΔuspA1/A2 was incubated with serum supplemented with UspA1$^{50-770}$ and UspA2$^{30-539}$ followed by determination of the number of surviving bacteria. Mg-EGTA was included in the reactions in order to inhibit the classical pathway. Interestingly, addition of recombinant UspA1$^{50-770}$ and UspA2$^{30-539}$ to NHS prevented killing of the UspA1/A2 deficient *M. catarrhalis* (FIG. 17C). UspA2$^{30-539}$ was most efficient in inhibiting bacterial killing as compared to UspA1$^{50-770}$. When both recombinant proteins were supplemented together, no additional inhibition of the alternative pathway was detected. Ten % NHS correspond to approximately 600 nM C3. To investigate whether more UspA1 molecules could neutralize the C3 activity, UspA1$^{50-770}$ and/or UspA2$^{30-539}$ up to 600 nM was added. However, higher concentrations of the recombinant proteins did not further increase the inhibition (not shown).

Figure 18:
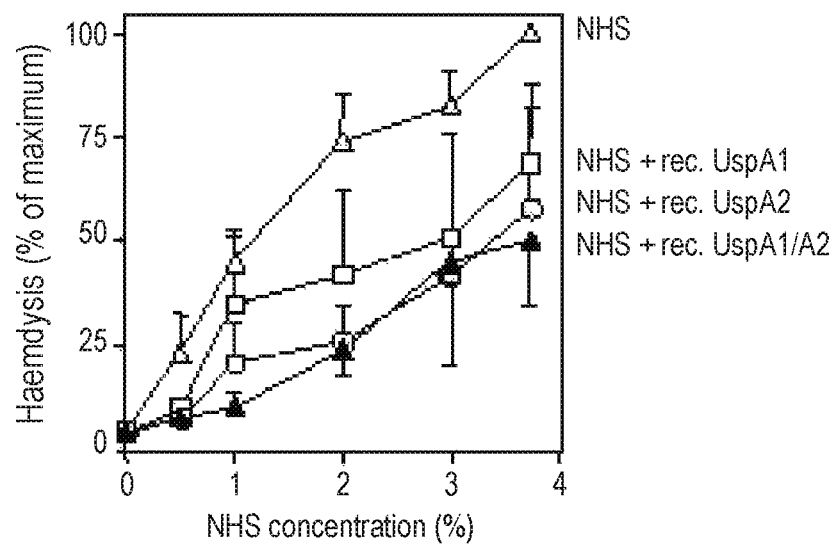
FIG. 18 illustrates that recombinant UspA1$^{50-770}$ and UspA2$^{30-539}$ decrease haemolysis of rabbit erythrocytes by inhibition of the alternative pathway. NHS was incubated with or without 100 nM UspA1$^{50-770}$ and/or UspA2$^{30-539}$ at 37° C. for 30 min. NHS at the indicated concentrations was thereafter added to rabbit erythrocytes. After incubation for 30 min, the suspensions were centrifuged and the supernatants were measured by spectrophotometry. Maximum haemolysis in each experiment was defined as 100%. Mean values of three separate experiments are shown and error bars correspond to S.D. The results obtained with NHS+UspA2$^{30-539}$ and NHS+UspA1$^{50-770}$/UspA2$^{30-539}$ at NHS concentrations of 2, 3 and 4% were significantly different from the NHS control (P<0.05).

We also included an alternative pathway haemolytic assay consisting of rabbit erythrocytes and NHS in order to establish the role of UspA1 and A2 as inhibitors of the alternative pathway. NHS was preincubated with recombinant UspA1$^{50-770}$, UspA2$^{30-539}$, or both proteins together followed by addition to the erythrocytes. After 1 h incubation, the amount of erythrocyte lysis was determined. Interestingly, a significantly decreased haemolysis was observed when NHS was preincubated with UspA1$^{50-770}$ or UspA2$^{30-539}$ as compared to untreated NHS (FIG. 18). In parallel with the increased survival of bacteria in the presence of UspA2$^{30-539}$ or UspA1$^{50-770}$ (FIG. 17C), preincubation with UspA2$^{30-539}$ alone resulted in a more efficient inhibition of the alternative pathway as compared to when NHS was preincubated with UspA1$^{50-770}$. In conclusion, recombinant UspA1$^{50-770}$ or UspA2$^{30-539}$ interfered with the activity of the alternative pathway due to their ability to capture C3.

In addition of being a key molecule in the complement cascade, deposited C3b and iC3b (inactivated C3b) target microbes for removal in the process of opsonophagocytosis. To investigate whether C3 or C3met that was non-covalently bound at the surface of M. catarrhalis could still function as an opsonin, a series of phagocytosis experiments was performed. M. catarrhalis was preincubated with C3met, NHS or NHS treated with EDTA followed by addition of polymorphonuclear leukocytes. Interestingly, M. catarrhalis was not engulfed in the presence of C3met, whereas NHS strongly promoted phagocytosis (data not shown). However, when NHS was pretreated with EDTA, M. catarrhalis was not phagocytosed by polymorphonuclear leukocytes. Thus, C3/C3met was inactive at the M. catarrhalis cell surface and did not function as an opsonin.

Discussion

Interaction Between M. catarrhalis and Fibronectin

UspA1$^{299-452}$ and UspA2$^{165-318}$ from the clinical M. catarrhalis strain Bc5 were the shortest fragments that still bound fibronectin. Interestingly, longer fragments encompassing the amino acid sequence found within UspA1$^{299-452}$ and UspA2$^{165-318}$ displayed a more efficient binding to fibronectin (FIGS. 5A and B). This may mean that these two regions represent partial binding domains or that the binding site is highly dependent on a specific molecular structure. UspA1$^{299-452}$ and UspA2$^{165-318}$ share a sequence of 31 identical amino acid residues including the 23 residues "NNINNIYELAQQQDQHSSDIKTL" (SEQ ID NO: 85) (NNINNIY (SEQ ID NO: 86) sequence). This sequence contains the epitope for the protective monoclonal antibody (mAb) 17C7 for which there is universal reactivity. [2, 50, 30] In a mouse model, passive immunization with mAb 17C7 provided protection and improved pulmonary clearance of M. catarrhalis. [30] It is hence most interesting that UspA1/A2 fibronectin binding domains contain these residues and argues for the importance of this region in the pathogenesis of M. catarrhalis respiratory tract infection.

The fibronectin binding M. catarrhalis BBH18 and RH4 used in our experiments also carry the 31 amino acid residues in their UspA1/A2 protein. Most M. catarrhalis have a part of this sequence (i.e., the NNINNIY (SEQ ID NO: 86) sequence). However, strains like the O35E which has the NNINNIY (SEQ ID NO: 86) sequence in their UspA2 gene do not express a fibronectin binding UspA2 protein. [49] A likely explanation would be that the variations in the flanking regions might affect the interaction with fibronectin. Also, the conserved NNINNIY (SEQ ID NO: 86) sequence itself can have minor single amino acid base changes. [28] It is thus likely that fibronectin binding would depend not just on UspA1/A2 expression, but also on the individual makeup of each UspA protein. Interestingly, an almost identical amino acid sequence can be found in the hybrid UspA2H protein with adhesive properties [M. catarrhalis TTA37 and O46E). [43] This give support to our findings that the 31 amino acid sequence is important in adhesion.

In our last set of experiments, we tested whether the adherence of M. catarrhalis to Chang conjunctival cells could be inhibited by the fibronectin binding fragments (UspA1$^{299-452}$ and UspA2$^{165-318}$) (FIG. 8B). Preincubation with UspA1$^{299-452}$, UspA2$^{165-318}$ or an anti-fibronectin pAb resulted in decreased binding to Chang epithelial cells. These results confirm the importance of these binding domains in the interactions of UspA1/A2 with Chang epithelial cells and further suggest that fibronectin is an important receptor for UspA. In addition, it is known that FnBP facilitate the adherence of bacteria to undifferentiated and injured airways.[54, 69] Fibronectin expression by lung fibroblasts is also increased by cigarette smoke extract.[87] The role of M. catarrhalis UspA1/A2 binding to ECM fibronectin or epithelial cell-associated fibronectin is thus of great importance in patients with COPD and may explain the common occurrence of M. catarrhalis infection in this group of patients. [40]

In conclusion, we have shown that UspA1/A2 of M. catarrhalis BBH18, RH4 and Bc5 are crucial FnBP. Both recombinant UspA1 and A2 derived from Bc5 bind fibronectin with a binding domain sharing identical amino acid residues including the conserved NNINNIY (SEQ ID NO: 86) sequence. Furthermore, an interaction of M. catarrhalis UspA1/A2 with epithelial cells is via cell-associated fibronectin. The definition of these fibronectin binding domains is therefore an important step forward in the development of a vaccine against M. catarrhalis.

Interaction Between M. catarrhalis and Laminin

M. catarrhalis is a common cause of infectious exacerbations in patients with COPD. The success of this species in patients with COPD is probably related in part to its large repertoire of adhesins. In addition, there are pathological changes such as loss of epithelial integrity with exposure of basement membrane where the laminin layer itself is thickened in smokers.[4] Some pathogens have been shown to be able to bind to laminin and thus may contribute to their ability to adhere to such damaged and denuded mucosal surfaces. These include pathogens known to cause significant disease in the airways such as S. aureus and P. aeruginosa amongst others.[7, 63]

We recently showed that both UspA1 and A2 bind fibronectin.[78] The fibronectin binding domains were located within UspA1$^{299-452}$ and UspA2$^{165-318}$. In this study, the N-terminal halves UspA1$^{50-491}$ and UspA2$^{30-351}$ (containing the fibronectin domains) also bound laminin. However, the smallest fragments that bound fibronectin, UspA1$^{299-452}$ and UspA2$^{165-318}$ did not bind laminin to any appreciable extent. In fact, fragments smaller than the N-terminal half of UspA1 (UspA1$^{50-491}$) losses all its laminin binding ability whereas with UspA2, only UspA2$^{30-170}$ bound laminin albeit at a lower level then the whole recombinant protein (UspA2$^{30-539}$). These findings suggest that perhaps different parts of the molecules might have different functional roles.

Comparing the smallest laminin binding regions of UspA1 and A2, we find that there is, however, little similarity by way of amino acid homology between UspA2$^{30-170}$ and UspA1$^{50-491}$ (data not shown). This is not surprising as it is a known fact that both proteins have a 'lollipop'-shaped globular head structure despite having only 22% identity in both N-terminal halves.[2, 32] We postulate that a tertiary structure is likely responsible for the interactions with laminin in the head region in vivo. The localization of the binding domains at the N-terminal end would be logical as this would be most exposed and in contact with the human basement membrane in vivo.

Bacterial factors mediating adherence to tissue and extracellular matrix (ECM) components are grouped together in a single family named "microbial surface components recognizing adhesive matrix molecules" (MSCRAMMS). Since UspA1/A2 bind both fibronectin and laminin, these proteins can be designated MSCRAMMS. Our results suggest that UspA1 and A2 are multifunctional adhesins with different domains interacting with different ligands in the respiratory tract. Similar broad-spectrum binding profiles have been reported for other bacterial proteins such as YadA of *Yersinia enterocolitica* for which UspA1 and A2 bear a structural relationship. [45, 70] YadA too binds both fibronectin and laminin. [32]

In summary we have shown that UspA1/A2 are crucial to *M. catarrhalis* interaction with the basement membrane glycoprotein laminin and this will play an important role in the pathogenesis of infections in patients with COPD. [74]

Interaction Between *M. catarrhalis* and C3 and C3met

Complement resistance is one of the most important bacterial virulence factors.[66] The majority (89%) of *M. catarrhalis* isolates from patients with lower respiratory tract infections are resistant to complement-mediated killing.[34] *M. catarrhalis* UspA1 and A2 are crucial for bacterial survival in human serum in vivo [1, 15], and we have shown that these two outer membrane proteins bind to the complement fluid phase regulator of the classical pathway, C4BP.[58] In the present study, we demonstrate that *M. catarrhalis* can inhibit the alternative pathway by non-covalently binding of C3 (FIGS. 17 and 18). The binding of C3 most likely also inhibits the classical pathway. This could, however, not be analysed in detail since *M. catarrhalis* also binds C4BP. Interestingly, the *M. catarrhalis*-dependent C3-binding is unique as several related *moraxella* subspecies as well as common human pathogenic bacteria do not bind C3 (Table 9). The interactions with C3 and methylamine-treated C3 are mediated mainly by UspA2, whereas UspA1 has a minor role (FIGS. 15 and 16). The C3-binding region of UspA2 was localized between the amino acid residues 200 to 458. This region contains a stretch of 140 amino acid residues that is 93% identical to a region in UspA1.[2] However, despite this sequence similarity, UspA1 binds C3 to a much lower extent. This might be due to a specific difference in conformation between the proteins. The discrepancy in the C3 binding of UspA1 and UspA2 stands in contrast to the UspA1/A2 interaction with C4BP.[58]

*M. catarrhalis* is equally resistant to both the classical and alternative pathways (FIG. 12B). The bacterium binds C4BP that inhibits the classical pathway [58] and in this paper we demonstrate an interaction with the alternative pathway through binding of C3. To determine which of these mechanisms that is of most importance for the *M. catarrhalis* serum resistance in various in vivo situations is difficult. For example, the importance of the classical pathway will strongly depend on history of infections with *M. catarrhalis* and ability to generate complement-activating antibodies. However, every mechanism providing protection from the complement is certainly beneficial for a pathogen. Since C3 is a key molecule in the complement system, the binding of C3 most likely results in regulation of all three activation pathways and may contribute the most to serum resistance.

The importance of the complement system as a primary defence mechanism is mirrored by the fact that microbes have developed various strategies to interfere with and/or neutralize components of the complement system.[42, 35, 88] In addition to *M. catarrhalis, S. pyogenes, Bordetella pertussis, E. coli* K1, *Candida albicans*, and *N. gonorrhoeae* express specific surface molecules that bind C4BP and as a consequence protect the bacteria against the classical complement pathway.[8, 9, 52, 58, 64, 65, 80] In addition to inhibition of the classical pathway, several bacteria (e.g., *C. albicans, N. meningitides, S. pyogenes*, and *S. pneumoniae*; for reviews see [68, 89] bind factor H and factor H-like molecule and hence are partially protected against the alternative complement pathway.

UspA1 and A2 absorb C3 from serum and hereby most likely inhibit the complement activation. Similarly, the Pneumococcal Surface Protein A (PspA) appears to inhibit the alternative pathway both in vitro and in vivo. PspA is an important virulence factor for *S. pneumoniae*. PspA-deficient pneumococcal strains are readily cleared from the blood, whereas the PspA-expressing strains survive.[82] Furthermore, in a murine model of bacteremia, PspA-deficient pneumococci have a significantly reduced virulence compared with pneumococci that express PspA.[11] It has been demonstrated that more C3b is deposited on PspA-negative pneumococci than on PspA-positive.[67, 82] Thus, expression of PspA reduces the complement-mediated clearance and phagocytosis of *S. pneumoniae* by limiting opsonization by C3b.[12, 67] PspA-deficient pneumococci that are not virulent in normal mice become virulent in C3-deficient and factor B-deficient mice.[82]

To our knowledge, there are only two examples of bacterial proteins that non-covalently bind C3 and thereby interfere with complement function. The first one is the extracellular fibrinogen-binding protein (Efb) of *Staphylococcus aureus*, which was found to bind C3b.[44] Efb inhibits both the classical and alternative pathways independently of the thioester conformation, i.e., the binding to C3b is non-covalent. The second example is the pneumococcal choline-binding protein (CbpA), which has been shown to bind methylamine-treated C3, suggesting a non-covalent interaction that is not dependent on complement activation. [16] CbpA is a component of the pneumococcal cell wall, but may only bind C3 when the CbpA is secreted. In order to test this hypothesis, which is not firmly established in the literature, we analyzed eleven different pneumococcal isolates for C3 binding (methylamine-treated C3 or NHS-EDTA) by flow cytometry (FIG. 12B and Table 9). No bound C3 could be detected on the surface of *S. pneumoniae*. When lysates of *S. pneumoniae* and culture supernatants were analyzed on Western blots using methylamine-treated C3 followed by an anti-human C3 pAb, we confirmed the results by Cheng and collaborators [16] (not shown). In the light of Efb and CbpA, which both are C3-binding proteins secreted by two Gram-positive bacteria, the Gram-negative *M. catarrhalis* is a unique species with membrane anchored proteins that bind C3 and inhibit the alternative pathway at the surface of the bacterium.

The yeast *Candida albicans* has been shown to bind C3b, iC3b and C3d. However, C3b is bound at a considerably lower affinity than iC3b and C3d.[29] We found a large difference between C3 binding to *M. catarrhalis* and *C. albicans* (not shown); despite that *candida* bound C3met (56% positive cells), the mean fluorescence intensity (mfi) was only <2.0 as compared to mfi 36.9 for *M. catarrhalis*. Furthermore, no detectable binding was seen when *C. albicans* was incubated with EDTA-treated serum. Two C3d-binding proteins have been isolated from *C. albicans* and the most characterized protein is a 60 kDa mannoprotein that initially was recognized by an antibody directed against human complement receptor 2 (CD21).[13] However, *M. catarrhalis* UspA1 and A2 were not recognized by a polyclonal antibody directed against CD21 (not shown). In parallel with staphylococci and pneumococci [52, 64], a secreted C3d-binding protein from *C. albicans* also exists. [72] Finally, a *C. albicans* iC3b receptor has been isolated and is structurally similar to human CR3 (CD11b).[3] The mechanisms by which these receptors may participate in pathogenesis are not fully known.

The above examples of C3 binding pathogens are notably different from *M. catarrhalis* in that these species often are blood stream isolates. *M. catarrhalis* is mucosal pathogen with rare instances of bacteremic infections. Hence, the binding and inactivating C3 most likely occur at the mucosal surface. This is supported by the fact that there is strong ongoing complement activation and consequent inflammation in disease state such as acute otitis media.[57] The complement proteins are believed to be transported to the mucosal surface due to exudation of plasma.[26, 62] In middle-ear effusions (MEEs) from children for example, strongly elevated concentrations of C3 products can also be found.[51] In addition, complement factors in MEEs fluid have been shown to be important in the bactericidal activity against other mucosal agents such as non-typable *H. influenzae*.[75] *M. catarrhalis* is a strict human pathogen. It does not cause diseases such as otitis media or pneumonia in animals. A mouse pulmonary clearance model and an otitis media model with chinchilla has been used at several occasions. However, neither otitis media nor pneumonia develops and bacteria are rapidly cleared.[19, 83] It is thus difficult to test the biological significance of bacterial C3 binding in vivo. Since UspA1 and A2 are multifunctional proteins [1, 15, 31, 43, 58, 78], it would be impossible to relate any differences in the clearance of *M. catarrhalis* to C3 binding. In particular the fact that UspA1 is an important adhesin of *M. catarrhalis* and binds both CEACAM1 and fibronectin [31, 78] would most likely affect the clearance. Nevertheless, due to the strong complement activation in disease states such as otitis media, *moraxella*-dependent binding of C3 may represent an important way of combating the mucosal defense.

The fact that *M. catarrhalis* hampers the human immune system in several ways might explain why *M. catarrhalis* is such a common inhabitant of the respiratory tract [73]. In conclusion, *M. catarrhalis* has developed sophisticated ways of combating both the humoral and innate immune systems. The present data show that *M. catarrhalis* has a unique C3-binding capacity at the bacterial cell surface that cannot be found in other bacterial species.

REFERENCES

1. Aebi C, Lafontaine E R, Cope L D, et al. Phenotypic effect of isogenic uspA1 and uspA2 mutations on *Moraxella catarrhalis* 035E. Infect Immun 1998; 66:3113-9.
2. Aebi C, Maciver I, Latimer J L, et al. A protective epitope of *Moraxella catarrhalis* is encoded by two different genes. Infect Immun 1997; 65:4367-77.
3. Alaei, S., C. Larcher, C. Ebenbichler, W. M. Prodinger, J. Janatova, and M. P. Dierich. 1993. Isolation and biochemical characterization of the iC3b receptor of *Candida albicans*. *Infect. Immun*. 61:1395-1399.
4. Amin K, Ekberg-Jansson A, Lofdahl C G and Venge P. Relationship between inflammatory cells and structural changes in the lungs of asymptomatic and never smokers: a biopsy study. Thorax 2003; 58:135-42.
5. Attia A S, Lafontaine E R, Latimer J L, Aebi C, Syrogiannopoulos G A and Hansen E J. The UspA2 protein of *Moraxella catarrhalis* is directly involved in the expression of serum resistance. Infect Immun 2005; 73:2400-10.
6. Bartos L C, Murphy T F. Comparison of the outer membrane proteins of 50 strains of *Branhamella catarrhalis*. J Infect Dis 1988; 158:761-5.
7. de Bentzmann S, Tristan A, Etienne J, Brousse N, Vandenesch F and Lina G. *Staphylococcus aureus* isolates associated with necrotizing pneumonia bind to basement membrane type I and IV collagens and laminin. J Infect Dis 2004; 190:1506-15.
8. Berggard, K., E. Johnsson, F. R. Mooi, and G. Lindahl. 1997. *Bordetella pertussis* binds the human complement regulator C4BP: role of filamentous hemagglutinin. *Infect. Immun*. 65:3638-3643.
9. Blom, A. M., A. Rytkonen, P. Vasquez, G. Lindahl, B. Dahlbäck, and A. B. Jonsson. 2001. A novel interaction between type IV pili of *Neisseria gonorrhoeae* and the human complement regulator C4B-binding protein. *J. Immunol*. 166:6764-6770.
10. Bootsma H J, van der Heide H G, van de Pas S, Schouls L M and Mooi F R. Analysis of *Moraxella catarrhalis* by DNA typing: evidence for a distinct subpopulation associated with virulence traits. J Infect Dis 2000; 181:1376-87.
11. Briles, D. E., J. Yother, L. S. McDaniel. 1988. Role of pneumococcal surface protein A in the virulence of *Streptococcus pneumoniae*. Rev. Infect. Dis. 10:(Suppl. 2):S372.
12. Briles, D. E., S. K. Hollingshead, E. Swiatlo, A. Brooks-Walter, A. Szalai, A. Virolainen, L. S. McDaniel, K. A. Benton, P. White, K. Prellner, A. Hermansson, P. C. Aerts, H. Van Dijk, and M. J. Crain. 1997. PspA and PspC: their potential for use as pneumococcal vaccines. Microb. Drug Resist. 3:401-408.
13. Calderone, R. A., L. Linehan, E. Wadsworth, and A. L. Sandberg. 1988. Identification of C3d receptors on *Candida albicans*. Infect. Immun. 56:252-258.
14. Catlin B W. *Branhamella catarrhalis*: an organism gaining respect as a pathogen. Clin Microbiol Rev 1990; 3:293-320.
15. Chen D, Barniak V, VanDerMeid K R and McMichael J C. The levels and bactericidal capacity of antibodies directed against the UspA1 and UspA2 outer membrane proteins of *Moraxella (Branhamella) catarrhalis* in adults and children. Infect Immun 1999; 67:1310-6.
16. Cheng, Q., D. Finkel, and M. K. Hostetter. 2000. Novel purification scheme and functions for a C3-binding protein from *Streptococcus pneumoniae*. Biochem. 39:5450-5457.
17. Cope L D, Lafontaine E R, Slaughter C A, et al. Characterization of the *Moraxella catarrhalis* uspA1 and uspA2 genes and their encoded products. J Bacteriol 1999; 181:4026-34.
18. De Saint Jean M, Baudouin C, Di Nolfo M, et al. Comparison of morphological and functional characteristics of primary-cultured human conjunctival epithelium and of Wong-Kilbourne derivative of Chang conjunctival cell line. Exp Eye Res 2004; 78:257-74.
19. Fulghum, R. S., and H. G. Marrow. 1996. Experimental otitis media with *Moraxella (Branhamella) catarrhalis*. Ann. Otol. Rhinol. Laryngol. 105:234-241.
20. Forsgren, A., and A. Grubb. 1979. Many bacterial species bind human IgD. *J. Immunol* 122:1468-1472.

21. Forsgren A, Brant M, Mollenkvist A, et al. Isolation and characterization of a novel IgD-binding protein from *Moraxella catarrhalis*. J Immunol 2001; 167:2112-20.
22. Forsgren A, Brant M, Karamehmedovic M and Riesbeck K. The immunoglobulin D-binding protein MID from *Moraxella catarrhalis* is also an adhesin. Infect Immun 2003; 71:3302-9.
23. Forsgren A, Brant M and Riesbeck K. Immunization with the truncated adhesion *moraxella catarrhalis* immunoglobulin D-binding protein (MID764-913) is protective against *M. catarrhalis* in a mouse model of pulmonary clearance. J Infect Dis 2004; 190:352-5.
24. Gjörloff-Wingren, A., R. Hadzic, A. Forsgren, and K. Riesbeck. 2002. A novel IgD-binding bacterial protein from *Moraxella catarrhalis* induces human B lymphocyte activation and isotype switching in the presence of Th2 cytokines. *J. Immunol.* 168:5582-5588.
25. Greenwood F C, Hunter W M and Glover J S. The Preparation of I-131-Labelled Human Growth Hormone of High Specific Radioactivity. Biochem J 1963; 89:114-23.
26. Greiff, D., I. Erjefält, C. Svensson, P. Wollmer, U. Alkner, M. Andersson, and C. G. Persson. 1993. Plasma exudation and solute absorbtion across the airway mucosa. *Clin. Physiol.* 13: 219-233.
27. Hanski E, Caparon M. Protein F, a fibronectin-binding protein, is an adhesin of the group A *streptococcus Streptococcus* pyogenes. Proc Natl Acad Sci USA 1992; 89:6172-6.
28. Hays J P, van der Schee C, Loogman A, et al. Total genome polymorphism and low frequency of intra-genomic variation in the uspA1 and uspA2 genes of *Moraxella catarrhalis* in otitis prone and non-prone children up to 2 years of age. Consequences for vaccine design? Vaccine 2003; 21:1118-24.
29. Heidenreich, F., and M. P. Dierich. 1985. *Candida albicans* and *Candida stellatoidea*, in contrast to other *Candida* species, bind iC3b and C3d but not C3b. *Infect. Immun.* 50:598-600.
30. Helminen M E, Maciver I, Latimer J L, et al. A large, antigenically conserved protein on the surface of *Moraxella catarrhalis* is a target for protective antibodies. J Infect Dis 1994; 170:867-72.
31. Hill D J, Virji M. A novel cell-binding mechanism of *Moraxella catarrhalis* ubiquitous surface protein UspA: specific targeting of the N-domain of carcinoembryonic antigen-related cell adhesion molecules by UspA1. Mol Microbiol 2003; 48:117-29.
32. Hoiczyk E, Roggenkamp A, Reichenbecher M, Lupas A and Heesemann J. Structure and sequence analysis of *Yersinia* YadA and *Moraxella* UspAs reveal a novel class of adhesins. EMBO J 2000; 19:5989-99.
33. Holm M M, Vanlerberg S L, Foley I M, Sledjeski D D and Lafontaine E R. The *Moraxella catarrhalis* porin-like outer membrane protein CD is an adhesin for human lung cells. Infect Immun 2004; 72:1906-13.
34. Hol, C., C. M. Verduin, E. E. Van Dijke, J. Verhoef, A. Fleer, H. van Dijk. 1995. Complement resistance is a virulence factor of *Branhamella* (*Moraxella*) *catarrhalis*. *FEMS Immunol. Med. Microbiol.* 11:207-211.
35. Hornef, M. W., M. J. Wick, M. Rhen, and S. Normark. 2002. Bacterial strategies for overcoming host innate and adaptive immune responses. *Nat. Immunol.* 3:1033-1040.
36. Hostetter, M. K., M. L. Thomas, F. S. Rosen, and B. F. Tack. 1982. Binding of C3b proceeds by a transesterification reaction at the thiolester site. *Nature* 298:72-75.
37. Hostetter, M. K., R. A. Krueger, and D. J. Schmeling. 1984. The biochemistry of opsonization: central role of the reactive thiolester of the third component of complement. *J. Infect. Dis.* 150:653-661.
38. Joh D, Wann E R, Kreikemeyer B, Speziale P and Hook M. Role of fibronectinbinding MSCRAMMs in bacterial adherence and entry into mammalian cells. Matrix Biol 1999; 18:211-23.
39. Joh H J, House-Pompeo K, Patti J M, Gurusiddappa S and Hook M. Fibronectin receptors from gram-positive bacteria: comparison of active sites. Biochemistry 1994; 33:6086-92.
40. Karalus R, Campagnari A. *Moraxella catarrhalis*: a review of an important human mucosal pathogen. Microbes Infect 2000; 2:547-59.
41. Kask, L., L. A. Trouw, B. Dahlback, and A. M. Blom. 2004. The C4b-binding protein-protein S complex inhibits the phagocytosis of apoptotic cells. *J. Biol. Chem.* 279:23869-23873.
42. Lachmann, P. J. 2002. Microbial subversion of the immune response. *Proc. Natl. Acad. Sci. U.S.A* 99:8461-8462.
43. Lafontaine E R, Cope L D, Aebi C, Latimer J L, McCracken G H, Jr. and Hansen E J. The UspA1 protein and a second type of UspA2 protein mediate adherence of *Moraxella catarrhalis* to human epithelial cells in vitro. J Bacteriol 2000; 182:1364-73.
44. Lee, L. Y. L., M. Höök, D. Haviland, R. A. Wetsel, E. O. Yonter, P. Syribeys, J. Vernachio, and E. L. Brown. 2004. Inhibition of complement activation by secreted *Staphylococcus aureus* protein. *J. Infect. Dis.* 190:571-579.
45. Mack D, Heesemann J and Laufs R. Characterization of different oligomeric species of the *Yersinia enterocolitica* outer membrane protein YadA. Med Microbiol Immunol (Berl) 1994; 183:217-27.
46. Maheshwari R K, Kedar V P, Bhartiya D, Coon H C and Kang Y H. Interferon enhances fibronectin expression in various cell types. J Biol Regul Homeost Agents 1990; 4:117-24.
47. McGavin M J, Gurusiddappa S, Lindgren P E, Lindberg M, Raucci G and Hook M. Fibronectin receptors from *Streptococcus dysgalactiae* and *Staphylococcus aureus*. Involvement of conserved residues in ligand binding. J Biol Chem 1993; 268:23946-53.
48. McMichael J C. Vaccines for *Moraxella catarrhalis*. Vaccine 2000; 19 Suppl 1:S101-7.
49. McMichael J C, Fiske M J, Fredenburg R A, et al. Isolation and characterization of two proteins from *Moraxella catarrhalis* that bear a common epitope. Infect Immun 1998; 66:4374-81.
50. Meier P S, Troller R, Grivea I N, Syrogiannopoulos G A and Aebi C. The outer membrane proteins UspA1 and UspA2 of *Moraxella catarrhalis* are highly conserved in nasopharyngeal isolates from young children. Vaccine 2002; 20:1754-60.
51. Meri, S., T. Lehtinen, and T. Palva. 1984. Complement in chronic secretory otitis media. C3 breakdown and C3 splitting activity. *Arch. Otolaryngol.* 110:774-778.
52. Meri, T., A. M. Blom, A. Hartmann, D. Lenk, S. Meri, P. F. Zipfel. 2004. The hyphal and yeast forms of *Candida albicans* bind the complement regulator C4b-binding protein. *Infect. Immun.* 72:6633-6641.
53. Mollenkvist A, Nordstrom T, Hallden C, Christensen J J, Forsgren A and Riesbeck K. The *Moraxella catarrhalis* immunoglobulin D-binding protein MID has conserved sequences and is regulated by a mechanism corresponding to phase variation. J Bacteriol 2003; 185:2285-95.

54. Mongodin E, Bajolet O, Cutrona J, et al. Fibronectin-binding proteins of *Staphylococcus aureus* are involved in adherence to human airway epithelium. Infect Immun 2002; 70:620-30.
55. Murphy T F. *Branhamella catarrhalis*: epidemiology, surface antigenic structure, and immune response. Microbiol Rev 1996; 60:267-79.
56. Murphy T F, Brauer A L, Aebi C and Sethi S. Identification of surface antigens of *Moraxella catarrhalis* as targets of human serum antibody responses in chronic obstructive pulmonary disease. Infect Immun 2005; 73:3471-8.
57. Närkiö-Mäkelä, M., J. Jero, and S. Meri 1999. Complement activation and expression of membrane regulators in the middle ear mucosa in otitis media with effusion. *Clin. Exp. Immunol.* 116:401-409.
58. Nordstrom T, Blom A M, Forsgren A and Riesbeck K. The emerging pathogen *Moraxella catarrhalis* Interacts with complement inhibitor C4b binding protein through ubiquitous surface proteins A1 and A2. J Immunol 2004; 173:4598-606.
59. Nordstrom T, Forsgren A and Riesbeck K. The immunoglobulin D-binding part of the outer membrane protein MID from *Moraxella catarrhalis* comprises 238 amino acids and a tetrameric structure. J Biol Chem 2002; 277:34692-9.
60. Nordstrom T, Blom A M, Tan T T, Forsgren A and Riesbeck K. Ionic binding of C3 to the human pathogen *Moraxella catarrhalis* is a unique mechanism for combating innate immunity. J Immunol 2005; MS#05-2213, in press.
61. Pearson M M, Lafontaine E R, Wagner N J, St Geme J W, 3rd and Hansen E J. A hag mutant of *Moraxella catarrhalis* strain O35E is deficient in hemagglutination, autoagglutination, and immunoglobulin D-binding activities. Infect Immun 2002; 70:4523-33.
62. Persson, C. G., I. Erjefält, U. Alkner, C. Baumgarten, L. Greiff, B. Gustafsson, A. Luts, U. Pipkorn, F. Sundler, C. Svensson et al. 1991. Plasma exudation as a first line respiratory mucosal defence. *Clin. Exp. Allergy* 21: 17-24.
63. Plotkowski M C, Tournier J M and Puchelle E. *Pseudomonas aeruginosa* strains possess specific adhesins for laminin. Infect Immun 1996; 64:600-5.
64. Prasadarao, N. V., A. M. Blom, B. O. Villoutreix, and L. C. Linsangan. 2002. A novel interaction of outer membrane protein A with C4b binding protein mediates serum resistance of *Escherichia coli* K1. *J. Immunol.* 169:6352-6360.
65. Ram, S., M. Cullinane, A. M. Blom, S. Gulati, D. P. McQuillen, B. G. Monks, C. O'Connell, R. Boden, C. Elkins, M. K. Pangburn, B. Dahlback, and P. A. Rice. 2001. Binding of C4b-binding protein to porin: a molecular mechanism of serum resistance of *Neisseria gonorrhoeae*. *J. Exp. Med.* 193:281-296.
66. Rautemaa, R., and S. Meri. 1999. Complement-resistance mechanisms of bacteria. *Microbes Infect.* 1:785-94.
67. Ren, B., A. J. Szalai, S. K. Hollingshead, D. E. Briles. 2004. Effects of PspA and antibodies to PspA on activation and deposition of complement on the pneumococcal surface. *Infect. Immun.* 72:114-122.
68. Rodríguez de Córdoba, S., J. Esparza-Gordillo, E. Goicoechea de Jorge, M. Lopez-Trascasa, and P. Sánchez-Corral. 2004. The human complement factor H: functional roles, genetic variations and disease associations. *Mol. Immunol.* 41:355-367
69. Roger P, Puchelle E, Bajolet-Laudinat O, et al. Fibronectin and alpha5beta1 integrin mediate binding of *Pseudomonas aeruginosa* to repairing airway epithelium. Eur Respir J 1999; 13:1301-9.
70. Roggenkamp A, Ackermann N, Jacobi C A, Truelzsch K, Hoffmann H and Heesemann J. Molecular analysis of transport and oligomerization of the *Yersinia enterocolitica* adhesin YadA. J Bacteriol 2003; 185:3735-44.
71. Rozalska B, Wadstrom T. Protective opsonic activity of antibodies against fibronectin-binding proteins (FnBPs) of *Staphylococcus aureus*. Scand J Immunol 1993; 37:575-80.
72. Saxena, A., and R. Calderone. 1990. Purification and characterization of the extracellular C3d-binding protein of *Candida albicans*. *Infect. Immun.* 58:309-314.
73. Schwarz-Linek U, Werner J M, Pickford A R, et al. Pathogenic bacteria attach to human fibronectin through a tandem beta-zipper. Nature 2003; 423:177-81.
74. Sethi, S., and T. F. Murphy. 2001. Bacterial infection in chronic obstructive pulmonary disease in 2000: a state-of-the-art review. *Clin. Microbiol. Rev.* 14:336-363.
75. Shimizu, T., T. Harada, Y. Majima, and Y. Sakakura. 1988. Bactericidal activity of middle ear effusion on a single isolate of non-typable *Haemophilus influenzae*. *Int. J. Pediatr. Otorhinolaryngol.* 16:211-217.
76. Tack, B. F., R. A. Harrison, J. Janatova, M. L. Thomas, and J. W. Prahl. 1980. Evidence for presence of an internal thiolester bond in third component of human complement. *Proc. Natl. Acad. Sci. U.S.A.* 77: 5764-5768.
77. Talay S R, Valentin-Weigand P, Jerlstrom P G, Timmis K N and Chhatwal G S. Fibronectin-binding protein of *Streptococcus* pyogenes: sequence of the binding domain involved in adherence of streptococci to epithelial cells. Infect Immun 1992; 60:3837-44.
78. Tan, T. T., T. Nordström, A. Forsgren, and K. Riesbeck. 2005. The Respiratory Pathogen *Moraxella catarrhalis* Adheres to Epithelial Cells by Interacting with Fibronectin through Ubiquitous Surface Proteins A1 and A2. *J. Infect. Dis.*, MS#33893, in press.
79. Tenner, A. J., P. H. Lesavre, and N. R. Cooper. 1981. Purification and radiolabeling of human C1q. *J. Immunol.* 127:648-653.
80. Thern, A., L. Stenberg, B. Dahlbäck, and G. Lindahl. 1995. Ig-binding surface proteins of *Streptococcus* pyogenes also bind human C4b-binding protein (C4BP), a regulatory component of the complement system. *J. Immunol.* 154:375-386.
81. Timpe J M, Holm M M, Vanlerberg S L, Basrur V and Lafontaine E R. Identification of a *Moraxella catarrhalis* outer membrane protein exhibiting both adhesin and lipolytic activities. Infect Immun 2003; 71:4341-50.
82. Tu, A. H., R. L. Fulgham, M. A. McCrory, D. E. Briles, A. J. Szalai. 1999. Pneumococcal surface protein A inhibits complement activation by *Streptococcus pneumoniae*. *Infect. Immun.* 67:4720.
83. Unhanand, M., I. Maciver, O. Ramilo, O. Arencibia-Mireles, J. C. Argyle, G. H. McCracken Jr, and E. J. Hansen. 1992. Pulmonary clearance of *Moraxella catarrhalis* in an animal model. *J. Infect. Dis.* 165:644-650.
84. Verduin C M, Hol C, Fleer A, van Dijk H and van Belkum A. *Moraxella catarrhalis*: from emerging to established pathogen. Clin Microbiol Rev 2002; 15:125-44.
85. Walport, M. J. 2001. Complement. First of two parts. *N. Engl. J. Med.* 344:1058-1066.

86. Walport, M. J. 2001. Complement. Second of two parts. *N. Engl. J. Med.* 344:1140-1144.
87. Wang H, Liu X, Umino T, et al. Effect of cigarette smoke on fibroblast-mediated gel contraction is dependent on cell density. Am J Physiol Lung Cell Mol Physiol 2003; 284:L205-13.
88. Wurzner, R. 1999. Evasion of pathogens by avoiding recognition or eradication by complement, in part via molecular mimicry. *Mol. Immunol.* 36:249-260.
89. Zipfel, P. F., C. Skerka, J. Hellwage, S. T. Jokiranta, S. Meri, V. Brade, P. Kraiczy, M. Noris, and G. Remuzzi. 2001. Factor H family proteins: on complement, microbes and human diseases. *Biochem. Soc. Trans.* 30:971-978.

SEQUENCE LISTING

<160> NUMBER OF SEQ ID NOS: 88

<210> SEQ ID NO 1
<211> LENGTH: 31
<212> TYPE: PRT
<213> ORGANISM: Moraxella catarrhalis

<400> SEQUENCE: 1

Asp Gln Lys Ala Asp Ile Asp Asn Asn Ile Asn Asn Ile Tyr Glu Leu
 1               5                  10                  15

Ala Gln Gln Gln Asp Gln His Ser Ser Asp Ile Lys Thr Leu Lys
             20                  25                  30

<210> SEQ ID NO 2
<211> LENGTH: 154
<212> TYPE: PRT
<213> ORGANISM: Moraxella catarrhalis

<400> SEQUENCE: 2

Thr Gly Asn Gly Thr Val Ser Val Gly Lys Lys Gly Lys Glu Arg Gln
 1               5                  10                  15

Ile Val His Val Gly Ala Gly Glu Ile Ser Asp Thr Asp Ala Val Asn
             20                  25                  30

Gly Ser Gln Leu His Val Leu Ala Thr Val Val Ala Gln Asn Lys Ala
         35                  40                  45

Asp Ile Lys Asp Leu Asp Asp Glu Val Gly Leu Leu Gly Glu Glu Ile
     50                  55                  60

Asn Ser Leu Glu Gly Glu Ile Phe Asn Asn Gln Asp Ala Ile Ala Lys
 65                  70                  75                  80

Asn Gln Ala Asp Ile Lys Thr Leu Glu Ser Asn Val Glu Glu Gly Leu
                 85                  90                  95

Leu Asp Leu Ser Gly Arg Leu Leu Ser Thr Asp Gln Lys Ala Asp Ile
            100                 105                 110

Asp Asn Asn Ile Asn Asn Ile Tyr Glu Leu Ala Gln Gln Gln Asp Gln
        115                 120                 125

His Ser Ser Asp Ile Lys Thr Leu Lys Asn Asn Val Glu Glu Gly Leu
    130                 135                 140

Leu Asp Leu Ser Gly Arg Leu Ile Asp Gln
145                 150

<210> SEQ ID NO 3
<211> LENGTH: 154
<212> TYPE: PRT
<213> ORGANISM: Moraxella catarrhalis

<400> SEQUENCE: 3

Lys Asp Ala Ile Ala Lys Asn Asn Glu Ser Ile Glu Asp Leu Tyr Asp
 1               5                  10                  15

Phe Gly His Glu Val Ala Glu Ser Ile Gly Glu Ile His Ala His Asn
             20                  25                  30

Glu Ala Gln Asn Glu Thr Leu Lys Gly Leu Ile Thr Asn Ser Ile Glu
         35                  40                  45

```
Asn Thr Asn Asn Ile Thr Lys Asn Lys Ala Asp Ile Gln Ala Leu Glu
            50                  55                  60

Asn Asn Val Val Glu Leu Phe Asn Leu Ser Gly Arg Leu Ile Asp
 65                  70                  75                  80

Gln Lys Ala Asp Ile Asp Asn Asn Ile Asn Asn Ile Tyr Glu Leu Ala
                 85                  90                  95

Gln Gln Gln Asp Gln His Ser Ser Asp Ile Lys Thr Leu Lys Lys Asn
            100                 105                 110

Val Glu Glu Gly Leu Leu Glu Leu Ser Asp His Ile Ile Asp Gln Lys
            115                 120                 125

Thr Asp Ile Ala Gln Asn Gln Ala Asn Ile Gln Asp Leu Ala Thr Tyr
            130                 135                 140

Asn Glu Leu Gln Asp Gln Tyr Ala Gln Lys
145                 150
```

<210> SEQ ID NO 4
<211> LENGTH: 721
<212> TYPE: PRT
<213> ORGANISM: Moraxella catarrhalis

<400> SEQUENCE: 4

```
Lys Val Gly Lys Ala Thr Asn Lys Ile Ser Gly Gly Asp Asn Asn Thr
  1               5                  10                  15

Ala Asn Gly Thr Tyr Leu Thr Ile Gly Gly Asp Tyr Asn Lys Thr
                 20                  25                  30

Lys Gly Arg Tyr Ser Thr Ile Gly Gly Gly Leu Phe Asn Glu Ala Thr
             35                  40                  45

Asn Glu Tyr Ser Thr Ile Gly Ser Gly Tyr Asn Lys Ala Lys Gly
 50                  55                  60

Arg Tyr Ser Thr Ile Gly Gly Gly Tyr Asn Glu Ala Thr Asn Gln
 65                  70                  75                  80

Tyr Ser Thr Ile Gly Gly Gly Asp Asn Asn Thr Ala Lys Gly Arg Tyr
                 85                  90                  95

Ser Thr Ile Gly Gly Gly Gly Tyr Asn Glu Ala Thr Ile Glu Asn Ser
            100                 105                 110

Thr Val Gly Gly Gly Gly Tyr Asn Gln Ala Lys Gly Arg Asn Ser Thr
            115                 120                 125

Val Ala Gly Gly Tyr Asn Asn Glu Ala Thr Gly Thr Asp Ser Thr Ile
            130                 135                 140

Ala Gly Gly Arg Lys Asn Gln Ala Thr Gly Lys Gly Ser Phe Ala Ala
145                 150                 155                 160

Gly Ile Asp Asn Lys Ala Asn Ala Asp Asn Ala Val Ala Leu Gly Asn
                165                 170                 175

Lys Asn Thr Ile Glu Gly Glu Asn Ser Val Ala Ile Gly Ser Asn Asn
            180                 185                 190

Thr Val Lys Lys Gly Gln Gln Asn Val Phe Ile Leu Gly Ser Asn Thr
            195                 200                 205

Asp Thr Thr Asn Ala Gln Asn Gly Ser Val Leu Leu Gly His Asn Thr
            210                 215                 220

Ala Gly Lys Ala Ala Thr Ile Val Asn Ser Ala Glu Val Gly Gly Leu
225                 230                 235                 240

Ser Leu Thr Gly Phe Ala Gly Ala Ser Lys Thr Gly Asn Gly Thr Val
                245                 250                 255

Ser Val Gly Lys Lys Gly Lys Glu Arg Gln Ile Val His Val Gly Ala
```

-continued

```
                260                 265                 270
Gly Glu Ile Ser Asp Thr Ser Thr Asp Ala Val Asn Gly Ser Gln Leu
            275                 280                 285
His Val Leu Ala Thr Val Val Ala Gln Asn Lys Ala Asp Ile Lys Asp
        290                 295                 300
Leu Asp Asp Glu Val Gly Leu Leu Gly Glu Ile Asn Ser Leu Glu
305                 310                 315                 320
Gly Glu Ile Phe Asn Asn Gln Asp Ala Ile Ala Lys Asn Gln Ala Asp
                325                 330                 335
Ile Lys Thr Leu Glu Ser Asn Val Glu Glu Gly Leu Leu Asp Leu Ser
            340                 345                 350
Gly Arg Leu Leu Asp Gln Lys Ala Asp Ile Asp Asn Asn Ile Asn Asn
        355                 360                 365
Ile Tyr Glu Leu Ala Gln Gln Gln Asp Gln His Ser Ser Asp Ile Lys
    370                 375                 380
Thr Leu Lys Asn Asn Val Glu Glu Gly Leu Leu Asp Leu Ser Gly Arg
385                 390                 395                 400
Leu Ile Asp Gln Lys Ala Asp Leu Thr Lys Asp Ile Lys Ala Leu Glu
                405                 410                 415
Ser Asn Val Glu Glu Gly Leu Leu Asp Leu Ser Gly Arg Leu Ile Asp
            420                 425                 430
Gln Lys Ala Asp Ile Ala Lys Asn Gln Ala Asp Ile Ala Gln Asn Gln
        435                 440                 445
Thr Asp Ile Gln Asp Leu Ala Ala Tyr Asn Glu Leu Gln Asp Ala Tyr
    450                 455                 460
Ala Lys Gln Gln Thr Glu Ala Ile Asp Ala Leu Asn Lys Ala Ser Ser
465                 470                 475                 480
Ala Asn Thr Asp Arg Ile Ala Thr Ala Glu Leu Gly Ile Ala Glu Asn
                485                 490                 495
Lys Lys Asp Ala Gln Ile Ala Lys Ala Gln Ala Asn Glu Asn Lys Asp
            500                 505                 510
Gly Ile Ala Lys Asn Gln Ala Asp Ile Gln Leu His Asp Lys Lys Ile
        515                 520                 525
Thr Asn Leu Gly Ile Leu His Ser Met Val Ala Arg Ala Val Gly Asn
    530                 535                 540
Asn Thr Gln Gly Val Ala Thr Asn Lys Ala Asp Ile Ala Lys Asn Gln
545                 550                 555                 560
Ala Asp Ile Ala Asn Asn Ile Lys Asn Ile Tyr Glu Leu Ala Gln Gln
                565                 570                 575
Gln Asp Gln His Ser Ser Asp Ile Lys Thr Leu Ala Lys Val Ser Ala
            580                 585                 590
Ala Asn Thr Asp Arg Ile Ala Lys Asn Lys Ala Glu Ala Asp Ala Ser
        595                 600                 605
Phe Glu Thr Leu Thr Lys Asn Gln Asn Thr Leu Ile Glu Gln Gly Glu
    610                 615                 620
Ala Leu Val Glu Gln Asn Lys Ala Ile Asn Gln Leu Glu Gly Phe
625                 630                 635                 640
Ala Ala His Ala Asp Val Gln Asp Lys Gln Ile Leu Gln Asn Gln Ala
                645                 650                 655
Asp Ile Thr Thr Asn Lys Thr Ala Ile Glu Gln Asn Ile Asn Arg Thr
            660                 665                 670
Val Ala Asn Gly Phe Glu Ile Glu Lys Asn Lys Ala Gly Ile Ala Thr
        675                 680                 685
```

```
Asn Lys Gln Glu Leu Ile Leu Gln Asn Asp Arg Leu Asn Arg Ile Asn
            690                 695                 700

Glu Thr Asn Asn His Gln Asp Gln Lys Ile Asp Gln Leu Gly Tyr Ala
705                 710                 715                 720

Leu

<210> SEQ ID NO 5
<211> LENGTH: 443
<212> TYPE: PRT
<213> ORGANISM: Moraxella catarrhalis

<400> SEQUENCE: 5

Lys Val Gly Lys Ala Thr Asn Lys Ile Ser Gly Gly Asp Asn Asn Thr
1               5                   10                  15

Ala Asn Gly Thr Tyr Leu Thr Ile Gly Gly Asp Tyr Asn Lys Thr
            20                  25                  30

Lys Gly Arg Tyr Ser Thr Ile Gly Gly Leu Phe Asn Glu Ala Thr
            35                  40                  45

Asn Glu Tyr Ser Thr Ile Gly Ser Gly Gly Tyr Asn Lys Ala Lys Gly
        50                  55                  60

Arg Tyr Ser Thr Ile Gly Gly Gly Tyr Asn Glu Ala Thr Asn Gln
65                  70                  75                  80

Tyr Ser Thr Ile Gly Gly Gly Asp Asn Asn Thr Ala Lys Gly Arg Tyr
                85                  90                  95

Ser Thr Ile Gly Gly Gly Gly Tyr Asn Glu Ala Thr Ile Glu Asn Ser
            100                 105                 110

Thr Val Gly Gly Gly Gly Tyr Asn Gln Ala Lys Gly Arg Asn Ser Thr
        115                 120                 125

Val Ala Gly Gly Tyr Asn Asn Glu Ala Thr Gly Thr Asp Ser Thr Ile
130                 135                 140

Ala Gly Gly Arg Lys Asn Gln Ala Thr Gly Lys Gly Ser Phe Ala Ala
145                 150                 155                 160

Gly Ile Asp Asn Lys Ala Asn Ala Asp Asn Ala Val Ala Leu Gly Asn
                165                 170                 175

Lys Asn Thr Ile Glu Gly Glu Asn Ser Val Ala Ile Gly Ser Asn Asn
            180                 185                 190

Thr Val Lys Lys Gly Gln Gln Asn Val Phe Ile Leu Gly Ser Asn Thr
        195                 200                 205

Asp Thr Thr Asn Ala Gln Asn Gly Ser Val Leu Leu Gly His Asn Thr
210                 215                 220

Ala Gly Lys Ala Ala Thr Ile Val Asn Ser Ala Glu Val Gly Gly Leu
225                 230                 235                 240

Ser Leu Thr Gly Phe Ala Gly Ala Ser Lys Thr Gly Asn Gly Thr Val
                245                 250                 255

Ser Val Gly Lys Lys Gly Lys Glu Arg Gln Ile Val His Val Gly Ala
            260                 265                 270

Gly Glu Ile Ser Asp Thr Ser Thr Asp Ala Val Asn Gly Ser Gln Leu
        275                 280                 285

His Val Leu Ala Thr Val Val Ala Gln Asn Lys Ala Asp Ile Lys Asp
290                 295                 300

Leu Asp Asp Glu Val Gly Leu Leu Gly Glu Glu Ile Asn Ser Leu Glu
305                 310                 315                 320

Gly Glu Ile Phe Asn Asn Gln Asp Ala Ile Ala Lys Asn Gln Ala Asp
                325                 330                 335
```

```
Ile Lys Thr Leu Glu Ser Asn Val Glu Glu Gly Leu Leu Asp Leu Ser
            340                 345                 350

Gly Arg Leu Leu Asp Gln Lys Ala Asp Ile Asp Asn Ile Asn Asn
            355                 360                 365

Ile Tyr Glu Leu Ala Gln Gln Asp Gln His Ser Ser Asp Ile Lys
    370                 375                 380

Thr Leu Lys Asn Asn Val Glu Glu Gly Leu Leu Asp Leu Ser Gly Arg
385                 390                 395                 400

Leu Ile Asp Gln Lys Ala Asp Leu Thr Lys Asp Ile Lys Ala Leu Glu
                405                 410                 415

Ser Asn Val Glu Glu Gly Leu Leu Asp Leu Ser Gly Arg Leu Ile Asp
            420                 425                 430

Gln Lys Ala Asp Ile Ala Lys Asn Gln Ala Asp
            435                 440
```

<210> SEQ ID NO 6
<211> LENGTH: 510
<212> TYPE: PRT
<213> ORGANISM: Moraxella catarrhalis

<400> SEQUENCE: 6

```
Gln Ala Lys Asn Asp Ile Thr Leu Glu Asp Leu Pro Tyr Leu Ile Lys
  1               5                  10                  15

Lys Ile Asp Gln Asn Glu Leu Glu Ala Asp Ile Gly Asp Ile Thr Ala
                 20                  25                  30

Leu Glu Lys Tyr Leu Ala Leu Ser Gln Tyr Gly Asn Ile Leu Ala Leu
             35                  40                  45

Glu Glu Leu Asn Lys Ala Leu Glu Glu Leu Asp Glu Asp Val Gly Trp
         50                  55                  60

Asn Gln Asn Asp Ile Ala Asn Leu Glu Asp Asp Val Glu Thr Leu Thr
 65                  70                  75                  80

Lys Asn Gln Asn Ala Phe Ala Glu Gln Gly Glu Ala Ile Lys Glu Asp
                 85                  90                  95

Leu Gln Gly Leu Ala Asp Phe Val Glu Gly Gln Glu Gly Lys Ile Leu
                100                 105                 110

Gln Asn Glu Thr Ser Ile Lys Lys Asn Thr Gln Arg Asn Leu Val Asn
            115                 120                 125

Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
    210                 215                 220

Asn Asn Ile Tyr Glu Leu Ala Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Asp His Ile Ile Asp Gln Lys Thr Asp Ile Ala Gln Asn Gln Ala Asn
```

```
            260                 265                 270
Ile Gln Asp Leu Ala Thr Tyr Asn Glu Leu Gln Asp Gln Tyr Ala Gln
            275                 280                 285

Lys Gln Thr Glu Ala Ile Asp Ala Leu Asn Lys Ala Ser Ser Glu Asn
            290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
            325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Ala Glu Ala Ile Asp Ala Leu Asn
            355                 360                 365

Lys Ala Ser Ser Glu Asn Thr Gln Asn Ile Ala Lys Asn Gln Ala Asp
            370                 375                 380

Ile Ala Asn Asn Ile Thr Asn Ile Tyr Glu Leu Ala Gln Gln Gln Asp
385                 390                 395                 400

Lys His Arg Ser Asp Ile Lys Thr Leu Ala Lys Thr Ser Ala Ala Asn
            405                 410                 415

Thr Asp Arg Ile Ala Lys Asn Lys Ala Asp Asp Ala Ser Phe Glu
            420                 425                 430

Thr Leu Thr Lys Asn Gln Asn Thr Leu Ile Glu Lys Asp Lys Glu His
            435                 440                 445

Asp Lys Leu Ile Thr Ala Asn Lys Thr Ala Ile Asp Ala Asn Lys Ala
            450                 455                 460

Ser Ala Asp Thr Lys Phe Ala Ala Thr Ala Asp Ala Phe Thr Lys Asn
465                 470                 475                 480

Gly Asn Ala Ile Thr Lys Asn Ala Lys Ser Ile Thr Asp Leu Gly Thr
            485                 490                 495

Lys Val Asp Gly Phe Asp Ser Arg Val Thr Ala Leu Asp Thr
            500                 505                 510

<210> SEQ ID NO 7
<211> LENGTH: 322
<212> TYPE: PRT
<213> ORGANISM: Moraxella catarrhalis

<400> SEQUENCE: 7

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Phe Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
            115                 120                 125
```

```
Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
                180                 185                 190

Ala Asp Ile Gln Ala Leu Glu Asn Val Val Glu Glu Leu Phe Asn
            195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Asp His Ile Ile Asp Gln Lys Thr Asp Ile Ala Gln Asn Gln Ala Asn
                260                 265                 270

Ile Gln Asp Leu Ala Thr Tyr Asn Glu Leu Gln Asp Gln Tyr Ala Gln
                275                 280                 285

Lys Gln Thr Glu Ala Ile Asp Ala Leu Asn Lys Ala Ser Ser Glu Asn
                290                 295                 300

Thr Gln Asn Ile Glu Asp Leu Ala Ala Tyr Asn Glu Leu Gln Asp Ala
305                 310                 315                 320

Tyr Ala

<210> SEQ ID NO 8
<211> LENGTH: 148
<212> TYPE: PRT
<213> ORGANISM: Moraxella catarrhalis

<400> SEQUENCE: 8

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
            35                  40                  45

Glu Glu Leu Asn Lys Ala Leu Glu Glu Leu Asp Glu Asp Val Gly Trp
        50                  55                  60

Asn Gln Asn Asp Ile Ala Asn Leu Glu Asp Asp Val Glu Thr Leu Thr
65                  70                  75                  80

Lys Asn Gln Asn Ala Phe Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
130                 135                 140

Ser Ile Glu Asp
145

<210> SEQ ID NO 9
<211> LENGTH: 340
```

<212> TYPE: PRT
<213> ORGANISM: Moraxella catarrhalis

<400> SEQUENCE: 9

```
Asn Glu Thr Leu Lys Gly Leu Ile Thr Asn Ser Ile Glu Asn Thr Asn
 1               5                  10                  15

Asn Ile Thr Lys Asn Lys Ala Asp Ile Gln Ala Leu Glu Asn Asn Val
             20                  25                  30

Val Glu Glu Leu Phe Asn Leu Ser Gly Arg Leu Ile Asp Gln Lys Ala
         35                  40                  45

Asp Ile Asp Asn Asn Ile Asn Asn Ile Tyr Glu Leu Ala Gln Gln Gln
     50                  55                  60

Asp Gln His Ser Ser Asp Ile Lys Thr Leu Lys Lys Asn Val Glu Glu
 65                  70                  75                  80

Gly Leu Leu Glu Leu Ser Asp His Ile Ile Asp Gln Lys Thr Asp Ile
                 85                  90                  95

Ala Gln Asn Gln Ala Asn Ile Gln Asp Leu Ala Thr Tyr Asn Glu Leu
            100                 105                 110

Gln Asp Gln Tyr Ala Gln Lys Gln Thr Glu Ala Ile Asp Ala Leu Asn
        115                 120                 125

Lys Ala Ser Ser Glu Asn Thr Gln Asn Ile Glu Asp Leu Ala Ala Tyr
130                 135                 140

Asn Glu Leu Gln Asp Ala Tyr Ala Lys Gln Gln Thr Glu Ala Ile Asp
145                 150                 155                 160

Ala Leu Asn Lys Ala Ser Ser Glu Asn Thr Gln Asn Ile Glu Asp Leu
                165                 170                 175

Ala Ala Tyr Asn Glu Leu Gln Asp Ala Tyr Ala Lys Gln Gln Ala Glu
            180                 185                 190

Ala Ile Asp Ala Leu Asn Lys Ala Ser Ser Glu Asn Thr Gln Asn Ile
        195                 200                 205

Ala Lys Asn Gln Ala Asp Ile Ala Asn Asn Ile Thr Asn Ile Tyr Glu
210                 215                 220

Leu Ala Gln Gln Gln Asp Lys His Arg Ser Asp Ile Lys Thr Leu Ala
225                 230                 235                 240

Lys Thr Ser Ala Ala Asn Thr Asp Arg Ile Ala Lys Asn Lys Ala Asp
                245                 250                 255

Asp Asp Ala Ser Phe Glu Thr Leu Thr Lys Asn Gln Asn Thr Leu Ile
            260                 265                 270

Glu Lys Asp Lys Glu His Asp Lys Leu Ile Thr Ala Asn Lys Thr Ala
        275                 280                 285

Ile Asp Ala Asn Lys Ala Ser Ala Asp Thr Lys Phe Ala Ala Thr Ala
290                 295                 300

Asp Ala Phe Thr Lys Asn Gly Asn Ala Ile Thr Lys Asn Ala Lys Ser
305                 310                 315                 320

Ile Thr Asp Leu Gly Thr Lys Val Asp Gly Phe Asp Ser Arg Val Thr
                325                 330                 335

Ala Leu Asp Thr
            340
```

<210> SEQ ID NO 10
<211> LENGTH: 157
<212> TYPE: PRT
<213> ORGANISM: Moraxella catarrhalis

<400> SEQUENCE: 10

```
Ile Gln Asp Leu Ala Thr Tyr Asn Glu Leu Gln Asp Gln Tyr Ala Gln
 1               5                  10                  15

Lys Gln Thr Glu Ala Ile Asp Ala Leu Asn Lys Ala Ser Ser Glu Asn
            20                  25                  30

Thr Gln Asn Ile Glu Asp Leu Ala Ala Tyr Asn Glu Leu Gln Asp Ala
        35                  40                  45

Tyr Ala Lys Gln Gln Thr Glu Ala Ile Asp Ala Leu Asn Lys Ala Ser
 50                  55                  60

Ser Glu Asn Thr Gln Asn Ile Glu Asp Leu Ala Ala Tyr Asn Glu Leu
 65                  70                  75                  80

Gln Asp Ala Tyr Ala Lys Gln Gln Ala Glu Ala Ile Asp Ala Leu Asn
            85                  90                  95

Lys Ala Ser Ser Glu Asn Thr Gln Asn Ile Ala Lys Asn Gln Ala Asp
        100                 105                 110

Ile Ala Asn Asn Ile Thr Asn Ile Tyr Glu Leu Ala Gln Gln Gln Asp
        115                 120                 125

Lys His Arg Ser Asp Ile Lys Thr Leu Ala Lys Thr Ser Ala Ala Asn
        130                 135                 140

Thr Asp Arg Ile Ala Lys Asn Lys Ala Asp Asp Ala
145                 150                 155

<210> SEQ ID NO 11
<211> LENGTH: 922
<212> TYPE: PRT
<213> ORGANISM: Moraxella catarrhalis

<400> SEQUENCE: 11

Met Asn Lys Ile Tyr Lys Val Lys Lys Asn Ala Ala Gly His Leu Val
 1               5                  10                  15

Ala Cys Ser Glu Phe Ala Lys Gly His Thr Lys Lys Ala Val Leu Gly
            20                  25                  30

Ser Leu Leu Ile Val Gly Ile Leu Gly Met Ala Thr Thr Ala Ser Ala
        35                  40                  45

Gln Lys Ala Ala Asn Thr Thr Asn Gln Ala Ser Gly Arg His Thr Tyr
 50                  55                  60

Val Gly Gly Gly Asp Asn Asn Gln Ala Thr Gly Met Tyr Ser Phe Ile
 65                  70                  75                  80

Gly Gly Gly Phe Phe Asn Gln Ala Thr Gly Asn His Leu Thr Ile Gly
            85                  90                  95

Gly Gly Ser Ala Asn Gln Ala Lys Gly Asn Tyr Ser Thr Ile Gly Gly
        100                 105                 110

Gly Asp Gly Asn Glu Thr Thr Gly Thr His Ser Thr Ile Gly Gly Gly
        115                 120                 125

Asp Ser Asn Lys Ala Glu Gly Thr His Ser Thr Ile Gly Gly Gly Tyr
        130                 135                 140

Asp Asn Thr Ala Lys Gly Thr His Ser Thr Ile Val Gly Gly Arg Lys
145                 150                 155                 160

Asn Arg Ala Glu Gly Asn Tyr Ser Thr Val Ala Gly Gly Asp Asn Asn
                165                 170                 175

Gln Ala Thr Gly Asn Asn Ser Thr Val Val Gly Gly Ser Lys Asn Gln
            180                 185                 190

Ala Thr Gly Ala Gly Ser Phe Ala Ala Gly Val Glu Asn Gln Ala Lys
        195                 200                 205

Thr Glu Asn Ala Val Ala Leu Gly Asn Lys Asn Thr Ile Gly Gly Thr
        210                 215                 220
```

```
Asn Ser Val Ala Ile Gly Ser Asn Asn Thr Val Glu Asp Gly Lys Gln
225                 230                 235                 240

Asp Val Phe Ile Leu Gly Ser Asn Thr Thr Asn Ala Gln Ser Gly Ser
            245                 250                 255

Val Leu Leu Gly Asn Asn Thr Ser Gly Lys Ala Ala Thr Ala Val Ser
        260                 265                 270

Ser Ala Thr Val Gly Arg Leu Lys Leu Thr Gly Phe Ala Gly Val Ser
    275                 280                 285

Gln Ala Asn Gln Ala Asn Ser Gly Thr Val Ser Val Gly Ser Ala Gly
290                 295                 300

Ser Glu Arg Gln Ile Val Asn Val Gly Ala Gly Gln Ile Ser Ala Thr
305                 310                 315                 320

Ser Thr Asp Ala Val Asn Gly Ser Gln Leu His Ala Leu Ala Thr Ala
                325                 330                 335

Val Ser Gln Asn Gln Asp Asn Ile Leu Thr Asn Arg Val Asp Ile Gln
            340                 345                 350

Glu Leu Lys Arg Lys Gln Glu Asn Asp Ile Lys Glu Val Val Glu Met
        355                 360                 365

Gln Asn Ala Ile Ala Glu Gln Ala Asp Ile Asn Lys Asn His Ile Gln
370                 375                 380

Asp Leu Ala Lys Ala Gln Leu Ala Gly Val Ala Val Met Glu Glu Leu
385                 390                 395                 400

Asp Lys His Val Glu Asp Leu Tyr Glu Ala Thr Asn Glu Asn Leu Asp
                405                 410                 415

Lys Ile Ser Gln Leu Asp Gly Ala Val Phe Asn Asn Thr Gln Asn Ile
            420                 425                 430

Glu Asp Leu Ala Ala Tyr Asn Glu Leu Gln Asp Ala Tyr Ala Lys Gln
        435                 440                 445

Gln Thr Glu Ala Ile Asp Ala Leu Asn Lys Ala Ser Ser Glu Asn Thr
450                 455                 460

Gln Asn Ile Ala Lys Asn Ser Asn His Ile Lys Thr Leu Glu Ser Asn
465                 470                 475                 480

Val Glu Glu Glu Leu Leu Asn Leu Ser Gly Arg Leu Ile Asp Gln Lys
                485                 490                 495

Ala Asp Ile Asp Asn Asn Ile Asn His Ile Tyr Glu Leu Ala Gln Gln
            500                 505                 510

Gln Asp Gln His Ser Ser Asp Ile Lys Thr Leu Lys Asn Asn Val Glu
        515                 520                 525

Glu Gly Leu Leu Asp Leu Ser Gly Arg Leu Ile Asp Gln Lys Ala Asp
530                 535                 540

Ile Ala Lys Asn Gln Ala Asp Ile Ala Gln Asn Gln Thr Asp Ile Gln
545                 550                 555                 560

Asp Leu Ala Ala Tyr Asn Glu Leu Gln Asp Ala Tyr Ala Lys Gln Gln
                565                 570                 575

Thr Glu Ala Ile Asp Ala Leu Asn Lys Ala Ser Ser Ala Asn Thr Asp
            580                 585                 590

Arg Ile Ala Thr Ala Glu Leu Gly Ile Ala Glu Asn Lys Lys Asp Ala
        595                 600                 605

Gln Ile Ala Lys Ala Gln Ala Asn Glu Asn Lys Asp Gly Ile Ala Lys
610                 615                 620

Asn Gln Ala Asp Ile Gln Leu His Asp Lys Lys Ile Thr Asn Leu Gly
625                 630                 635                 640
```

Ile Leu His Ser Met Val Ala Arg Ala Val Gly Asn Asn Thr Gln Gly
            645                 650                 655

Val Ala Thr Asn Lys Ala Asp Ile Ala Lys Asn Gln Ala Asp Ile Ala
        660                 665                 670

Asn Asn Ile Lys Asn Ile Tyr Glu Leu Ala Gln Gln Asp Gln His
    675                 680                 685

Ser Ser Asp Ile Lys Thr Leu Ala Lys Val Ser Ala Ala Asn Thr Asp
690                 695                 700

Arg Ile Ala Lys Asn Lys Ala Glu Ala Asp Ser Phe Glu Thr Leu
705                 710                 715                 720

Thr Lys Asn Gln Asn Thr Leu Ile Glu Gln Gly Glu Ala Leu Val Glu
                725                 730                 735

Gln Asn Lys Ala Ile Asn Gln Glu Leu Glu Gly Phe Ala Ala His Ala
            740                 745                 750

Asp Val Gln Asp Lys Gln Ile Leu Gln Asn Gln Ala Asp Ile Thr Thr
        755                 760                 765

Asn Lys Thr Ala Ile Glu Gln Asn Ile Asn Arg Thr Val Ala Asn Gly
    770                 775                 780

Phe Glu Ile Glu Lys Asn Lys Ala Gly Ile Ala Thr Asn Lys Gln Glu
785                 790                 795                 800

Leu Ile Leu Gln Asn Asp Arg Leu Asn Arg Ile Asn Glu Thr Asn Asn
                805                 810                 815

His Gln Asp Gln Lys Ile Asp Gln Leu Gly Tyr Ala Leu Lys Glu Gln
            820                 825                 830

Gly Gln His Phe Asn Asn Arg Ile Ser Ala Val Glu Arg Gln Thr Ala
        835                 840                 845

Gly Gly Ile Ala Asn Ala Ile Ala Ile Ala Thr Leu Pro Ser Pro Ser
    850                 855                 860

Arg Ala Gly Glu His His Val Leu Phe Gly Ser Gly Tyr His Asn Gly
865                 870                 875                 880

Gln Ala Ala Val Ser Leu Gly Ala Gly Leu Ser Asp Thr Gly Lys
                885                 890                 895

Ser Thr Tyr Lys Ile Gly Leu Ser Trp Ser Asp Ala Gly Gly Leu Ser
            900                 905                 910

Gly Gly Val Gly Gly Ser Tyr Arg Trp Lys
        915                 920

<210> SEQ ID NO 12
<211> LENGTH: 913
<212> TYPE: PRT
<213> ORGANISM: Moraxella catarrhalis

<400> SEQUENCE: 12

Met Asn Lys Ile Tyr Lys Val Lys Lys Asn Ala Ala Gly His Leu Val
1               5                   10                  15

Ala Cys Ser Glu Phe Ala Lys Gly His Thr Lys Lys Ala Val Leu Gly
            20                  25                  30

Ser Leu Leu Ile Val Gly Ile Leu Gly Met Ala Thr Thr Ala Ser Ala
        35                  40                  45

Gln Ala Ile Asn Thr Gly Gln Gly Thr Val Val Asp Gln Asn Gly Asn
    50                  55                  60

Glu Ala Ile Gly Asn Tyr Ser Thr Ala Ser Gly Gly Asp Tyr Asn Gln
65                  70                  75                  80

Ala Lys Gly Asn Tyr Ser Thr Ala Ser Gly Gly Ser Gly Asn Thr Ala
                85                  90                  95

-continued

```
Glu Gly Asn Tyr Ser Thr Ala Ser Gly Gly Leu Gly Asn Thr Ala Glu
                100                 105                 110

Gly Asn Tyr Ser Thr Ala Ser Gly Gly Leu Gly Asn Thr Ala Lys Gly
            115                 120                 125

Lys Tyr Ser Thr Val Ala Gly Gly Ala Asn Gln Ala Lys Gly Asp
130                 135                 140

Tyr Ser Thr Ala Ser Gly Gly Ser Gly Asn Thr Ala Glu Gly Asn Tyr
145                 150                 155                 160

Ser Thr Val Ala Gly Gly Lys Asn Asn Gln Ala Thr Gly Leu Asn Ser
                165                 170                 175

Thr Val Ala Gly Gly Ser Asp Asn Gln Ala Thr Gly Thr Gly Ser Phe
                180                 185                 190

Ala Ala Gly Val Gly Asn Lys Ala Asn Ala Glu Asn Ala Val Ala Leu
                195                 200                 205

Gly Asn Lys Asn Thr Ile Glu Gly Glu Asn Ser Val Ala Ile Gly Ser
                210                 215                 220

Asn Asn Thr Val Glu Thr Gly Lys Glu Asn Val Phe Ile Leu Gly Ser
225                 230                 235                 240

Gly Thr Thr Gly Val Thr Ser Asn Ser Val Leu Leu Gly Asn Lys Thr
                245                 250                 255

Ala Gly Lys Glu Ala Thr Ala Val Asn Asp Ala Thr Val Asn Gly Leu
                260                 265                 270

Thr Leu Lys Asn Phe Ala Gly Val Ser Lys Thr Gly Asn Gly Thr Val
                275                 280                 285

Ser Val Gly Ser Glu Asn His Glu Arg Gln Ile Val Asn Val Gly Ala
                290                 295                 300

Gly Lys Ile Ser Ala Asp Ser Thr Asp Ala Val Asn Gly Ser Gln Leu
305                 310                 315                 320

His Ala Leu Ala Thr Val Val Ala Lys Asn Lys Ser Asp Ile Thr Lys
                325                 330                 335

Asn Gln Ala Glu Thr Leu Val Asn Arg Val Asn Ile Lys Glu Leu Glu
                340                 345                 350

Arg Lys Gln Glu Asn Asp Ile Lys Glu Val Val Glu Met Gln Asn Ala
                355                 360                 365

Ile Ala Glu Gln Ala Asp Lys Asn Lys Asn His Ile Gln Asp Leu Ala
                370                 375                 380

Lys Ala Gln Leu Ala Gly Val Thr Val Met Glu Glu Leu Asn Lys His
385                 390                 395                 400

Val Glu Asp Leu Tyr Glu Ala Thr Asn Asp Asn Leu Asp Lys Ile Ser
                405                 410                 415

Gln Leu Asp Gly Ala Val Phe Asn Asn Thr Gln Asn Ile Ala Lys Asn
                420                 425                 430

Ser Asn His Ile Lys Thr Leu Glu Asn Asn Val Glu Glu Glu Leu Leu
                435                 440                 445

Asn Leu Ser Gly Arg Leu Leu Asp Gln Lys Ala Asp Ile Asp Asn Asn
                450                 455                 460

Ile Asn Asn Ile Tyr Glu Leu Ala Gln Gln Asp Gln His Ser Ser
465                 470                 475                 480

Asp Ile Lys Thr Leu Lys Asn Asn Val Glu Glu Gly Leu Leu Asp Leu
                485                 490                 495

Ser Gly Arg Leu Ile Asp Gln Lys Ala Asp Leu Thr Lys Asp Ile Lys
                500                 505                 510
```

Ala Leu Glu Asn Asn Val Glu Glu Gly Leu Leu Asp Leu Ser Gly Arg
            515                 520                 525

Leu Ile Asp Gln Lys Ala Asp Ile Ala Lys Asn Gln Ala Asp Ile Ala
530                 535                 540

Gln Asn Gln Thr Asp Ile Gln Asp Leu Ala Ala Tyr Asn Glu Leu Gln
545                 550                 555                 560

Asp Ala Tyr Ala Lys Gln Gln Thr Glu Ala Ile Asp Ala Leu Asn Lys
                565                 570                 575

Ala Ser Ser Ala Asn Thr Asp Arg Ile Ala Thr Ala Glu Leu Gly Ile
            580                 585                 590

Ala Glu Asn Lys Lys Asp Ala Gln Ile Ala Lys Ala Gln Ala Asn Glu
        595                 600                 605

Asn Lys Asp Gly Ile Ala Lys Asn Gln Ala Asp Ile Gln Leu His Asp
    610                 615                 620

Lys Lys Ile Thr Asn Leu Gly Ile Leu His Ser Met Val Ala Arg Ala
625                 630                 635                 640

Val Gly Asn Asn Thr Gln Gly Val Ala Thr Asn Lys Ala Asp Ile Ala
                645                 650                 655

Lys Asn Gln Ala Asp Ile Ala Asn Asn Ile Lys Asn Ile Tyr Glu Leu
            660                 665                 670

Ala Gln Gln Gln Asp Gln His Ser Ser Asp Ile Lys Thr Leu Ala Lys
        675                 680                 685

Val Ser Ala Ala Asn Thr Asp Arg Ile Ala Lys Asn Lys Ala Glu Ala
    690                 695                 700

Asp Ala Ser Phe Glu Thr Leu Thr Lys Asn Gln Asn Thr Leu Ile Glu
705                 710                 715                 720

Gln Gly Glu Ala Leu Val Glu Gln Asn Lys Ala Ile Asn Gln Glu Leu
                725                 730                 735

Glu Gly Phe Ala Ala His Ala Asp Val Gln Asp Lys Gln Ile Leu Gln
            740                 745                 750

Asn Gln Ala Asp Ile Thr Thr Asn Lys Thr Ala Ile Glu Gln Asn Ile
        755                 760                 765

Asn Arg Thr Val Ala Asn Gly Phe Glu Ile Glu Lys Asn Lys Ala Gly
    770                 775                 780

Ile Ala Thr Asn Lys Gln Glu Leu Ile Leu Gln Asn Asp Arg Leu Asn
785                 790                 795                 800

Arg Ile Asn Glu Thr Asn Asn Arg Gln Asp Gln Lys Ile Asp Gln Leu
                805                 810                 815

Gly Tyr Ala Leu Lys Glu Gln Gly Gln His Phe Asn Asn Arg Ile Ser
            820                 825                 830

Ala Val Glu Arg Gln Thr Ala Gly Gly Ile Ala Asn Ala Ile Ala Ile
        835                 840                 845

Ala Thr Leu Pro Ser Pro Ser Arg Ala Gly Glu His Val Leu Phe
850                 855                 860

Gly Ser Gly Tyr His Asn Gly Gln Ala Ala Val Ser Leu Gly Ala Ala
865                 870                 875                 880

Gly Leu Ser Asp Thr Gly Lys Ser Thr Tyr Lys Ile Gly Leu Ser Trp
                885                 890                 895

Ser Asp Ala Gly Gly Leu Ser Gly Val Gly Gly Ser Tyr Arg Trp
            900                 905                 910

Lys

<210> SEQ ID NO 13

```
<211> LENGTH: 863
<212> TYPE: PRT
<213> ORGANISM: Moraxella catarrhalis

<400> SEQUENCE: 13
```

| | | | | | | | | | | | | | | |
|---|---|---|---|---|---|---|---|---|---|---|---|---|---|---|
|Met|Asn|Lys|Ile|Tyr|Lys|Val|Lys|Lys|Asn|Ala|Ala|Gly|His|Leu|Val|
|1| | | |5| | | | |10| | | | |15|
|Ala|Cys|Ser|Glu|Phe|Ala|Lys|Gly|His|Thr|Lys|Lys|Ala|Val|Leu|Gly|
| | | |20| | | | |25| | | | |30| | |
|Ser|Leu|Leu|Ile|Val|Gly|Ile|Leu|Gly|Met|Ala|Thr|Ala|Ser|Ala|
| | |35| | | | |40| | | | |45| | |
|Gln|Lys|Val|Gly|Lys|Ala|Thr|Asn|Lys|Ile|Ser|Gly|Gly|Asp|Asn|Asn|
| |50| | | | |55| | | | |60| | | | |
|Thr|Ala|Asn|Gly|Thr|Tyr|Leu|Thr|Ile|Gly|Gly|Asp|Tyr|Asn|Lys|
|65| | | | |70| | | | |75| | | | |80|
|Thr|Lys|Gly|Arg|Tyr|Ser|Thr|Ile|Gly|Gly|Leu|Phe|Asn|Glu|Ala|
| | | | |85| | | | |90| | | | |95| |
|Thr|Asn|Glu|Tyr|Ser|Thr|Ile|Gly|Ser|Gly|Gly|Tyr|Asn|Lys|Ala|Lys|
| | | |100| | | | |105| | | | |110| | |
|Gly|Arg|Tyr|Ser|Thr|Ile|Gly|Gly|Gly|Tyr|Asn|Glu|Ala|Thr|Asn|
| | |115| | | | |120| | | | |125| | | |
|Gln|Tyr|Ser|Thr|Ile|Gly|Gly|Gly|Asp|Asn|Asn|Thr|Ala|Lys|Gly|Arg|
| |130| | | | |135| | | | |140| | | | |
|Tyr|Ser|Thr|Ile|Gly|Gly|Gly|Tyr|Asn|Glu|Ala|Thr|Ile|Glu|Asn|
|145| | | | |150| | | | |155| | | | |160|
|Ser|Thr|Val|Gly|Gly|Gly|Tyr|Asn|Gln|Ala|Lys|Gly|Arg|Asn|Ser|
| | | | |165| | | | |170| | | | |175| |
|Thr|Val|Ala|Gly|Gly|Tyr|Asn|Asn|Glu|Ala|Thr|Gly|Thr|Asp|Ser|Thr|
| | | |180| | | | |185| | | | |190| | |
|Ile|Ala|Gly|Gly|Arg|Lys|Asn|Gln|Ala|Thr|Gly|Lys|Gly|Ser|Phe|Ala|
| | |195| | | | |200| | | | |205| | | |
|Ala|Gly|Ile|Asp|Asn|Lys|Ala|Asn|Ala|Asp|Asn|Ala|Val|Ala|Leu|Gly|
| |210| | | | |215| | | | |220| | | | |
|Asn|Lys|Asn|Thr|Ile|Glu|Gly|Glu|Asn|Ser|Val|Ala|Ile|Gly|Ser|Asn|
|225| | | | |230| | | | |235| | | | |240|
|Asn|Thr|Val|Lys|Lys|Gly|Gln|Gln|Asn|Val|Phe|Ile|Leu|Gly|Ser|Asn|
| | | | |245| | | | |250| | | | |255| |
|Thr|Asp|Thr|Thr|Asn|Ala|Gln|Asn|Gly|Ser|Val|Leu|Leu|Gly|His|Asn|
| | | |260| | | | |265| | | | |270| | |
|Thr|Ala|Gly|Lys|Ala|Ala|Thr|Ile|Val|Asn|Ser|Ala|Glu|Val|Gly|Gly|
| | |275| | | | |280| | | | |285| | | |
|Leu|Ser|Leu|Thr|Gly|Phe|Ala|Gly|Ala|Ser|Lys|Thr|Gly|Asn|Gly|Thr|
| |290| | | | |295| | | | |300| | | | |
|Val|Ser|Val|Gly|Lys|Lys|Gly|Lys|Glu|Arg|Gln|Ile|Val|His|Val|Gly|
|305| | | | |310| | | | |315| | | | |320|
|Ala|Gly|Glu|Ile|Ser|Asp|Thr|Ser|Thr|Asp|Ala|Val|Asn|Gly|Ser|Gln|
| | | | |325| | | | |330| | | | |335| |
|Leu|His|Ala|Leu|Ala|Thr|Val|Val|Ala|Gln|Asn|Lys|Ala|Asp|Ile|Lys|
| | | |340| | | | |345| | | | |350| | |
|Asp|Leu|Asp|Asp|Glu|Val|Gly|Leu|Gly|Glu|Glu|Ile|Asn|Ser|Leu|
| | |355| | | | |360| | | | |365| | | |
|Glu|Gly|Glu|Ile|Phe|Asn|Asn|Gln|Asp|Ala|Ile|Ala|Lys|Asn|Gln|Ala|
| |370| | | | |375| | | | |380| | | | |
|Asp|Ile|Lys|Thr|Leu|Glu|Ser|Asn|Val|Glu|Glu|Gly|Leu|Leu|Asp|Leu|

-continued

```
            385                 390                 395                 400
        Ser Gly Arg Leu Leu Asp Gln Lys Ala Asp Ile Asp Asn Asn Ile Asn
                    405                 410                 415
        Asn Ile Tyr Glu Leu Ala Gln Gln Asp Gln His Ser Ser Asp Ile
                    420                 425                 430
        Lys Thr Leu Lys Asn Asn Val Glu Glu Gly Leu Leu Asp Leu Ser Gly
                    435                 440                 445
        Arg Leu Ile Asp Gln Lys Ala Asp Leu Thr Lys Asp Ile Lys Ala Leu
        450                 455                 460
        Glu Ser Asn Val Glu Glu Gly Leu Leu Asp Leu Ser Gly Arg Leu Ile
        465                 470                 475                 480
        Asp Gln Lys Ala Asp Ile Ala Lys Asn Gln Ala Asp Ile Ala Gln Asn
                    485                 490                 495
        Gln Thr Asp Ile Gln Asp Leu Ala Ala Tyr Asn Glu Leu Gln Asp Ala
                    500                 505                 510
        Tyr Ala Lys Gln Gln Thr Glu Ala Ile Asp Ala Leu Asn Lys Ala Ser
                    515                 520                 525
        Ser Ala Asn Thr Asp Arg Ile Ala Thr Ala Glu Leu Gly Ile Ala Glu
                    530                 535                 540
        Asn Lys Lys Asp Ala Gln Ile Ala Lys Ala Gln Ala Asn Glu Asn Lys
        545                 550                 555                 560
        Asp Gly Ile Ala Lys Asn Gln Ala Asp Ile Gln Leu His Asp Lys Lys
                    565                 570                 575
        Ile Thr Asn Leu Gly Ile Leu His Ser Met Val Ala Arg Ala Val Gly
                    580                 585                 590
        Asn Asn Thr Gln Gly Val Ala Thr Asn Lys Ala Asp Ile Ala Lys Asn
                    595                 600                 605
        Gln Ala Asp Ile Ala Asn Asn Ile Lys Asn Ile Tyr Glu Leu Ala Gln
                    610                 615                 620
        Gln Gln Asp Gln His Ser Ser Asp Ile Lys Thr Leu Ala Lys Val Ser
        625                 630                 635                 640
        Ala Ala Asn Thr Asp Arg Ile Ala Lys Asn Lys Ala Glu Ala Asp Ala
                    645                 650                 655
        Ser Phe Glu Thr Leu Thr Lys Asn Gln Asn Thr Leu Ile Glu Gln Gly
                    660                 665                 670
        Glu Ala Leu Val Glu Gln Asn Lys Ala Ile Asn Gln Glu Leu Glu Gly
                    675                 680                 685
        Phe Ala Ala His Ala Asp Val Gln Asp Lys Gln Ile Leu Gln Asn Gln
                    690                 695                 700
        Ala Asp Ile Thr Thr Asn Lys Thr Ala Ile Glu Gln Asn Ile Asn Arg
        705                 710                 715                 720
        Thr Val Ala Asn Gly Phe Glu Ile Glu Lys Asn Lys Ala Gly Ile Ala
                    725                 730                 735
        Thr Asn Lys Gln Glu Leu Ile Leu Gln Asn Asp Arg Leu Asn Arg Ile
                    740                 745                 750
        Asn Glu Thr Asn Asn His Gln Asp Gln Lys Ile Asp Gln Leu Gly Tyr
                    755                 760                 765
        Ala Leu Lys Glu Gln Gly Gln His Phe Asn Asn Arg Ile Ser Ala Val
                    770                 775                 780
        Glu Arg Gln Thr Ala Gly Gly Ile Ala Asn Ala Ile Ala Ile Ala Thr
        785                 790                 795                 800
        Leu Pro Ser Pro Ser Arg Ala Gly Glu His His Val Leu Phe Gly Ser
                    805                 810                 815
```

```
Gly Tyr His Asn Gly Gln Ala Ala Val Ser Leu Gly Ala Ala Gly Leu
                820                 825                 830

Ser Asp Thr Gly Lys Ser Thr Tyr Lys Ile Gly Leu Ser Trp Ser Asp
            835                 840                 845

Ala Gly Gly Leu Ser Gly Val Gly Gly Ser Tyr Arg Trp Lys
    850                 855                 860
```

<210> SEQ ID NO 14
<211> LENGTH: 892
<212> TYPE: PRT
<213> ORGANISM: Moraxella catarrhalis

<400> SEQUENCE: 14

```
Met Asn Lys Ile Tyr Lys Val Lys Asn Ala Ala Gly His Leu Val
  1               5                  10                  15

Ala Cys Ser Glu Phe Ala Lys Gly His Thr Lys Lys Ala Val Leu Gly
                 20                  25                  30

Ser Leu Leu Ile Val Gly Ala Leu Gly Met Ala Thr Thr Ala Ser Ala
             35                  40                  45

Gln Ala Thr Lys Gly Thr Gly Lys His Val Val Asp Asn Lys Asp Asn
         50                  55                  60

Lys Ala Lys Gly Asp Tyr Ser Thr Ala Ser Gly Gly Lys Asp Asn Glu
 65                  70                  75                  80

Ala Lys Gly Asn Tyr Ser Thr Val Gly Gly Asp Tyr Asn Glu Ala
                 85                  90                  95

Lys Gly Asn Tyr Ser Thr Val Gly Gly Ser Ser Asn Thr Ala Lys
                100                 105                 110

Gly Glu Lys Ser Thr Ile Gly Gly Asp Thr Asn Asp Ala Asn Gly
            115                 120                 125

Thr Tyr Ser Thr Ile Gly Gly Tyr Tyr Ser Arg Ala Ile Gly Asp
        130                 135                 140

Ser Ser Thr Ile Gly Gly Tyr Tyr Asn Gln Ala Thr Gly Glu Lys
145                 150                 155                 160

Ser Thr Val Ala Gly Gly Arg Asn Asn Gln Ala Thr Gly Asn Asn Ser
                165                 170                 175

Thr Val Ala Gly Gly Ser Tyr Asn Gln Ala Thr Gly Asn Asn Ser Thr
            180                 185                 190

Val Ala Gly Gly Ser His Asn Gln Ala Thr Gly Glu Gly Ser Phe Ala
        195                 200                 205

Ala Gly Val Glu Asn Lys Ala Asn Ala Asn Asn Ala Val Ala Leu Gly
    210                 215                 220

Lys Asn Asn Thr Ile Asp Gly Asp Asn Ser Val Ala Ile Gly Ser Asn
225                 230                 235                 240

Asn Thr Ile Asp Ser Gly Lys Gln Asn Val Phe Ile Leu Gly Ser Ser
                245                 250                 255

Thr Asn Thr Asn Ala Gln Ser Gly Ser Val Leu Leu Gly His Asn
            260                 265                 270

Thr Ala Gly Lys Lys Ala Thr Ala Val Ser Ser Ala Lys Val Asn Gly
        275                 280                 285

Leu Thr Leu Gly Asn Phe Ala Gly Ala Ser Lys Thr Gly Asn Gly Thr
    290                 295                 300

Val Ser Val Gly Ser Glu Asn Asn Glu Arg Gln Ile Val Asn Val Gly
305                 310                 315                 320

Ala Gly Asn Ile Ser Ala Asp Ser Thr Asp Ala Val Asn Gly Ser Gln
```

```
            325                 330                 335
Leu Tyr Ala Leu Ala Thr Ala Val Lys Ala Asp Ala Asp Glu Asn Phe
            340                 345                 350

Lys Ala Leu Thr Lys Thr Gln Asn Thr Leu Ile Glu Gln Gly Glu Ala
            355                 360                 365

Gln Asp Ala Leu Ile Ala Gln Asn Gln Thr Asp Ile Thr Ala Asn Lys
            370                 375                 380

Thr Ala Ile Glu Arg Asn Phe Asn Arg Thr Val Val Asn Gly Phe Glu
385                 390                 395                 400

Ile Glu Lys Asn Lys Ala Gly Ile Ala Lys Asn Gln Ala Asp Ile Gln
            405                 410                 415

Thr Leu Glu Asn Asn Val Gly Glu Glu Leu Leu Asn Leu Ser Gly Arg
            420                 425                 430

Leu Leu Asp Gln Lys Ala Asp Ile Asp Asn Asn Ile Asn Asn Ile Tyr
            435                 440                 445

Asp Leu Ala Gln Gln Gln Asp Gln His Ser Ser Asp Ile Lys Thr Leu
450                 455                 460

Lys Lys Asn Val Glu Glu Gly Leu Leu Asp Leu Ser Gly Arg Leu Ile
465                 470                 475                 480

Asp Gln Lys Ala Asp Leu Thr Lys Asp Ile Lys Thr Leu Glu Asn Asn
            485                 490                 495

Val Glu Glu Gly Leu Leu Asp Leu Ser Gly Arg Leu Ile Asp Gln Lys
            500                 505                 510

Ala Asp Ile Ala Lys Asn Gln Ala Asp Ile Ala Gln Asn Gln Thr Asp
            515                 520                 525

Ile Gln Asp Leu Ala Ala Tyr Asn Glu Leu Gln Asp Gln Tyr Ala Gln
            530                 535                 540

Lys Gln Thr Glu Ala Ile Asp Ala Leu Asn Lys Ala Ser Ser Ala Asn
545                 550                 555                 560

Thr Asp Arg Ile Ala Thr Ala Glu Leu Gly Ile Ala Glu Asn Lys Lys
            565                 570                 575

Asp Ala Gln Ile Ala Lys Ala Gln Ala Asn Glu Asn Lys Asp Gly Ile
            580                 585                 590

Ala Lys Asn Gln Ala Asp Ile Gln Leu His Asp Lys Lys Ile Thr Asn
            595                 600                 605

Leu Gly Ile Leu His Ser Met Val Ala Arg Ala Val Gly Asn Asn Thr
            610                 615                 620

Gln Gly Val Ala Thr Asn Lys Ala Asp Ile Ala Lys Asn Gln Ala Asp
625                 630                 635                 640

Ile Ala Asn Asn Ile Lys Asn Ile Tyr Glu Leu Ala Gln Gln Gln Asp
            645                 650                 655

Gln His Ser Ser Asp Ile Lys Thr Leu Ala Lys Val Ser Ala Ala Asn
            660                 665                 670

Thr Asp Arg Ile Ala Lys Asn Lys Ala Glu Ala Asp Ala Ser Phe Glu
            675                 680                 685

Thr Leu Thr Lys Asn Gln Asn Thr Leu Ile Glu Gln Gly Glu Ala Leu
            690                 695                 700

Val Glu Gln Asn Lys Ala Ile Asn Gln Glu Leu Glu Gly Phe Ala Ala
705                 710                 715                 720

His Ala Asp Val Gln Asp Lys Gln Ile Leu Gln Asn Gln Ala Asp Ile
            725                 730                 735

Thr Thr Asn Lys Ala Ala Ile Glu Gln Asn Ile Asn Arg Thr Val Ala
            740                 745                 750
```

```
Asn Gly Phe Glu Ile Glu Lys Asn Lys Ala Gly Ile Ala Thr Asn Lys
        755                 760                 765

Gln Glu Leu Ile Leu Gln Asn Asp Arg Leu Asn Gln Ile Asn Glu Thr
770                 775                 780

Asn Asn Arg Gln Asp Gln Lys Ile Asp Gln Leu Gly Tyr Ala Leu Lys
785                 790                 795                 800

Glu Gln Gly Gln His Phe Asn Asn Arg Ile Ser Ala Val Glu Arg Gln
                805                 810                 815

Thr Ala Gly Gly Ile Ala Asn Ala Ile Ala Ile Ala Thr Leu Pro Ser
            820                 825                 830

Pro Ser Arg Ala Gly Glu His His Val Leu Phe Gly Ser Gly Tyr His
        835                 840                 845

Asn Gly Gln Ala Ala Val Ser Leu Gly Ala Ala Gly Leu Ser Asp Thr
850                 855                 860

Gly Lys Ser Thr Tyr Lys Ile Gly Leu Ser Trp Ser Asp Ala Gly Gly
865                 870                 875                 880

Leu Ser Gly Gly Val Gly Gly Ser Tyr Arg Trp Lys
                885                 890

<210> SEQ ID NO 15
<211> LENGTH: 873
<212> TYPE: PRT
<213> ORGANISM: Moraxella catarrhalis

<400> SEQUENCE: 15

Met Asn Lys Ile Tyr Lys Val Lys Lys Asn Ala Ala Gly His Leu Val
1               5                   10                  15

Ala Cys Ser Glu Phe Ala Lys Gly His Thr Lys Lys Ala Val Leu Gly
            20                  25                  30

Ser Leu Leu Ile Val Gly Ile Leu Gly Met Ala Thr Thr Ala Ser Ala
        35                  40                  45

Gln Gln Thr Ile Ala Arg Gln Gly Lys Gly Met His Ser Ile Ile Gly
    50                  55                  60

Gly Gly Asn Asp Asn Glu Ala Asn Gly Asp Tyr Ser Thr Val Ser Gly
65                  70                  75                  80

Gly Asp Tyr Asn Glu Ala Lys Gly Asp Ser Ser Thr Ile Gly Gly Gly
                85                  90                  95

Tyr Tyr Asn Glu Ala Asn Gly Asp Ser Ser Thr Ile Gly Gly Gly Phe
            100                 105                 110

Tyr Asn Glu Ala Lys Gly Glu Ser Ser Thr Ile Gly Gly Gly Asp Asn
        115                 120                 125

Asn Ser Ala Thr Gly Met Tyr Ser Thr Ile Gly Gly Gly Asp Asn Asn
    130                 135                 140

Ser Ala Thr Gly Arg Tyr Ser Thr Ile Ala Gly Gly Trp Leu Asn Gln
145                 150                 155                 160

Ala Thr Gly His Ser Ser Thr Val Ala Gly Gly Trp Leu Asn Gln Ala
                165                 170                 175

Thr Asn Glu Asn Ser Thr Val Gly Gly Gly Arg Phe Asn Gln Ala Thr
            180                 185                 190

Gly Arg Asn Ser Thr Val Ala Gly Gly Tyr Lys Asn Lys Ala Thr Gly
        195                 200                 205

Val Asp Ser Thr Ile Ala Gly Gly Arg Asn Asn Gln Ala Asn Gly Ile
    210                 215                 220

Gly Ser Phe Ala Ala Gly Ile Asp Asn Gln Ala Asn Ala Asn Asn Thr
```

```
            225                 230                 235                 240
    Val Ala Leu Gly Asn Lys Asn Ile Ile Lys Gly Lys Asp Ser Val Ala
                    245                 250                 255
    Ile Gly Ser Asn Asn Thr Val Glu Thr Gly Lys Glu Asn Val Phe Ile
                    260                 265                 270
    Leu Gly Ser Asn Thr Lys Asp Ala His Ser Asn Ser Val Leu Leu Gly
                    275                 280                 285
    Asn Glu Thr Thr Gly Lys Ala Ala Thr Val Glu Asn Ala Lys Val
            290                 295                 300
    Gly Gly Leu Ser Leu Thr Gly Phe Val Gly Ala Ser Lys Ala Asn Thr
    305                 310                 315                 320
    Asn Asn Gly Thr Val Ser Val Gly Lys Gln Gly Lys Glu Arg Gln Ile
                    325                 330                 335
    Val Asn Val Gly Ala Gly Gln Ile Arg Ala Asp Ser Thr Asp Ala Val
                    340                 345                 350
    Asn Gly Ser Gln Leu His Ala Leu Ala Thr Ala Val Asp Ala Glu Phe
                    355                 360                 365
    Arg Thr Leu Thr Gln Thr Gln Asn Ala Leu Ile Glu Gln Gly Glu Ala
            370                 375                 380
    Ile Asn Gln Glu Leu Glu Gly Leu Ala Asp Tyr Thr Asn Ala Gln Asp
    385                 390                 395                 400
    Glu Lys Ile Leu Lys Asn Gln Thr Asp Ile Thr Ala Asn Lys Thr Ala
                    405                 410                 415
    Ile Glu Gln Asn Phe Asn Arg Thr Val Thr Asn Gly Phe Glu Ile Glu
                    420                 425                 430
    Lys Asn Lys Ala Gly Ile Ala Lys Asn Gln Ala Asp Ile Gln Thr Leu
                    435                 440                 445
    Glu Asn Asp Val Gly Lys Glu Leu Leu Asn Leu Ser Gly Arg Leu Leu
            450                 455                 460
    Asp Gln Lys Ala Asp Ile Asp Asn Asn Ile Asn Asn Ile Tyr Glu Leu
    465                 470                 475                 480
    Ala Gln Gln Gln Asp Gln His Ser Ser Asp Ile Lys Thr Leu Lys Asn
                    485                 490                 495
    Asn Val Glu Glu Gly Leu Leu Asp Leu Ser Gly Arg Leu Ile Asp Gln
                    500                 505                 510
    Lys Ala Asp Leu Thr Lys Asp Ile Lys Ala Leu Glu Asn Asn Val Glu
                    515                 520                 525
    Glu Gly Leu Leu Asp Leu Ser Gly Arg Leu Ile Asp Gln Lys Ala Asp
            530                 535                 540
    Ile Ala Lys Asn Gln Ala Asp Ile Gln Asp Leu Ala Ala Tyr Asn Glu
    545                 550                 555                 560
    Leu Gln Asp Gln Tyr Ala Gln Lys Gln Thr Glu Ala Ile Asp Ala Leu
                    565                 570                 575
    Asn Lys Ala Ser Ser Ala Asn Thr Asp Arg Ile Ala Thr Ala Glu Leu
                    580                 585                 590
    Gly Ile Ala Glu Asn Lys Lys Asp Ala Gln Ile Ala Lys Ala Gln Ala
                    595                 600                 605
    Asn Glu Asn Lys Asp Gly Ile Ala Lys Asn Gln Ala Asp Ile Ala Asn
            610                 615                 620
    Asn Ile Lys Asn Ile Tyr Glu Leu Ala Gln Gln Gln Asp Gln His Ser
    625                 630                 635                 640
    Ser Asp Ile Lys Thr Leu Ala Lys Val Ser Ala Ala Asn Thr Asp Arg
                    645                 650                 655
```

-continued

Ile Ala Lys Asn Lys Ala Glu Ala Asp Ala Ser Phe Glu Thr Leu Thr
            660                 665                 670

Lys Asn Gln Asn Thr Leu Ile Glu Gln Gly Glu Ala Leu Val Glu Gln
        675                 680                 685

Asn Lys Ala Ile Asn Gln Glu Leu Glu Gly Phe Ala Ala His Ala Asp
    690                 695                 700

Val Gln Asp Lys Gln Ile Leu Gln Asn Gln Ala Asp Ile Thr Ala Asn
705                 710                 715                 720

Lys Thr Ala Ile Glu Gln Asn Ile Asn Arg Thr Val Ala Asn Gly Phe
                725                 730                 735

Glu Ile Glu Lys Asn Lys Ala Gly Ile Ala Thr Asn Lys Gln Glu Leu
            740                 745                 750

Ile Leu Gln His Asp Arg Leu Asn Arg Ile Asn Glu Thr Asn Asn Arg
        755                 760                 765

Gln Asp Gln Lys Ile Asp Gln Leu Gly Tyr Ala Leu Lys Glu Gln Gly
    770                 775                 780

Gln His Phe Asn Asn Arg Ile Ser Ala Val Glu Arg Gln Thr Ala Gly
785                 790                 795                 800

Gly Ile Ala Asn Ala Ile Ala Ile Ala Thr Leu Pro Ser Pro Ser Arg
                805                 810                 815

Ala Gly Glu His His Val Leu Phe Gly Ser Gly Tyr His Asn Gly Gln
            820                 825                 830

Ala Ala Val Ser Leu Gly Ala Ala Gly Leu Ser Asp Thr Gly Lys Ser
        835                 840                 845

Thr Tyr Lys Ile Gly Leu Ser Trp Ser Asp Ala Gly Gly Leu Ser Gly
    850                 855                 860

Gly Val Gly Gly Ser Tyr Arg Trp Lys
865                 870

<210> SEQ ID NO 16
<211> LENGTH: 832
<212> TYPE: PRT
<213> ORGANISM: Moraxella catarrhalis

<400> SEQUENCE: 16

Met Asn Lys Ile Tyr Lys Val Lys Lys Asn Ala Ala Gly His Leu Val
1               5                   10                  15

Ala Cys Ser Glu Phe Ala Lys Gly His Thr Lys Lys Ala Val Leu Gly
            20                  25                  30

Ser Leu Leu Ile Val Gly Ala Leu Gly Met Ala Thr Thr Ala Ser Ala
        35                  40                  45

Gln Ala Thr Asn Ser Lys Gly Thr Gly Ala His Ile Gly Val Asn Asn
    50                  55                  60

Asn Asn Glu Ala Pro Gly Asp Tyr Ser Phe Ile Gly Ser Gly Gly Tyr
65                  70                  75                  80

Asn Lys Ala Glu Gly Arg Tyr Ser Ala Ile Gly Gly Gly Leu Phe Asn
                85                  90                  95

Lys Ala Thr Asn Glu Tyr Ser Thr Ile Val Gly Gly Gly Tyr Asn Lys
            100                 105                 110

Ala Glu Gly Arg Tyr Ser Thr Ile Gly Gly Gly Ser Asn Asn Glu Ala
        115                 120                 125

Thr Asn Glu Tyr Ser Thr Ile Val Gly Gly Asp Asp Asn Lys Ala Thr
    130                 135                 140

Gly Arg Tyr Ser Thr Ile Gly Gly Gly Asp Asn Asn Thr Ala Glu Gly

```
            145                 150                 155                 160
Glu Tyr Ser Thr Val Ala Gly Lys Asn Asn Gln Ala Thr Gly Thr
                165                 170                 175
Gly Ser Phe Ala Ala Gly Val Glu Asn Gln Ala Asn Ala Glu Asn Ala
                180                 185                 190
Val Ala Val Gly Lys Lys Asn Ile Ile Glu Gly Glu Asn Ser Val Ala
                195                 200                 205
Ile Gly Ser Glu Asn Thr Val Lys Thr Glu His Lys Asn Val Phe Ile
210                 215                 220
Leu Gly Ser Gly Thr Thr Gly Val Thr Ser Asn Ser Val Leu Leu Gly
225                 230                 235                 240
Asn Glu Thr Ala Gly Lys Gln Ala Thr Thr Val Lys Asn Ala Glu Val
                245                 250                 255
Gly Gly Leu Ser Leu Thr Gly Phe Ala Gly Glu Ser Lys Ala Glu Asn
                260                 265                 270
Gly Val Val Ser Val Gly Ser Glu Gly Gly Glu Arg Gln Ile Val Asn
                275                 280                 285
Val Gly Ala Gly Gln Ile Ser Asp Thr Ser Thr Asp Ala Val Asn Gly
                290                 295                 300
Ser Gln Leu His Ala Leu Ala Thr Val Val Asp Asp Asn Gln Tyr Asp
305                 310                 315                 320
Ile Val Asn Asn Arg Ala Asp Ile Leu Asn Asn Gln Asp Asp Ile Lys
                325                 330                 335
Asp Leu Gln Lys Glu Val Lys Gly Leu Asp Asn Glu Val Gly Glu Leu
                340                 345                 350
Ser Arg Asp Ile Asn Ser Leu His Asp Val Thr Asp Asn Gln Gln Asp
                355                 360                 365
Asp Ile Lys Glu Leu Lys Arg Gly Val Lys Glu Leu Asp Asn Glu Val
                370                 375                 380
Gly Val Leu Ser Arg Asp Ile Asn Ser Leu His Asp Asp Val Ala Asp
385                 390                 395                 400
Asn Gln Asp Asp Ile Ala Lys Asn Lys Ala Asp Ile Lys Gly Leu Asn
                405                 410                 415
Lys Glu Val Lys Glu Leu Asp Lys Glu Val Gly Val Leu Ser Arg Asp
                420                 425                 430
Ile Gly Ser Leu His Asp Asp Val Ala Thr Asn Gln Ala Asp Ile Ala
                435                 440                 445
Lys Asn Gln Ala Asp Ile Lys Thr Leu Glu Asn Asn Val Glu Glu Glu
                450                 455                 460
Leu Leu Asn Leu Ser Gly Arg Leu Leu Asp Gln Lys Ala Asp Ile Asp
465                 470                 475                 480
Asn Asn Ile Asn Asn Ile Tyr Glu Leu Ala Gln Gln Asp Gln His
                485                 490                 495
Ser Ser Asp Ile Lys Thr Leu Lys Asn Asn Val Glu Glu Gly Leu Leu
                500                 505                 510
Asp Leu Ser Gly Arg Leu Ile Asp Gln Lys Ala Asp Ile Ala Lys Asn
                515                 520                 525
Gln Ala Asp Ile Ala Gln Asn Gln Thr Asp Ile Gln Asp Leu Ala Ala
                530                 535                 540
Tyr Asn Glu Leu Gln Asp Gln Tyr Ala Gln Lys Gln Thr Glu Ala Ile
545                 550                 555                 560
Asp Ala Leu Asn Lys Ala Ser Ser Glu Asn Thr Gln Asn Ile Ala Lys
                565                 570                 575
```

```
Asn Gln Ala Asp Ile Ala Asn Ile Asn Asn Ile Tyr Glu Leu Ala
            580                 585                 590

Gln Gln Gln Asp Gln His Ser Ser Asp Ile Lys Thr Leu Ala Lys Val
        595                 600                 605

Ser Ala Ala Asn Thr Asp Arg Ile Ala Lys Asn Lys Ala Glu Ala Asp
610                 615                 620

Ala Ser Phe Glu Thr Leu Thr Lys Asn Gln Asn Thr Leu Ile Glu Gln
625                 630                 635                 640

Gly Glu Ala Leu Val Glu Gln Asn Lys Ala Ile Asn Gln Glu Leu Glu
                645                 650                 655

Gly Phe Ala Ala His Ala Asp Ile Gln Asp Lys Gln Ile Leu Gln Asn
            660                 665                 670

Gln Ala Asp Ile Thr Thr Asn Lys Thr Ala Ile Glu Gln Asn Ile Asn
        675                 680                 685

Arg Thr Val Ala Asn Gly Phe Glu Ile Glu Lys Asn Lys Ala Gly Ile
690                 695                 700

Ala Thr Asn Lys Gln Glu Leu Ile Leu Gln Asn Asp Arg Leu Asn Arg
705                 710                 715                 720

Ile Asn Glu Thr Asn Asn Arg Gln Asp Gln Lys Ile Asp Gln Leu Gly
                725                 730                 735

Tyr Ala Leu Lys Glu Gln Gly Gln His Phe Asn Asn Arg Ile Ser Ala
            740                 745                 750

Val Glu Arg Gln Thr Ala Gly Gly Ile Ala Asn Ala Ile Ala Ile Ala
        755                 760                 765

Thr Leu Pro Ser Pro Ser Arg Ala Gly Glu His Val Leu Phe Gly
770                 775                 780

Ser Gly Tyr His Asn Gly Gln Ala Ala Val Ser Leu Gly Ala Ala Gly
785                 790                 795                 800

Leu Ser Asp Thr Gly Lys Ser Thr Tyr Lys Ile Gly Leu Ser Trp Ser
                805                 810                 815

Asp Ala Gly Gly Leu Ser Gly Gly Val Gly Ser Tyr Arg Trp Lys
            820                 825                 830

<210> SEQ ID NO 17
<211> LENGTH: 941
<212> TYPE: PRT
<213> ORGANISM: Moraxella catarrhalis

<400> SEQUENCE: 17

Met Asn Lys Ile Tyr Lys Val Lys Lys Asn Ala Ala Gly His Leu Val
1               5                   10                  15

Ala Cys Ser Glu Phe Ala Lys Gly His Thr Lys Lys Ala Val Leu Gly
            20                  25                  30

Ser Leu Leu Ile Val Gly Ile Leu Gly Met Ala Thr Ala Ser Ala
        35                  40                  45

Gln Met Ala Thr Thr Pro Ser Ala Gln Val Val Lys Thr Asn Asn Lys
    50                  55                  60

Lys Asn Gly Thr His Pro Phe Ile Gly Gly Asp Tyr Asn Thr Thr
65                  70                  75                  80

Lys Gly Asn Tyr Pro Thr Ile Gly Gly His Phe Asn Thr Ala Glu
                85                  90                  95

Gly Asn Tyr Ser Thr Val Gly Gly Phe Thr Asn Glu Ala Ile Gly
            100                 105                 110

Lys Asn Ser Thr Val Gly Gly Phe Thr Asn Glu Ala Met Gly Glu
```

```
                115                 120                 125
Tyr Ser Thr Val Ala Gly Gly Ala Asn Asn Gln Ala Lys Gly Asn Tyr
    130                 135                 140

Ser Thr Val Gly Gly Gly Asn Gly Asn Lys Ala Ile Gly Asn Asn Ser
145                 150                 155                 160

Thr Val Val Gly Gly Ser Asn Asn Gln Ala Lys Gly Glu His Ser Thr
                165                 170                 175

Ile Ala Gly Gly Lys Asn Asn Gln Ala Thr Gly Asn Gly Ser Phe Ala
            180                 185                 190

Ala Gly Val Glu Asn Lys Ala Asp Ala Asn Asn Ala Val Ala Leu Gly
                195                 200                 205

Asn Lys Asn Thr Ile Glu Gly Thr Asn Ser Val Ala Ile Gly Ser Asn
        210                 215                 220

Asn Thr Val Lys Thr Gly Lys Glu Asn Val Phe Ile Leu Gly Ser Asn
225                 230                 235                 240

Thr Asn Thr Glu Asn Ala Gln Ser Gly Ser Val Leu Leu Gly Asn Asn
                245                 250                 255

Thr Ala Gly Lys Ala Ala Thr Thr Val Asn Asn Ala Glu Val Asn Gly
                260                 265                 270

Leu Thr Leu Glu Asn Phe Ala Gly Ala Ser Lys Ala Asn Ala Asn Asn
        275                 280                 285

Ile Gly Thr Val Ser Val Gly Ser Glu Asn Asn Glu Arg Gln Ile Val
        290                 295                 300

Asn Val Gly Ala Gly Gln Ile Ser Ala Thr Ser Thr Asp Ala Val Asn
305                 310                 315                 320

Gly Ser Gln Leu His Ala Leu Ala Lys Ala Val Ala Lys Asn Lys Ser
                325                 330                 335

Asp Ile Lys Gly Leu Asn Lys Gly Val Lys Glu Leu Asp Lys Glu Val
                340                 345                 350

Gly Val Leu Ser Arg Asp Ile Asn Ser Leu His Asp Asp Val Ala Asp
                355                 360                 365

Asn Gln Asp Ser Ile Ala Lys Asn Lys Ala Asp Ile Lys Gly Leu Asn
        370                 375                 380

Lys Glu Val Lys Glu Leu Asp Lys Glu Val Gly Val Leu Ser Arg Asp
385                 390                 395                 400

Ile Gly Ser Leu His Asp Asp Val Ala Asp Asn Gln Asp Ser Ile Ala
                405                 410                 415

Lys Asn Lys Ala Asp Ile Lys Gly Leu Asn Lys Glu Val Lys Glu Leu
                420                 425                 430

Asp Lys Glu Val Gly Val Leu Ser Arg Asp Ile Gly Ser Leu His Asp
        435                 440                 445

Asp Val Ala Thr Asn Gln Ala Asp Ile Ala Lys Asn Gln Ala Asp Ile
        450                 455                 460

Lys Thr Leu Glu Asn Asn Val Glu Glu Leu Leu Asn Leu Ser Gly
465                 470                 475                 480

Arg Leu Ile Asp Gln Lys Ala Asp Ile Asp Asn Asn Ile Asn Asn Ile
                485                 490                 495

Tyr Glu Leu Ala Gln Gln Asp Gln His Ser Ser Asp Ile Lys Thr
                500                 505                 510

Leu Lys Asn Asn Val Glu Glu Gly Leu Leu Asp Leu Ser Gly Arg Leu
        515                 520                 525

Ile Asp Gln Lys Ala Asp Leu Thr Lys Asp Ile Lys Thr Leu Lys Asn
        530                 535                 540
```

```
Asn Val Glu Glu Gly Leu Leu Asp Leu Ser Gly Arg Leu Ile Asp Gln
545                 550                 555                 560

Lys Ala Asp Ile Ala Lys Asn Gln Ala Asp Ile Ala Gln Asn Gln Thr
                565                 570                 575

Asp Ile Gln Asp Leu Ala Ala Tyr Asn Glu Leu Gln Asp Gln Tyr Ala
                580                 585                 590

Gln Lys Gln Thr Glu Ala Ile Asp Ala Leu Asn Lys Ala Ser Ser Ala
                595                 600                 605

Asn Thr Asp Arg Ile Ala Thr Ala Glu Leu Gly Ile Ala Glu Asn Lys
610                 615                 620

Lys Asp Ala Gln Ile Ala Lys Ala Gln Ala Asn Glu Asn Lys Asp Gly
625                 630                 635                 640

Ile Ala Lys Asn Gln Ala Asp Ile Gln Leu His Asp Lys Lys Ile Thr
                645                 650                 655

Asn Leu Gly Ile Leu His Ser Met Val Ala Arg Ala Val Gly Asn Asn
                660                 665                 670

Thr Gln Gly Val Ala Thr Asn Lys Ala Asp Ile Ala Lys Asn Gln Ala
                675                 680                 685

Asp Ile Ala Asn Asn Ile Lys Asn Ile Tyr Glu Leu Ala Gln Gln Gln
690                 695                 700

Asp Gln His Ser Ser Asp Ile Lys Thr Leu Ala Lys Val Ser Ala Ala
705                 710                 715                 720

Asn Thr Asp Arg Ile Ala Lys Asn Lys Ala Glu Ala Asp Ala Ser Phe
                725                 730                 735

Glu Thr Leu Thr Lys Asn Gln Asn Thr Leu Ile Glu Gln Gly Glu Ala
                740                 745                 750

Leu Val Glu Gln Asn Lys Ala Ile Asn Gln Glu Leu Glu Gly Phe Ala
                755                 760                 765

Ala His Ala Asp Val Gln Asp Lys Gln Ile Leu Gln Asn Gln Ala Asp
                770                 775                 780

Ile Thr Thr Asn Lys Thr Ala Ile Glu Gln Asn Ile Asn Arg Thr Val
785                 790                 795                 800

Ala Asn Gly Phe Glu Ile Glu Lys Asn Lys Ala Gly Ile Ala Thr Asn
                805                 810                 815

Lys Gln Glu Leu Ile Leu Gln Asn Asp Arg Leu Asn Gln Ile Asn Glu
                820                 825                 830

Thr Asn Asn His Gln Asp Gln Lys Ile Asp Gln Leu Gly Tyr Ala Leu
                835                 840                 845

Lys Glu Gln Gly Gln His Phe Asn Asn Arg Ile Ser Ala Val Glu Arg
                850                 855                 860

Gln Thr Ala Gly Ile Ala Asn Ala Ile Ala Ile Ala Thr Leu Pro
865                 870                 875                 880

Ser Pro Ser Arg Ala Gly Glu His His Val Leu Phe Gly Ser Gly Tyr
                885                 890                 895

His Asn Gly Gln Ala Ala Val Ser Leu Gly Ala Ala Gly Leu Ser Asp
                900                 905                 910

Thr Gly Lys Ser Thr Tyr Lys Ile Gly Leu Ser Trp Ser Asp Ala Gly
                915                 920                 925

Gly Leu Ser Gly Gly Val Gly Gly Ser Tyr Arg Trp Lys
930                 935                 940

<210> SEQ ID NO 18
<211> LENGTH: 912
```

```
<212> TYPE: PRT
<213> ORGANISM: Moraxella catarrhalis

<400> SEQUENCE: 18

Met Asn Lys Ile Tyr Lys Val Lys Lys Asn Ala Ala Gly His Leu Val
  1               5                  10                  15

Ala Cys Ser Glu Phe Ala Lys Gly His Thr Lys Lys Ala Val Leu Gly
             20                  25                  30

Ser Leu Leu Ile Val Gly Ile Leu Gly Met Ala Thr Thr Ala Ser Ala
         35                  40                  45

Gln Gln Asn Asn Gln Lys Ser Gly Lys Tyr Pro Phe Ile Gly Gly Gly
     50                  55                  60

Gly Tyr Asn Asn Val Asp Gly Lys Tyr Pro Thr Ile Gly Gly Gly Leu
 65                  70                  75                  80

Phe Asn Ile Ala Asn Gly Lys Tyr Pro Thr Ile Gly Gly Gly Ala His
                 85                  90                  95

Asn Lys Ala Asn Gly Thr Tyr Ser Thr Ile Gly Gly Gly Ser Tyr Asn
            100                 105                 110

Glu Ala Asn Gly Glu Lys Ser Thr Ile Gly Gly Gly Asp Asn Asn Thr
        115                 120                 125

Ala Lys Gly Asn His Ser Thr Val Val Gly Gly Tyr Lys Asn Glu Ala
    130                 135                 140

Thr Gly Lys Tyr Ser Thr Val Gly Gly Gly Asn Ser Asn Lys Ala Glu
145                 150                 155                 160

Gly Thr Asp Ser Thr Ile Ala Gly Gly Lys Asn Asn Gln Ala Lys Gly
                165                 170                 175

Glu Gly Ser Phe Ala Ala Gly Val Glu Asn Lys Ala Asn Ala Glu Asn
            180                 185                 190

Ala Val Ala Val Gly Lys Lys Asn Ser Ile Glu Gly Lys Asp Ser Val
        195                 200                 205

Ala Ile Gly Ser Glu Asn Thr Val Glu Asn Asn Lys Gln Asn Val Phe
    210                 215                 220

Ile Leu Gly Ser Lys Thr Ser Gly Ala Gln Ser Asn Ser Val Leu Leu
225                 230                 235                 240

Gly Asn Glu Thr Thr Gly Lys Ala Ala Thr Thr Val Glu Asn Ala Glu
                245                 250                 255

Val Gly Gly Leu Ser Leu Thr Gly Phe Ala Gly Ala Ser Lys Ala Asn
            260                 265                 270

Ala Asn Ala Asn Ile Gly Thr Val Ser Val Gly Ser Gln Gly Lys Glu
        275                 280                 285

Arg Gln Ile Val Asn Val Gly Ala Gly Gln Ile Ser Ala Thr Ser Thr
    290                 295                 300

Asp Ala Val Asn Gly Ser Gln Leu His Ala Leu Ala Ser Thr Ile Asp
305                 310                 315                 320

Glu Glu Val Asp Leu Leu Gly Glu Ile Asn Ser Leu Glu Gly Glu
                325                 330                 335

Ile Phe Asn Asn Gln Asp Ala Ile Ala Lys Asn Gln Ala Asp Ile Ala
            340                 345                 350

Thr Asn Lys Thr Asn Ile Glu Thr Asn Gly Ser Lys Ile Thr Asn Leu
        355                 360                 365

Gly Thr Leu Tyr Ala Thr Val Thr Lys Ala Val Gly Asn Asn Thr Gln
    370                 375                 380

Gly Val Ala Ala Asn Lys Ala Asp Ile Thr Lys Asn Lys Ala Asp Ile
385                 390                 395                 400
```

```
Gln Asp Leu Asp Asp Glu Val Gly Val Leu Ser Gln Asp Ile Gly Ser
                405                 410                 415

Leu His Asp Asp Val Ala Thr Asn Gln Ala Asp Ile Ala Lys Asn Gln
            420                 425                 430

Ala Asp Ile Gln Thr Leu Glu Asn Asn Val Glu Glu Leu Leu Asn
        435                 440                 445

Leu Ser Gly Arg Leu Leu Asp Gln Lys Ala Asp Ile Asp Asn Asn Ile
    450                 455                 460

Asn Asn Ile Tyr Glu Leu Ala Gln Gln Gln Asp Gln His Ser Ser Asp
465                 470                 475                 480

Ile Lys Thr Leu Lys Asn Asn Val Glu Glu Gly Leu Leu Asp Leu Ser
                485                 490                 495

Gly Arg Leu Ile Asp Gln Lys Ala Asp Leu Thr Lys Asp Ile Lys Thr
            500                 505                 510

Leu Glu Ser Asn Val Glu Glu Gly Leu Leu Asp Leu Ser Gly Arg Leu
        515                 520                 525

Ile Asp Gln Lys Ala Asp Ile Ala Lys Asn Gln Ala Asp Ile Ala Gln
    530                 535                 540

Asn Gln Thr Asp Ile Gln Asp Leu Ala Ala Tyr Asn Glu Leu Gln Asp
545                 550                 555                 560

Gln Tyr Ala Gln Lys Gln Thr Glu Ala Ile Asp Ala Leu Asn Lys Ala
                565                 570                 575

Ser Ser Ala Asn Thr Asp Arg Ile Ala Thr Ala Glu Leu Gly Ile Ala
            580                 585                 590

Glu Asn Lys Lys Asp Ala Gln Ile Ala Lys Ala Gln Ala Asn Glu Asn
        595                 600                 605

Lys Asp Gly Ile Ala Lys Asn Gln Ala Asp Ile Gln Leu His Asp Lys
    610                 615                 620

Lys Ile Thr Asn Leu Gly Ile Leu His Ser Met Val Ala Arg Ala Val
625                 630                 635                 640

Gly Asn Asn Thr Gln Gly Val Ala Thr Asn Lys Ala Asp Ile Ala Lys
                645                 650                 655

Asn Gln Ala Asp Ile Ala Asn Asn Ile Lys Asn Ile Tyr Glu Leu Ala
            660                 665                 670

Gln Gln Gln Asp Gln His Ser Ser Asp Ile Lys Thr Leu Ala Lys Val
        675                 680                 685

Ser Ala Ala Asn Thr Asp Arg Ile Ala Lys Asn Lys Ala Glu Ala Asp
    690                 695                 700

Ala Ser Phe Glu Thr Leu Thr Lys Asn Gln Asn Thr Leu Ile Glu Gln
705                 710                 715                 720

Gly Glu Ala Leu Val Glu Gln Asn Lys Ala Ile Asn Gln Glu Leu Glu
                725                 730                 735

Gly Phe Ala Ala His Ala Asp Val Gln Asp Lys Gln Ile Leu Gln Asn
            740                 745                 750

Gln Ala Asp Ile Thr Thr Asn Lys Thr Ala Ile Glu Gln Asn Ile Asn
        755                 760                 765

Arg Thr Val Ala Asn Gly Phe Glu Ile Glu Lys Asn Lys Ala Gly Ile
    770                 775                 780

Ala Thr Asn Lys Gln Glu Leu Ile Leu Gln Asn Asp Arg Leu Asn Arg
785                 790                 795                 800

Ile Asn Glu Thr Asn Asn His Gln Asp Gln Lys Ile Asp Gln Leu Gly
                805                 810                 815
```

```
Tyr Ala Leu Lys Glu Gln Gly Gln His Phe Asn Asn Arg Ile Ser Ala
            820                 825                 830

Val Glu Arg Gln Thr Ala Gly Gly Ile Ala Asn Ala Ile Ala Ile Ala
        835                 840                 845

Thr Leu Pro Ser Pro Ser Arg Ala Gly Glu His His Val Leu Phe Gly
850                 855                 860

Ser Gly Tyr His Asn Gly Gln Ala Ala Val Ser Leu Gly Ala Ala Gly
865                 870                 875                 880

Leu Ser Asp Thr Gly Lys Ser Thr Tyr Lys Ile Gly Leu Ser Trp Ser
                885                 890                 895

Asp Ala Gly Gly Leu Ser Gly Gly Val Gly Gly Ser Tyr Arg Trp Lys
            900                 905                 910

<210> SEQ ID NO 19
<211> LENGTH: 877
<212> TYPE: PRT
<213> ORGANISM: Moraxella catarrhalis

<400> SEQUENCE: 19

Met Asn Lys Ile Tyr Lys Val Lys Lys Asn Ala Ala Gly His Ser Val
1               5                   10                  15

Ala Cys Ser Glu Phe Ala Lys Gly His Thr Lys Lys Ala Val Leu Gly
            20                  25                  30

Ser Leu Leu Ile Val Gly Ala Leu Gly Met Ala Thr Thr Ala Ser Ala
        35                  40                  45

Gln Leu Val Ser Thr Thr Gln Pro Asn Asp Tyr Arg Ser Ser Thr Thr
    50                  55                  60

Gly Asn Asn His Leu Gly Ser Ser Trp Ser Ile Ile Gly Ala Gly His
65              70                  75                  80

Asp Asn Ile Val Tyr Arg Ser Ala Ser Asn Ser Gly Ile Leu Ser Gly
                85                  90                  95

Tyr Lys Asn Arg Val Asn Gly Ser Thr Ser Ala Ile Val Gly Gly Tyr
            100                 105                 110

Asp Asn Glu Thr Arg Gly Lys Tyr Thr Phe Val Gly Gly Tyr Lys
        115                 120                 125

Asn Leu Ala Glu Gly His Gln Ser Ala Ile Gly Gly Gly Tyr Ala Asn
    130                 135                 140

Trp Ala Glu Gly Asp Asn Ala Thr Ile Ala Gly Gly Phe Glu Asn Phe
145                 150                 155                 160

Ala Ala Gly Asn Gln Ser Ala Ile Gly Gly Gly Tyr Ala Asn Leu Ala
                165                 170                 175

Glu Gly Asp Asp Ala Thr Ile Ala Gly Gly Phe Glu Asn Arg Ala Glu
            180                 185                 190

Gly Asn Gln Ser Ala Ile Gly Gly Gly Tyr Ala Asn Phe Ala Ala Gly
        195                 200                 205

Asp Tyr Thr Phe Val Gly Gly Gly Tyr Glu Asn Arg Ala Glu Gly Asn
    210                 215                 220

Gln Ser Ala Ile Gly Gly Gly Tyr Ala Asn Leu Ala Glu Gly Asp Asn
225                 230                 235                 240

Ala Thr Ile Ala Gly Gly Phe Glu Asn Arg Ala Lys Gly Ile Asn Ser
                245                 250                 255

Val Val Ser Gly Gly Tyr Ala Asn Gln Ala Thr Gly Glu Ser Ser Thr
            260                 265                 270

Ile Ala Gly Gly Phe Glu Asn Arg Ala Glu Gly Ile Asp Ser Val Val
        275                 280                 285
```

```
Ser Gly Gly Tyr Ala Asn Gln Ala Asn Gly Ala Gln Ser Thr Val Ala
    290                 295                 300

Gly Gly Tyr Asn Asn Gln Ala Thr Gly Glu Ser Ser Thr Ile Ala Gly
305                 310                 315                 320

Gly Ser Asn Asn Gln Ala Thr Gly Thr Gly Ser Phe Ala Ala Gly Val
                325                 330                 335

Glu Asn Lys Ala Asn Ala Asp Asn Ala Val Ala Leu Gly Lys Asn Asn
            340                 345                 350

Ile Ile Asn Gly Asp Asn Ser Ala Ala Ile Gly Ser Asn Asn Thr Val
        355                 360                 365

Lys Lys Gly Gln Lys Asp Val Phe Ile Leu Gly Ser Asn Thr Ser Gly
    370                 375                 380

Ala Gln Ser Asn Ser Val Leu Leu Gly Asn Glu Thr Thr Gly Lys Lys
385                 390                 395                 400

Ala Thr Ala Val Glu Asn Ala Thr Val Gly Asp Leu Ser Leu Thr Gly
                405                 410                 415

Phe Ala Gly Val Ser Lys Ala Asn Ser Gly Thr Val Ser Val Gly Ser
            420                 425                 430

Glu Gly Lys Glu Arg Gln Ile Val His Val Gly Ala Gly Arg Ile Ser
        435                 440                 445

Asn Asp Ser Thr Asp Ala Val Asn Gly Ser Gln Leu Tyr Ala Leu Ala
    450                 455                 460

Ala Ala Val Asp Asp Asn Gln Tyr Asp Ile Glu Lys Asn Gln Asp Asp
465                 470                 475                 480

Ile Lys Glu Leu Lys Arg Gly Val Lys Glu Leu Asp Lys Glu Met Asn
                485                 490                 495

Val Leu Ser Arg Asp Ile Val Ser Leu Asn Asp Asp Val Ala Gln Asn
            500                 505                 510

Gln Ser Asp Ile Lys Thr Leu Lys Asn Asn Val Glu Glu Gly Leu Leu
    515                 520                 525

Glu Leu Ser Gly His Leu Ile Asp Gln Lys Ala Asp Leu Thr Lys Asp
    530                 535                 540

Ile Lys Ala Leu Glu Asn Asn Val Glu Glu Gly Leu Leu Asp Leu Ser
545                 550                 555                 560

Gly Arg Leu Leu Asp Gln Lys Ala Asp Ile Ala Lys Asn Gln Ala Asp
                565                 570                 575

Ile Ala Gln Asn Gln Thr Asp Ile Gln Asp Leu Ala Ala Tyr Asn Glu
            580                 585                 590

Leu Gln Asp Ala Tyr Ala Lys Gln Gln Thr Glu Ala Ile Asp Ala Leu
    595                 600                 605

Asn Lys Ala Ser Ser Glu Asn Thr Gln Asn Ile Glu Asp Leu Ala Ala
    610                 615                 620

Tyr Asn Glu Leu Gln Asp Ala Tyr Ala Lys Gln Gln Thr Glu Ala Ile
625                 630                 635                 640

Asp Ala Leu Asn Lys Ala Ser Ser Glu Asn Thr Gln Asn Ile Ala Lys
                645                 650                 655

Asn Gln Ala Asp Ile Ala Asn Asn Ile Asn Asn Ile Tyr Glu Leu Ala
            660                 665                 670

Gln Gln Gln Asp Gln His Ser Ser Asp Ile Lys Thr Leu Ala Lys Ala
    675                 680                 685

Ser Ala Ala Asn Thr Asp Arg Ile Ala Lys Asn Lys Ala Asp Ala Asp
    690                 695                 700
```

```
Ala Ser Phe Glu Thr Leu Thr Lys Asn Gln Asn Thr Leu Ile Glu Lys
705                 710                 715                 720

Asp Lys Glu His Asp Lys Leu Ile Thr Ala Asn Lys Thr Ala Ile Asp
            725                 730                 735

Ala Asn Lys Ala Ser Ala Asp Thr Lys Phe Ala Ala Thr Ala Asp Ala
        740                 745                 750

Ile Thr Lys Asn Gly Asn Ala Ile Thr Lys Asn Ala Lys Ser Ile Thr
            755                 760                 765

Asp Leu Gly Thr Lys Val Asp Gly Phe Asp Gly Arg Val Thr Ala Leu
        770                 775                 780

Asp Thr Lys Val Asn Ala Phe Asp Gly Arg Ile Thr Ala Leu Asp Ser
785                 790                 795                 800

Lys Val Glu Asn Gly Met Ala Ala Gln Ala Ala Leu Ser Gly Leu Phe
                805                 810                 815

Gln Pro Tyr Ser Val Gly Lys Phe Asn Ala Thr Ala Ala Leu Gly Gly
            820                 825                 830

Tyr Gly Ser Lys Ser Ala Val Ala Ile Gly Ala Gly Tyr Arg Val Asn
        835                 840                 845

Pro Asn Leu Ala Phe Lys Ala Gly Ala Ala Ile Asn Thr Ser Gly Asn
850                 855                 860

Lys Lys Gly Ser Tyr Asn Ile Gly Val Asn Tyr Glu Phe
865                 870                 875
```

<210> SEQ ID NO 20
<211> LENGTH: 889
<212> TYPE: PRT
<213> ORGANISM: Moraxella catarrhalis

<400> SEQUENCE: 20

```
Met Asn Lys Ile Tyr Lys Val Lys Asn Ala Ala Gly His Leu Val
1               5                   10                  15

Ala Cys Ser Glu Phe Ala Lys Gly His Thr Lys Lys Ala Val Leu Gly
            20                  25                  30

Ser Leu Leu Ile Val Gly Ala Leu Gly Met Ala Thr Thr Ala Ser Ala
        35                  40                  45

Gln Pro Leu Val Ser Thr Asn Lys Pro Asn Gln Gln Val Lys Gly Tyr
    50                  55                  60

Trp Ser Ile Ile Gly Ala Gly Arg His Asn Asn Val Gly Gly Ser Ala
65                  70                  75                  80

His His Ser Gly Ile Leu Gly Gly Trp Lys Asn Thr Val Asn Gly Tyr
                85                  90                  95

Thr Ser Ala Ile Val Gly Gly Tyr Gly Asn Glu Thr Gln Gly Asp Tyr
            100                 105                 110

Thr Phe Val Gly Gly Gly Tyr Lys Asn Leu Ala Lys Gly Asn Tyr Thr
        115                 120                 125

Phe Val Gly Gly Gly Tyr Lys Asn Leu Ala Glu Gly Asp Asn Ala Thr
    130                 135                 140

Ile Ala Gly Gly Phe Ala Asn Leu Ala Glu Gly Asp Asn Ala Thr Ile
145                 150                 155                 160

Ala Gly Gly Phe Glu Asn Arg Ala Glu Gly Ile Asp Ser Val Val Ser
                165                 170                 175

Gly Gly Tyr Ala Asn Gln Ala Thr Gly Glu Ser Ser Thr Val Ala Gly
            180                 185                 190

Gly Ser Asn Asn Leu Ala Glu Gly Lys Ser Ser Ala Ile Gly Gly Gly
        195                 200                 205
```

```
Arg Gln Asn Glu Ala Ser Gly Asp Arg Ser Thr Val Ser Gly Gly Tyr
    210                 215                 220
Asn Asn Leu Ala Glu Gly Lys Ser Ser Ala Ile Gly Gly Gly Glu Phe
225                 230                 235                 240
Asn Leu Ala Leu Gly Asn Asn Ala Thr Ile Ser Gly Gly Arg Gln Asn
                245                 250                 255
Glu Ala Ser Gly Asp Arg Ser Thr Val Ala Gly Gly Glu Gln Asn Gln
            260                 265                 270
Ala Ile Gly Lys Tyr Ser Thr Ile Ser Gly Gly Arg Gln Asn Glu Ala
        275                 280                 285
Ser Gly Asp Arg Ser Thr Val Ala Gly Gly Glu Gln Asn Gln Ala Ile
    290                 295                 300
Gly Lys Tyr Ser Thr Val Ser Gly Gly Tyr Arg Asn Gln Ala Thr Gly
305                 310                 315                 320
Lys Gly Ser Phe Ala Ala Gly Ile Asp Asn Lys Ala Asn Ala Asp Asn
                325                 330                 335
Ala Val Ala Leu Gly Asn Lys Asn Thr Ile Glu Gly Glu Asn Ser Val
            340                 345                 350
Ala Ile Gly Ser Asn Asn Thr Val Lys Lys Asn Gln Lys Asn Val Phe
        355                 360                 365
Ile Leu Gly Ser Asn Thr Asp Thr Lys Asp Ala Gln Ser Gly Ser Val
    370                 375                 380
Leu Leu Gly Asp Asn Thr Ser Gly Lys Ala Ala Thr Ala Val Glu Asp
385                 390                 395                 400
Ala Thr Val Gly Asp Leu Ser Leu Thr Gly Phe Ala Gly Val Ser Lys
                405                 410                 415
Ala Asn Ser Gly Thr Val Ser Val Gly Ser Glu Gly Lys Glu Arg Gln
            420                 425                 430
Ile Val His Val Gly Ala Gly Arg Ile Ser Asn Asp Ser Thr Asp Ala
        435                 440                 445
Val Asn Gly Ser Gln Leu Tyr Ala Leu Ala Ala Val Asp Asp Asn
450                 455                 460
Gln Tyr Asp Ile Glu Lys Asn Gln Asp Ile Ala Lys Asn Gln Ala
465                 470                 475                 480
Asp Ile Ala Lys Asn Gln Ala Asp Ile Gln Thr Leu Glu Asn Asp Val
                485                 490                 495
Gly Lys Glu Leu Leu Asn Leu Ser Gly Arg Leu Ile Asp Gln Lys Ala
            500                 505                 510
Asp Ile Asp Asn Asn Ile Asn His Ile Tyr Glu Leu Ala Gln Gln Gln
        515                 520                 525
Asp Gln His Ser Ser Asp Ile Lys Thr Leu Lys Lys Asn Val Glu Glu
    530                 535                 540
Gly Leu Leu Glu Leu Ser Gly His Leu Ile Asp Gln Lys Ala Asp Leu
545                 550                 555                 560
Thr Lys Asp Ile Lys Ala Leu Glu Ser Asn Val Glu Glu Gly Leu Leu
                565                 570                 575
Asp Leu Ser Gly Arg Leu Ile Asp Gln Lys Ala Asp Ile Ala Gln Asn
            580                 585                 590
Gln Ala Asn Ile Gln Asp Leu Ala Ala Tyr Asn Glu Leu Gln Asp Gln
        595                 600                 605
Tyr Ala Gln Lys Gln Thr Glu Ala Ile Asp Ala Leu Asn Lys Ala Ser
    610                 615                 620
```

-continued

Ser Glu Asn Thr Gln Asn Ile Glu Asp Leu Ala Ala Tyr Asn Glu Leu
625                 630                 635                 640

Gln Asp Ala Tyr Ala Lys Gln Thr Glu Ala Ile Asp Ala Leu Asn
            645                 650                 655

Lys Ala Ser Ser Glu Asn Thr Gln Asn Ile Ala Lys Asn Gln Ala Asp
        660                 665                 670

Ile Ala Asn Asn Ile Asn Asn Ile Tyr Glu Leu Ala Gln Gln Gln Asp
            675                 680                 685

Gln His Ser Ser Asp Ile Lys Thr Leu Ala Lys Ala Ser Ala Ala Asn
        690                 695                 700

Thr Asp Arg Ile Ala Lys Asn Lys Ala Asp Ala Asp Ala Ser Phe Glu
705                 710                 715                 720

Thr Leu Thr Lys Asn Gln Asn Thr Leu Ile Glu Lys Asp Lys Glu His
            725                 730                 735

Asp Lys Leu Ile Thr Ala Asn Lys Thr Ala Ile Asp Ala Asn Lys Ala
        740                 745                 750

Ser Ala Asp Thr Lys Phe Ala Ala Thr Ala Asp Ala Ile Thr Lys Asn
    755                 760                 765

Gly Asn Ala Ile Thr Lys Asn Ala Lys Ser Ile Thr Asp Leu Gly Thr
770                 775                 780

Lys Val Asp Gly Phe Asp Gly Arg Val Thr Ala Leu Asp Thr Lys Val
785                 790                 795                 800

Asn Ala Phe Asp Gly Arg Ile Thr Ala Leu Asp Ser Lys Val Glu Asn
            805                 810                 815

Gly Met Ala Ala Gln Ala Ala Leu Ser Gly Leu Phe Gln Pro Tyr Ser
        820                 825                 830

Val Gly Lys Phe Asn Ala Thr Ala Ala Leu Gly Gly Tyr Gly Ser Lys
    835                 840                 845

Ser Ala Val Ala Ile Gly Ala Gly Tyr Arg Val Asn Pro Asn Leu Ala
850                 855                 860

Phe Lys Ala Gly Ala Ala Ile Asn Thr Ser Gly Asn Lys Lys Gly Ser
865                 870                 875                 880

Tyr Asn Ile Gly Val Asn Tyr Glu Phe
            885

<210> SEQ ID NO 21
<211> LENGTH: 686
<212> TYPE: PRT
<213> ORGANISM: Moraxella catarrhalis

<400> SEQUENCE: 21

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asn Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Gln Leu Asn Gly Phe
                85                  90                  95

Lys Glu Gly Asp Thr Ile Ile Pro Leu Asp Glu Asn Gly Lys Pro Val
            100                 105                 110

```
Tyr Lys Leu Asp Glu Ile Thr Glu Asn Gly Val Lys Arg Lys Val Tyr
            115                 120                 125

Ser Val Thr Thr Lys Thr Ala Thr Arg Glu Asp Val Glu Gln Ser Ala
130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Asp Gln His Ser Ser Asp
            195                 200                 205

Ile Lys Thr Leu Lys Lys Asn Val Glu Glu Gly Leu Leu Glu Leu Ser
        210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270

Thr Gln Asn Ile Ala Lys Asn Ser Asn His Ile Lys Thr Leu Glu Asn
        275                 280                 285

Asn Ile Glu Glu Gly Leu Leu Glu Leu Ser Gly His Leu Ile Asp Gln
        290                 295                 300

Lys Ala Asp Leu Thr Lys Asp Ile Lys Ala Leu Glu Ser Asn Val Glu
305                 310                 315                 320

Glu Gly Leu Leu Asp Leu Ser Gly Arg Leu Leu Asp Gln Lys Ala Asp
                325                 330                 335

Ile Ala Lys Asn Gln Ala Asp Ile Ala Gln Asn Gln Thr Asp Ile Gln
            340                 345                 350

Asp Leu Ala Ala Tyr Asn Glu Leu Gln Asp Gln Tyr Ala Gln Lys Gln
        355                 360                 365

Thr Glu Ala Ile Asp Ala Leu Asn Lys Ala Ser Ser Glu Asn Thr Gln
370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
            405                 410                 415

Asn Thr Gln Asn Ile Glu Asp Leu Ala Ala Tyr Asn Glu Leu Gln Asp
        420                 425                 430

Ala Tyr Ala Lys Gln Gln Thr Glu Ala Ile Asp Ala Leu Asn Lys Ala
        435                 440                 445

Ser Ser Glu Asn Thr Gln Asn Ile Ala Lys Asn Gln Ala Asp Ile Ala
    450                 455                 460

Asn Asn Ile Asn Asn Ile Tyr Glu Leu Ala Gln Gln Asp Gln His
465                 470                 475                 480

Ser Ser Asp Ile Lys Thr Leu Ala Lys Ala Ser Ala Ala Asn Thr Asp
            485                 490                 495

Arg Ile Ala Lys Asn Lys Ala Asp Ala Asp Ala Ser Phe Glu Thr Leu
        500                 505                 510

Thr Lys Asn Gln Asn Thr Leu Ile Glu Lys Asp Lys Glu His Asp Lys
        515                 520                 525
```

```
Leu Ile Thr Ala Asn Lys Thr Ala Ile Asp Ala Asn Lys Ala Ser Ala
    530                 535                 540

Asp Thr Lys Phe Ala Ala Thr Ala Asp Ala Ile Thr Lys Asn Gly Asn
545                 550                 555                 560

Ala Ile Thr Lys Asn Ala Lys Ser Ile Thr Asp Leu Gly Thr Lys Val
                565                 570                 575

Asp Gly Phe Asp Gly Arg Val Thr Ala Leu Asp Thr Lys Val Asn Ala
            580                 585                 590

Leu Asp Thr Lys Val Asn Ala Phe Asp Gly Arg Ile Thr Ala Leu Asp
        595                 600                 605

Ser Lys Val Glu Asn Gly Met Ala Ala Gln Ala Leu Ser Gly Leu
    610                 615                 620

Phe Gln Pro Tyr Ser Val Gly Lys Phe Asn Ala Thr Ala Leu Gly
625                 630                 635                 640

Gly Tyr Gly Ser Lys Ser Ala Val Ala Ile Gly Ala Gly Tyr Arg Val
                645                 650                 655

Asn Pro Asn Leu Ala Phe Lys Ala Gly Ala Ala Ile Asn Thr Ser Gly
            660                 665                 670

Asn Lys Lys Gly Ser Tyr Asn Ile Gly Val Asn Tyr Glu Phe
        675                 680                 685

<210> SEQ ID NO 22
<211> LENGTH: 684
<212> TYPE: PRT
<213> ORGANISM: Moraxella catarrhalis

<400> SEQUENCE: 22

Met Lys Thr Met Lys Leu Leu Pro Leu Lys Ile Ala Val Thr Ser Ala
  1               5                  10                  15

Met Met Val Gly Leu Gly Met Ala Ser Thr Ala Asn Ala Gln Gln Gln
                20                  25                  30

Lys Ser Pro Lys Thr Glu Ile Phe Leu Pro Asn Leu Phe Asp Asn Asp
            35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Asp Thr Ile Ile Pro Leu Asp
            100                 105                 110

Glu Asn Gly Lys Pro Val Tyr Lys Leu Asp Ser Ile Val Glu Gln Gly
    115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
    195                 200                 205

Gln His Ser Ser Asp Ile Lys Thr Leu Lys Lys Asn Val Glu Lys Asp
210                 215                 220
```

```
Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
            245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
            275                 280                 285

Lys Thr Leu Glu Asn Asn Ile Glu Glu Gly Leu Leu Glu Leu Ser Gly
            290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
            325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
            370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
            405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
            450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Ala Asn Thr Asp Arg Ile
            485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
            530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
            565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
            610                 615                 620

Pro Tyr Ser Val Gly Lys Phe Asn Ala Thr Ala Ala Leu Gly Gly Tyr
625                 630                 635                 640
```

```
Gly Ser Lys Ser Ala Val Ala Ile Gly Ala Gly Tyr Arg Val Asn Pro
            645                 650                 655

Asn Leu Ala Phe Lys Ala Gly Ala Ile Asn Thr Ser Gly Asn Lys
            660                 665                 670

Lys Gly Ser Tyr Asn Ile Gly Val Asn Tyr Glu Phe
        675                 680

<210> SEQ ID NO 23
<211> LENGTH: 576
<212> TYPE: PRT
<213> ORGANISM: Moraxella catarrhalis

<400> SEQUENCE: 23

Met Lys Thr Met Lys Leu Leu Pro Leu Lys Ile Ala Val Thr Ser Ala
  1               5                  10                  15

Met Ile Val Gly Leu Gly Ala Thr Ser Thr Val Asn Ala Gln Val Val
             20                  25                  30

Glu Gln Phe Phe Pro Asn Ile Phe Phe Asn Glu Asn His Asp Glu Leu
         35                  40                  45

Asp Asp Ala Tyr His Asn Met Ile Leu Gly Asp Thr Ala Ile Val Ser
     50                  55                  60

Asn Ser Gln Asp Asn Ser Thr Gln Leu Lys Phe Tyr Ser Asn Asp Glu
 65                  70                  75                  80

Asp Ser Val Pro Asp Ser Leu Leu Phe Ser Lys Leu Leu His Glu Gln
                 85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Glu Glu Gly
    210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
                245                 250                 255

Leu Ser Gly His Leu Ile Asp Gln Lys Ala Asp Leu Thr Lys Asp Ile
            260                 265                 270

Lys Ala Leu Glu Ser Asn Val Glu Glu Gly Leu Leu Asp Leu Ser Gly
        275                 280                 285

Arg Leu Leu Asp Gln Lys Ala Asp Ile Ala Lys Asn Gln Ala Asp Ile
    290                 295                 300

Ala Gln Asn Gln Thr Asp Ile Gln Asp Leu Ala Ala Tyr Asn Glu Leu
305                 310                 315                 320

Gln Asp Ala Tyr Ala Lys Gln Gln Thr Glu Ala Ile Asp Ala Leu Asn
                325                 330                 335
```

Lys Ala Ser Ser Glu Asn Thr Gln Asn Ile Ala Lys Asn Gln Ala Asp
              340                 345                 350

Ile Ala Asn Asn Ile Asn Asn Ile Tyr Glu Leu Ala Gln Gln Gln Asp
              355                 360                 365

Gln His Ser Ser Asp Ile Lys Thr Leu Ala Lys Ala Ser Ala Ala Asn
370                 375                 380

Thr Asp Arg Ile Ala Lys Asn Lys Ala Asp Ala Asp Ala Ser Phe Glu
385                 390                 395                 400

Thr Leu Thr Lys Asn Gln Asn Thr Leu Ile Glu Lys Asp Lys Glu His
              405                 410                 415

Asp Lys Leu Ile Thr Ala Asn Lys Thr Ala Ile Asp Ala Asn Lys Ala
              420                 425                 430

Ser Ala Asp Thr Lys Phe Ala Ala Thr Ala Asp Ala Ile Thr Lys Asn
              435                 440                 445

Gly Asn Ala Ile Thr Lys Asn Ala Lys Ser Ile Thr Asp Leu Gly Thr
              450                 455                 460

Lys Val Asp Gly Phe Asp Gly Arg Val Thr Ala Leu Asp Thr Lys Val
465                 470                 475                 480

Asn Ala Leu Asp Thr Lys Val Asn Ala Phe Asp Gly Arg Ile Thr Ala
              485                 490                 495

Leu Asp Ser Lys Val Glu Asn Gly Met Ala Gln Ala Ala Leu Ser
              500                 505                 510

Gly Leu Phe Gln Pro Tyr Ser Val Gly Lys Phe Asn Ala Thr Ala Ala
              515                 520                 525

Leu Gly Gly Tyr Gly Ser Lys Ser Ala Val Ala Ile Gly Ala Gly Tyr
              530                 535                 540

Arg Val Asn Pro Asn Leu Ala Phe Lys Ala Gly Ala Ala Ile Asn Thr
545                 550                 555                 560

Ser Gly Asn Lys Lys Gly Ser Tyr Asn Ile Gly Val Asn Tyr Glu Phe
              565                 570                 575

<210> SEQ ID NO 24
<211> LENGTH: 674
<212> TYPE: PRT
<213> ORGANISM: Moraxella catarrhalis

<400> SEQUENCE: 24

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
              20                  25                  30

Glu Gln Phe Phe Pro Asn Ile Phe Phe Asn Glu Asn His Asp Glu Leu
              35                  40                  45

Asp Asp Ala Tyr His Asn Met Ile Leu Gly Asp Thr Ala Ile Val Ser
        50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
              85                  90                  95

Gln Leu Asn Gly Phe Lys Ala Gly Asp Thr Ile Ile Pro Leu Asp Lys
              100                 105                 110

Asp Gly Lys Pro Val Tyr Thr Lys Asp Thr Arg Thr Lys Asp Gly Lys
              115                 120                 125

Val Glu Thr Val Tyr Ser Val Thr Thr Lys Ile Ala Thr Gln Asp Asp

```
                130               135               140
    Val Glu Gln Ser Ala Tyr Ser Arg Gly Ile Gln Gly Asp Ile Asp Asp
    145               150               155               160

Leu Tyr Asp Ile Asn Arg Glu Val Asn Glu Tyr Leu Lys Ala Thr His
                    165               170               175

Asp Tyr Asn Glu Arg Gln Thr Glu Ala Ile Asp Ala Leu Asn Lys Ala
                    180               185               190

Ser Ser Ala Asn Thr Asp Arg Ile Asp Thr Ala Glu Glu Arg Ile Asp
                    195               200               205

Lys Asn Glu Tyr Asp Ile Lys Ala Leu Glu Ser Asn Val Glu Glu Gly
            210               215               220

Leu Leu Glu Leu Ser Gly His Leu Ile Asp Gln Lys Ala Asp Leu Thr
    225               230               235               240

Lys Asp Ile Lys Ala Leu Glu Ser Asn Val Glu Glu Gly Leu Leu Glu
                    245               250               255

Leu Ser Gly His Leu Ile Asp Gln Lys Ala Asp Leu Thr Lys Asp Ile
                    260               265               270

Lys Ala Leu Glu Ser Asn Val Glu Glu Gly Leu Leu Asp Leu Ser Gly
                    275               280               285

Arg Leu Ile Asp Gln Lys Ala Asp Ile Ala Gln Asn Gln Ala Asn Ile
    290               295               300

Gln Asp Leu Ala Ala Tyr Asn Glu Leu Gln Asp Ala Tyr Ala Lys Gln
    305               310               315               320

Gln Thr Glu Ala Ile Asp Ala Leu Asn Lys Ala Ser Ser Glu Asn Thr
                    325               330               335

Gln Asn Ile Glu Asp Leu Ala Ala Tyr Asn Glu Leu Gln Asp Ala Tyr
                    340               345               350

Ala Lys Gln Gln Thr Glu Ala Ile Asp Ala Leu Asn Lys Ala Ser Ser
                    355               360               365

Glu Asn Thr Gln Asn Ile Glu Asp Leu Ala Ala Tyr Asn Glu Leu Gln
            370               375               380

Asp Ala Tyr Ala Lys Gln Gln Thr Glu Ala Ile Asp Ala Leu Asn Lys
    385               390               395               400

Ala Ser Ser Glu Asn Thr Gln Asn Ile Glu Asp Leu Ala Ala Tyr Asn
                    405               410               415

Glu Leu Gln Asp Ala Tyr Ala Lys Gln Gln Thr Glu Ala Ile Asp Ala
                    420               425               430

Leu Asn Lys Ala Ser Ser Glu Asn Thr Gln Asn Ile Ala Lys Asn Gln
                    435               440               445

Ala Asp Ile Ala Asn Asn Ile Asn Asn Ile Tyr Glu Leu Ala Gln Gln
    450               455               460

Gln Asp Gln His Ser Ser Asp Ile Lys Thr Leu Ala Lys Ala Ser Ala
    465               470               475               480

Ala Asn Thr Asp Arg Ile Ala Lys Asn Lys Ala Asp Ala Asp Ala Ser
                    485               490               495

Phe Glu Thr Leu Thr Lys Asn Gln Asn Thr Leu Ile Glu Lys Asp Lys
                    500               505               510

Glu His Asp Lys Leu Ile Thr Ala Asn Lys Thr Ala Ile Asp Ala Asn
                    515               520               525

Lys Ala Ser Ala Asp Thr Lys Phe Ala Thr Ala Asp Ala Ile Thr
                    530               535               540

Lys Asn Gly Asn Ala Ile Thr Lys Asn Ala Lys Ser Ile Thr Asp Leu
    545               550               555               560
```

-continued

```
Gly Thr Lys Val Asp Gly Phe Asp Gly Arg Val Thr Ala Leu Asp Thr
                565                 570                 575
Lys Val Asn Ala Leu Asp Thr Lys Val Asn Ala Phe Asp Gly Arg Ile
            580                 585                 590
Thr Ala Leu Asp Ser Lys Val Glu Asn Gly Met Ala Gln Ala Ala
        595                 600                 605
Leu Ser Gly Leu Phe Gln Pro Tyr Ser Val Gly Lys Phe Asn Ala Thr
    610                 615                 620
Ala Ala Leu Gly Gly Tyr Gly Ser Lys Ser Ala Val Ala Ile Gly Ala
625                 630                 635                 640
Gly Tyr Arg Val Asn Pro Asn Leu Ala Phe Lys Ala Gly Ala Ala Ile
                645                 650                 655
Asn Thr Ser Gly Asn Lys Lys Gly Ser Tyr Asn Ile Gly Val Asn Tyr
            660                 665                 670
Glu Phe

<210> SEQ ID NO 25
<211> LENGTH: 650
<212> TYPE: PRT
<213> ORGANISM: Moraxella catarrhalis

<400> SEQUENCE: 25

Met Lys Thr Met Lys Leu Leu Pro Leu Lys Ile Ala Val Thr Ser Ala
  1               5                  10                  15
Leu Ile Val Gly Leu Gly Ala Ala Ser Thr Ala Asn Ala Gln Gln Gln
             20                  25                  30
Gln Lys Thr Lys Thr Glu Val Phe Leu Pro Asn Leu Phe Tyr Asn Asp
         35                  40                  45
Tyr Ile Glu Glu Thr Asp Leu Leu Tyr His Asn Met Ile Leu Gly Asp
     50                  55                  60
Thr Ala Ala Leu Val Asp Arg Gln Asn Tyr Ser Asn Ser Gln Leu Lys
 65                  70                  75                  80
Phe Tyr Ser Asn Asp Glu Glu Ser Val Pro Asp Ser Leu Leu Phe Ser
                 85                  90                  95
Lys Met Leu Asn Asn Gln Gln Leu Asn Gly Phe Lys Ala Gly Asp Ile
            100                 105                 110
Ile Ile Pro Val Asp Ala Asn Gly Gln Val Ile Tyr Gln Lys Asp Thr
        115                 120                 125
Arg Val Glu Gly Gly Lys Thr Arg Thr Val Leu Ser Val Thr Thr Lys
    130                 135                 140
Ile Ala Thr Gln Gln Asp Val Asp Ser Ala Tyr Ser Arg Gly Ile Gln
145                 150                 155                 160
Gly Lys Val Asn Asp Leu Asp Asp Glu Met Asn Phe Leu Asn His Asp
                165                 170                 175
Ile Thr Ser Leu Tyr Asp Val Thr Ala Asn Gln Gln Asp Asp Ile Lys
            180                 185                 190
Gly Leu Lys Lys Gly Val Lys Asp Leu Lys Lys Gly Val Lys Gly Leu
        195                 200                 205
Asn Lys Glu Leu Lys Glu Leu Asp Lys Glu Val Gly Val Leu Ser Arg
    210                 215                 220
Asp Ile Gly Ser Leu Asn Asp Val Ala Gln Asn Asn Glu Ser Ile
225                 230                 235                 240
Glu Asp Leu Tyr Asp Phe Ser Gln Glu Val Ala Asp Ser Ile Gly Glu
                245                 250                 255
```

Ile His Ala His Asn Lys Ala Gln Asn Glu Thr Leu Gln Asp Leu Ile
        260                 265                 270

Thr Asn Ser Val Glu Asn Thr Asn Ile Thr Lys Asn Lys Ala Asp
            275                 280                 285

Ile Gln Ala Leu Glu Asn Val Val Glu Glu Leu Phe Asn Leu Ser
290                 295                 300

Gly Arg Leu Ile Asp Gln Lys Ala Asp Leu Thr Lys Asp Ile Lys Thr
305                 310                 315                 320

Leu Glu Ser Asn Val Glu Gly Leu Leu Glu Leu Ser Gly His Leu
                325                 330                 335

Ile Asp Gln Lys Ala Asp Ile Ala Lys Asn Gln Ala Asp Ile Ala Gln
            340                 345                 350

Asn Gln Ala Asn Ile Gln Asp Leu Ala Ala Tyr Asn Glu Leu Gln Asp
            355                 360                 365

Ala Tyr Ala Lys Gln Gln Thr Glu Ala Ile Asp Ala Leu Asn Lys Ala
370                 375                 380

Ser Ser Glu Asn Thr Gln Asn Ile Glu Asp Leu Ala Ala Tyr Asn Glu
385                 390                 395                 400

Leu Gln Asp Ala Tyr Ala Lys Gln Gln Thr Glu Ala Ile Asp Ala Leu
                405                 410                 415

Asn Lys Ala Ser Ser Glu Asn Thr Gln Asn Ile Ala Lys Asn Gln Ala
            420                 425                 430

Asp Ile Ala Asn Asn Ile Asn Asn Ile Tyr Glu Leu Ala Gln Gln Gln
            435                 440                 445

Asp Gln His Ser Ser Asp Ile Lys Thr Leu Ala Lys Ser Ala Ala
            450                 455                 460

Asn Thr Asp Arg Ile Ala Lys Asn Lys Ala Asp Ala Asp Ala Ser Phe
465                 470                 475                 480

Glu Thr Leu Thr Lys Asn Gln Asn Thr Leu Ile Glu Lys Asp Lys Glu
                485                 490                 495

His Asp Lys Leu Ile Thr Ala Asn Lys Thr Ala Ile Asp Glu Asn Lys
                500                 505                 510

Ala Ser Ala Asp Thr Lys Phe Ala Ala Thr Ala Asp Ala Ile Thr Lys
            515                 520                 525

Asn Gly Asn Ala Ile Thr Lys Asn Ala Lys Ser Ile Thr Asp Leu Gly
530                 535                 540

Thr Lys Val Asp Gly Phe Asp Gly Arg Val Thr Ala Leu Asp Thr Lys
545                 550                 555                 560

Val Asn Ala Phe Asp Gly Arg Ile Thr Ala Leu Asp Ser Lys Val Glu
                565                 570                 575

Asn Gly Met Ala Ala Gln Ala Ala Leu Ser Gly Leu Phe Gln Pro Tyr
            580                 585                 590

Ser Val Gly Lys Phe Asn Ala Thr Ala Ala Leu Gly Gly Tyr Gly Ser
            595                 600                 605

Lys Ser Ala Val Ala Ile Gly Ala Gly Tyr Arg Val Asn Pro Asn Leu
610                 615                 620

Ala Phe Lys Ala Gly Ala Ala Ile Asn Thr Ser Gly Asn Lys Lys Gly
625                 630                 635                 640

Ser Tyr Asn Ile Gly Val Asn Tyr Glu Phe
            645                 650

<210> SEQ ID NO 26
<211> LENGTH: 668

<212> TYPE: PRT
<213> ORGANISM: Moraxella catarrhalis

<400> SEQUENCE: 26

Met Lys Thr Met Lys Leu Leu Pro Leu Lys Ile Ala Val Thr Ser Ala
1               5                   10                  15

Leu Ile Val Gly Leu Gly Thr Ala Ser Thr Ala Asn Ala Gln Val Ala
            20                  25                  30

Ser Pro Ala Asn Gln Lys Ile Gln Gln Lys Ile Lys Lys Val Arg Lys
        35                  40                  45

Glu Leu Arg Gln Asp Ile Lys Ser Leu Arg Asn Asp Ile Asp Ser Asn
    50                  55                  60

Thr Ala Asp Ile Gly Ser Leu Asn Asp Asp Val Ala Asp Asn Gln Asp
65                  70                  75                  80

Asp Ile Leu Asp Asn Gln Ala Asp Ile Ala Lys Asn Gln Asp Asp Ile
                85                  90                  95

Glu Lys Asn Gln Ala Asp Ile Lys Glu Leu Asp Lys Glu Val Gly Val
            100                 105                 110

Leu Ser Arg Glu Ile Gly Ser Leu Asn Asp Asp Ile Ala Asp Asn Tyr
        115                 120                 125

Thr Asp Ile Ile Asp Asn Tyr Thr Asp Ile Ile Asp Asn Gln Ala Asn
    130                 135                 140

Ile Ala Lys Asn Gln Asp Asp Ile Glu Lys Asn Gln Ala Asp Ile Lys
145                 150                 155                 160

Glu Leu Asp Lys Glu Val Gly Val Leu Ser Arg Glu Ile Gly Ser Leu
                165                 170                 175

Asn Asp Asp Val Ala Asp Asn Gln Asp Asp Ile Ala Lys Asn Gln Ala
            180                 185                 190

Asp Ile Gln Thr Leu Glu Asn Asn Val Glu Glu Gly Leu Leu Glu Leu
        195                 200                 205

Ser Gly His Leu Leu Asp Gln Lys Ala Asp Ile Asp Asn Asn Ile Asn
    210                 215                 220

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Glu
        275                 280                 285

Gln Thr Glu Ala Ile Asp Ala Leu Asn Lys Ala Ser Ser Glu Asn Thr
    290                 295                 300

Gln Asn Ile Ala Lys Asn Ser Asn Arg Ile Lys Ala Leu Glu Ser Asn
305                 310                 315                 320

Val Glu Glu Gly Leu Leu Glu Leu Ser Gly His Leu Ile Asp Gln Lys
                325                 330                 335

Ala Asp Leu Thr Lys Asp Ile Lys Ala Leu Glu Ser Asn Val Glu Glu
            340                 345                 350

Gly Leu Leu Glu Leu Ser Gly His Leu Ile Asp Gln Lys Ala Asp Ile
        355                 360                 365

Ala Gln Asn Gln Ala Asn Ile Gln Asp Leu Ala Ala Tyr Asn Glu Leu
    370                 375                 380

Gln Asp Gln Tyr Ala Gln Lys Gln Thr Glu Ala Ile Asp Ala Leu Asn
385                 390                 395                 400

```
Lys Ala Ser Ser Glu Asn Thr Gln Asn Ile Glu Asp Leu Ala Ala Tyr
                405                 410                 415

Asn Glu Leu Gln Asp Ala Tyr Ala Lys Gln Gln Thr Glu Ala Ile Asp
            420                 425                 430

Ala Leu Asn Lys Ala Ser Ser Glu Asn Thr Gln Asn Ile Ala Lys Asn
        435                 440                 445

Gln Ala Asp Ile Ala Asn Asn Ile Asn Ile Tyr Glu Leu Ala Gln
    450                 455                 460

Gln Gln Asp Gln His Ser Ser Asp Ile Lys Thr Leu Ala Lys Ala Ser
465                 470                 475                 480

Ala Ala Asn Thr Asp Arg Ile Ala Lys Asn Lys Ala Asp Ala Asp Ala
                485                 490                 495

Ser Phe Glu Thr Leu Thr Lys Asn Gln Asn Thr Leu Ile Glu Lys Asp
            500                 505                 510

Lys Glu His Asp Lys Leu Ile Thr Ala Asn Lys Thr Ala Ile Asp Ala
        515                 520                 525

Asn Lys Val Ser Ala Asp Thr Lys Phe Ala Ala Thr Ala Asp Ala Ile
    530                 535                 540

Thr Lys Asn Gly Asn Ala Ile Thr Lys Asn Ala Lys Ser Ile Thr Asp
545                 550                 555                 560

Leu Gly Thr Lys Val Asp Ala Phe Asp Ser Arg Val Thr Ala Leu Asp
                565                 570                 575

Thr Lys Val Asn Ala Phe Asp Gly Arg Ile Thr Ala Leu Asp Ser Lys
            580                 585                 590

Val Glu Asn Gly Met Ala Ala Gln Ala Ala Leu Ser Gly Leu Phe Gln
        595                 600                 605

Pro Tyr Ser Val Gly Lys Phe Asn Ala Thr Ala Ala Leu Gly Gly Tyr
    610                 615                 620

Gly Ser Lys Ser Ala Val Ala Ile Gly Ala Gly Tyr Arg Val Asn Pro
625                 630                 635                 640

Asn Leu Ala Phe Lys Ala Gly Ala Ile Asn Thr Ser Gly Asn Lys
                645                 650                 655

Lys Gly Ser Tyr Asn Ile Gly Val Asn Tyr Glu Phe
            660                 665

<210> SEQ ID NO 27
<211> LENGTH: 894
<212> TYPE: PRT
<213> ORGANISM: Moraxella catarrhalis

<400> SEQUENCE: 27

Met Asn Lys Ile Tyr Lys Val Lys Lys Asn Ala Ala Gly His Ser Val
1               5                   10                  15

Ala Cys Ser Glu Phe Ala Lys Gly His Thr Lys Lys Ala Val Leu Gly
            20                  25                  30

Ser Leu Leu Ile Val Gly Ala Leu Gly Met Ala Thr Thr Ala Ser Ala
        35                  40                  45

Gln Thr Gly Ser Thr Asn Ala Ala Asn Gly Asn Ile Ile Ser Gly Val
    50                  55                  60

Gly Ala Tyr Val Gly Gly Val Ile Asn Gln Ala Lys Gly Asn Tyr
65                  70                  75                  80

Pro Thr Val Gly Gly Phe Asp Asn Arg Ala Thr Gly Asn Tyr Ser
                85                  90                  95

Val Ile Ser Gly Gly Phe Asp Asn Gln Ala Lys Gly Glu His Ser Thr
```

```
            100                 105                 110
Ile Ala Gly Gly Glu Ser Asn Gln Ala Thr Gly Arg Asn Ser Thr Val
            115                 120                 125
Ala Gly Gly Ser Asn Asn Gln Ala Val Gly Thr Asn Ser Thr Val Ala
            130                 135                 140
Gly Gly Ser Asn Asn Gln Ala Lys Gly Ala Asn Ser Phe Ala Ala Gly
145                 150                 155                 160
Val Gly Asn Gln Ala Asn Thr Asp Asn Ala Val Ala Leu Gly Lys Asn
                        165                 170                 175
Asn Thr Ile Asn Gly Asn Asn Ser Ala Ala Ile Gly Ser Glu Asn Thr
                    180                 185                 190
Val Asn Glu Asn Gln Lys Asn Val Phe Ile Leu Gly Ser Asn Thr Thr
                195                 200                 205
Asn Ala Gln Ser Gly Ser Val Leu Leu Gly His Glu Thr Ser Gly Lys
            210                 215                 220
Glu Ala Thr Ala Val Ser Arg Ala Arg Val Asn Gly Leu Thr Leu Lys
225                 230                 235                 240
Asn Phe Ser Gly Val Ser Lys Ala Asp Asn Gly Thr Val Ser Val Gly
                        245                 250                 255
Ser Gln Gly Lys Glu Arg Gln Ile Val His Val Gly Ala Gly Gln Ile
                    260                 265                 270
Ser Asp Asp Ser Thr Asp Ala Val Asn Gly Ser Gln Leu Tyr Ala Leu
                275                 280                 285
Ala Thr Ala Val Asp Asp Asn Gln Tyr Asp Ile Glu Ile Asn Gln Asp
            290                 295                 300
Asn Ile Lys Asp Leu Gln Lys Glu Val Lys Gly Leu Asp Lys Glu Val
305                 310                 315                 320
Gly Val Leu Ser Arg Asp Ile Gly Ser Leu His Asp Asp Val Ala Asp
                        325                 330                 335
Asn Gln Ala Asp Ile Ala Lys Asn Lys Ala Asp Ile Lys Glu Leu Asp
                    340                 345                 350
Lys Glu Met Asn Val Leu Ser Arg Asp Ile Val Ser Leu Asn Asp Asp
                355                 360                 365
Val Ala Asp Asn Gln Ala Asp Ile Ala Lys Asn Gln Ala Asp Ile Lys
            370                 375                 380
Thr Leu Glu Asn Asn Val Glu Glu Gly Leu Leu Asp Leu Ser Gly Arg
385                 390                 395                 400
Leu Ile Asp Gln Lys Ala Asp Ile Asp Asn Asn Ile Asn His Ile Tyr
                        405                 410                 415
Glu Leu Ala Gln Gln Gln Asp Gln His Ser Ser Asp Ile Lys Thr Leu
                    420                 425                 430
Lys Lys Asn Val Glu Glu Gly Leu Leu Glu Leu Ser Gly His Leu Ile
                435                 440                 445
Asp Gln Lys Ala Asp Ile Ala Gln Asn Gln Thr Asp Ile Gln Asp Leu
            450                 455                 460
Ala Thr Tyr Asn Glu Leu Gln Asp Gln Tyr Ala Gln Lys Gln Thr Glu
465                 470                 475                 480
Ala Ile Asp Ala Leu Asn Lys Ala Ser Ser Glu Asn Thr Gln Asn Ile
                        485                 490                 495
Glu Asp Leu Ala Ala Tyr Asn Glu Leu Gln Asp Ala Tyr Ala Lys Gln
                    500                 505                 510
Gln Thr Glu Ala Ile Asp Ala Leu Asn Lys Ala Ser Ser Glu Asn Thr
                515                 520                 525
```

Gln Asn Ile Glu Asp Leu Ala Ala Tyr Asn Glu Leu Gln Asp Ala Tyr
              530                 535                 540

Ala Lys Gln Gln Thr Glu Ala Ile Asp Ala Leu Asn Lys Ala Ser Ser
545                 550                 555                 560

Glu Asn Thr Gln Asn Ile Glu Asp Leu Ala Ala Tyr Asn Glu Leu Gln
                565                 570                 575

Asp Ala Tyr Ala Lys Gln Gln Thr Glu Ala Ile Asp Ala Leu Asn Lys
            580                 585                 590

Ala Ser Ser Glu Asn Thr Gln Asn Ile Gln Asp Leu Ala Ala Tyr Asn
        595                 600                 605

Glu Leu Gln Asp Ala Tyr Ala Lys Gln Gln Thr Glu Ala Ile Asp Ala
    610                 615                 620

Leu Asn Lys Ala Ser Ser Glu Asn Thr Gln Asn Ile Gln Asp Leu Ala
625                 630                 635                 640

Ala Tyr Asn Glu Leu Gln Asp Ala Tyr Ala Lys Gln Gln Thr Glu Ala
                645                 650                 655

Ile Asp Ala Leu Asn Lys Ala Ser Ser Glu Asn Thr Gln Asn Ile Ala
            660                 665                 670

Lys Asn Gln Ala Asp Ile Ala Asn Asn Ile Asn Asn Ile Tyr Glu Leu
        675                 680                 685

Ala Gln Gln Gln Asp Gln His Ser Ser Asp Ile Lys Thr Leu Ala Lys
    690                 695                 700

Ala Ser Ala Ala Asn Thr Asp Arg Ile Ala Lys Asn Lys Ala Asp Ala
705                 710                 715                 720

Asp Ala Ser Phe Glu Thr Leu Thr Lys Asn Gln Asn Thr Leu Ile Glu
                725                 730                 735

Lys Asp Lys Glu His Asp Lys Leu Ile Thr Ala Asn Lys Thr Ala Ile
            740                 745                 750

Asp Ala Asn Lys Ala Ser Ala Asp Thr Lys Phe Ala Ala Thr Ala Asp
        755                 760                 765

Ala Ile Thr Lys Asn Gly Asn Ala Ile Thr Lys Asn Ala Lys Ser Ile
    770                 775                 780

Thr Asp Leu Gly Thr Lys Val Asp Gly Phe Asp Gly Arg Val Thr Ala
785                 790                 795                 800

Leu Asp Thr Lys Val Asn Ala Phe Asp Gly Arg Ile Thr Ala Leu Asp
                805                 810                 815

Ser Lys Val Glu Asn Gly Met Ala Ala Gln Ala Ala Leu Ser Gly Leu
            820                 825                 830

Phe Gln Pro Tyr Ser Val Gly Lys Phe Asn Ala Thr Ala Ala Leu Gly
        835                 840                 845

Gly Tyr Gly Ser Lys Ser Ala Val Ala Ile Gly Ala Gly Tyr Arg Val
    850                 855                 860

Asn Pro Asn Leu Ala Phe Lys Ala Gly Ala Ala Ile Asn Thr Ser Gly
865                 870                 875                 880

Asn Lys Lys Gly Ser Tyr Asn Ile Gly Val Asn Tyr Glu Phe
                885                 890

<210> SEQ ID NO 28
<211> LENGTH: 630
<212> TYPE: PRT
<213> ORGANISM: Moraxella catarrhalis

<400> SEQUENCE: 28

Met Lys Thr Met Lys Leu Leu Pro Leu Lys Ile Ala Val Thr Ser Ala

```
  1               5                  10                 15
Met Ile Ile Gly Leu Gly Ala Ala Ser Thr Ala Asn Ala Gln Ala Lys
             20                 25                 30
Asn Asp Ile Thr Leu Glu Asp Leu Pro Tyr Leu Ile Lys Lys Ile Asp
             35                 40                 45
Gln Asn Glu Leu Glu Ala Asp Ile Gly Asp Ile Thr Ala Leu Glu Lys
 50                 55                 60
Tyr Leu Ala Leu Ser Gln Tyr Gly Asn Ile Leu Ala Leu Glu Glu Leu
 65                 70                 75                 80
Asn Lys Ala Leu Glu Glu Leu Asp Glu Asp Val Gly Trp Asn Gln Asn
                 85                 90                 95
Asp Ile Ala Asn Leu Glu Asp Val Glu Thr Leu Thr Lys Asn Gln
                100                105                110
Asn Ala Phe Ala Glu Gln Gly Glu Ala Ile Lys Glu Asp Leu Gln Gly
                115                120                125
Leu Ala Asp Phe Val Glu Gly Gln Gly Lys Ile Leu Gln Asn Glu
                130                135                140
Thr Ser Ile Lys Lys Asn Thr Gln Arg Asn Leu Val Asn Gly Phe Glu
145                150                155                160
Ile Glu Lys Asn Lys Asp Ala Ile Ala Lys Asn Asn Glu Ser Ile Glu
                165                170                175
Asp Leu Tyr Asp Phe Gly His Glu Val Ala Glu Ser Ile Gly Glu Ile
                180                185                190
His Ala His Asn Glu Ala Gln Asn Glu Thr Leu Lys Gly Leu Ile Thr
                195                200                205
Asn Ser Ile Glu Asn Thr Asn Asn Ile Thr Lys Asn Lys Ala Asp Ile
210                215                220
Gln Ala Leu Glu Asn Asn Val Val Glu Leu Phe Asn Leu Ser Gly
225                230                235                240
Arg Leu Ile Asp Gln Lys Ala Asp Ile Asp Asn Asn Ile Asn Asn Ile
                245                250                255
Tyr Glu Leu Ala Gln Gln Gln Asp Gln His Ser Ser Asp Ile Lys Thr
                260                265                270
Leu Lys Lys Asn Val Glu Glu Gly Leu Leu Glu Leu Ser Asp His Ile
                275                280                285
Ile Asp Gln Lys Thr Asp Ile Ala Gln Asn Gln Ala Asn Ile Gln Asp
                290                295                300
Leu Ala Thr Tyr Asn Glu Leu Gln Asp Gln Tyr Ala Gln Lys Gln Thr
305                310                315                320
Glu Ala Ile Asp Ala Leu Asn Lys Ala Ser Ser Glu Asn Thr Gln Asn
                325                330                335
Ile Glu Asp Leu Ala Ala Tyr Asn Glu Leu Gln Asp Ala Tyr Ala Lys
                340                345                350
Gln Gln Thr Glu Ala Ile Asp Ala Leu Asn Lys Ala Ser Ser Glu Asn
                355                360                365
Thr Gln Asn Ile Glu Asp Leu Ala Ala Tyr Asn Glu Leu Gln Asp Ala
                370                375                380
Tyr Ala Lys Gln Gln Ala Glu Ala Ile Asp Ala Leu Asn Lys Ala Ser
385                390                395                400
Ser Glu Asn Thr Gln Asn Ile Ala Lys Asn Gln Ala Asp Ile Ala Asn
                405                410                415
Asn Ile Thr Asn Ile Tyr Glu Leu Ala Gln Gln Gln Asp Lys His Arg
                420                425                430
```

```
Ser Asp Ile Lys Thr Leu Ala Lys Thr Ser Ala Ala Asn Thr Asp Arg
        435                 440                 445

Ile Ala Lys Asn Lys Ala Asp Asp Ala Ser Phe Glu Thr Leu Thr
    450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
            485                 490                 495

Thr Lys Phe Ala Ala Thr Ala Asp Ala Phe Thr Lys Asn Gly Asn Ala
                500                 505                 510

Ile Thr Lys Asn Ala Lys Ser Ile Thr Asp Leu Gly Thr Lys Val Asp
            515                 520                 525

Gly Phe Asp Ser Arg Val Thr Ala Leu Asp Thr Lys Val Asn Ala Phe
530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
                565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
        595                 600                 605

Gly Ala Ala Ile Asn Thr Ser Gly Asn Lys Lys Gly Ser Tyr Asn Ile
    610                 615                 620

Gly Val Asn Tyr Glu Phe
625                 630

<210> SEQ ID NO 29
<211> LENGTH: 630
<212> TYPE: PRT
<213> ORGANISM: Moraxella catarrhalis

<400> SEQUENCE: 29

Met Lys Thr Met Lys Leu Leu Pro Leu Lys Ile Ala Val Thr Ser Ala
 1               5                  10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Glu Gly Lys Ile Leu Gln Asn Glu
    130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
```

```
                    165                 170                 175
Asp Leu Tyr Asp Phe Gly His Glu Val Ala Glu Ser Ile Gly Glu Ile
                180                 185                 190
His Ala His Asn Glu Ala Gln Asn Glu Thr Leu Lys Gly Leu Ile Thr
                195                 200                 205
Asn Ser Ile Glu Asn Thr Asn Asn Ile Thr Lys Asn Lys Ala Asp Ile
            210                 215                 220
Gln Ala Leu Glu Asn Asn Val Val Glu Leu Phe Asn Leu Ser Gly
225                 230                 235                 240
Arg Leu Ile Asp Gln Lys Ala Asp Ile Asp Asn Ile Asn Asn Ile
                245                 250                 255
Tyr Glu Leu Ala Gln Gln Asp Gln His Ser Ser Asp Ile Lys Thr
            260                 265                 270
Leu Lys Lys Asn Val Glu Glu Gly Leu Leu Glu Leu Ser Gly His Leu
        275                 280                 285
Ile Asp Gln Lys Thr Asp Ile Ala Gln Asn Gln Ala Asn Ile Gln Asp
        290                 295                 300
Leu Ala Thr Tyr Asn Glu Leu Gln Asp Gln Tyr Ala Gln Lys Gln Thr
305                 310                 315                 320
Glu Ala Ile Asp Ala Leu Asn Lys Ala Ser Ser Glu Asn Thr Gln Asn
                325                 330                 335
Ile Glu Asp Leu Ala Ala Tyr Asn Glu Leu Gln Asp Ala Tyr Ala Lys
            340                 345                 350
Gln Gln Thr Glu Ala Ile Asp Ala Leu Asn Lys Ala Ser Ser Glu Asn
            355                 360                 365
Thr Gln Asn Ile Glu Asp Leu Ala Ala Tyr Asn Glu Leu Gln Asp Ala
        370                 375                 380
Tyr Ala Lys Gln Gln Thr Glu Ala Ile Asp Ala Leu Asn Lys Ala Ser
385                 390                 395                 400
Ser Glu Asn Thr Gln Asn Ile Ala Lys Asn Gln Ala Asp Ile Ala Asn
                405                 410                 415
Asn Ile Asn Asn Ile Tyr Glu Leu Ala Gln Gln Gln Asp Gln His Ser
            420                 425                 430
Ser Asp Ile Lys Thr Leu Ala Lys Ala Ser Ala Ala Asn Thr Asp Arg
        435                 440                 445
Ile Ala Lys Asn Lys Ala Asp Ala Asp Ala Ser Phe Glu Thr Leu Thr
        450                 455                 460
Lys Asn Gln Asn Thr Leu Ile Glu Lys Asp Lys Glu His Asp Lys Leu
465                 470                 475                 480
Ile Thr Ala Asn Lys Thr Ala Ile Asp Ala Asn Lys Ala Ser Ala Asp
                485                 490                 495
Thr Lys Phe Ala Ala Thr Ala Asp Ala Ile Thr Lys Asn Gly Asn Ala
            500                 505                 510
Ile Thr Lys Asn Ala Lys Ser Ile Thr Asp Leu Gly Thr Lys Val Asp
            515                 520                 525
Gly Phe Asp Ser Arg Val Thr Ala Leu Asp Thr Lys Val Asn Ala Phe
        530                 535                 540
Asp Gly Arg Ile Thr Ala Leu Asp Ser Lys Val Glu Asn Gly Met Ala
545                 550                 555                 560
Ala Gln Ala Ala Leu Ser Gly Leu Phe Gln Pro Tyr Ser Val Gly Lys
                565                 570                 575
Phe Asn Ala Thr Ala Ala Leu Gly Gly Tyr Gly Ser Lys Ser Ala Val
            580                 585                 590
```

Ala Ile Gly Ala Gly Tyr Arg Val Asn Pro Asn Leu Ala Phe Lys Ala
            595                 600                 605

Gly Ala Ala Ile Asn Thr Ser Gly Asn Lys Lys Gly Ser Tyr Asn Ile
    610                 615                 620

Gly Val Asn Tyr Glu Phe
625                 630

<210> SEQ ID NO 30
<211> LENGTH: 616
<212> TYPE: PRT
<213> ORGANISM: Moraxella catarrhalis

<400> SEQUENCE: 30

Met Lys Thr Met Lys Leu Leu Pro Leu Lys Ile Ala Val Thr Ser Ala
 1               5                  10                  15

Leu Ile Val Gly Leu Gly Ala Val Ser Thr Thr Asn Ala Gln Ala Gln
            20                  25                  30

Ser Arg Ser Leu Asp Gln Ile Gln Thr Lys Leu Ala Asp Leu Ala Gly
        35                  40                  45

Lys Ile Ala Ala Gly Lys Asn Gly Gly Gln Asn Asn Gln Asn Asn
    50                  55                  60

Gln Asn Asp Ile Asn Lys Tyr Leu Phe Leu Ser Gln Tyr Ala Asn Ile
65                  70                  75                  80

Leu Thr Met Glu Glu Leu Asn Asn Asn Val Val Lys Asn Ser Ser Ser
                85                  90                  95

Ile Glu Thr Leu Glu Thr Asp Phe Gly Trp Leu Glu Asn Asp Val Ala
            100                 105                 110

Asp Leu Glu Asp Gly Val Glu Glu Leu Thr Lys Asn Gln Asn Thr Leu
        115                 120                 125

Ile Glu Lys Asp Glu Glu His Asp Arg Leu Ile Ala Gln Asn Gln Ala
    130                 135                 140

Asp Ile Gln Thr Leu Glu Asn Asn Val Val Glu Glu Leu Phe Asn Leu
145                 150                 155                 160

Ser Asp Arg Leu Ile Asp Gln Lys Ala Asp Ile Ala Lys Asn Gln Ala
                165                 170                 175

Asp Ile Ala Gln Asn Asn Glu Ser Ile Glu Glu Leu Tyr Asp Phe Asp
            180                 185                 190

Asn Glu Val Ala Glu Lys Ile Gly Glu Ile His Ala Tyr Thr Glu Glu
        195                 200                 205

Val Asn Lys Thr Leu Gln Asp Leu Ile Thr Asn Ser Val Lys Asn Thr
    210                 215                 220

Asp Asn Ile Asp Lys Asn Lys Ala Asp Ile Asp Asn Asn Ile Asn His
225                 230                 235                 240

Ile Tyr Glu Leu Ala Gln Gln Asp Gln His Ser Ser Asp Ile Lys
                245                 250                 255

Thr Leu Lys Asn Asn Val Glu Glu Gly Leu Leu Glu Leu Ser Gly His
            260                 265                 270

Leu Ile Asp Gln Lys Ala Asp Leu Thr Lys Asp Ile Lys Thr Leu Glu
        275                 280                 285

Asn Asn Val Glu Glu Gly Leu Leu Asp Leu Ser Gly Arg Leu Ile Asp
    290                 295                 300

Gln Lys Ala Asp Ile Ala Lys Asn Gln Ala Asp Ile Ala Gln Asn Gln
305                 310                 315                 320

Thr Asp Ile Gln Asp Leu Ala Ala Tyr Asn Glu Leu Gln Asp Gln Tyr 325                 330                 335
Ala Gln Lys Gln Thr Glu Ala Ile Asp Ala Leu Asn Lys Ala Ser Ser
                340                 345                 350

Glu Asn Thr Gln Asn Ile Glu Asp Leu Ala Ala Tyr Asn Glu Leu Gln
            355                 360                 365

Asp Ala Tyr Ala Lys Gln Gln Thr Glu Ala Ile Asp Ala Leu Asn Lys
        370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Ala Ser Ala Ala Asn Thr
            420                 425                 430

Asp Arg Ile Ala Lys Asn Lys Ala Asp Ala Asp Ala Ser Phe Glu Thr
        435                 440                 445

Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Glu Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
            500                 505                 510

Val Asp Gly Phe Asp Gly Arg Val Thr Ala Leu Asp Thr Lys Val Asn
        515                 520                 525

Ala Phe Asp Gly Arg Ile Thr Ala Leu Asp Ser Lys Val Glu Asn Gly
    530                 535                 540

Met Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
    610                 615

<210> SEQ ID NO 31
<211> LENGTH: 613
<212> TYPE: PRT
<213> ORGANISM: Moraxella catarrhalis

<400> SEQUENCE: 31

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
                20                  25                  30

Asp Arg Ser Leu Glu Asp Ile Gln Asp Ser Ile Ser Lys Leu Val Gln
            35                  40                  45

Asp Asp Ile Asp Thr Leu Lys Gln Asp Gln Gln Lys Met Asn Lys Tyr
        50                  55                  60

Leu Leu Leu Asn Gln Leu Ala Asn Thr Leu Ile Thr Asp Glu Leu Asn
65                  70                  75                  80

```
Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu Glu His
        115                 120                 125

Asp Arg Leu Ile Ala Gln Asn Ala Asp Ile Gln Thr Leu Glu Asn
    130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Asn Leu Ile Thr Asn Ser Val Lys
        195                 200                 205

Asn Thr Asp Asn Ile Asp Lys Asn Lys Ala Asp Ile Asp Asn Asn Ile
    210                 215                 220

Asn His Ile Tyr Glu Leu Ala Gln Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
            260                 265                 270

Leu Glu Ser Asn Val Glu Glu Gly Leu Leu Asp Leu Ser Gly Arg Leu
        275                 280                 285

Leu Asp Gln Lys Ala Asp Leu Thr Lys Asp Ile Lys Ala Leu Glu Ser
    290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
            340                 345                 350

Asp Ala Leu Asn Lys Ala Ser Ser Glu Asn Thr Gln Asn Ile Glu Asp
        355                 360                 365

Leu Ala Ala Tyr Asn Glu Leu Gln Asp Ala Tyr Ala Lys Gln Gln Thr
    370                 375                 380

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Asn Ile Asn Asn Ile Tyr
                405                 410                 415

Glu Leu Ala Gln Gln Gln Asp Gln His Ser Ser Asp Ile Lys Thr Leu
            420                 425                 430

Ala Lys Ala Ser Ala Ala Asn Thr Asn Arg Ile Ala Thr Ala Glu Leu
        435                 440                 445

Gly Ile Ala Glu Asn Lys Lys Asp Ala Gln Ile Ala Lys Ala Gln Ala
    450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
```

```
                500             505             510
Phe Asp Gly Arg Val Thr Ala Leu Asp Thr Lys Val Asn Ala Phe Asp
            515                 520             525

Gly Arg Ile Thr Ala Leu Asp Ser Lys Val Glu Asn Gly Met Ala Ala
530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
        595                 600                 605

Val Asn Tyr Glu Phe
    610

<210> SEQ ID NO 32
<211> LENGTH: 863
<212> TYPE: PRT
<213> ORGANISM: Moraxella catarrhalis

<400> SEQUENCE: 32

Met Asn Lys Ile Tyr Lys Val Lys Lys Asn Ala Ala Gly His Leu Val
 1               5                  10                  15

Ala Cys Ser Glu Phe Ala Lys Gly His Thr Lys Lys Ala Val Leu Gly
                20                  25                  30

Ser Leu Leu Ile Val Gly Ile Leu Gly Met Ala Thr Thr Ala Ser Ala
            35                  40                  45

Gln Lys Val Gly Lys Ala Thr Asn Lys Ile Ser Gly Gly Asp Asn Asn
        50                  55                  60

Thr Ala Asn Gly Thr Tyr Leu Thr Ile Gly Gly Asp Tyr Asn Lys
65                  70                  75                  80

Thr Lys Gly Arg Tyr Ser Thr Ile Gly Gly Leu Phe Asn Glu Ala
                85                  90                  95

Thr Asn Glu Tyr Ser Thr Ile Gly Ser Gly Gly Tyr Asn Lys Ala Lys
                100                 105                 110

Gly Arg Tyr Ser Thr Ile Gly Gly Gly Tyr Asn Glu Ala Thr Asn
            115                 120                 125

Gln Tyr Ser Thr Ile Gly Gly Asp Asn Asn Thr Ala Lys Gly Arg
        130                 135                 140

Tyr Ser Thr Ile Gly Gly Gly Tyr Asn Glu Ala Thr Ile Glu Asn
145                 150                 155                 160

Ser Thr Val Gly Gly Gly Gly Tyr Asn Gln Ala Lys Gly Arg Asn Ser
                165                 170                 175

Thr Val Ala Gly Gly Tyr Asn Asn Glu Ala Thr Gly Thr Asp Ser Thr
            180                 185                 190

Ile Ala Gly Gly Arg Lys Asn Gln Ala Thr Gly Lys Gly Ser Phe Ala
        195                 200                 205

Ala Gly Ile Asp Asn Lys Ala Asn Ala Asp Asn Ala Val Ala Leu Gly
    210                 215                 220

Asn Lys Asn Thr Ile Glu Gly Glu Asn Ser Val Ala Ile Gly Ser Asn
225                 230                 235                 240

Asn Thr Val Lys Lys Gly Gln Gln Asn Val Phe Ile Leu Gly Ser Asn
                245                 250                 255
```

```
Thr Asp Thr Thr Asn Ala Gln Asn Gly Ser Val Leu Leu Gly His Asn
        260                 265                 270

Thr Ala Gly Lys Ala Ala Thr Ile Val Asn Ser Ala Glu Val Gly Gly
            275                 280                 285

Leu Ser Leu Thr Gly Phe Ala Gly Ala Ser Lys Thr Gly Asn Gly Thr
        290                 295                 300

Val Ser Val Gly Lys Lys Gly Lys Glu Arg Gln Ile Val His Val Gly
305                 310                 315                 320

Ala Gly Glu Ile Ser Asp Thr Ser Thr Asp Ala Val Asn Gly Ser Gln
                325                 330                 335

Leu His Val Leu Ala Thr Val Val Ala Gln Asn Lys Ala Asp Ile Lys
            340                 345                 350

Asp Leu Asp Asp Glu Val Gly Leu Leu Gly Glu Glu Ile Asn Ser Leu
        355                 360                 365

Glu Gly Glu Ile Phe Asn Asn Gln Asp Ala Ile Ala Lys Asn Gln Ala
    370                 375                 380

Asp Ile Lys Thr Leu Glu Ser Asn Val Glu Glu Gly Leu Leu Asp Leu
385                 390                 395                 400

Ser Gly Arg Leu Leu Asp Gln Lys Ala Asp Ile Asp Asn Asn Ile Asn
                405                 410                 415

Asn Ile Tyr Glu Leu Ala Gln Gln Gln Asp Gln His Ser Ser Asp Ile
            420                 425                 430

Lys Thr Leu Lys Asn Asn Val Glu Glu Gly Leu Leu Asp Leu Ser Gly
        435                 440                 445

Arg Leu Ile Asp Gln Lys Ala Asp Leu Thr Lys Asp Ile Lys Ala Leu
    450                 455                 460

Glu Ser Asn Val Glu Glu Gly Leu Leu Asp Leu Ser Gly Arg Leu Ile
465                 470                 475                 480

Asp Gln Lys Ala Asp Ile Ala Lys Asn Gln Ala Asp Ile Ala Gln Asn
                485                 490                 495

Gln Thr Asp Ile Gln Asp Leu Ala Ala Tyr Asn Glu Leu Gln Asp Ala
            500                 505                 510

Tyr Ala Lys Gln Gln Thr Glu Ala Ile Asp Ala Leu Asn Lys Ala Ser
        515                 520                 525

Ser Ala Asn Thr Asp Arg Ile Ala Thr Ala Glu Leu Gly Ile Ala Glu
    530                 535                 540

Asn Lys Lys Asp Ala Gln Ile Ala Lys Ala Gln Ala Asn Glu Asn Lys
545                 550                 555                 560

Asp Gly Ile Ala Lys Asn Gln Ala Asp Ile Gln Leu His Asp Lys Lys
                565                 570                 575

Ile Thr Asn Leu Gly Ile Leu His Ser Met Val Ala Arg Ala Val Gly
            580                 585                 590

Asn Asn Thr Gln Gly Val Ala Thr Asn Lys Ala Asp Ile Ala Lys Asn
        595                 600                 605

Gln Ala Asp Ile Ala Asn Asn Ile Lys Asn Ile Tyr Glu Leu Ala Gln
    610                 615                 620

Gln Gln Asp Gln His Ser Ser Asp Ile Lys Thr Leu Ala Lys Val Ser
625                 630                 635                 640

Ala Ala Asn Thr Asp Arg Ile Ala Lys Asn Lys Ala Glu Ala Asp Ala
                645                 650                 655

Ser Phe Glu Thr Leu Thr Lys Asn Gln Asn Thr Leu Ile Glu Gln Gly
        660                 665                 670

Glu Ala Leu Val Glu Gln Asn Lys Ala Ile Asn Gln Glu Leu Glu Gly
```

```
                675                 680                 685
Phe Ala Ala His Ala Asp Val Gln Asp Lys Gln Ile Leu Gln Asn Gln
    690                 695                 700
Ala Asp Ile Thr Thr Asn Lys Thr Ala Ile Glu Gln Asn Ile Asn Arg
705                 710                 715                 720
Thr Val Ala Asn Gly Phe Glu Ile Glu Lys Asn Lys Ala Gly Ile Ala
                725                 730                 735
Thr Asn Lys Gln Glu Leu Ile Leu Gln Asn Asp Arg Leu Asn Arg Ile
                740                 745                 750
Asn Glu Thr Asn Asn His Gln Asp Gln Lys Ile Asp Gln Leu Gly Tyr
                755                 760                 765
Ala Leu Lys Glu Gln Gly Gln His Phe Asn Asn Arg Ile Ser Ala Val
    770                 775                 780
Glu Arg Gln Thr Ala Gly Gly Ile Ala Asn Ala Ile Ala Ile Ala Thr
785                 790                 795                 800
Leu Pro Ser Pro Ser Arg Ala Gly Glu His His Val Leu Phe Gly Ser
                805                 810                 815
Gly Tyr His Asn Gly Gln Ala Ala Val Ser Leu Gly Ala Ala Gly Leu
                820                 825                 830
Ser Asp Thr Gly Lys Ser Thr Tyr Lys Ile Gly Leu Ser Trp Ser Asp
                835                 840                 845
Ala Gly Gly Leu Ser Gly Gly Val Gly Gly Ser Tyr Arg Trp Lys
    850                 855                 860

<210> SEQ ID NO 33
<211> LENGTH: 630
<212> TYPE: PRT
<213> ORGANISM: Moraxella catarrhalis

<400> SEQUENCE: 33

Met Lys Thr Met Lys Leu Leu Pro Leu Lys Ile Ala Val Thr Ser Ala
  1               5                  10                  15
Met Ile Ile Gly Leu Gly Ala Ala Ser Thr Ala Asn Ala Gln Ala Lys
                 20                  25                  30
Asn Asp Ile Thr Leu Glu Asp Leu Pro Tyr Leu Ile Lys Lys Ile Asp
             35                  40                  45
Gln Asn Glu Leu Glu Ala Asp Ile Gly Asp Ile Thr Ala Leu Glu Lys
         50                  55                  60
Tyr Leu Ala Leu Ser Gln Tyr Gly Asn Ile Leu Ala Leu Glu Glu Leu
 65                  70                  75                  80
Asn Lys Ala Leu Glu Glu Leu Asp Glu Asp Val Gly Trp Asn Gln Asn
                 85                  90                  95
Asp Ile Ala Asn Leu Glu Asp Asp Val Glu Thr Leu Thr Lys Asn Gln
            100                 105                 110
Asn Ala Phe Ala Glu Gln Gly Glu Ala Ile Lys Glu Asp Leu Gln Gly
        115                 120                 125
Leu Ala Asp Phe Val Glu Gly Gln Gly Lys Ile Leu Gln Asn Glu
    130                 135                 140
Thr Ser Ile Lys Lys Asn Thr Gln Arg Asn Leu Val Asn Gly Phe Glu
145                 150                 155                 160
Ile Glu Lys Asn Lys Asp Ala Ile Ala Lys Asn Asn Glu Ser Ile Glu
                165                 170                 175
Asp Leu Tyr Asp Phe Gly His Glu Val Ala Glu Ser Ile Gly Glu Ile
                180                 185                 190
```

```
His Ala His Asn Glu Ala Gln Asn Glu Thr Leu Lys Gly Leu Ile Thr
        195                 200                 205

Asn Ser Ile Glu Asn Thr Asn Ile Thr Lys Asn Lys Ala Asp Ile
210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
            245                 250                 255

Tyr Glu Leu Ala Gln Gln Gln Asp Gln His Ser Ser Asp Ile Lys Thr
            260                 265                 270

Leu Lys Lys Asn Val Glu Glu Gly Leu Leu Glu Leu Ser Asp His Ile
        275                 280                 285

Ile Asp Gln Lys Thr Asp Ile Ala Gln Asn Gln Ala Asn Ile Gln Asp
    290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
            325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

Thr Gln Asn Ile Glu Asp Leu Ala Ala Tyr Asn Glu Leu Gln Asp Ala
    370                 375                 380

Tyr Ala Lys Gln Gln Ala Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
            405                 410                 415

Asn Ile Thr Asn Leu Tyr Glu Leu Ala Gln Gln Gln Asp Lys His Arg
            420                 425                 430

Ser Asp Ile Lys Thr Leu Ala Lys Thr Ser Ala Ala Asn Thr Asp Arg
        435                 440                 445

Ile Ala Lys Asn Lys Ala Asp Asp Asp Ala Ser Phe Glu Thr Leu Thr
    450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
            485                 490                 495

Thr Lys Phe Ala Ala Thr Ala Asp Ala Phe Thr Lys Asn Gly Asn Ala
            500                 505                 510

Ile Thr Lys Asn Ala Lys Ser Ile Thr Asp Leu Gly Thr Lys Val Asp
        515                 520                 525

Gly Phe Asp Ser Arg Val Thr Ala Leu Asp Thr Lys Val Asn Ala Phe
    530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
            565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
        595                 600                 605

Gly Ala Ala Ile Asn Thr Ser Gly Asn Lys Lys Gly Ser Tyr Asn Ile
```

```
                610                 615                 620

Gly Val Asn Tyr Glu Phe
625                 630

<210> SEQ ID NO 34
<211> LENGTH: 42
<212> TYPE: PRT
<213> ORGANISM: Moraxella catarrhalis
<220> FEATURE:
<221> NAME/KEY: MOD_RES
<222> LOCATION: (2)
<223> OTHER INFORMATION: Thr or Val
<220> FEATURE:
<221> NAME/KEY: MOD_RES
<222> LOCATION: (7)
<223> OTHER INFORMATION: Ser or Lys
<220> FEATURE:
<221> NAME/KEY: MOD_RES
<222> LOCATION: (8)
<223> OTHER INFORMATION: Gln, Glu, Lys or Ala
<220> FEATURE:
<221> NAME/KEY: MOD_RES
<222> LOCATION: (9)
<223> OTHER INFORMATION: Gly or Asn
<220> FEATURE:
<221> NAME/KEY: MOD_RES
<222> LOCATION: (10)
<223> OTHER INFORMATION: Lys, Asn, Gly, His or Ser
<220> FEATURE:
<221> NAME/KEY: MOD_RES
<222> LOCATION: (16)
<223> OTHER INFORMATION: Asn or His
<220> FEATURE:
<221> NAME/KEY: MOD_RES
<222> LOCATION: (21)
<223> OTHER INFORMATION: Gln, Asn, Glu or Lys
<220> FEATURE:
<221> NAME/KEY: MOD_RES
<222> LOCATION: (23)
<223> OTHER INFORMATION: Ser or Arg
<220> FEATURE:
<221> NAME/KEY: MOD_RES
<222> LOCATION: (24)
<223> OTHER INFORMATION: Ala or Asp
<220> FEATURE:
<221> NAME/KEY: MOD_RES
<222> LOCATION: (25)
<223> OTHER INFORMATION: Thr or Asp
<220> FEATURE:
<221> NAME/KEY: MOD_RES
<222> LOCATION: (36)
<223> OTHER INFORMATION: His or Tyr
<220> FEATURE:
<221> NAME/KEY: MOD_RES
<222> LOCATION: (40)
<223> OTHER INFORMATION: Ser, Lys or Thr
<220> FEATURE:
<221> NAME/KEY: MOD_RES
<222> LOCATION: (41)
<223> OTHER INFORMATION: Thr, Ala or Val
<220> FEATURE:
<221> NAME/KEY: MOD_RES
<222> LOCATION: (42)
<223> OTHER INFORMATION: Ile or Val

<400> SEQUENCE: 34

Gly Xaa Val Ser Val Gly Xaa Xaa Xaa Xaa Glu Arg Gln Ile Val Xaa
  1               5                  10                  15

Val Gly Ala Gly Xaa Ile Xaa Xaa Xaa Ser Thr Asp Ala Val Asn Gly
                 20                  25                  30

Ser Gln Leu Xaa Ala Leu Ala Xaa Xaa Xaa
                 35                  40
```

-continued

```
<210> SEQ ID NO 35
<211> LENGTH: 10
<212> TYPE: PRT
<213> ORGANISM: Moraxella catarrhalis

<400> SEQUENCE: 35

Ser Thr Asp Ala Val Asn Gly Ser Gln Leu
1               5                   10

<210> SEQ ID NO 36
<211> LENGTH: 40
<212> TYPE: PRT
<213> ORGANISM: Moraxella catarrhalis
<220> FEATURE:
<221> NAME/KEY: MOD_RES
<222> LOCATION: (3)
<223> OTHER INFORMATION: Asn or Asp
<220> FEATURE:
<221> NAME/KEY: MOD_RES
<222> LOCATION: (9)
<223> OTHER INFORMATION: Leu or Ile
<220> FEATURE:
<221> NAME/KEY: MOD_RES
<222> LOCATION: (21)
<223> OTHER INFORMATION: Asn or His
<220> FEATURE:
<221> NAME/KEY: MOD_RES
<222> LOCATION: (24)
<223> OTHER INFORMATION: Glu or Asp

<400> SEQUENCE: 36

Leu Leu Xaa Leu Ser Gly Arg Leu Xaa Asp Gln Lys Ala Asp Ile Asp
1               5                   10                  15

Asn Asn Ile Asn Xaa Ile Tyr Xaa Leu Ala Gln Gln Asp Gln His
            20                  25                  30

Ser Ser Asp Ile Lys Thr Leu Lys
        35                  40

<210> SEQ ID NO 37
<211> LENGTH: 11
<212> TYPE: PRT
<213> ORGANISM: Moraxella catarrhalis

<400> SEQUENCE: 37

Asp Gln Lys Ala Asp Ile Asp Asn Asn Ile Asn
1               5                   10

<210> SEQ ID NO 38
<211> LENGTH: 16
<212> TYPE: PRT
<213> ORGANISM: Moraxella catarrhalis

<400> SEQUENCE: 38

Leu Ala Gln Gln Gln Asp Gln His Ser Ser Asp Ile Lys Thr Leu Lys
1               5                   10                  15

<210> SEQ ID NO 39
<211> LENGTH: 24
<212> TYPE: PRT
<213> ORGANISM: Moraxella catarrhalis
<220> FEATURE:
<221> NAME/KEY: MOD_RES
<222> LOCATION: (10)
<223> OTHER INFORMATION: Asn or His

<400> SEQUENCE: 39

Lys Ala Asp Ile Asp Asn Asn Ile Asn Xaa Ile Tyr Glu Leu Ala Gln
1               5                   10                  15
```

Gln Gln Asp Gln His Ser Ser Asp
            20

<210> SEQ ID NO 40
<211> LENGTH: 29
<212> TYPE: PRT
<213> ORGANISM: Moraxella catarrhalis
<220> FEATURE:
<221> NAME/KEY: MOD_RES
<222> LOCATION: (2)
<223> OTHER INFORMATION: Lys or Gln
<220> FEATURE:
<221> NAME/KEY: MOD_RES
<222> LOCATION: (3)
<223> OTHER INFORMATION: Thr or Ala
<220> FEATURE:
<221> NAME/KEY: MOD_RES
<222> LOCATION: (5)
<223> OTHER INFORMATION: Lys or Glu
<220> FEATURE:
<221> NAME/KEY: MOD_RES
<222> LOCATION: (6)
<223> OTHER INFORMATION: Lys, Asn or Ser
<220> FEATURE:
<221> NAME/KEY: MOD_RES
<222> LOCATION: (8)
<223> OTHER INFORMATION: Val or Ile
<220> FEATURE:
<221> NAME/KEY: MOD_RES
<222> LOCATION: (9)
<223> OTHER INFORMATION: Glu or Val
<220> FEATURE:
<221> NAME/KEY: MOD_RES
<222> LOCATION: (11)
<223> OTHER INFORMATION: Gly or Glu
<220> FEATURE:
<221> NAME/KEY: MOD_RES
<222> LOCATION: (13)
<223> OTHER INFORMATION: Leu or Phe
<220> FEATURE:
<221> NAME/KEY: MOD_RES
<222> LOCATION: (14)
<223> OTHER INFORMATION: Glu or Asn
<220> FEATURE:
<221> NAME/KEY: MOD_RES
<222> LOCATION: (17)
<223> OTHER INFORMATION: Asp or Gly
<220> FEATURE:
<221> NAME/KEY: MOD_RES
<222> LOCATION: (18)
<223> OTHER INFORMATION: His or Arg
<220> FEATURE:
<221> NAME/KEY: MOD_RES
<222> LOCATION: (19)
<223> OTHER INFORMATION: Ile or Leu
<220> FEATURE:
<221> NAME/KEY: MOD_RES
<222> LOCATION: (24)
<223> OTHER INFORMATION: Thr or Ala
<220> FEATURE:
<221> NAME/KEY: MOD_RES
<222> LOCATION: (26)
<223> OTHER INFORMATION: Ile or Leu
<220> FEATURE:
<221> NAME/KEY: MOD_RES
<222> LOCATION: (27)
<223> OTHER INFORMATION: Ala or Thr
<220> FEATURE:
<221> NAME/KEY: MOD_RES
<222> LOCATION: (28)
<223> OTHER INFORMATION: Gln or Lys
<220> FEATURE:
<221> NAME/KEY: MOD_RES
<222> LOCATION: (29)
<223> OTHER INFORMATION: Asn or Asp

<400> SEQUENCE: 40

```
Ile Xaa Xaa Leu Xaa Xaa Asn Xaa Xaa Glu Xaa Leu Xaa Xaa Leu Ser
1               5                   10                  15

Xaa Xaa Xaa Ile Asp Gln Lys Xaa Asp Xaa Xaa Xaa Xaa
            20                  25
```

```
<210> SEQ ID NO 41
<211> LENGTH: 78
<212> TYPE: PRT
<213> ORGANISM: Moraxella catarrhalis
<220> FEATURE:
<221> NAME/KEY: MOD_RES
<222> LOCATION: (2)
<223> OTHER INFORMATION: Glu or Gln
<220> FEATURE:
<221> NAME/KEY: MOD_RES
<222> LOCATION: (19)
<223> OTHER INFORMATION: Ala or Thr
<220> FEATURE:
<221> NAME/KEY: MOD_RES
<222> LOCATION: (48)
<223> OTHER INFORMATION: Thr or Asn
<220> FEATURE:
<221> NAME/KEY: MOD_RES
<222> LOCATION: (59)
<223> OTHER INFORMATION: Lys or Gln
<220> FEATURE:
<221> NAME/KEY: MOD_RES
<222> LOCATION: (61)
<223> OTHER INFORMATION: Arg or Ser
<220> FEATURE:
<221> NAME/KEY: MOD_RES
<222> LOCATION: (70)
<223> OTHER INFORMATION: Thr or Ala
<220> FEATURE:
<221> NAME/KEY: MOD_RES
<222> LOCATION: (76)
<223> OTHER INFORMATION: Asp or Asn

<400> SEQUENCE: 41

Ile Xaa Asp Leu Ala Ala Tyr Asn Glu Leu Gln Asp Ala Tyr Ala Lys
1               5                   10                  15

Gln Gln Xaa Glu Ala Ile Asp Ala Leu Asn Lys Ala Ser Ser Glu Asn
            20                  25                  30

Thr Gln Asn Ile Ala Lys Asn Gln Ala Asp Ile Ala Asn Asn Ile Xaa
        35                  40                  45

Asn Ile Tyr Glu Leu Ala Gln Gln Gln Asp Xaa His Xaa Ser Asp Ile
    50                  55                  60

Lys Thr Leu Ala Lys Xaa Ser Ala Ala Asn Thr Xaa Arg Ile
65                  70                  75
```

```
<210> SEQ ID NO 42
<211> LENGTH: 16
<212> TYPE: PRT
<213> ORGANISM: Moraxella catarrhalis

<400> SEQUENCE: 42

Asp Leu Ala Ala Tyr Asn Glu Leu Gln Asp Ala Tyr Ala Lys Gln Gln
1               5                   10                  15
```

```
<210> SEQ ID NO 43
<211> LENGTH: 28
<212> TYPE: PRT
<213> ORGANISM: Moraxella catarrhalis

<400> SEQUENCE: 43

Glu Ala Ile Asp Ala Leu Asn Lys Ala Ser Ser Glu Asn Thr Gln Asn
1               5                   10                  15
```

```
Ile Ala Lys Asn Gln Ala Asp Ile Ala Asn Asn Ile
            20                  25
```

<210> SEQ ID NO 44
<211> LENGTH: 42
<212> TYPE: PRT
<213> ORGANISM: Moraxella catarrhalis
<220> FEATURE:
<221> NAME/KEY: MOD_RES
<222> LOCATION: (2)
<223> OTHER INFORMATION: Thr or Val
<220> FEATURE:
<221> NAME/KEY: MOD_RES
<222> LOCATION: (7)
<223> OTHER INFORMATION: Ser or Lys
<220> FEATURE:
<221> NAME/KEY: MOD_RES
<222> LOCATION: (8)
<223> OTHER INFORMATION: Gln, Glu, Lys or Ala
<220> FEATURE:
<221> NAME/KEY: MOD_RES
<222> LOCATION: (9)
<223> OTHER INFORMATION: Gly or Asn
<220> FEATURE:
<221> NAME/KEY: MOD_RES
<222> LOCATION: (10)
<223> OTHER INFORMATION: Lys, Asn, Gly, His or Ser
<220> FEATURE:
<221> NAME/KEY: MOD_RES
<222> LOCATION: (16)
<223> OTHER INFORMATION: Asn or His
<220> FEATURE:
<221> NAME/KEY: MOD_RES
<222> LOCATION: (21)
<223> OTHER INFORMATION: Gln, Asn, Glu or Lys
<220> FEATURE:
<221> NAME/KEY: MOD_RES
<222> LOCATION: (23)
<223> OTHER INFORMATION: Ser or Arg
<220> FEATURE:
<221> NAME/KEY: MOD_RES
<222> LOCATION: (24)
<223> OTHER INFORMATION: Ala or Asp
<220> FEATURE:
<221> NAME/KEY: MOD_RES
<222> LOCATION: (25)
<223> OTHER INFORMATION: Thr or Asp
<220> FEATURE:
<221> NAME/KEY: MOD_RES
<222> LOCATION: (36)
<223> OTHER INFORMATION: His or Tyr
<220> FEATURE:
<221> NAME/KEY: MOD_RES
<222> LOCATION: (40)
<223> OTHER INFORMATION: Ser, Lys or Thr
<220> FEATURE:
<221> NAME/KEY: MOD_RES
<222> LOCATION: (41)
<223> OTHER INFORMATION: Thr, Ala or Val
<220> FEATURE:
<221> NAME/KEY: MOD_RES
<222> LOCATION: (42)
<223> OTHER INFORMATION: Ile or Val

<400> SEQUENCE: 44

```
Gly Xaa Val Ser Val Gly Xaa Xaa Xaa Xaa Glu Arg Gln Ile Val Xaa
 1               5                  10                  15

Val Gly Ala Gly Xaa Ile Xaa Xaa Xaa Ser Thr Asp Ala Val Asn Gly
            20                  25                  30

Ser Gln Leu Xaa Ala Leu Ala Xaa Xaa Xaa
        35                  40
```

<210> SEQ ID NO 45

```
<211> LENGTH: 10
<212> TYPE: PRT
<213> ORGANISM: Moraxella catarrhalis

<400> SEQUENCE: 45

Ser Thr Asp Ala Val Asn Gly Ser Gln Leu
1               5                   10

<210> SEQ ID NO 46
<211> LENGTH: 40
<212> TYPE: PRT
<213> ORGANISM: Moraxella catarrhalis
<220> FEATURE:
<221> NAME/KEY: MOD_RES
<222> LOCATION: (3)
<223> OTHER INFORMATION: Asn or Asp
<220> FEATURE:
<221> NAME/KEY: MOD_RES
<222> LOCATION: (9)
<223> OTHER INFORMATION: Leu or Ile
<220> FEATURE:
<221> NAME/KEY: MOD_RES
<222> LOCATION: (21)
<223> OTHER INFORMATION: Asn or His
<220> FEATURE:
<221> NAME/KEY: MOD_RES
<222> LOCATION: (24)
<223> OTHER INFORMATION: Glu or Asp

<400> SEQUENCE: 46

Leu Leu Xaa Leu Ser Gly Arg Leu Xaa Asp Gln Lys Ala Asp Ile Asp
1               5                   10                  15

Asn Asn Ile Asn Xaa Ile Tyr Xaa Leu Ala Gln Gln Gln Asp Gln His
            20                  25                  30

Ser Ser Asp Ile Lys Thr Leu Lys
        35                  40

<210> SEQ ID NO 47
<211> LENGTH: 11
<212> TYPE: PRT
<213> ORGANISM: Moraxella catarrhalis

<400> SEQUENCE: 47

Asp Gln Lys Ala Asp Ile Asp Asn Asn Ile Asn
1               5                   10

<210> SEQ ID NO 48
<211> LENGTH: 16
<212> TYPE: PRT
<213> ORGANISM: Moraxella catarrhalis

<400> SEQUENCE: 48

Leu Ala Gln Gln Gln Asp Gln His Ser Ser Asp Ile Lys Thr Leu Lys
1               5                   10                  15

<210> SEQ ID NO 49
<211> LENGTH: 24
<212> TYPE: PRT
<213> ORGANISM: Moraxella catarrhalis
<220> FEATURE:
<221> NAME/KEY: MOD_RES
<222> LOCATION: (10)
<223> OTHER INFORMATION: Asn or His

<400> SEQUENCE: 49

Lys Ala Asp Ile Asp Asn Asn Ile Asn Xaa Ile Tyr Glu Leu Ala Gln
1               5                   10                  15
```

Gln Gln Asp Gln His Ser Ser Asp
            20

<210> SEQ ID NO 50
<211> LENGTH: 29
<212> TYPE: PRT
<213> ORGANISM: Moraxella catarrhalis
<220> FEATURE:
<221> NAME/KEY: MOD_RES
<222> LOCATION: (2)
<223> OTHER INFORMATION: Lys or Gln
<220> FEATURE:
<221> NAME/KEY: MOD_RES
<222> LOCATION: (3)
<223> OTHER INFORMATION: Thr or Ala
<220> FEATURE:
<221> NAME/KEY: MOD_RES
<222> LOCATION: (5)
<223> OTHER INFORMATION: Lys or Glu
<220> FEATURE:
<221> NAME/KEY: MOD_RES
<222> LOCATION: (6)
<223> OTHER INFORMATION: Lys, Asn or Ser
<220> FEATURE:
<221> NAME/KEY: MOD_RES
<222> LOCATION: (8)
<223> OTHER INFORMATION: Val or Ile
<220> FEATURE:
<221> NAME/KEY: MOD_RES
<222> LOCATION: (9)
<223> OTHER INFORMATION: Glu or Val
<220> FEATURE:
<221> NAME/KEY: MOD_RES
<222> LOCATION: (11)
<223> OTHER INFORMATION: Gly or Glu
<220> FEATURE:
<221> NAME/KEY: MOD_RES
<222> LOCATION: (13)
<223> OTHER INFORMATION: Leu or Phe
<220> FEATURE:
<221> NAME/KEY: MOD_RES
<222> LOCATION: (14)
<223> OTHER INFORMATION: Glu or Asn
<220> FEATURE:
<221> NAME/KEY: MOD_RES
<222> LOCATION: (17)
<223> OTHER INFORMATION: Asp or Gly
<220> FEATURE:
<221> NAME/KEY: MOD_RES
<222> LOCATION: (18)
<223> OTHER INFORMATION: His or Arg
<220> FEATURE:
<221> NAME/KEY: MOD_RES
<222> LOCATION: (19)
<223> OTHER INFORMATION: Ile or Leu
<220> FEATURE:
<221> NAME/KEY: MOD_RES
<222> LOCATION: (24)
<223> OTHER INFORMATION: Thr or Ala
<220> FEATURE:
<221> NAME/KEY: MOD_RES
<222> LOCATION: (26)
<223> OTHER INFORMATION: Ile or Leu
<220> FEATURE:
<221> NAME/KEY: MOD_RES
<222> LOCATION: (27)
<223> OTHER INFORMATION: Ala or Thr
<220> FEATURE:
<221> NAME/KEY: MOD_RES
<222> LOCATION: (28)
<223> OTHER INFORMATION: Gln or Lys
<220> FEATURE:
<221> NAME/KEY: MOD_RES
<222> LOCATION: (29)
<223> OTHER INFORMATION: Asn or Asp

<400> SEQUENCE: 50

```
Ile Xaa Xaa Leu Xaa Xaa Asn Xaa Xaa Glu Xaa Leu Xaa Xaa Leu Ser
1               5                   10                  15

Xaa Xaa Xaa Ile Asp Gln Lys Xaa Asp Xaa Xaa Xaa Xaa
            20                  25
```

<210> SEQ ID NO 51
<211> LENGTH: 78
<212> TYPE: PRT
<213> ORGANISM: Moraxella catarrhalis
<220> FEATURE:
<221> NAME/KEY: MOD_RES
<222> LOCATION: (2)
<223> OTHER INFORMATION: Glu or Gln
<220> FEATURE:
<221> NAME/KEY: MOD_RES
<222> LOCATION: (19)
<223> OTHER INFORMATION: Ala or Thr
<220> FEATURE:
<221> NAME/KEY: MOD_RES
<222> LOCATION: (48)
<223> OTHER INFORMATION: Thr or Asn
<220> FEATURE:
<221> NAME/KEY: MOD_RES
<222> LOCATION: (59)
<223> OTHER INFORMATION: Lys or Gln
<220> FEATURE:
<221> NAME/KEY: MOD_RES
<222> LOCATION: (61)
<223> OTHER INFORMATION: Arg or Ser
<220> FEATURE:
<221> NAME/KEY: MOD_RES
<222> LOCATION: (70)
<223> OTHER INFORMATION: Thr or Ala
<220> FEATURE:
<221> NAME/KEY: MOD_RES
<222> LOCATION: (76)
<223> OTHER INFORMATION: Asp or Asn

<400> SEQUENCE: 51

```
Ile Xaa Asp Leu Ala Ala Tyr Asn Glu Leu Gln Asp Ala Tyr Ala Lys
1               5                   10                  15

Gln Gln Xaa Glu Ala Ile Asp Ala Leu Asn Lys Ala Ser Ser Glu Asn
            20                  25                  30

Thr Gln Asn Ile Ala Lys Asn Gln Ala Asp Ile Ala Asn Asn Ile Xaa
        35                  40                  45

Asn Ile Tyr Glu Leu Ala Gln Gln Gln Asp Xaa His Xaa Ser Asp Ile
    50                  55                  60

Lys Thr Leu Ala Lys Xaa Ser Ala Ala Asn Thr Xaa Arg Ile
65                  70                  75
```

<210> SEQ ID NO 52
<211> LENGTH: 16
<212> TYPE: PRT
<213> ORGANISM: Moraxella catarrhalis

<400> SEQUENCE: 52

```
Asp Leu Ala Ala

Ile Ala Lys Asn Gln Ala Asp Ile Ala Asn Asn Ile
            20                  25

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caaagctgac atccaagcac ttg                                              23

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcgtctgcgg atccagtagg caaggcaacc                                       30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcgtctgcgg atccagtagg caaggcaacc                                       30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcgtctgcgg atccagtagg caaggcaacc                                       30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcgtctgcgg atccagtagg caaggcaacc                                       30

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggatttgcag gtgcatcgga tcctggtaat ggtact         36

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
catagctctg atatggatcc acttaaaaac               30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gccaaagcac aagcggatcc aaataaagac               30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gttgagcaaa aggatcccat caatcaagag               30

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cgaatgcgga tcctaaaaat gatataactt tagagg         36

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgaatgcgga tcctaaaaat gatataactt tagagg         36

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gatattgcgg atccggaaga tgatgttgaa ac             32

<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gatattgcgg atccggaaga tgatgttgaa ac                                32

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gagattgaga aggatccaga tgctattgct                                   30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gctcaaaacc aagcggatcc ccaagatctg                                   30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gcaagtgctg cggatcctga tcgtattgct                                   30

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccctgaagct ttagtgcata acctaattg                                    29

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ttgagcaagc ttagcttggt ttttagcg                                     28

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
acctgtggca agcttcttcc tgcc                                          24

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ggtgtcacta agcttacctg caccaacatg aac                                33

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
gtcttttgta agatcaagct tttgatcaat                                    30

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
catgctgaga agcttaccta gattgg                                        26

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggtcttattg gtagtaagct tagcttggtt ttg                                33

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
ccctgaagct ttagtgcata acctaattg                                     29

```
<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cattaagctt ggtgtctaat gcagttac                                           28

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctcatgacca aaatcaagct tatcttcgat agactc                                  36

<210> SEQ ID NO 80
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gatcaataag cttaccgctt agattgaata gttcttc                                 37

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gtcaatcgct tcaagcttct tttgagcata ctg                                     33

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gtcaatcgct tcaagcttct tttgagcata ctg                                     33

<210> SEQ ID NO 83
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggtgagcgtt tcaagctttg catcagcatc ggc                                     33

<210> SEQ ID NO 84
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cattaagctt ggtgtctaat gcagttac                                        28

<210> SEQ ID NO 85
<211> LENGTH: 23
<212> TYPE: PRT
<213> ORGANISM: Moraxella catarrhalis

<400> SEQUENCE: 85

Asn Asn Ile Asn Asn Ile Tyr Glu Leu Ala Gln Gln Gln Asp Gln His
1               5                   10                  15

Ser Ser Asp Ile Lys Thr Leu
            20

<210> SEQ ID NO 86
<211> LENGTH: 7
<212> TYPE: PRT
<213> ORGANISM: Moraxella catarrhalis

<400> SEQUENCE: 86

Asn Asn Ile Asn Asn Ile Tyr
1               5

<210> SEQ ID NO 87
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Thr Gly Asn Gly Thr Val Ser Val Gly Lys Lys Gly Lys Glu Arg Gln
1               5                   10                  15

Ile Val His Val Gly Ala Gly Glu Ile Ser Asp Thr Ser Thr Asp Ala
            20                  25                  30

Val Asn Gly Ser Gln Leu His Val Leu Ala Thr Val Val Ala Gln Asn
        35                  40                  45

Lys Ala Asp Ile Lys Asp Leu Asp Asp Glu Val Gly Leu Leu Gly Glu
    50                  55                  60

Glu Ile Asn Ser Leu Glu Gly Glu Ile Phe Asn Asn Gln Asp Ala Ile
65                  70                  75                  80

Ala Lys Asn Gln Ala Asp Ile Lys Thr Leu Glu Ser Asn Val Glu Glu
                85                  90                  95

Gly Leu Leu Asp Leu Ser Gly Arg Leu Leu Asp Gln Lys Ala Asp Ile
            100                 105                 110

Asp Asn Asn Ile Asn Asn Ile Tyr Glu Leu Ala Gln Gln Gln Asp Gln
        115                 120                 125

His Ser Ser Asp Ile Lys Thr Leu Lys Asn Asn Val Glu Glu Gly Leu
    130                 135                 140

Leu Asp Leu Ser Gly Arg Leu Ile Asp Gln
145                 150

<210> SEQ ID NO 88
```

```
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Thr Gly Asn Gly Thr Val Ser Val Gly Lys Lys Gly Lys Glu Arg
 1               5                  10                  15

Gln Ile Val His Val Gly Ala Gly Glu Ile Ser Asp Thr Ser Thr Asp
             20                  25                  30

Ala Val Asn Gly Ser Gln Leu His Val Leu Ala Thr Val Val Ala Gln
         35                  40                  45

Asn Lys Ala Asp Ile Lys Asp Leu Asp Asp Glu Val Gly Leu Leu Gly
     50                  55                  60

Glu Glu Ile Asn Ser Leu Glu Gly Glu Ile Phe Asn Asn Gln Asp Ala
 65                  70                  75                  80

Ile Ala Lys Asn Gln Ala Asp Ile Lys Thr Leu Glu Ser Asn Val Glu
                 85                  90                  95

Glu Gly Leu Leu Asp Leu Ser Gly Arg Leu Leu Asp Gln Lys Ala Asp
            100                 105                 110

Ile Asp Asn Asn Ile Asn Asn Ile Tyr Glu Leu Ala Gln Gln Gln Asp
        115                 120                 125

Gln His Ser Ser Asp Ile Lys Thr Leu Lys Asn Asn Val Glu Glu Gly
    130                 135                 140

Leu Leu Asp Leu Ser Gly Arg Leu Ile Asp
145                 150
```

The invention claimed is:

1. An isolated polypeptide consisting of an amino acid sequence that is at least 95% identical to SEQ ID NO: 6.

2. The isolated polypeptide of claim 1, comprising SEQ ID NO: 1.

3. A fusion protein comprising an isolated polypeptide according to any one of claims 1 and 2.

4. An immunogenic composition comprising at least one polypeptide according to any one of claims 1 and 2, or at least one fusion protein according to claim 3, and one or more components chosen from pharmaceutically acceptable adjuvants, vehicles, excipients, binders, carriers, and preservatives.

5. The immunogenic composition of claim 4, comprising at least one polypeptide according to any one of claims 1 and 2 and a pharmaceutically acceptable adjuvant.

* * * * *